United States Patent [19]
Wissner et al.

[11] Patent Number: 6,002,008
[45] Date of Patent: Dec. 14, 1999

[54] SUBSTITUTED 3-CYANO QUINOLINES

[75] Inventors: Allan Wissner, Ardsley; Bernard D. Johnson, Stony Point; Marvin F. Reich; Middleton B. Floyd, Jr., both of Suffern; Douglas B. Kitchen, Schenectady; Hwei-Ru Tsou, New City, all of N.Y.

[73] Assignee: American Cyanamid Company

[21] Appl. No.: 09/049,718

[22] Filed: Mar. 27, 1998

Related U.S. Application Data

[60] Provisional application No. 60/041,963, Apr. 3, 1997.
[51] Int. Cl.⁶ .................. A01A 43/42; C07D 215/16; C07D 215/38
[52] U.S. Cl. .................. 546/160; 514/313; 546/156; 546/157; 546/159; 546/160; 546/161
[58] Field of Search .................. 546/153, 156, 546/157, 159, 150, 161; 514/312, 313

[56] References Cited

U.S. PATENT DOCUMENTS

| | | | |
|---|---|---|---|
| 5,480,883 | 1/1996 | Spada et al. | 514/249 |
| 5,686,457 | 11/1997 | Traxler et al. | 514/258 |

FOREIGN PATENT DOCUMENTS

| | | |
|---|---|---|
| 0520722 | 12/1992 | European Pat. Off. . |
| 0566226 | 10/1993 | European Pat. Off. . |
| 0602851 | 6/1994 | European Pat. Off. . |
| 0635498 | 1/1995 | European Pat. Off. . |
| 0635507 | 1/1995 | European Pat. Off. . |
| 9515758 | 6/1995 | WIPO . |
| 9519774 | 7/1995 | WIPO . |
| 9519970 | 7/1995 | WIPO . |
| 9521613 | 8/1995 | WIPO . |
| 9523141 | 8/1995 | WIPO . |
| 9524190 | 9/1995 | WIPO . |
| 9615118 | 5/1996 | WIPO . |
| 9616960 | 6/1996 | WIPO . |
| 9630347 | 10/1996 | WIPO . |
| 9633978 | 10/1996 | WIPO . |
| 9633979 | 10/1996 | WIPO . |
| 9633981 | 10/1996 | WIPO . |
| 9714681 | 4/1997 | WIPO . |
| 9609294 | 3/1998 | WIPO . |

OTHER PUBLICATIONS

Bridges A. J. et al., Tyrosine Kinase Inhibitors. 8. An Unusually Steep Structure—Activity Relationship for Analogues of 4–(3–Bromoaniline)–6,7–dimethoxyquinazoline. (PD 153035), a Potent Inhibitor of the Epidermal Growth Factor Receptor, J. Med. Chem., 1996, 39, 267–276.

Dolle R. E. et al., 5,7–Dimethoxy–3–(4–pyridinyl)quinoline Is a Potent and Selective Inhibitor of Human Vascular β–Type Platelet–Derived Growth factor Receptor Tyrosine Kinase, J. Med. Chem., 1994, 37, 2627–2629.

Ife, R. J. et al., Reversible Inhibitors of the Gastric (H⁺/K⁺)–ATPase.
3.3–Substituted–4–(phenylamine)quinolines, J. Med. Chem., 1992, 35, 3413–3422.

Maguire M. P. et al., A New Series of PDGF Receptor Tyrosine Kinase Inhibitors: 3–Substituted Quinoline Derivatives, J. Med. Chem., 1994, 37, 2129–2137.

Rewcastle G. W. et al., Tyrosine Kinase Inhibitors. 5. Synthesis and Structure–Activity Relationships for 4–[(Phenylmethyl)amino]–and 4–(Phenylamino) quinazolines as Potent Adenosine 5'–Triphosphate Binding Site Inhibitors of the Tyrosine Kinase Domain of the Epidermal Growth Factor Receptor, J. Med. Chem,. 1995, 38, 3482–3487.

Fry, D. W. et al., A Specific Inhibitor of the Epidermal Growth Factor Receptor Tyrosine Kinase, Science, 265, 1994, 1093–1095.

Gazit A. et al., Tyrphostins. 5. Potent Inhibitors of Platelet–Derived Growth Factor Receptor Tyrosine Kinase: Structure–Activity Relationships in Quinoxalines, Quinolines, and Indole Tyrpostins, J. Med. Chem., 1996, 39, 2170–2177.

Price, C. C. et al., J. Amer. Chem. Soc., vol. 68, (1946) pp. 1246–1250.

*Primary Examiner*—D Margaret M. Mach
*Attorney, Agent, or Firm*—Arnold S. Milowsky

[57] ABSTRACT

This invention provides compounds having the formula:

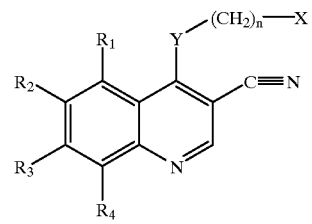

wherein:
X is cycloalkyl which may be optionally substituted; or is a pyridinyl, pyrimidinyl, or phenyl ring; wherein the pyridinyl, pyrimidinyl, or phenyl ring may be optionally substituted;

n is 0–1;

Y is —NH—, —O—, —S—, or —NR—;

R is alkyl of 1–6 carbon atoms;

$R_1$, $R_2$, $R_3$, and $R_4$ are each, independently, hydrogen, halogen, alkyl, alkenyl, alkynyl, alkenyloxy, alkynyloxy, hydroxymethyl, halomethyl, alkanoyloxy, alkenoyloxy, alkynoyloxy, alkanoyloxymethyl, alkenoyloxymethyl, alkynoyloxymethyl, alkoxymethyl, alkoxy, alkylthio, alkylsulphinyl, alkylsulphonyl, alkylsulfonamido, alkenylsulfonamido, alkynylsulfonamido, hydroxy, trifluoromethyl, cyano, nitro, carboxy, carboalkoxy, carboalkyl, phenoxy, phenyl, thiophenoxy, benzyl, amino, hydroxyamino, alkoxyamino, alkylamino, dialkylamino, aminoalkyl, N-alkylaminoalkyl, N,N-dialkylaminoalkyl, phenylamino, benzylamino, $R_5$—CONH(CH_2)_p—, $R_5$—S—(C(R_6)_2)_q—CONH(CH_2)_p—, $R_8$≡≡—CONH(CH_2)_p—,

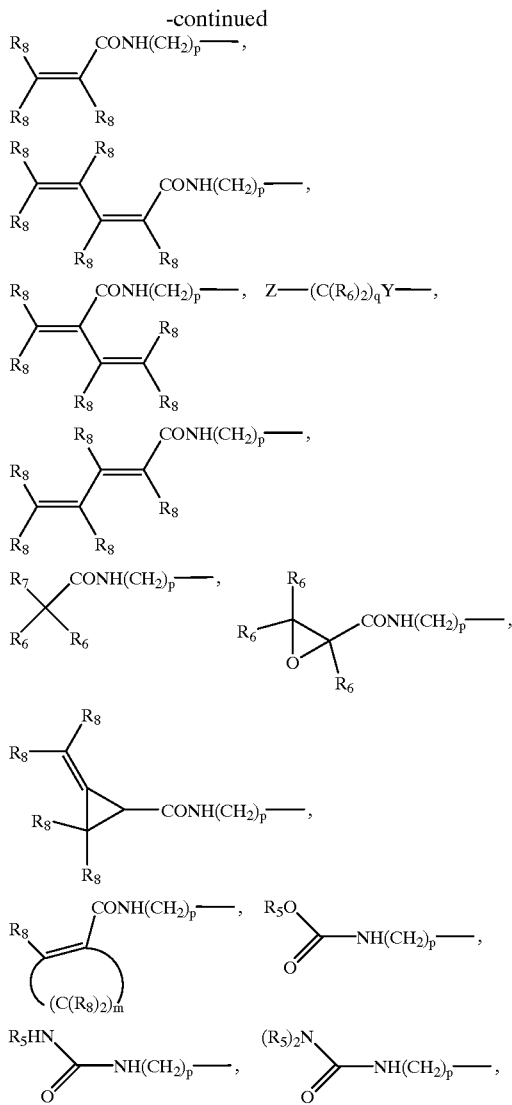

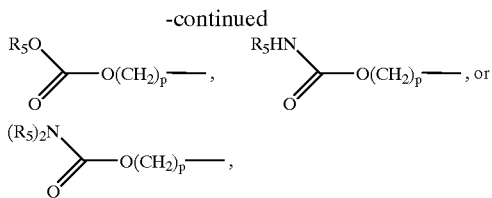

$R_5$ is alkyl which may be optionally substituted, or phenyl which may be optionally substituted;

$R_6$ is hydrogen, alkyl, or alkenyl;

$R_7$ is chloro or bromo $R_8$ is hydrogen, alkyl, aminoalkyl, N-alkylaminoalkyl, N,N-dialkylaminoalkyl, N-cycloalkylaminoalkyl, N-cycloalkyl-N-alkylaminoalkyl, N,N-dicycloalkylaminoalkyl, morpholino-N-alkyl, piperidino-N-alkyl, N-alkyl-piperidino-N-alkyl, azacycloalkyl-N-alkyl, hydroxyalkyl, alkoxyalkyl, carboxy, carboalkoxy, phenyl, carboalkyl+, chloro, fluoro, or bromo;

Z is amino, hydroxy, alkoxy, alkylamino, dialkylamino, morpholino, piperazino, N-alkylpiperazino, or pyrrolidino;

m=1–4, q=1–3, and p=0–3;

any of the substituents $R_1$, $R_2$, $R_3$, or $R_4$ that are located on contiguous carbon atoms can together be the divalent radical —O—C($R_8$)$_2$—O—;

or a pharmaceutically acceptable salt thereof with the proviso that when Y is —NH—, $R_1$, $R_2$, $R_3$, and $R_4$ are hydrogen, and n is 0, X is not 2-methylphenyl, which are inhibitors of protein tyrosine kinase.

29 Claims, No Drawings

SUBSTITUTED 3-CYANO QUINOLINES

This application claims the benefit of U.S. Provisional Application Ser. No. 60/041,963, filed Apr. 3, 1997.

BACKGROUND OF THE INVENTION

This invention relates to certain substituted 3-cyano quinoline compounds as well as the pharmaceutically acceptable salts thereof. The compounds of the present invention inhibit the action of certain growth factor receptor protein tyrosine kinases (PTK) thereby inhibiting the abnormal growth of certain cell types. The compounds of this invention are therefore useful for the treatment of certain diseases that are the result of deregulation of these PTKs. The compounds of this invention are anti-cancer agents and are useful for the treatment of cancer in mammals. In addition, the compounds of this invention are useful for the treatment of polycystic kidney disease in mammals. This invention also relates to the manufacture of said 3-cyano quinolines, their use for the treatment of cancer and polycystic kidney disease, and the pharmaceutical preparations containing them.

Protein tyrosine kinases are a class of enzymes that catalyze the transfer of a phosphate group from ATP to a tyrosine residue located on a protein substrate. Protein tyrosine kinases clearly play a role in normal cell growth. Many of the growth factor receptor proteins function as tyrosine kinases and it is by this process that they effect signaling. The interaction of growth factors with these receptors is a necessary event in normal regulation of cell growth. However, under certain conditions, as a result of either mutation or overexpression, these receptors can become deregulated; the result of which is uncontrolled cell proliferation which can lead to tumor growth and ultimately to the disease known as cancer [Wilks A. F., *Adv. Cancer Res.*, 60, 43 (1993) and Parsons, J. T.; Parsons, S. J., *Important Advances in Oncology,* DeVita V. T. Ed., J. B. Lippincott Co., Phila., 3 (1993) ]. Among the growth factor receptor kinases and their proto-oncogenes that have been identified and which are targets of the compounds of this invention are the epidermal growth factor receptor kinase (EGF-R kinase, the protein product of the erbB oncogene), and the product produced by the erbB-2 (also referred to as the neu or HER2) oncogene. Since the phosphorylation event is a necessary signal for cell division to occur and since overexpressed or mutated kinases have been associated with cancer, an inhibitor of this event, a protein tyrosine kinase inhibitor, will have therapeutic value for the treatment of cancer and other diseases characterized by uncontrolled or abnormal cell growth. For example, overexpression of the receptor kinase product of the erbB-2 oncogene has been associated with human breast and ovarian cancers [Slamon, D. J., et. al., *Science,* 244, 707 (1989) and *Science,* 235, 1146 (1987)]. Deregulation of EGF-R kinase has been associated with epidermoid tumors [Reiss, M., et. al., *Cancer Res.*, 51, 6254 (1991)], breast tumors [Macias, A., et. al., *Anticancer Res.,* 7, 459 (1987)], and tumors involving other major organs [Gullick, W. J., *Brit. Med Bull.,* 47, 87 (1991)]. Because of the importance of the role played by deregulated receptor kinases in the pathogenesis of cancer, many recent studies have dealt with the development of specific PTK inhibitors as potential anti-cancer therapeutic agents [some recent reviews: Burke. T. R., *Drugs Future,* 17, 119 (1992) and Chang, C. J.; Geahlen, R. L., *J. Nat. Prod.,* 55, 1529 (1992)].

It is also known that deregulation of EGF receptors is a factor in the growth of epithelial cysts in the disease described as polycystic kidney disease [Du J., Wilson P. D., *Amer. J. Physiol.,* 269(2 Pt 1), 487 (1995); Nauta J., et al., *Pediatric Research,* 37(6), 755 (1995); Gattone V. H., et al., *Developmental. Biology,* 169(2), 504 (1995); Wilson P. D., et al., *Eur. J. Cell Biol.,* 61(1), 131, (1993)]. The compounds of this invention, which inhibit the catalytic function of the EGF receptors, are consequently useful for the treatment of this disease.

The mitogen-activated protein kinase (MAPK) pathway is a major pathway in the cellular signal transduction cascade from growth factors to the cell nucleus. The pathway involves kinases at two levels: MAP kinase kinases (MAPKK), and their substrates MAP kinases (MAPK). There are different isoforms in the MAP kinase family. (For review, see Rony Seger and Edwin G. Krebs, FASEB, Vol. 9, 726, June 1995). The compounds of this invention can inhibit the action of two of these kinases: MEK, a MAP kinase kinase, and its substrate ERK, a MAP kinase. MEK is activated by phosphorylation on two serine residues by upstream kinases such as members of the raf family. When activated, MEK catalyzes phosphorylation on a threonine and a tyrosine residue of ERK. The activated ERK then phosphorylates and activates transcription factors in the nucleus, such as fos and jun, or other cellular targets with PXT/SP sequences. ERK, a p42 MAPK is found to be essential for cell proliferation and differentiation. Overexpression and/or over-activation of Mek or ERK has been found to be associated with various human cancers (For example, Vimala S. Sivaraman, Hsien-yu Wang, Gerard J. Nuovo, and Craig C. Malbon, J. Clin. Invest. Vol. 99, No. 7April 1997). It has been demonstrated that inhibition of MEK prevents activation of ERK and subsequent activation of ERK substrates in cells, resulting in inhibition of cell growth stimulation and reversal of the phenotype of ras-transformed cells (David T. Dudley, Long Pang, Stuart J. Decker, Alexander J. Bridges, and Alan R. Saltiel, PNAS, Vol. 92, 7686, August 1995). Since, as demonstrated below, the compounds of this invention can inhibit the coupled action of MEK and ERK, they are useful for the treatment of diseases such as cancer which are characterized by uncontrolled cell proliferation and which, at least in part, depend on the MAPK pathway.

Epithelial Cell Kinase (ECK) is a receptor protein tyrosine kinase (RPTK) belonging to the EPH (Erythropoietin Producing Hepatoma) family. Although originally identified as an epithelial lineage-specific tyrosine kinase, ECK has subsequently been shown to be expressed on vascular endothelial cells, smooth muscle cells, and fibroblasts. ECK is a type I transmembrane glycoprotein with the extracellular ligand-binding domain consisting of a cysteine-rich region followed by three fibronectin type III repeats. The intracellular domain of ECK possesses a tyrosine kinase catalytic domain that initiates a signal transduction cascade reflecting the ECK function. ECK binds and is subsequently activated by its counter-receptor, Ligand for Eph-Related Kinase (LERK)-1, which is an immediate early response gene product readily inducible in a lineage-unrestricted manner with proinflammatory cytokines such as IL-1 or TNF. Soluble LERK-1 has been shown to stimulate angiogenesis in part by stimulating ECK in a murine model of corneal angiogenesis. Unlike their normal counterparts, tumor cells of various lineages constitutively express LERK-1 and this expression can further be upregulated by hypoxia and proinflammatory cytokines. Many of these tumor cells also express ECK at higher levels than their normal counterparts, thereby creating an opportunity for autocrine stimulation via ECK LERK-1 interaction. The increased expression of both ECK and LERK-1 has been correlated with the transformation of melanomas from the noninvasive horizontal phase of growth into very invasive vertically growing metastatic melanomas. Together, the ECK:LERK-1 interaction is believed to promote tumor growth via its tumor growth promoting and angiogenic effects. Thus, the inhibition of the ECK tyrosine kinase activity mediating signaling cascade induced by its binding and cross-linking to LERK-1 may be therapeutically beneficial in cancer, inflammatory diseases, and hyperproliferative disorders. As is shown below, the compounds of this invention inhibit the tyrosine kinase activity of ECK and are therefore useful for the treatment of the aforementioned disorders.

Growth of most solid tumors is dependent on the angiogenesis involving activation, proliferation and migration of vascular endothelial cells and their subsequent differentiation into capillary tubes. Angiogenization of tumors allows them access to blood-derived oxygen and nutrients, and also provides them adequate perfusion. Hence inhibiting angiogenesis is an important therapeutic strategy in not only cancer but also in a number of chronic diseases such as rheumatoid arthritis, psoriasis, diabetic retinopathy, age-related macular degeneration, and so on. Tumor cells produce a number of angiogenic molecules. Vascular Endothelial Growth Factor (VEGF) is one such angiogenic factor. VEGF, a homodimeric disulfide-linked member of the PDGF family, is an endothelial cell-specific mitogen and is known to cause profound increase in the vascular endothelial permeability in the affected tissues. VEGF is also a senescence-preventing survival factor for endothelial cells. Almost all nucleated tissues in the body possess the capability to express VEGF in response to various stimuli including hypoxia, glucose deprivation, advanced glycation products, inflammatory cytokines, etc. Growth-promoting angiogenic effects of VEGF are mediated predominantly via its signaling receptor Kinase insert Domain containing Receptor (KDR). The expression of KDR is low on most endothelial cells; however, activation with angiogenic agents results in a significant upregulation of KDR on endothelial cells. Most angiogenized blood vessels express high levels of KDR. KDR is a receptor protein tyrosine kinase with an extracellular VEGF-binding domain consisting of 7 immunoglobulin-like domains and a cytoplasmic domain containing the catalytic tyrosine kinase domain split by a kinase-insert region. Binding to VEGF causes dimerization of KDR resulting in its autophosphorylation and initiation of signaling cascade. Tyrosine kinase activity of KDR is essential for mediation of its functional effects as a receptor for VEGF. Inhibition of KDR-mediated functional effects by inhibiting KDR's catalytic activity is considered to be an important therapeutic strategy in the treatment of angiogenized disease states including cancer. As is shown below, the compounds of this invention inhibit the tyrosine kinase activity of KDR and are therefore useful for the treatment of the aforementioned disease states.

In addition to the above utilities some of the compounds of this invention are useful for the preparation of other compounds of this invention.

The compounds of this invention are certain substituted 3-cyano quinolines. Throughout this patent application, the quinoline ring system will be numbered as indicated in the formula below; the numbering for the quinazoline ring system is also shown:

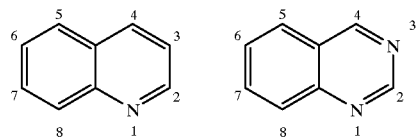

No 3-cyano quinolines have been reported that have biological activity as inhibitors of protein tyrosine kinases. A 3-cyano quinoline with a 4-(2-methyl anilino) substituent having gastric (H$^+$/K$^+$)-ATPase inhibitory activity at high concentrations has been described [Ife R. J., et al., J. Med. Chem., 35(18), 3413 (1992)].

There are quinolines that do not have the 3-cyano substituent and, unlike the compounds of this invention, are unsubstituted at the 4-position but are reported to be inhibitors of protein tyrosine kinases [Gazit A., et al., J. Med. Chem., 39(11), 2170 (1996)]. A series of quinolines that have a 3-pyridyl substituent and no substituent at the 4-position have been described as inhibitors of platelet derived growth factor receptor kinase [Dolle R. E., et al., J. Med. Chem., 372, 2627 (1994) and Maguire M. P., et al., J. Med. Chem., 372, 129 (1994)]. The patent application WO 96/09294 describes inhibitors of protein tyrosine kinases that include 4-anilino quinolines with a large variety of substituents on positions 5–8 but which must also have a hydrogen atom at position 3. The U.S. Pat. No. 5,480,883 describes quinoline derivatives that are inhibitors of protein tyrosine kinases but these derivatives do not have the unique combination of substituents, including the 3-cyano group, contained in the compounds of the present invention.

In addition to quinolines, certain quinazoline derivatives that are similar, in some respects, to the compounds of this invention are known to be inhibitors of protein tyrosine kinases. The application EP-92305703.8 describes 4-anilinoquinazolines that contain simple substituents such as chloro, trifluoromethyl, or nitro groups at positions 5 to 8. The application EP-93300270.1 is similar but with a much larger variety of substituents now allowed at positions 5 to 8. The application WO-9609294 describes compounds with similar substituents at positions 5 to 8 and with the substituent at to 4-position consisting of some polycyclic ring systems. Some simple substituted quinazolines are also described in the applications WO-9524190, WO-9521613, and WO-9515758. The applications EP-93309680.2 and WO9523141 cover similar quinazoline derivatives where the aryl group attached at position 4 can be a variety of heterocyclic ring structures. The application EP-94305195.3 describes certain quinazoline derivatives that have alkenoylamino and alkynoylamino groups among the substituents at position 6 and a halogen atom at position 7. The application WO 9519774 describes compounds where one or more of the carbon atoms at positions 5–8 can be replaced with heteroatoms resulting in a large variety of bicyclic systems where the left-hand ring is a 5 and 6-membered heterocyclic ring; in addition, a variety of substituents are allowed on the left-hand ring. The application EP-682027-A1 describes certain pyrrolopyrimidine inhibitors of PTKs. The application WO-9519970 describes compounds in which the left-hand aromatic ring of the basic quinazoline structure has been replaced with a wide variety of different heterocyclic rings so that the resulting inhibitors are tricyclic. The application WO-94305194.6 describes quinazolines where an additional 5 or 6-membered heterocyclic ring with optional substitution is fused at positions 5 and 6.

In addition to the aforementioned patent applications, a number of publications describe 4-anilinoquinazolines: Fry, D. W., et. al., *Science,* 265, 1093 (1994), Rewcastle G. W., et. al., *J. Med. Chem.,* 38, 3482 (1995), and Bridges, A. J., et. al., *J. Med. Chem.,* 39 , 267, (1996). There are no publications that describe 3-cyano quinolines as PTK inhibitors.

DESCRIPTION OF THE INVENTION

This invention provides a compound of formula 1:

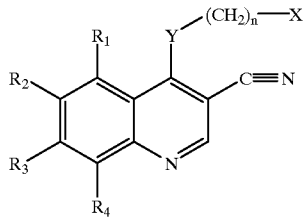

wherein:

X is cycloalkyl of 3 to 7 carbon atoms, which may be optionally substituted with one or more alkyl of 1 to 6 carbon atom groups; or is a pyridinyl, pyrimidinyl, or phenyl ring; wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

n is 0–1;

Y is —NH—, —O—, —S—, or —NR—;

R is alkyl of 1–6 carbon atoms;

$R_1$, $R_2$, $R_3$, and $R_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, aminoalkyl of 1–4 carbon atoms, N-alkylaminoalkyl of 2–7 carbon atoms, N,N-dialkylaminoalkyl of 3–14 carbon atoms, phenylamino, benzylamino,

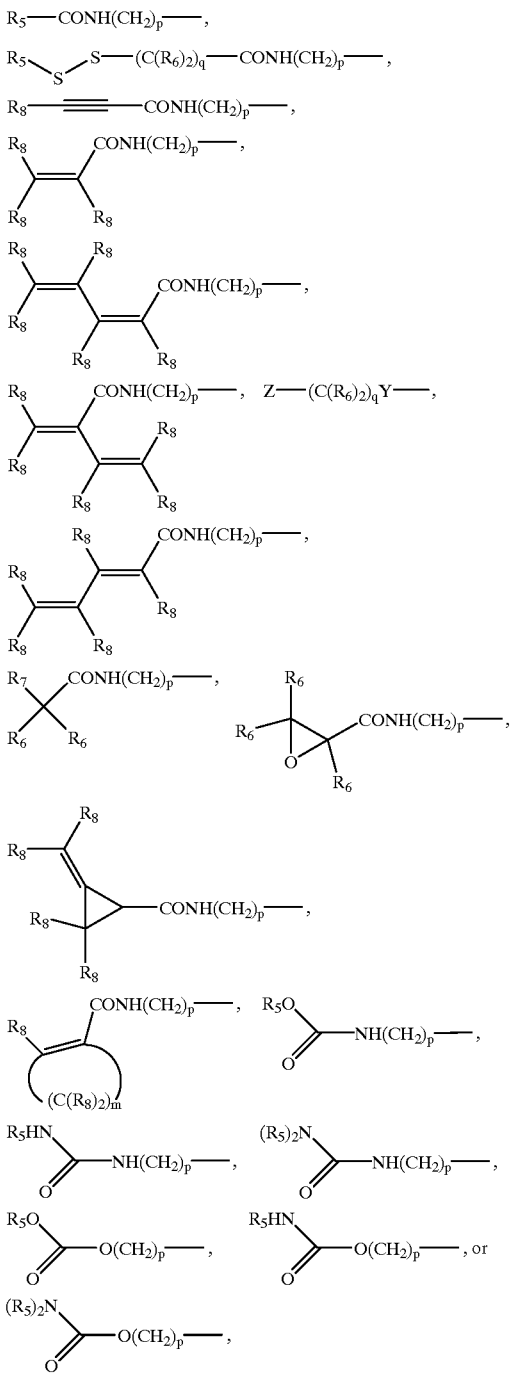

$R_5$ is alkyl of 1–6 carbon atoms, alkyl optionally substituted with one or more halogen atoms, phenyl, or phenyl optionally substituted with one or more halogen, alkoxy of 1–6 carbon atoms, trifluoromethyl, amino, nitro, cyano, or alkyl of 1–6 carbon atoms groups;

$R_6$ is hydrogen, alkyl of 1–6 carbon atoms, or alkenyl of 2–6 carbon atoms;

$R_7$ is chloro or bromo $R_8$ is hydrogen, alkyl of 1–6 carbon atoms, aminoalkyl of 1–6 carbon atoms, N-alkylaminoalkyl of 2–9 carbon atoms, N,N-dialkylaminoalkyl of 3–12 carbon atoms, N-cycloalkylaminoalkyl of 4–12 carbon atoms, N-cycloalkyl-N-alkylaminoalkyl of 5–18 carbon atoms, N,N-dicycloalkylaminoalkyl of 7–18 carbon atoms, morpholino-N-alkyl wherein the alkyl group is 1–6 carbon atoms, piperidino-N-alkyl wherein the alkyl group is 1–6 carbon atoms, N-alkyl-piperidino-N-alkyl wherein either alkyl group is 1–6 carbon atoms, azacycloalkyl-N-alkyl of 3–11 carbon atoms, hydroxyalkyl of 1–6 carbon atoms, alkoxyalkyl of 2–8 carbon atoms, carboxy, carboalkoxy of 1–6 carbon atoms, phenyl, carboalkyl of 2–7 carbon atoms, chloro, fluoro, or bromo;

Z is amino, hydroxy, alkoxy of 1–6 carbon atoms, alkylamino wherein the alkyl moiety is of 1–6 carbon atoms, dialkylamino wherein each of the alkyl moieties is of 1–6 carbon atoms, morpholino, piperazino, N-alkylpiperazino wherein the alkyl moiety is of 1–6 carbon atoms, or pyrrolidino;

m=1–4, q=1–3, and p=0–3;

any of the substituents $R_1$, $R_2$, $R_3$, or $R_4$ that are located on contiguous carbon atoms can together be the divalent radical —O—C($R_8$)$_2$—O—;

or a pharmaceutically acceptable salt thereof with the proviso that when Y is —NH—, $R_1$, $R_2$, $R_3$, and $R_4$ are hydrogen, and n is 0, X is not 2-methylphenyl.

The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The alkyl portion of the alkyl, alkoxy, alkanoyloxy, alkoxymethyl, alkanoyloxymethyl, alkylsulphinyl, alkylsulphonyl, alkylsulfonamido, carboalkoxy, carboalkyl, alkanoylamino aminoalkyl, alkylaminoalkyl, N,N-dicycloalkylaminoalkyl, hydroxyalkyl, and alkoxyalkyl substituents include both straight chain as well as branched carbon chains. The cycloalkyl portions of N-cycloalkyl-N-alkylaminoalkyl and N,N-dicycloalkylaminoalkyl substituents include both simple carbocycles as well as carbocycles containing alkyl substituents. The alkenyl portion of the alkenyl, alkenoyloxymethyl, alkenyloxy, alkenylsulfonamido, substituents include both straight chain as well as branched carbon chains and one or more sites of unsaturation. The alkynyl portion of the alkynyl, alkynoyloxymethyl, alkynylsulfonamido, alkynyloxy, substituents include both straight chain as well as branched carbon chains and one or more sites of unsaturation. Carboxy is defined as a —CO$_2$H radical. Carboalkoxy of 2–7 carbon atoms is defined as a —CO$_2$R" radical, where R" is an alkyl radical of 1–6 carbon atoms. Carboalkyl is defined as a —COR" radical, where R" is an alkyl radical of 1–6 carbon atoms. Alkanoyloxy is defined as a —OCOR" radical, where R" is an alkyl radical of 1–6 carbon atoms. Alkanoyloxymethyl is defined as R"CO$_2$CH$_2$— radical, where R" is an alkyl radical of 1–6 carbon atoms. Alkoxymethyl is defined as R"OCH$_2$— radical, where R" is an alkyl radical of 1–6 carbon atoms. Alkylsulphinyl is defined as R"SO— radical, where R" is an alkyl radical of 1–6 carbon atoms. Alkylsulphonyl is defined as R"SO$_2$— radical, where R" is an alkyl radical of 1–6 carbon atoms. Alkylsulfonamido, alkenylsulfonamido, alkynylsulfonamido are defined as R"SO$_2$NH— radical, where R" is an alkyl radical of 1–6 carbon atoms, an alkenyl radical of 2–6 carbon atoms, or an alkynyl radical of 2–6 carbon atoms, respectively. N-alkylcarbamoyl is defined as R"NHCO— radical, where R" is an alkyl radical of 1–6 carbon atoms. N,N-dialkylcarbamoyl is defined as R"R'NCO— radical, where R" is an alkyl radical of 1–6 carbon atoms, R' is an alkyl radical of 1–6 carbon atoms and R', and R" may be the same or different. When X is substituted, it is preferred that it is mono-, di-, or tri-substituted, with monosubstituted being most preferred. It is preferred that of the substituents $R_1$, $R_2$, $R_3$, and $R_4$, at least one is hydrogen and it is most preferred that two or three be hydrogen. An azacycloalkyl-N-alkyl substituent refers to a monocyclic heterocycle that contains a nitrogen atom on which is substituted a straight or branched chain alkyl radical. A morpholino-N-alkyl substituent is a morpholine ring substituted on the nitrogen atom with a straight or branch chain alkyl radical. A piperidino-N-alkyl substituent is a piperidine ring substituted on one of the nitrogen atoms with a straight or branch chain alkyl radical. A N-alkyl-piperidino-N-alkyl substituent is a piperidine ring substituted on one of the nitrogen atoms with a straight or branched chain alkyl group and on the other nitrogen atom with a straight or branch chain alkyl radical.

The compounds of this invention may contain an asymmetric carbon; in such cases, the compounds of this invention cover the racemate and the individual R and S entantiomers, and in the case were more than one asymmetric carbon exists, the individual diastereomers, their racemates and individual entantiomers The preparation of the compounds of this invention encompassed by Formula 5 is described below in Flowsheet A where Y and n are as described above and X' is cycloalkyl or phenyl optionally substituted with one or more substituents selected from the group consisting of hydrogen, halogeno, alkyl of 1–6 carbon atoms, alkenyl of 2–6 carbon atoms, alkynyl of 2–6 carbon atoms, halomethyl, alkoxy of 1–6 carbon atoms, alkylthio of 1–6 carbon atoms, trifluoromethyl, cyano, nitro, carboalkyl of 2–7 carbon atoms, phenoxy, phenyl, thiophenoxy, benzyl, dialkylamino of 2 to 12 carbon atoms. $R_1'$, $R_2'$, $R_3'$, and $R_4'$ are each, independently, hydrogen, halogeno, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, halomethyl, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, trifluoromethyl, cyano, nitro, carboxy, carboalkyl of 2–7 carbon atoms, phenoxy, phenyl, thiophenoxy, benzyl, alkoxyamino of 1–4 carbon atoms, dialkylamino of 2 to 12 carbon atom, N,N-dialkylaminoalkyl of 3–14 carbon atoms, phenylamino, benzylamino, N-alkylcarbamoyl of 1–6 carbon atoms, N,N-dialkylcarbamoyl of 2–12 carbon atoms. Any of the substituents $R_{1'}$, $R_{2'}$, $R_{3'}$, or $R_{4'}$ that are located on contiguous carbon atoms can together be the divalent radical —O—C($R_8$)$_2$—O—. According to the sequence of reaction outlined in flowsheet A, a quinoline-3-carboxylic acid ester of Formula 2 is hydrolyzed with base to furnish a carboxylic acid of Formula 3. The carboxylic acid group of 3 is converted to an acyl imidazole by heating it with carbonyldiimidazole in an inert solvent such as dimethylformamide (DMF) followed by the addition of ammonia to give the amide 4. Dehydration of the amide functional group with a dehydrating agent such as trifluoroacetic anhydride in pyridine, phosphorous pentoxide in an inert solvent, or the like gives the 3-cyano quinolines, 5, of this invention. In those cases where any of the intermediates have an asymmetric carbon atom, they can be used as the racemate or as the individual R or S entantiomers in which case the compounds of this invention will be in the racemic or R and S optically active forms, respectively. The quinoline-3-carboxylic acid esters of Formula 2, the quinoline-3-carboxylic acids of Formula 3, and the quinoline-3-carboxylic amides of Formula 4 needed to prepare the compounds of this invention are either already known to the art or can be prepared by procedures known in the art as detailed in the following references:

Sarges, Reinhard; Gallagher, Andrea; Chambers, Timothy J.; Yeh, Li An, *J. Med. Chem.*, 36, 2828 (1993); Savini, Luisa;

Massarelli, Paola; Pellerano, Cesare; Bruni, Giancarlo, *Farmaco*, 48(6), 805 (1993); Ife, Robert J.; Brown, Thomas H.; Keeling, David J.; Leach, Colin, *J. Med. Chem*, 35, 3413 (1992); Hanifin, J. William; Capuzzi, Rosemary; Cohen, Elliott, *J. Med Chem.*, 12(5), 1096 (1969); Marecki, Paul E.; Bambury, Ronald E., *J. Pharm. Sci.*, 73(8), 1141 (1984); Pellerano, C.; Savini, L.; Massarelli, P.; Bruni, G.; Fiaschi, A. I., *Farmaco*, 45(3), 269, (1990); Marecki, Paul E.; Bambury, Ronald E., *J. Pharm. Sci.*, 73(8), 114 (1984); patent application WO 8908105; U.S. Pat. No. 4,343,804; U.S. Pat. No. 3,470,186.

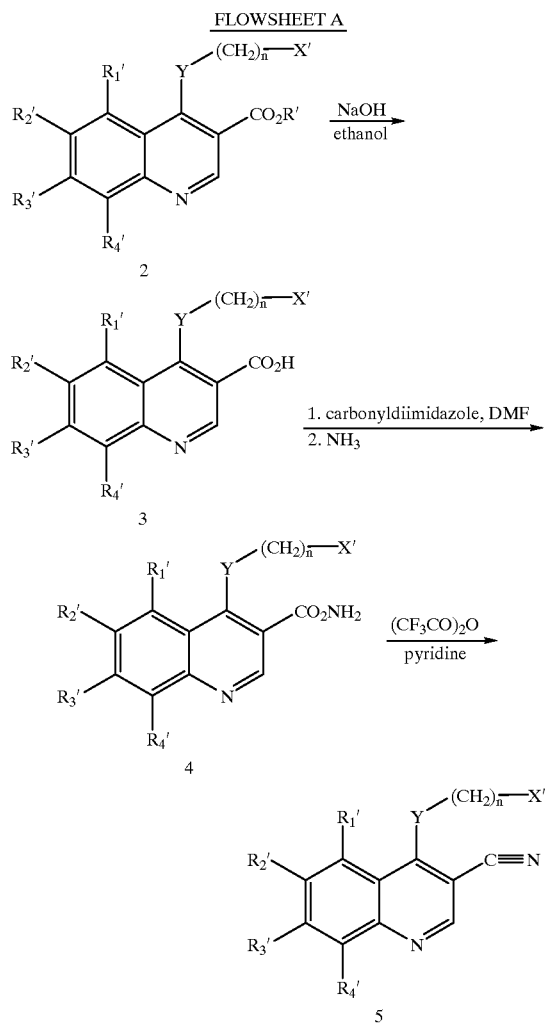

The preparation of the compounds of this invention encompassed by Formula 10 and Formula 11 are described below in Flowsheet B where Y, p, and n are as described above. X" is selected from the group consisting of cycloalkyl or phenyl optionally substituted with one or more substituents selected from the group consisting of hydrogen, halogeno, alkyl of 1–6 carbon atoms, alkenyl of 2–6 carbon atoms, alkynyl of 2–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino. Each $R_9$ is independently hydrogen, phenyl, or alkyl of 1–6 carbon atoms. The moieties $(R_{10})_k$ represent 1 to 3 substituents on the aromatic ring that can be the same or different and are selected independently from the group hydrogen, halogeno, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, halomethyl, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, trifluoromethyl, cyano, nitro, carboxy, carboalkyl of 2–7 carbon atoms, phenoxy, phenyl, thiophenoxy, benzyl, alkoxyamino of 1–4 carbon atoms, dialkylamino of 2 to 12 carbon atom, N,N-dialkylaminoalkyl of 3–14 carbon atoms, phenylamino, benzylamino, N-alkylcarbamoyl of 1–6 carbon atoms, N,N-dialkylcarbamoyl of 2–12 carbon atoms. $R_{11}$ is a radical and is selected from the group:

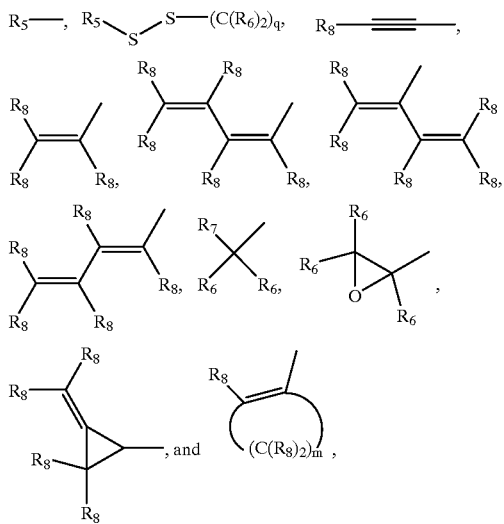

wherein q, $R_5$, $R_6$, $R_7$, and $R_8$ are as defined above. R'" is alkyl from 1 to 6 carbon atoms preferably isobutyl. According to the sequence of reactions outlined in Flowsheet B, acylation of 6 with either an acid chloride of Formula 8 or a mixed anhydride of Formula 9 (which is prepared from the corresponding carboxylic acid) in an inert solvent such as tetrahydrofuran (THF) in the presence of an organic base such as pyridine, triethylamine, or N-methyl morpholine gives the compounds of this invention represented by Formula 11. In those cases where 8 or 9 have an asymmetric carbon atom, they can be used as the racemate or as the individual R or S entantiomers in which case the compounds of this invention will be in the racemic or R and S optically active forms, respectively. Acylation of 6 with a cyclic anhydride of Formula 7 in an inert solvent such as tetrahydrofuran in the presence of a basic catalyst such as pyridine or triethylamine gives the compounds of the invention of Formula 10. The compounds of Formula 6 with p=0 can be prepared from the aromatic nitro substituted compounds by reducing the nitro group with a reducing agent such as iron and ammonium chloride in alcohol, sodium hydrosulfite in an aqueous mixture, or the like.

FLOWSHEET B

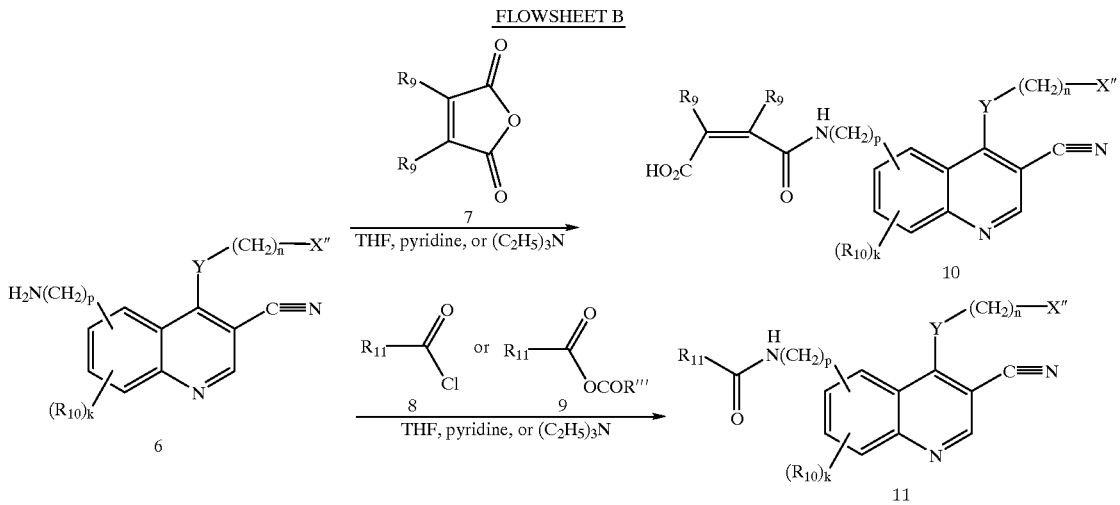

The preparation of the compounds of this invention encompassed by Formula 18 is described below in Flowsheet C where X, Y, n, $R_1'$, $R_2'$, $R_3'$ and $R_4'$ are as described above. The substituted aniline of Formula 12 is heated with or without a solvent with the reagent 13 to give intermediate 14 as a mixture of isomers.

Thermolysis of 14 in a high boiling solvent such as diphenyl ether at 200–350° C. gives the 3-cyano quinolones of Formula 15; these intermediates may also exist in the 4-hydroxy quinoline tautomeric form. In those cases where $R_4'$ is a hydrogen atom, the intermediates 15 may be formed as a mixture of two regioisomers. These isomers can be separated by methods well known in the art including, but not limited to, fractional crystallization and chromatographic methods. The separated isomers can then be converted separately to the compounds of the invention. Alternatively, the isomers can be separated at a later stage of the synthesis. Heating compounds 15 with or without solvent with a chlorinating agent such as phosphorous oxychloride or phosphorous pentachloride gives the 4-chloro-3-cyano quinolines of Formula 16. Condensation of 16 with a nucleophilic amine, aniline, mercaptan, thiophenol, phenol, or alcohol reagent of Formula 17 gives the 3-cyano quinolines of this invention of Formula 18; this condensation can be accelerated by heating the reaction mixture or by using basic catalysts such as trialkylamines, sodium hydride in an inert solvent, sodium or potassium alkoxides in an alcohol solvents, and the like. In those cases where the substituents X, $R_1'$, $R_2'$, $R_3'$, and $R_4'$ may contribute an asymmetric carbon atom, the intermediates can be used as the racemate or as the individual R or S entantiomers in which case the compounds of this invention will be in the racemic or R and S optically active forms, respectively. In cases where the substituents X, $R_1'$, $R_2'$, $R_3''$, and $R_4'$ may contribute more than one asymmetric carbon atoms, diasteriomers may be present; these can be separated by methods well known in the art including, but not limited to, fractional crystallization and chromatographic methods.

FLOWSHEET C

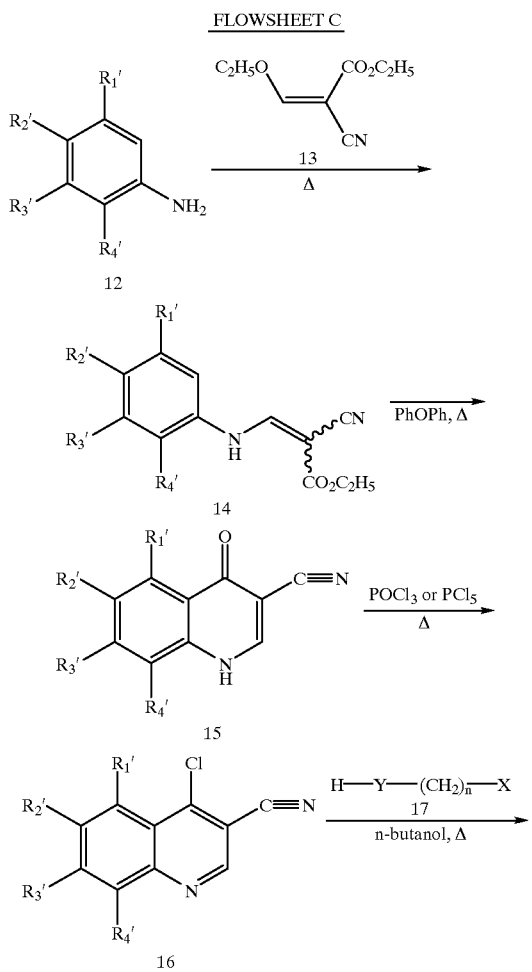

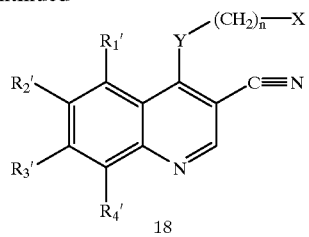
18

The preparation of intermediate 21 (identical to intermediate 15 of Flowsheet C) can also be prepared as describe below in Flowsheet D. Heating the substituted aniline of Formula 19 with dimethylformamide dimethyl acetal with or without a solvent gives intermediates for Formula 20. The reaction of 20 with one to ten equivalents of acetonitrile using a base such as sodium methoxide or the like in an inert solvent gives the 3-cyano quinolones, 21, or the 3-cyano-4-hydroxy quinoline tautomers thereof which can be converted to the compounds of this invention using the procedures outlined above in Flowsheet C.

FLOWSHEET D

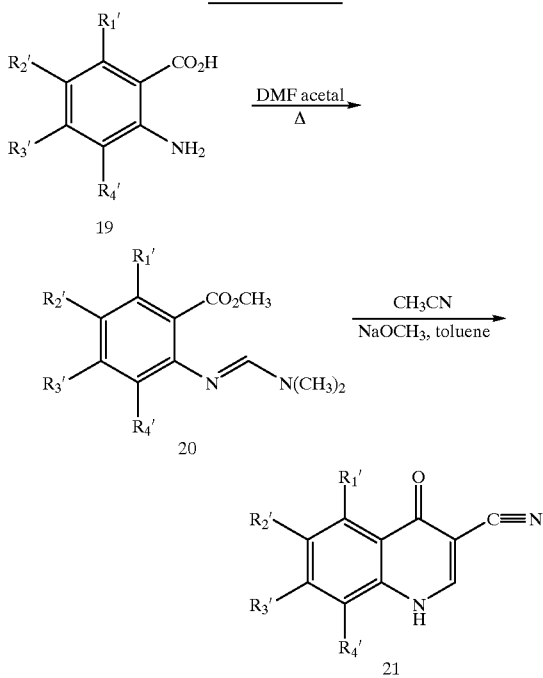

Formula 22 is given below wherein $R_1$, $R_2$, $R_3$, $R_4$, n, and X' are as defined above.

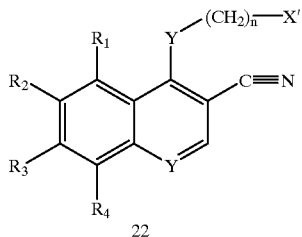
22

Where one or more of $R_1$, $R_2$, $R_3$, or $R_4$ of Formula 22 is a nitro group, it can be converted to the corresponding amino group by reduction using a reducing agent such as iron in acetic acid.

Where one or more of $R_1$, $R_2$, $R_3$, or $R_4$ of Formula 22 is an amino group, it can be converted to the corresponding dialkyamino group of 2 to 12 carbon atoms by alkylation with at least two equivalents of an alkyl halide of 1 to 6 carbon atoms by heating in an inert solvent.

Where one or more of $R_1$, $R_2$, $R_3$, or $R_4$ of Formula 22 is a methoxy group, it can be converted to the corresponding hydroxy group by reaction with a demethylating agent such as boron tribromide in an inert solvent or by heating with pyridinium chloride with or without solvent.

Where one or more of $R_1$, $R_2$, $R_3$, or $R_4$ of Formula 22 is an amino group, it can be converted to the corresponding alkylsulfonamido, alkenylsulfonamido, or alkynylsulfonamido group of 2 to 6 carbon atoms by the reaction with an alkylsulfonyl chloride, alkenylsulfonyl chloride, or alkynylsulfonyl chloride, respectively, in an inert solvent using a basic catalyst such as triethylamine or pyridine. Alternatively, when one or more of $R_1$, $R_2$, $R_3$, or $R_4$ of Formula 22 is an amino group, it can be converted to the corresponding alkenylsulfonamido group by the reaction with a reagent Cl—C(R'$_6$)$_2$—CHR'$_6$SO2Cl, wherein R'$_6$ is hydrogen or alkyl of 1–4 carbon atoms, in an inert solvent using an excess of an organic base such as triethylamine.

Where two of $R_1$, $R_2$, $R_3$, or $R_4$ of Formula 22 is are contiguous methoxy groups, the corresponding compound with contiguous hydroxy groups can be prepared by using a demethylating agent such as boron tribromide in an inert solvent or by heating with pyridinium chloride with or without solvent.

Where two of $R_1$, $R_2$, $R_3$, or $R_4$ of Formula 22 is are contiguous hydroxy groups, they can be converted to the compound where together the two contiguous $R_1$, $R_2$, $R_3$, or $R_4$ groups are the divalent radical —O—C(R$_8$)$_2$—O— wherein R$_8$ is defined above by the reaction with a reagent, J—C(R$_8$)$_2$—J, wherein J is chloro, bromo, or iodo, and each J can be the same or different, using a base such as cesium carbonate or potassium carbonate in an inert solvent and heating as required.

Where one or more of $R_1$, $R_2$, $R_3$, or $R_4$ of Formula 22 is an amino group, it can be converted to the corresponding alkyamino group of 1 to 6 carbon atoms by alkylation with one equivalent of an alkyl halide of 1 to 6 carbon atoms by heating in an inert solvent or by reductive alkylation using an aldehyde of 1 to 6 carbon atoms and a reducing agent such as sodium cyanoborohydride in a protic solvent such as water or alcohol, or mixtures thereof.

Where one or more of $R_1$, $R_2$, $R_3$, or $R_4$ of Formula 22 is hydroxy, it can be converted to the corresponding alkanoyloxy, group of 1–6 carbon atoms by reaction with an appropriate carboxylic acid chloride, anhydride, or mixed anhydride in a inert solvent using pyridine or a trialkylamine as a catalyst.

Where one or more of $R_1$, $R_2$, $R_3$, or $R_4$ of Formula 22 is hydroxy, it can be converted to the corresponding alkenoyloxy group of 1–6 carbon atoms by reaction with an appropriate carboxylic acid chloride, anhydride, or mixed anhydride in an inert solvent using pyridine or a trialkylamine as a catalyst.

Where one or more of $R_1$, $R_2$, $R_3$, or $R_4$ of Formula 22 is hydroxy, it can be converted to the corresponding alkynoyloxy group of 1–6 carbon atoms by reaction with an appropriate carboxylic acid chloride, anhydride, or mixed anhydride in a inert solvent using pyridine or a trialkylamine as a catalyst.

Where one or more of $R_1$, $R_2$, $R_3$, or $R_4$ of Formula 22 is carboxy or a carboalkoxy group of 2–7 carbon atoms, it can be converted to the corresponding hydroxymethyl group by reduction with an appropriate reducing agent such as borane, lithium borohydride, or lithium aluminum hydride in a inert solvent; the hydroxymethyl group, in turn, can be converted to the corresponding halomethyl group by reaction in an inert solvent with a halogenating reagent such as phosphorous tribromide to give a bromomethyl group, or phosphorous pentachloride to give a chloromethyl group. The hydroxymethyl group can be acylated with an appropriate acid chloride, anhydride, or mixed anhydride in an inert solvent using pyridine or a trialkylamine as a catalyst to give the compounds of this invention with the corresponding alkanoyloxymethyl group of 2–7 carbon atoms, alkenoyloxymethyl group of 2–7 carbon atoms, or alkynoyloxymethyl group of 2–7 carbon atoms.

Where one or more of $R_1$, $R_2$, $R_3$, or $R_4$ of Formula 22 is a halomethyl group, it can be converted to an alkoxymethyl group of 2–7 carbon atoms by displacing the halogen atom with a sodium alkoxide in an inert solvent.

Where one or more of $R_1$, $R_2$, $R_3$, or $R_4$ of Formula 22 is a halomethyl group, it can be converted to an aminomethyl group, N-alkylaminomethyl group of 2–7 carbon atoms or N,N-dialkylaminomethyl group of 3–14 carbon atoms by displacing the halogen atom with ammonia, a primary, or secondary amine, respectively, in an inert solvent.

Where one or more of $R_1$, $R_2$, $R_3$, or $R_4$ of Formula 22 is a $H_2N(CH_2)_p-$ group, it can be converted to the corresponding groups:

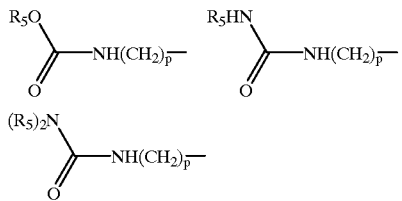

wherein $R_5$ and p are as defined above by reacting with phosgene in an inert solvent such as toluene in the presence of a base such as pyridine to give an isocyanate which, in turn, is treated with an excess of the alcohol $R_5-OH$ or amines $R_5-NH_2$ or $(R_5)_2NH$ respectively.

Where one or more of $R_1$, $R_2$, $R_3$, or $R_4$ of Formula 22 is a $HO-(CH_2)_p-$ group, it can be converted to the corresponding groups:

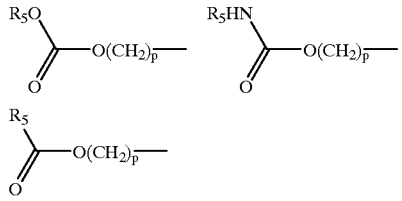

wherein $R_5$ and p are as defined above by the reaction, in an inert solvent using a basic catalyst such a pyridine, with an appropriate alkyl or phenyl chloroformate, $R_5-OCOCl$, alkyl or phenyl substituted isocyanate, $R_5-N=C=O$, or alkyl or phenyl substituted carboxylic acid chloride, $R_5-COCl$, respectively.

Where one or more of $R_1$, $R_2$, $R_3$, or $R_4$ of Formula 22 is a $HO-(CH_2)_p-$ group, it can be converted to the corresponding group:

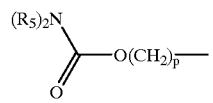

wherein $R_5$ and p are as defined above by the reaction, in an inert solvent using a basic catalyst such a pyridine, with a reagent $(R_5)_2NCOCl$.

Representative compounds of this invention were evaluated in several standard pharmacological test procedures that showed that the compounds of this invention possess significant activity as inhibitors of protein tyrosine kinase and are antiproliferative agents. Based on the activity shown in the standard pharmacological test procedures, the compounds of this invention are therefore useful as antineoplastic agents. The test procedures used and results obtained are shown below.

Inhibition of Epidermal Growth Factor Receptor Kinase (EGF-R, membrane extract)

Representative compounds of the invention were evaluated for their ability to inhibit the phosphorylation of the tyrosine residue of a peptide substrate catalyzed by the enzyme epidermal growth factor receptor kinase in the standard pharmacological test procedure described below. The peptide substrate (RR-SRC) has the sequence arg-arg-leu-ile-glu-asp-ala-glu-tyr-ala-ala-arg-gly. The enzyme was obtained as a membrane extract of A431 cells (American Type Culture Collection, Rockville, Md.). A431 cells were grown in T175 flasks to 80% confluency. The cells were washed twice with phosphate buffered saline (PBS) without $Ca^{2+}$. Flasks were rotated for 1.5 hours in 20 ml PBS with 1.0 mM ethylenediaminetetraacetic acid (EDTA) at room temperature and centrifuged at 600 g for 10 minutes. The cells were solubilized in 1 ml per $5 \times 10^6$ cells of cold lysis buffer {10 mM 4-(2-hydroxyethyl)-1-piperazineethanesulfonic acid (HEPES), pH 7.6, 10 mM NaCl, 2 mM EDTA, 1 mM phenylmethylsulfonyl-fluoride (PMSF), 10 mg/ml aprotinin, 10 mg/ml leupeptin, 0.1 mM sodium orthovanadate} in a Dounce homogenizer with 10 strokes on ice. The lysate was centrifuged at 600 g for 10 minutes first to clear cell debris and the supernatant further centrifuged at 100,000 g for min at 4° C. The membrane pellet was suspended in 1.5 ml HNG buffer (50 mM HEPES, pH 7.6, 125 mM NaCl, 10% glycerol). The membrane extract was divided into aliquots, immediately frozen in liquid nitrogen and stored at −70° C.

Compounds to be evaluated were made into 10 mg/ml stock solutions in 100% dimethylsulfoxide (DMSO). Prior to experiment, stock solutions were diluted to 500 mM with buffer (30 mM Hepes pH 7.4) and then serially diluted to the desired concentration.

An aliquot of the A431 membrane extract (10 mg/ml) was diluted in 30 mM HEPES (pH 7.4) to give a protein concentration of 50 ug/ml. To 4 $\mu$l of enzyme preparation, EGF (1 $\mu$l at 12 $\mu$g/ml) was added and incubated for 10 min on ice followed by 4 $\mu$l of the test compound or buffer; this mix was incubated on ice for 30 min. To this was added the $^{33}$P-ATP (10 mCi/ml) diluted 1:10 in assay buffer along with the substrate peptide at a concentration of 0.5 mM (control reactions get no test compound) and the reaction was allowed to proceed for 30 min at 30° C. The reaction was stopped with 10% TCA and left on ice for at least 10 min after which tubes were microcentrifuged at full speed for 15 min. The a portion of the supernatants were spotted on P81 phosphocellulose discs and washed twice in 1% acetic acid then water for 5 min each followed by scintillation counting.

The inhibition data for representative compounds of the invention are shown below in TABLE 1. The $IC_{50}$ is the concentration of test compound needed to reduce the total amount of phosphorylated substrate by 50%. The % inhibition of the test compound was determined for at least three different concentrations and the $IC_{50}$ value was evaluated from the dose response curve. The % inhibition was evaluated with the following formula:

% inhibition=100−[CPM(drug)/CPM(control)]×100 where CPM(drug) is in units of counts per minute and is a number expressing the amount of radiolabeled ATP (g-$^{33}$P) incorporated onto the RR-SRC peptide substrate by the enzyme after 30 minutes at 30° C. in the presence of test compound as measured by liquid scintillation counting. CPM(control) is in units of counts per minute and was a number expressing the amount of radiolabeled ATP (g-$^{33}$P) incorporated into the RR-SCR SRC peptide substrate by the enzyme after 30 minutes at 30° C. in the absence of test compound as measured by liquid scintillation counting. The CPM values were corrected for the background counts produced by ATP in the absence of the enzymatic reaction. The $IC_{50}$ values reported in TABLE 1 are averages of the number of tests conducted.

TABLE 1

Inhibition of Epidermal Growth Factor Receptor Kinase (membrane extract)

| Compound | IC50 (μM) | Number of Tests |
| --- | --- | --- |
| Example 31 | $1.5 \times 10^{-3}$ | 6 |
| Example 35 | 0.20 | 4 |
| Example 8 | 0.15 | 3 |
| Example 15 | $6 \times 10^{-4}$ | 1 |
| Example 16 | $1.5 \times 10^{-3}$ | 2 |
| Example 17 | 9.0 | 2 |
| Example 19 | $9.2 \times 10^{-2}$ | 3 |
| Example 18 | $2.1 \times 10^{-5}$ | 3 |
| Example 41 | 0.20 | 1 |
| Example 42 | 1.5 | 3 |
| Example 43 | 8.0 | 1 |
| Example 45 | 1.67 | 3 |
| Example 46 | 8.83 | 3 |
| Example 47 | 0.13 | 5 |
| Example 22 | 3.0 | 1 |
| Example 50 | 5.0 | 1 |
| Example 51 | $5 \times 10^{-5}$ | 1 |
| Example 52 | $1 \times 10^{-2}$ | 1 |
| Example 53 | $7 \times 10^{-3}$ | 1 |
| Example 54 | $7 \times 10^{-3}$ | 1 |
| Example 57 | $8 \times 10^{-3}$ | 1 |
| Example 58 | $2 \times 10^{-3}$ | 1 |
| Example 59 | $1 \times 10^{-4}$ | 1 |

As shown by the data presented in TABLE 1, the compounds of this invention are effective inhibitors of the epidermal growth factor receptor kinase and are, as such, useful for the treatment of diseases such as cancer and polycystic kidney disease where deregulation of the kinase is a component of the disease.

Inhibition of Epidermal Growth Factor Receptor Kinase (EGF-R) using recombinant enzyme Representative compounds of the invention were evaluated for their ability to inhibit the phosphorylation of the tyrosine residue of a peptide substrate catalyzed by the enzyme epidermal growth factor receptor kinase. The peptide substrate (RR-SRC) has the sequence arg-arg-leu-ile-glu-asp-ala-glu-tyr-ala-ala-arg-gly. The enzyme used in this assay is the His-tagged cytoplasmic domain of EGFR. A recombinant baculovirus (vHcEGFR52) was constructed containing the EGFR cDNA encoding amino acids 645–1186 preceded by Met-Ala-(His)$_6$. Sf9 cells in 100 mm plates were infected at an moi of 10 pfu/cell and cells were harvested 48 h post infection. A cytoplasmic extract was prepared using 1% Triton X-100 and applied to Ni-NTA column. After washing the column with 20 mM imidazole, HcEGFR was eluted with 250 mM imidazole (in 50 mM NaHPO$_4$, pH 8.0, 300 mM NaCl). Fractions collected were dialyzed against mM HEPES, pH 7.0, 50 mM NaCl, 10% glycerol, 1 μg/mL antipain and leupeptin and 0.1 mM Pefabloc SC. The protein was frozen in dry ice/methanol and stored −70° C.

Compounds to be evaluated were made into 10 mg/mL stock solutions in 100% dimethylsulfoxide (DMSO). Prior to experiment, stock solutions were diluted to 500 μM with 100% DMSO and then serially diluted to the desired concentration with HEPES buffer (30 mM HEPES pH 7.4).

For the enzyme reaction, 10 μL of each inhibitor (at various concentrations) were added to each well of a 96-well plate. To this was added 3 μL of enzyme (1:10 dilution in 10 mM HEPES, pH 7.4 for final conc. of 1:120). This was allowed to sit for min on ice and was followed by the addition of 5 μl peptide (80 μM final conc.), 10 μl of 4× Buffer (Table A), 0.25 μL $^{33}$P-ATP and 12 μL H$_2$O. The reaction was allowed to run for 90 min at room temperature and was followed by spotting the entire volume on to precut P81 filter papers. The filter discs were washed 2× with 0.5% phosphoric acid and radioactivity was measured using a liquid scintillation counter.

TABLE A

| Reagent | Final | 100 Rxns |
| --- | --- | --- |
| 1M HEPES (pH 7.4) | 12.5 mM | 50 μL |
| 10 mM Na$_3$VO$_4$ | 50 uM | 20 μL |
| 1M MnCl$_2$ | 10 mM | 40 μL |
| 1 mM ATP | 20 uM | 80 μL |
| $^{33}$P-ATP | 2.5 uCi | 25 μL |

The inhibition data for representative compounds of the invention are shown below in TABLE 2. The $IC_{50}$ is the concentration of test compound needed to reduce the total amount of phosphorylated substrate by 50%. The % inhibition of the test compound was determined for at least three different concentrations and the $IC_{50}$ value was evaluated from the dose response curve. The % inhibition was evaluated with the following formula:

% inhibition=100−[CPM(drug)/CPM(control)]×100 where CPM(drug) is in units of counts per minute and is a number expressing the amount of radiolabeled ATP (g-$^{33}$P) incorporated onto the RR-SRC peptide substrate by the enzyme after 90 minutes at room temperature in the presence of test compound as measured by liquid scintillation counting. CPM(control) is in units of counts per minute and was a number expressing the amount of radiolabeled ATP (g-$^{33}$P) incorporated into the RR-SRC peptide substrate by the enzyme after 90 minutes at room temperature in the absence of test compound as measured by liquid scintillation counting. The CPM values were corrected for the background counts produced by ATP in the absence of the enzymatic reaction. The $IC_{50}$ values reported in TABLE 2 are averages of the number of tests conducted.

TABLE 2

(recombinant enzyme)
Inhibition of Epidermal Growth Factor Receptor Kinase

| Compound | IC$_{50}$ ($\mu$M) | Number of Tests |
|---|---|---|
| Example 88 | 0.08 | 1 |
| Example 89 | 0.1 | 1 |
| Example 99 | 0.03 | 1 |
| Example 100 | 0.1 | 1 |
| Example 101 | 0.1 | 1 |
| Example 105 | 0.001 | 1 |
| Example 126 | 0.4 | 1 |
| Example 129 | 0.04 | 1 |
| Example 130 | 0.1 | 1 |
| Example 132 | 0.6 | 1 |
| Example 133 | 0.006 | 1 |
| Example 135 | 0.01 | 1 |
| Example 138 | 0.0035 | 2 |
| Example 139 | 0.5 | 1 |
| Example 140 | 0.0006 | 2 |
| Example 143 | 0.03 | 1 |
| Example 144 | 0.065 | 2 |
| Example 145 | 0.06 | 1 |
| Example 146 | 0.03 | 1 |
| Example 147 | 0.1 | 1 |
| Example 148 | 0.001 | 2 |
| Example 151 | 0.5 | 1 |
| Example 152 | 0.1 | 1 |
| Example 154 | 0.15 | 2 |
| Example 156 | 0.5 | 1 |
| Example 157 | 0.045 | 2 |
| Example 160 | 0.002 | 1 |
| Example 161 | 0.00035 | 2 |
| Example 164 | 0.09 | 1 |
| Example 165 | 0.0005 | 2 |
| Example 166 | 0.02 | 1 |
| Example 169 | 0.005 | 1 |
| Example 170 | 0.06 | 1 |
| Example 171 | 0.0065 | 2 |
| Example 172 | 0.005 | 2 |
| Example 173 | 0.03 | 1 |
| Example 174 | 0.2 | 1 |
| Example 175 | 0.3 | 1 |
| Example 184 | 1.7 | 1 |
| Example 185 | 10 | 1 |
| Example 186 | 0.1 | 1 |
| Example 187 | 0.0007 | 2 |
| Example 188 | 0.001 | 4 |
| Example 189 | 0.002 | 2 |
| Example 190 | 0.04 | 1 |
| Example 191 | 0.006 | 1 |
| Example 192 | 0.0006 | 1 |
| Example 193 | 0.0019 | 2 |
| Example 194 | 0.0017 | 3 |
| Example 197 | 0.002 | 1 |
| Example 198 | 0.000008 | 2 |
| Example 199 | 0.0005 | 2 |
| Example 200 | 0.02 | 1 |
| Example 203 | 0.0007 | 2 |
| Example 204 | 0.01 | 1 |
| Example 205 | 0.1 | 1 |
| Example 208 | 0.0015 | 2 |
| Example 209 | 0.005 | 3 |
| Example 216 | 0.0006 | 2 |
| Example 217 | 0.002 | 2 |
| Example 218 | 0.017 | 2 |
| Example 224 | 1. | 1 |
| Example 227 | 0.01 | 1 |
| Example 255 | 0.1 | 1 |
| Example 256 | 0.1 | 1 |
| Example 262 | 0.05 | 1 |
| Example 264 | 0.5 | 1 |
| Example 270 | 0.01 | 1 |
| Example 311 | 0.5 | 2 |
| Example 62 | 0.4 | 1 |
| Example 63 | 10 | 1 |
| Example 64 | 10 | 1 |
| Example 312 | 0.05 | 1 |
| Example 318 | 0.08 | 1 |
| Example 313 | 0.4 | 1 |
| Example 326 | 0.00005 | 1 |
| Example 327 | 0.01 | 1 |
| Example 328 | 0.0045 | 2 |
| Example 329 | 0.00045 | 2 |
| Example 330 | 0.00028 | 3 |
| Example 331 | 0.1 | 1 |
| Example 332 | 0.0009 | 1 |
| Example 347 | 0.04 | 2 |
| Example 358 | 0.1 | 1 |
| Example 363 | 0.1 | 1 |
| Example 360 | 0.5 | 1 |
| Example 347 | 0.04 | 2 |
| Example 383 | 0.007 | 1 |
| Example 380 | 0.007 | 1 |
| Example 395 | 0.5 | 1 |

Inhibition of Cancer Cell Growth as Measured by the Incorporation of [$^3$H]-Thymidine Representative compounds of this invention were evaluated for their ability to inhibit the growth of the cell lines described below in vitro. The inhibition is quantitated by measuring the decrease in the incorporation of radio-labeled thymidine when the cells are grown in the presence of the inhibitor. A431 and SKBR3 cell lines are obtained from American Type Culture Collection, Rockville, Md. Neu-3T3 cells are obtained by transfecting NIH 3T3 mouse fibroblasts with an activated rat Neu oncogene. NHEK cells are obtained from Clonetics (San Diego, Calif.). Cells were routinely grown in a humidified incubator in 5% $CO_2$ in air. These cell lines are dependent on growth factors which are ligands to the receptor tyrosine kinases that are the targets of the compounds of this invention, and have the following characteristics:

A431: human epidermoid carcinoma cells overexpressing EGFR

Neu-3T3: NIH 3T3 cells transfected with activated Neu oncogene

NHEK: EGF dependent normal human epidermal keratinocytes

SKBR3: Human breast cancer cells overexpressing ErbB2 gene

The cell lines were grown in appropriate media as described below:

A431: Dulbecco's Modified Eagles Media, high glucose, BRL/Gibco (10% Fetal Bovine Serum (FBS), Glutamine, Penicillin-Streptomycin) Dulbecco, R., Freeman, G. *Virology* 8, 396 (1959).

Neu-3T3: Dulbeccos Modified Eagles Media, high glucose (10% Fetal Bovine Serum, Glutamine, Penicillin-Streptomycin)

SKBR3: Roswell Park Memorial Institute 1640 W/GLU (10% FBS, GLU, PS) Moore, G. E., Gerner, R. E. and Franklin, H. A. *A.M.A.*, 199, 516 (1967).

NHEK: Keratinocyte Growth Media, Clonetics Boyce, S. T. and Ham, R. G. In Vitro 17, 239 (Abstract No. 159) (1981)

Cells were seeded at 10,000 cells/well in 96 well plates in complete media and allowed to grow to log phase. At this stage the complete media was replaced with media containing 0.5% FBS (for cells growing in 10% FBS) or media lacking epidermal growth factor (EGF) (for cells growing in serum free media). After overnight incubation in low serum (or EGF lacking) media, the compounds to be evaluated were added and cells remained in the presence of compounds for 48 to 72 hours. Media with test compound was then removed and complete media was added back The cells were allowed to grow for 18 hours. This is followed by incubation in [$^3$H]thymidine (1 mCi/ml in serum/EGF media) for 4 hours. Cells were lysed in 0.5 M NaOH for at least 30 min at 37° C. and radioactivity analyzed.

The cell growth inhibition data is provided below in TABLE 3. The IC$_{50}$ is the concentration of test compound needed to reduce the amount of [$^3$H]thymidine incorporation by 50%. The % inhibition of the compound evaluated was determined for at least three different concentrations and the IC$_{50}$ value evaluated from the dose response curve. The % inhibition is evaluated with the following formula:

% inhibition=100−[CPM(drug)/CPM(control)]×100 where CPM(drug) is in units of counts per minute and is a number expressing the amount of [$^3$H]thymidine incorporated into the DNA when cells are grown in the presence of test compound as measured by liquid scintillation counting. CPM(control) is in units of counts per minute and is a number expressing the amount of [$^3$H]thymidine incorporated onto the DNA when cells are grown in the absence of test compound as measured by liquid scintillation counting.

TABLE 3

Inhibition of Cell Growth as Measured by the Incorporation of [$^3$H]-Thymidine (IC$_{50}$)

| Compound | A431 (μM) | NEU-3T3 (μM) | NHEK (μM) | SKBR3 (μM) |
|---|---|---|---|---|
| Example 31 | 0.2 | | 0.003 | 25 |
| Example 15 | 35 | | 4.0 | |
| Example 41 | 1.5 | | | |
| Example 42 | 7 | | 0.01 | |
| Example 43 | 10 | | 4.0 | |
| Example 44 | 15 | | 1.5 | |
| Example 33 | 18 | | | |
| Example 45 | 0.15 | | | |
| Example 46 | 1.0 | | | |
| Example 47 | 1.5 | | 0.03 | |
| Example 20 | 35 | | 0.65 | |
| Example 3 | >50 | | 0.35 | |
| Example 7 | >50 | | 4.5 | |
| Example 8 | 40 | | 0.2 | |
| Example 13 | 50 | | | |
| Example 14 | 0.1 | | | |
| Example 23 | 0.1 | | | |
| Example 16 | 1.8 | | 0.06 | |
| Example 17 | 25 | | 9.0 | |
| Example 19 | 15 | | 2.0 | |

TABLE 3-continued

Inhibition of Cell Growth as Measured by the Incorporation of [$^3$H]-Thymidine (IC$_{50}$)

| Compound | A431 (μM) | NEU-3T3 (μM) | NHEK (μM) | SKBR3 (μM) |
|---|---|---|---|---|
| Example 18 | 0.00001 | | 0.007 | |
| Example 26 | 0.1 | >50 | 0.4 | >50 |
| Example 22 | 0.15 | >50 | 0.035 | >50 |
| Example 38 | 35 | | | |
| Example 48 | 10 | | | |

As illustrated by the data presented in TABLE 3, the compounds of this invention are effective inhibitors of cancer cell growth and are therefore useful as antineoplastic agents.

Inhibition of Cancer Cell Growth as Measured by Cell Number

Human tumor cell lines were plated in 96-well plates (250 ml/well, 1–6×10$^4$ cells/ml) in RPMI 1640 medium, containing 5% FBS (Fetal Bovine Serum). Twenty four hours after plating, test compounds were added at five log concentrations (0.01–100 mg/ml) or at lower concentrations for the more potent compounds. After 48 hours exposure to test compounds, cells were fixed with trichloroacetic acid, and stained with Sulforhodamine B according to the methods of Skehan et al (*J. Natl. Canc. Inst.* 1990,, 82, 1107–1112. After washing with trichloroacetic acid, bound dye was solubilized in 10 mM Tris base and optical density was determined using plate reader. Under conditions of the assay the optical density is proportional to the number of cells in the well. IC$_{50}$s (concentrations causing 50% inhibition of cell growth) were determined from the growth inhibition plots. These data are shown below in Tables 4–8 . The cell lines were chosen since they overexpressed epidermal growth factor receptor (EGFR) (i.e. A431) or HER2/neu (SKBR3), or had little to no expression of the these receptors (SW620, LOX, MCF7). Expression levels of these receptors were determined by antibody staining methods using EGFR or HER/neu directed antibodies and was similar to previously published data (Lewis et al., Cancer Immunol. Immunother., 1993, 37: 255–262). Other information about some of the cell lines used in these test procedures is available from the American Type Tissue Collection: Cell Lines and Hybridomas, 1994 Reference Guide, 8th Edition. In the Tables below, there may be separate entries for the same compound; this is an indication that the compound was tested more than one time. In the tables below, if a compound is missing a data value for a particular cell line, this is an indication that that compound was not tested against that cell line.

TABLE 4

Inhibition of Cancer Cell Growth as Measured by Cell Number (IC$_{50}$ μg/ml)

| Example No. | HTB161 | A27805 | A2780DDP | MIP | SW620 | COLO205 | CX1 |
|---|---|---|---|---|---|---|---|
| 31 | 0.7933 | 2.03 | 1.165 | 0.7475 | 4.54 | 3.095 | 0.9695 |
| 15 | 33 | 33 | 33 | 33 | 33 | 33 | 33 |
| 41 | 7.87 | 7.726 | 6.255 | 4.089 | 14.65 | 6.133 | 7.252 |
| 42 | 5.18 | 6.434 | 8.223 | 11 | 31.18 | 5.966 | 9.131 |
| 43 | 0.5337 | 3.424 | 4.445 | 3.296 | 4.325 | 4.179 | 3.427 |
| 44 | 5.2 | 5.888 | 9.276 | 11.13 | 7.462 | 7.792 | 6.336 |

TABLE 4-continued

Inhibition of Cancer Cell Growth as Measured by Cell Number (IC$_{50}$ μg/ml)

| Example No. | HTB161 | A27805 | A2780DDP | MIP | SW620 | COLO205 | CX1 |
|---|---|---|---|---|---|---|---|
| 35 | 2.976 | 2.953 | 0.8381 | 0.6496 | 9.572 | | 3.128 |
| 45 | 4.212 | 8.664 | 39.26 | >100 | >100 | >100 | 89.66 |
| 46 | 9.586 | 7.406 | 5.856 | 5.597 | >100 | | 9.7 |
| 47 | 0.003947 | 0.05304 | 0.06454 | 0.06935 | 0.06723 | 0.07567 | 0.06179 |
| 3 | 3.645 | 4.065 | 5.1 | 1.214 | 9.554 | 8.934 | 4.342 |
| 7 | 2.123 | 4.656 | 4.905 | 2.392 | 5.837 | 4.83 | 4.878 |
| 8 | 98.81 | 0.9119 | 6.79 | 0.3541 | 2.503 | 2.489 | 7.549 |
| 13 | 97.14 | 9.937 | 56.95 | 7.803 | 100 | 45.84 | >100 |
| 14 | 1.793 | 3.594 | 5.924 | 6.19 | 88.77 | >100 | 8.899 |
| 23 | 5.039 | 1.548 | 7.544 | 33.89 | >100 | >100 | 4.859 |
| 16 | 0.6672 | 0.6018 | 0.5958 | 0.5336 | >100 | | 0.9775 |
| 17 | 7.887 | 9.799 | 60.35 | 100 | >100 | >100 | 81.9 |
| 38 | 3.195 | 4.578 | 6.56 | 7.754 | 31.72 | 6.429 | 5.622 |
| 39 | 0.5963 | 1.574 | 0.4968 | 6.104 | 4.429 | 1.996 | 5.407 |
| 40 | 0.6626 | 0.8827 | 2.497 | 0.7401 | 2.263 | 1.483 | 2.568 |
| 19 | 0.08544 | 0.001 | 0.001 | 0.001 | 0.006484 | 0.001 | 0.02891 |
| 18 | 0.4146 | 0.6284 | 0.8843 | 1.472 | 1.395 | 1.902 | 1.56 |
| 22 | 0.2478 | 0.0567 | 0.2112 | 0.3784 | 0.5262 | 4.302 | 0.775 |
| 48 | 70.9 | 40.18 | 58.88 | 63.34 | >100 | 50.4 | 59.24 |
| 49 | 70.63 | 34.76 | 51.84 | >100 | >100 | 88.01 | 98.43 |
| 50 | 4.46 | 4.677 | 6.424 | 7.349 | 32.85 | 28.46 | 8.724 |
| 6 | 1.657 | 2.487 | 3.217 | 0.9502 | 4.713 | 5.513 | 3.024 |
| 9 | 0.3412 | 0.5424 | 0.5134 | 0.7313 | 1.937 | 2.565 | 0.9102 |

TABLE 5

Inhibition of Cancer Cell Growth as Measured by Cell Number (IC$_{50}$ μg/ml)

| Example | CACO2 | HCT15 | LS174T | SW948 | CCL228 | MCF7 |
|---|---|---|---|---|---|---|
| 31 | 0.9255 | 0.7269 | 0.8852 | 5.477 | 4.909 | 5.656 |
| 15 | 2.409 | >33 | >33 | >33 | >33 | >33 |
| 41 | 2.111 | 4.213 | 2.924 | 14.12 | 18.48 | 24.84 |
| 42 | 3.84 | 6.714 | 5.971 | 17.17 | 8.934 | 6.142 |
| 43 | 2.58 | 0.8229 | 4.225 | 4.756 | 2.557 | 5.829 |
| 44 | 5.681 | 5.098 | 6.79 | 6.756 | 7.446 | 9.411 |
| 35 | 1.933 | 0.8809 | 0.8185 | 7.827 | 12.09 | |
| 45 | 0.9109 | 79.71 | 87.1 | >100 | >100 | 57.84 |
| 46 | 6.03 | 5.597 | 7.129 | >100 | 54.01 | |
| 47 | 0.07006 | 0.03952 | 0.04683 | 0.06835 | 0.07154 | 0.07198 |
| 3 | 2.739 | 5.885 | 0.9281 | 0.8765 | 7.033 | 6.174 |
| 7 | 2.297 | 3.975 | 3.232 | 5.854 | 6.246 | 5.675 |
| 8 | 2.328 | 10.92 | 2.027 | 86.86 | 8.666 | 53.17 |
| 13 | 31.53 | 100 | 94.03 | >100 | >100 | 65 |
| 14 | 0.9885 | 6.628 | 39.29 | >100 | 39.36 | 80.7 |
| 23 | 6.19 | 9.321 | 98.16 | >100 | 95.33 | 47.91 |
| 16 | 0.7099 | 0.6409 | 0.4344 | 0.9284 | 4.383 | |
| 17 | 5.631 | 98.9 | 87.03 | >100 | >100 | 68.19 |
| 38 | 5.615 | 5.161 | 5.367 | 10.42 | 8.49 | 6 |
| 39 | 4.331 | 3.344 | 4.297 | 5.935 | 0.7774 | 6.642 |
| 40 | 0.7859 | 0.7268 | 1.346 | 4.467 | 0.9178 | 3.766 |
| 19 | 0.3773 | 0.002159 | 0.03099 | 0.09688 | 0.05037 | 0.05528 |
| 18 | 0.5761 | 1.672 | 1.593 | 1.937 | 1.171 | 2.169 |
| 22 | 0.4755 | 0.3723 | 0.8466 | 0.5934 | 0.2552 | |
| 48 | 30.1 | 83.6 | 48.48 | >100 | >100 | 79.3 |
| 49 | 42.15 | 97.36 | >100 | >100 | 99.04 | 57.45 |
| 50 | 4.886 | 8.535 | 7.684 | 17.9 | 6.787 | 7.138 |
| 6 | 0.8083 | 1.747 | 2.675 | 5.199 | 2.347 | 4.267 |
| 9 | 0.3407 | 0.9843 | 0.7118 | 3.3 | 0.7065 | 3.255 |

TABLE 6

Inhibition of Cancer Cell Growth as Measured by Cell Number (IC$_{50}$ μg/ml)

| Example No. | B7474 | T47D | LX1 | A549 | LOX | A431 | NFC |
|---|---|---|---|---|---|---|---|
| 31 | 1.577 | 3.331 | 6.88 | 2.269 | 0.8708 | 0.4339 | 2.231 |
| 15 | >33 | >33 | >33 | >33 | >33 | 22.01 | >33 |
| 41 | 6.261 | 8.503 | 48.74 | 24.96 | 0.961 | 0.8126 | 8.465 |
| 42 | 6.78 | 6.78 | 18.37 | 7.57 | 5.147 | 3.28 | 6.473 |
| 43 | 8.178 | 4.498 | 6.123 | 5.725 | 2.861 | 1.211 | 4.554 |
| 44 | 18.48 | 9.025 | 7.622 | 8.723 | 5.411 | 6.792 | 23.14 |
| 35 | 3.048 | 100 | 5.207 | 0.8654 | 0.6487 | 3.793 | |
| 45 | 86.76 | 30.04 | 100 | 100 | 9.06 | 2.609 | 72.08 |
| 46 | 32.91 | >100 | 34.02 | 4.853 | 5.351 | 8.013 | |
| 47 | 0.2332 | 0.04675 | 0.07596 | 0.06786 | 0.06053 | 0.04457 | 0.06708 |
| 3 | 4.265 | 4.321 | 6.739 | 5.679 | 1.417 | 2.479 | 5.013 |
| 7 | 3.885 | 5.172 | 6.296 | 5.93 | 1.448 | 1.056 | 5.179 |
| 8 | 55.45 | 39.47 | 0.932 | 7.278 | 0.6472 | 9.585 | 9.299 |
| 13 | 98.79 | 47.74 | >100 | >100 | >100 | 90.99 | >100 |
| 14 | 20.55 | 7.388 | 69.61 | 7.685 | 2.812 | 1.499 | 8.278 |
| 23 | 61.44 | 7.85 | 100 | 9.99 | 7.918 | 8.98 | 37.94 |
| 16 | 0.8995 | 6.555 | 0.644 | 0.2136 | 0.3157 | 0.7664 | |
| 17 | 95.68 | >100 | >100 | >100 | 74.16 | 38.06 | >100 |
| 38 | 16.97 | 5.977 | 7.522 | 7.327 | 8.115 | 4.728 | 6.531 |
| 39 | 6.649 | 0.5526 | 1.257 | 4.164 | 0.278 | 3.709 | 0.534 |
| 40 | 5.784 | 3.304 | 2.709 | 3.488 | 1.154 | 0.6946 | 3.415 |
| 19 | 0.3246 | 0.007921 | 0.001275 | 0.05804 | 0.001 | 0.03393 | 0.005082 |
| 18 | 0.1522 | 1.315 | 1.117 | 1.611 | 0.08508 | 0.249 | 1.414 |
| 22 | 0.3138 | 0.7042 | 0.8101 | 0.3754 | 0.02253 | 0.04428 | 0.4923 |
| 48 | 99.89 | >100 | >100 | >100 | 46.96 | 39.2 | >100 |
| 49 | 87.09 | 71.23 | >100 | >100 | 55.1 | 100 | 85.32 |
| 50 | 7.166 | 5.418 | 7.205 | 6.816 | 4.696 | 7.346 | 6.887 |
| 6 | 3.756 | 3.264 | 5.55 | 4.445 | 0.8133 | 0.8448 | 4.171 |
| 9 | 0.4432 | 0.8375 | 0.06716 | 2.915 | 0.4382 | 0.4334 | 0.9521 |

TABLE 7

Inhibition of Cancer Cell Growth as Measured by Cell Number (IC$_{50}$ μg/ml)

| Example No. | DU145 | PC3 | LNCAP | HL60 | CCRF-CEM | SKBR3 |
|---|---|---|---|---|---|---|
| 31 | 0.5852 | 5.159 | 0.7721 | 0.8939 | 3.19 | |
| 15 | 18.01 | >33 | >33 | >33 | >33 | >33 |
| 41 | 0.913 | 17.5 | 3.534 | 3.234 | 8.293 | 20.65 |
| 42 | 5.56 | 29.09 | 2.392 | 5.431 | 5.23 | 12.53 |
| 43 | 3.13 | 7.024 | 4.53 | 1.655 | 3.59 | 5.188 |
| 44 | 7.92 | 7.652 | 5.157 | 3.792 | 4.673 | 14.37 |
| 35 | 0.537 | 7.843 | | 1.978 | 3.862 | |
| 45 | 8.939 | 88.92 | 57.79 | >1.00 | >100 | 60.53 |
| 46 | 3.635 | >100 | | 6.023 | 61.73 | |
| 47 | 0.06799 | 0.11 | 0.03366 | 0.06254 | 0.06796 | 0.04668 |
| 3 | 4.448 | 5.689 | 6.659 | 3.672 | 3.687 | 6.897 |
| 7 | 1.09 | 7.219 | 2.187 | 2.633 | 3.435 | 5.598 |
| 8 | 6.474 | 53.35 | 59.44 | 18.95 | 0.8227 | 38.26 |
| 13 | 65.79 | >100 | >100 | 70.25 | >100 | 100 |
| 14 | 0.9097 | 41.24 | 8.979 | 4.044 | 7.603 | 43.61 |
| 23 | 41.89 | 100 | 6.633 | 6.388 | 6.797 | 48.01 |
| 16 | 0.1134 | 3.038 | | 0.6964 | 0.7286 | |
| 17 | 7.806 | >100 | 90.03 | >100 | >100 | 79.73 |
| 38 | 5.153 | 9.333 | 4.577 | 4.274 | 4.393 | 7.145 |
| 39 | 0.6365 | 5.697 | 3.479 | 2.97 | 0.8566 | 3.647 |
| 40 | 0.8375 | 5.645 | 2.692 | 0.7764 | 3.134 | 3.596 |
| 19 | 0.07054 | 0.05741 | 0.06975 | 0.07788 | 0.001 | 0.02646 |
| 18 | 0.3215 | 2.346 | 0.1462 | 1.427 | 1.038 | 1.852 |
| 22 | 0.2651 | 0.6952 | 0.7217 | 0.6077 | 0.4031 | |
| 48 | 20.81 | >100 | 40.65 | 44.65 | >100 | 64.5 |
| 49 | 79.79 | >100 | 52.39 | 48.39 | >100 | 74.57 |
| 50 | 5.601 | 8.527 | 5.336 | 4.721 | 4.603 | 6.831 |
| 6 | 1.034 | 4.689 | 4.186 | 0.9471 | 2.572 | 4.204 |
| 9 | 0.3877 | 1.658 | 0.6608 | 0.7581 | 0.5509 | 0.8621 |

TABLE 8

Inhibition of Cancer Cell Growth as Measured by Cell Number (IC$_{50}$ µg/ml)

| Example | A431 | SKBR3 | SW620 | LOX | MCF7 |
|---|---|---|---|---|---|
| 156 | 3.77 | 7.43 | 7.91 | 67 | 7.57 |
| 158 | 2.97 | 0.80 | 4.08 | 2.44 | 5.44 |
| 155 | 4.30 | 3.28 | 7.55 | 6.08 | 7.49 |
| 258 | 5.42 | 50.45 | 36.21 | 10.72 | 9.69 |
| 261 | 0.61 | 0.80 | 2.92 | 1.32 | 7.50 |
| 260 | 0.06 | 0.08 | 0.32 | 0.26 | 9.98 |
| 154 | 0.07 | 0.05 | 0.55 | 0.44 | 2.57 |
| 262 | 0.04 | 0.06 | 0.56 | 0.07 | 0.09 |
| 151 | 0.09 | 0.07 | <0.01 | 0.08 | 0.61 |
| 263 | 6.90 | 7.50 | 5.79 | 5.66 | 8.44 |
| 105 | 0.13 | 1.84 | 0.06 | 0.72 | 2.09 |
| 138 | 0.44 | <0.01 | 3.52 | 1.12 | 3.51 |
| 186 | 37.61 | 21.48 | 62.56 | 46.36 | 42.49 |
| 163 | 7.02 | 7.28 | 47.28 | 64.22 | 17.45 |
| 162 | 6.87 | 7.15 | 33.54 | 8.13 | 16.35 |
| 187 | 0.06 | 0.06 | 0.05 | 0.07 | 0.42 |
| 108 | 6.6 | 6.34 | 14.55 | 6.85 | 7.97 |
| 168 | 1.57 | 1.38 | 9.10 | 1.76 | 5.94 |
| 109 | 38.85 | 30.67 | 40.8 | 35.09 | 37.91 |
| 270 | 14.34 | 46.12 | 47.99 | 0.06 | 27.06 |
| 270 | 6.95 | >10 | >10 | >10 | >10 |
| 41 | 0.24 | 0.48 | 2.23 | 1.33 | 6.86 |
| 44 | 6.29 | 7.46 | 6.61 | 6.58 | 17.96 |
| 35 | 0.51 | 0.93 | 6.40 | 4.10 | 40.86 |
| 47 | <0.01 | <0.01 | <0.01 | 0.03 | 0.02 |
| 255 | 0.59 | 0.35 | 0.58 | 0.69 | 2.85 |
| 254 | 0.07 | 0.01 | 0.03 | 0.07 | 0.07 |
| 258 | 4.67 | 3.70 | 5.76 | 6.12 | 7.87 |
| 262 | 0.02 | <0.01 | N.A. | 0.03 | 0.07 |
| 31 | 0.1 | 0.48 | 0.82 | 1.65 | 6.04 |
| 188 | 0.54 | 0.16 | 8.77 | 0.62 | 1.43 |
| 110 | 0.9 | 1.3 | 0.7 | 0.8 | N.A. |
| 311 | 0.8 | 0.7 | 1.0 | 2.8 | N.A. |
| 167 | 2.6 | 3.7 | 8.1 | 5.3 | 8.5 |
| 165 | 0.2 | 0.1 | 3.0 | 0.8 | 5.8 |
| 65 | 48 | 60 | >100 | 84 | 84 |
| 188 | 0.4 | 0.5 | 0.7 | 0.3 | 0.8 |
| 164 | 0.6 | 0.7 | >100 | 0.9 | 57 |
| 192 | 0.05 | 0.03 | 0.1 | | |
| 169 | 0.01 | 0.02 | 0.1 | | |
| 189 | 0.04 | 0.03 | 0.1 | | |
| 62 | 0.01 | 0.3 | 0.3 | | |
| 194 | 0.1 | 0.2 | 0.2 | | |
| 193 | 0.01 | 0.003 | 0.1 | | |
| 99 | 0.3 | 0.1 | 4.4 | | |
| 101 | >10 | >10 | >10 | | |
| 100 | 0.1 | 0.1 | 0.8 | | |
| 161 | 0.1 | 0.04 | 0.2 | | |
| 227 | 0.02 | 0.2 | 0.1 | | |
| 166 | 0.02 | 0.02 | 0.04 | | |
| 145 | 0.03 | 0.03 | 0.4 | | |
| 140 | 0.02 | 0.02 | 0.1 | | |
| 170 | 0.03 | 0.03 | 0.1 | | |
| 160 | 0.2 | 0.5 | 2.3 | | |
| 190 | 1.6 | 2.7 | >5 | | |
| 146 | 0.03 | 0.03 | 0.6 | | |
| 198 | 0.002 | 0.03 | 0.4 | | |
| 188 | 0.579 | 0.479 | 2.177 | | |
| 99 | 0.159 | 0.078 | 1.153 | | |
| 191 | 0.048 | 0.060 | 0.084 | | |
| 190 | 1.733 | 0.494 | 4.882 | | |
| 164 | 0.322 | 0.684 | >5 | | |
| 200 | 0.128 | 0.247 | >5 | | |
| 203 | 0.048 | 0.1 | 1.733 | | |
| 204 | 0.032 | 0.026 | 0.340 | | |
| 63 | 0.095 | 0.144 | 0.208 | | |
| 64 | 0.806 | 1.965 | 1.603 | | |
| 199 | 0.048 | 0.076 | 0.433 | | |
| 61 | 0.341 | 1.094 | 1.066 | | |
| 312 | 0.491 | 2.255 | 3.534 | | |
| 184 | 0.158 | 0.300 | 0.463 | | |
| 185 | 0.340 | 1.108 | 2.182 | | |
| 112 | >5 | >5 | >5 | | |
| 111 | 3.046 | 3.324 | 2.019 | | |
| 197 | 0.121 | 0.197 | 0.266 | | |
| 205 | 0.049 | 0.243 | >5 | | |
| 204 | 0.038 | 0.029 | 0.347 | | |
| 157 | 3.26 | 2.601 | 4.17 | | |
| 229 | 0.469 | >5 | >5 | | |
| 174 | 0.345 | 0.298 | >5 | | |
| 172 | 0.255 | 0.067 | 1.591 | | |
| 209 | 0.113 | 0.048 | 0.380 | | |
| 208 | 0.067 | 0.038 | 0.453 | | |
| 148 | 0.195 | 0.043 | 0.260 | | |
| 175 | 0.144 | 0.180 | 4.948 | | |
| 218 | 0.102 | 0.029 | 1.855 | | |
| 217 | 0.050 | 0.019 | 1.387 | | |
| 216 | 0.032 | 0.012 | 0.730 | | |
| 76 | 2.206 | 1.886 | 2.310 | | |
| 81 | 1.402 | 1.441 | 2.084 | | |
| 216 | 0.024 | 0.015 | 0.240 | | |
| 217 | 0.046 | 0.033 | 0.455 | | |
| 218 | 0.044 | 0.047 | 1.235 | | |
| 318 | 0.8 | 1.5 | >10 | | |
| 328 | 0.19 | 0.02 | 0.15 | 0.33 | 0.78 |
| 329 | 0.22 | 0.21 | 0.03 | 0.58 | 0.75 |
| 330 | 0.05 | 0.23 | 0.02 | 0.02 | 0.36 |
| 331 | 0.03 | 0.16 | 0.04 | 0.04 | 0.44 |
| 332 | 0.60 | 0.08 | 0.44 | 0.51 | 54.9 |
| 347 | 0.04 | 0.2 | 0.2 | | |
| 358 | 0.5 | 0.7 | 4.1 | 2.5 | 7.8 |
| 363 | 0.07 | 0.06 | 0.08 | 0.08 | 0.8 |
| 391 | 0.34 | 0.4 | 5.23 | 0.10 | 6.53 |
| 392 | 0.46 | 2.61 | 73.3 | 1.99 | 3.66 |
| 393 | 0.45 | 0.84 | 2.25 | 0.85 | 4.0 |
| 396 | 0.3 | 0.2 | 2.7 | | |

In Vivo Inhibition of the Growth of Human Epidermoid Tumors (A431)

Representative compounds of this invention (listed below) were evaluated in an in vivo standard pharmacological test procedure which measured its ability to inhibit the growth of human epidermoid tumors. Human epidermoid carcinoma cells A-431 (American Type Culture Collection, Rockville, Md. # CRL-155) were grown in vitro as described above. BALB/c nu/nu female mice (Charles River, Wilmington, Mass.) were used in this in vivo standard pharmacological test procedure. A unit of $5 \times 10^6$ cells were injected SC into mice. When tumors attained a mass of between 100 and 150 mg, the mice were randomized into treatment groups (day zero). Mice were treated IP once a day either on days 1, 5, and 9 or on days 1 through 10 post staging with doses of either 80, 40 or 20 mg/kg/dose of the compound to be evaluated in 0.2% Klucel. Control animals received no drug. Tumor mass was determined every 7 days [(length X width$^2$)/2] for 28 days post staging. Relative tumor growth (Mean tumor mass on days 7, 14, 21, and 28 divided by the mean tumor mass on day zero) is determined for each treatment group.

When evaluated in this test procedure, the compound of Example 18 (80 mg/kg administered on days 1, 5, and 9) reduced tumor size by 29% on day 7 and by 45% (p<0.01) on day 14. Tumor growth was not reduced versus control when mice treated with the compound of Example 18 were evaluated on days 21 and 28.

The compound of Example 47 was similarly evaluated for its ability to inhibit the growth of human epidermoid tumors in vivo using the standard pharmacological test procedure described above. The results obtained are shown in Table 9.

TABLE 9

In Vivo Inhibition of the Growth of Human Epidermoid Tumors (A431) in Mice
by the Compound of Example 47

| a<br>Drug Treatment<br>mg/kg/dose | b<br>Day 7 | c<br>% T/C | b<br>Day 14 | c<br>% T/C | b<br>Day 21 | c<br>% T/C | b<br>Day 28 | c<br>% T/C | e<br>S/T |
|---|---|---|---|---|---|---|---|---|---|
| Placebo (Klucel) | 4.68 |  | 9.09 |  | 11.51 |  | 13.67 |  | 10/10 |
| Example 47 (100) | 1.57 | 34 (d) | 3.36 | 37 (d) | 5.90 | 51 | 5.85 | 43 | 5/5 |
| Example 47 (50) | 2.05 | 44 (d) | 5.04 | 55 (d) | 10.02 | 87 | 14.01 | 102 | 5/5 |
| Example 47 (40) | 3.22 | 69 | 6.75 | 74 | 13.38 | 116 | 18.59 | 136 | 5/5 | a) Drugs administered IP on days. 1 through 10 IP with exception of the placebo control which was administered on days 1 through 10 PO.

b) Relative Tumor Growth = $\dfrac{\text{Tumor Mass on Day 7, 14, 21, 28}}{\text{Mean Tumor Mass on Day 0}}$ c) % T/C = $\dfrac{\text{Relative Tumor Growth of Treated Group}}{\text{Relative Tumor Growth of Placebo Group}} \times 100$ d) Statistically (p < 0.05) significant; Student-t-test. significant reduction in Relative Tumor Growth of Treated Group, compared to Placebo Control.

e) S/T = No. Survivors/No. Treated on Day +28 post tumor staging.

As shown in Table 9, the compound of Example 47 inhibited tumor growth; for example at 100 mg/kg (administered i.p. during days 1–10), tumor growth was inhibited by 66% at day 7, 63% at day 14, 49% at day 21, and 57% at day 28. Tumor growth inhibition also appeared to be dose dependent The compound of Examples 203, 204, and 205 were similarly evaluated for their ability to inhibit the growth of human epidermoid tumors in vivo using the standard pharmacological test procedure described above. The results obtained are shown in Table 10.

As shown in Table 10, the compounds of Examples 203, 204, and 205 significantly inhibited tumor growth in animals that were treated with either drug relative to animals that did not receive any drug.

The compound of Examples 208, 216, and 217 were similarly evaluated for their ability to inhibit the growth of human epidermoid tumors in vivo using the standard pharmacological test procedure described above. The results obtained are shown in Table 11.

TABLE 10

In Vivo Inhibition of the Growth of Human Epidermoid Tumors (A431) in Mice
by the Compounds of Examples 203, 204, and 205

| a<br>Drug Treatment<br>mg/kg/dose | b<br>Day 7 | c<br>% T/C | b<br>Day 14 | c<br>% T/C | b<br>Day 21 | c<br>% T/C | b<br>Day 28 | c<br>% T/C | e<br>S/T |
|---|---|---|---|---|---|---|---|---|---|
| Klucel (Placebo Control) | 4.71 |  | 9.01 |  | 13.42 |  | 18.65 |  | 10/10 |
| Example 203 (80 PO) | 0.71 | 15 | 0.76 | 8 | 1.65 | 12 | 3.09 | 17 | 4/5 |
| Example 203 (80 IP) | 0.94 | 20 | 1.13 | 12 | 1.86 | 14 | 3.07 | 16 | 5/5 |
| Example 204 (80 PO) | 1.16 | 25 | 1.69 | 18 | 5.83 | 43 | 9.45 | 51 | 4/5 |
| Example 204 (80 IP) | 2.11 | 45 | 3.84 | 42 | 7.44 | 55 | 9.08 | 49 | 5/5 |
| Example 205 (80 PO) | 1.09 | 23 | 1.72 | 19 | 3.07 | 23 | 5.51 | 29 | 5/5 |
| Example 205 (80 IP) | 1.43 | 30 | 2.27 | 25 | 5.06 | 38 | 11.38 | 61 | 5/5 | a) All 80 PO doses administered on days 1 through 10. All 80 IP doses administered on days 1, 5, 9.

b) Relative Tumor Growth = $\dfrac{\text{Tumor Mass on Day 7, 14, 21, 28}}{\text{Mean Tumor Mass on Day 0}}$ c) % T/C = $\dfrac{\text{Relative Tumor Growth of Treated Group}}{\text{Relative Tumor Growth of Placebo Group}} \times 100$ d) Statistical analysis (Student-t-test) of Log Relative Tumor Growth. All data had p ≤ 0.05 indicating statistically significant reduction in Relative Tumor Growth of Treated Group, compared to Placebo Control.

e) S/T = No. Survivors/No. Treated on Day +28 post tumor staging.

TABLE 11

In Vivo Inhibition of the Growth of Human Epidermoid Tumors (A431) in Mice by the Compounds of Examples 298, 216, and 217

| a<br>Drug Treatment<br>mg/kg/dose | b<br>Day 7 | c<br>% T/C | b<br>Day 14 | c<br>% T/C | b<br>Day 21 | c<br>% T/C | b<br>Day 28 | c<br>% T/C | e<br>S/T |
|---|---|---|---|---|---|---|---|---|---|
| Klucel | 5.74 | | 14.99 | | 17.90 | | 24.85 | | 8/10 |
| Example 208 (80 PO) | 0.40 | 6 | 0.99 | 6 | 1.46 | 8 | 2.63 | 10 | 5/5 |
| Example 208 (80 IP) | 0.82 | 14 | 2.29 | 15 | 4.80 | 26 | 8.09 | 32 | 5/5 |
| Example 216 (80 PO) | 0.40 | 6 | 1.02 | 6 | 2.20 | 12 | 5.28 | 21 | 5/5 |
| Example 216 (80 IP) | 0.84 | 14 | 1.81 | 12 | 3.06 | 17 | 4.92 | 19 | 5/5 |
| Example 217 (80 PO) | 1.73 | 30 | 5.01 | 33 | 7.84 | 43 | 10.54 | 42 | 5/5 |
| Example 217 (80 IP) | 1.47 | 25 | 5.50 | 36 | 9.20 | 51 | 14.04 | 56 | 5/5 | a) All compounds administered IP received drug on days 1, 5 and 9. All compounds administered PO were received on days 1 through 10.

b) Relative Tumor Growth = $\dfrac{\text{Tumor Mass on Day 7, 14, 21, 28}}{\text{Mean Tumor Mass on Day 0}}$ c) % T/C = $\dfrac{\text{Relative Tumor Growth of Treated Group}}{\text{Relative Tumor Growth of Placebo Group}} \times 100$ d) Statistical analysis (Student-t-test) of Log Relative Tumor Growth. All data had p < 0.05 indicatiug a statisfically significant reduction in Relative Tumor Growth of Treated Group, compared to Placebo Control.

e) S/T = No. Survivors/No. Treated on Day +28 post tumor staging.

As shown in Table 11, the compounds of Examples 208, 216, and 217 significantly inhibited tumor growth in animals that were treated with either drug relative to animals that did not receive any drug.

Inhibition of Epithelial Cell Kinase (ECK)

In this standard pharmacological test procedure, a biotinylated peptide substrate is first immobilized on neutravidin-coated microtiter plates. The test drug, the Epithelial Cell Kinase (ECK), $Mg^{++}$, sodium vanadate (a protein tyrosine phosphatase inhibitor), and an appropriate buffer to maintain pH (7.2) are then added to the immobilized substrate-containing microtiter wells. ATP is then added to initiate phosphorylation. After incubation, the assay plates are washed with a suitable buffer leaving behind phosphorylated peptide which is exposed to horse radish peroxidase (HRP)-conjugated anti-phosphotyrosine monoclonal antibody. The antibody-treated plates are washed again and the HRP activity in individual wells is quantified as a reflection of degree of substrate phosphorylation. This nonradioactive format was used to identify inhibitors of ECK tyrosine kinase activity where the $IC_{50}$ is the concentration of drug that inhibits substrate phosphorylation by 50%.

TABLE 12

Inhibition of Epithelial Cell Kinase (ECK)

| Example<br>No. | Eck $IC_{50}$<br>($\mu$M) |
|---|---|
| 3 | 28.2318 |
| 6 | >25.0495 |
| 7 | >27.0834 |
| 8 | <0.0459 |
| 9 | >47.2500 |
| 13 | >27.0871 |
| 14 | >29.4814 |
| 15 | <0.0494 |
| 18 | >50.8587 |
| 19 | 24.0570 |
| 23 | 27.9110 |
| 35 | >61.8563 |
| 39 | 28.0756 |
| 40 | 27.1597 |
| 41 | >58.8616 |
| 42 | >53.5719 |
| 43 | >54.7360 |
| 44 | >62.6253 |
| 45 | >60.5418 |
| 46 | >61.8563 |
| 47 | >24.2548 |
| 48 | >59.6363 |
| 49 | >51.9184 |
| 65 | >22.8676 |
| 76 | 0.4663 |
| 81 | 0.4247 |
| 82 | 50.9606 |
| 83 | >46.0299 |
| 84 | 0.4495 |
| 85 | 0.0411 |
| 86 | >46.4177 |
| 87 | >42.2913 |
| 88 | >60.1793 |
| 89 | >28.5714 |
| 97 | >28.6533 |
| 100 | 41.8064 |
| 105 | >26.0960 |
| 108 | >23.4577 |
| 109 | >25.2334 |
| 110 | >43.2526 |
| 112 | >22.8154 |
| 125 | 42.4719 |
| 126 | <0.0402 |
| 127 | >42.4719 |
| 128 | >44.5931 |
| 129 | 22.7169 |
| 130 | >25.8933 |
| 131 | >24.0269 |
| 132 | >58.7544 |
| 133 | >72.9129 |
| 134 | >32.8623 |
| 135 | >57.3394 |
| 136 | >67.8656 |
| 138 | >58.0720 |
| 139 | >56.1167 |

TABLE 12-continued

Inhibition of Epithelial Cell Kinase (ECK)

| Example No. | Eck IC$_{50}$ ($\mu$M) |
|---|---|
| 140 | >45.5063 |
| 141 | >68.8942 |
| 143 | >52.7983 |
| 144 | >54.5256 |
| 145 | >47.1809 |
| 147 | 43.1127 |
| 148 | >42.9277 |
| 149 | >63.9591 |
| 150 | >29.1800 |
| 151 | >50.8647 |
| 152 | >29.4811 |
| 153 | >27.0856 |
| 154 | <0.0571 |
| 155 | >67.4992 |
| 156 | >30.6466 |
| 157 | >42.6439 |
| 158 | >49.6401 |
| 159 | >23.1000 |
| 160 | <0.0589 |
| 161 | >46.0299 |
| 162 | >35.0508 |
| 163 | >31.7158 |
| 164 | >57.0776 |
| 165 | >59.1017 |
| 166 | >46.1361 |
| 167 | >70.3482 |
| 168 | >31.8167 |
| 169 | 40.9500 |
| 170 | 11.8953 |
| 171 | >40.6174 |
| 174 | 39.1850 |
| 175 | >37.0096 |
| 176 | 0.0100 |
| 177 | 0.0057 |
| 186 | >22.1590 |
| 187 | >41.9842 |
| 188 | >38.6548 |
| 189 | >44.4543 |
| 190 | 39.7298 |
| 191 | 41.9842 |
| 192 | 39.6495 |
| 193 | 47.4091 |
| 194 | >48.9213 |
| 197 | 42.8894 |
| 200 | 38.2844 |
| 202 | >58.3494 |
| 203 | 2.2031 |
| 204 | 20.7485 |
| 205 | 40.3963 |
| 208 | >40.1317 |
| 209 | >37.9930 |
| 216 | >40.4535 |
| 217 | 0.1148 |
| 218 | >37.2833 |
| 227 | >41.8102 |
| 228 | >55.9011 |
| 232 | >52.8499 |
| 238 | >30.3251 |
| 239 | >29.8187 |
| 240 | >26.0261 |
| 241 | 7.2418 |
| 242 | >28.7018 |
| 243 | >26.7544 |
| 244 | 24.7647 |
| 246 | 0.0060 |
| 248 | 25.1091 |
| 249 | >28.1069 |
| 254 | >21.0084 |
| 255 | >44.6478 |
| 256 | >51.8403 |
| 257 | >53.2765 |
| 258 | >28.7853 |
| 259 | >29.9940 |
| 260 | >28.4576 |
| 261 | >152.9052 |
| 262 | >27.1887 |
| 264 | >62.4317 |
| 265 | >55.1861 |
| 266 | 51.7585 |
| 267 | >59.6363 |
| 268 | >56.5274 |
| 269 | >50.8298 |
| 270 | <0.0569 |
| 275 | >61.0225 |
| 276 | >65.5010 |
| 277 | >62.8176 |
| 278 | >54.0237 |
| 279 | >62.2396 |
| 280 | >30.3689 |
| 281 | 0.0033 |
| 282 | 0.0029 |
| 283 | 9.1534 |
| 284 | 32.7505 |
| 288 | 0.0014 |
| 290 | >28.1069 |
| 291 | >20.8711 |
| 292 | 0.0018 |
| 293 | 32.6449 |
| 294 | 0.0020 |
| 295 | >29.8182 |
| 302 | 28.0756 |
| 303 | >22.7118 |
| 305 | >42.8266 |
| 307 | >61.0128 |
| 308 | >63.7552 |
| 311 | >21.1730 |
| 319 | 0.001 |

Inhibition of Kinase insert Domain containing Receptor (KDR; the catalytic domain of the VEGF receptor)

In this standard pharmacological test procedure, KDR protein is mixed, in the presence or absence of a inhibitor compound, with a substrate peptide to be phosphorylated (a copolymer of glutamic acid and tyrosine, E:Y::4:1) and other cofacters such as Mg$^{++}$ and sodium vanadate (a protein tyrosine phosphatase inhibitor) in an appropriate buffer to maintain pH (7.2). ATP and a radioactive tracer (either P$^{32}$- or P$^{33}$-labeled ATP) is then add to initiate phosphorylation. After incubation, the radioactive phosphate associated with the acid-insoluble fraction of the assay mixture is then qualified as reflection of substrate phosphorylation. This radioactive format was used to identify inhibitors of KDR tyrosine kinase activity where the IC$_{50}$ is the concentration of drug that inhibits substrate phosphorylation by 50%.

TABLE 13

Inhibition of Kinase insert Domain containing Receptor (KDR)

| Example No. | KDR IC$_{50}$ $\mu$g/mL | Example No. | KDR IC$_{50}$ $\mu$g/mL |
|---|---|---|---|
| 9 | >30 | 241 | >30 |
| 18 | >30 | 242 | >30 |
| 49 | >30 | 243 | >30 |
| 76 | 0.7 | 244 | >30 |
| 82 | 3 | 246 | >10 |
| 84 | 0.3 | 248 | 10 |
| 85 | 0.3 | 249 | >10 |
| 86 | 3 | 250 | >10 |
| 87 | 3 | 275 | >30 |
| 97 | 0.1 | 276 | >30 |

TABLE 13-continued

Inhibition of Kinase insert Domain containing Receptor (KDR)

| Example No. | KDR IC$_{50}$ µg/mL | Example No. | KDR IC$_{50}$ µg/mL |
|---|---|---|---|
| 127 | 10 | 277 | >30 |
| 128 | 8 | 278 | >30 |
| 145 | >30 | 279 | >30 |
| 154 | >30 | 280 | >30 |
| 160 | 30 | 281 | 3 |
| 176 | 3 | 282 | 2 |
| 177 | 0.05 | 283 | 30 |
| 208 | 10 | 284 | 30 |
| 209 | 30 | 288 | 10 |
| 216 | 30 | 290 | 10 |
| 217 | 30 | 291 | 10 |
| 218 | >30 | 292 | 10 |
| 229 | 0.2 | 293 | 10 |
| 232 | >30 | 294 | 6 |
| 233 | >30 | 295 | 10 |
| 234 | >30 | 305 | 30 |
| 238 | >30 | 307 | 30 |
| 239 | >30 | 308 | 30 |
| 240 | >30 | 319 | 0.5 |

Mitogen Activated Protein Kinase (MAPK) Assay

To evaluate inhibitors of the MAP (mitogen activated protein) kinase a two component coupled standard pharmacological test procedure, which measures phosphorylation of a serine/threonine residue in an appropriate sequence in the substrate in the presence and absence of a putative inhibitor, was used. Recombinant human MEK 1 (MAPKK) was first used to activate recombinant human ERK2 (MAPK) and the activated MAPK (ERK) was incubated with substrate (MBP peptide or MYC peptide) in the presence of ATP, Mg$^{+2}$ and radiolabeled $^{33}$P ATP. The phosphorylated peptide was captured on a P 81 phosphocellulose filter (paper filter or embedded in microtiter plate) washed and counted by scintillation methods.

The peptide substrates used in the assay are MBP, peptide substrate (APRTPGGRR), or synthetic Myc substrate, (KKFELLPTPPLSPSRR•5 TFA. The recombinant enzymes used were prepared as GST fusion proteins of human ERK 2 and human MEK 1. Inhibitor samples were prepared as 10× stocks in 10% DMSO and an appropriate aliquot was used to deliver either 10 ug/ml for a single point screening dose or 100, 10, 1, and 0.1 uM final concentration for a dose response curve. Final DMSO concentrations were less than or equal to 1%.

The reaction was run as follows in 50 mM Tris kinase buffer, pH 7.4 in a reaction volume of 50 ul. The appropriate volume of kinase buffer and inhibitor sample was added to the tube. Appropriate dilution of enzyme was delivered to give 2–5 ug recombinant MAPK (Erk) per tube. The inhibitor was incubated with MAPK (Erk) for min at 0 deg. C. Recombinant Mek (MAPKK) (0.5–2.5 ug) or fully activated Mek (0.05–0.1 units) was added to activate the Erk and incubated for 30 min at 30° C. Then substrate and gamma $^{33}$P ATP was were added to give a final concentration of 0.5–1 mM MBPP or 250–500 uM Myc; 0.2–0.5 uCi gamma P 33 ATP/tube; 50 µM ATP final concentration. Samples were incubated at 30° C. for 30 minutes and the reaction was stopped by adding 25 µl of ice cold 10% TCA After samples were chilled on ice for 30 min, 20 µl of sample was transferred onto P 81 phosphocellulose filter paper or appropriate MTP with embedded P 81 filter. Filter papers or MTP were washed 2 times with a large volume of 1% acetic acid, then 2 times with water. The filters or MTP were briefly air dried before addition of scintillant and samples were counted in the appropriate scintillation counter set up for reading $^{33}$P isotope. Samples included a positive control (activated enzyme plus substrate); a no enzyme control; a no substrate control; samples with different concentrations of putative inhibitor; and samples with reference inhibitors (other active compounds or non-specific inhibitors such as staurosporine or K252 B).

The raw data was captured as cpm. Sample replicates were averaged and corrected for background count. Mean cpm data was tabulated by group and % inhibition by a test compound was calculated as (corrected cpm control-corrected. cpm sample/control)×100=% inhibition. If several concentrations of inhibitor were tested, IC$_{50}$ values (the concentration which gives 50% inhibition) were determined graphically from the dose response curve for % inhibition or by an appropriate computer program. In the Table below, there may be separate entries for the same compound; this is an indication that the compound was evaluated more than one time.

TABLE 14

Mitogen Activated Protein Kinase (MAPK) Assay

| Example | IC$_{50}$(µM) |
|---|---|
| 3 | >100 |
| 6 | >100 |
| 7 | 25 |
| 8 | >100 |
| 9 | >100 |
| 13 | >100 |
| 14 | >100 |
| 15 | >100 |
| 16 | 3.3 |
| 16 | 34 |
| 17 | >100 |
| 18 | >100 |
| 19 | 29 |
| 23 | >100 |
| 31 | 8 |
| 31 | <1 |
| 31 | 2 |
| 35 | 2.5 |
| 35 | 9 |
| 38 | 45 |
| 39 | 40 |
| 40 | >100 |
| 41 | 1.4 |
| 43 | 30 |
| 44 | 18 |
| 45 | >100 |
| 46 | >100 |
| 46 | >100 |
| 46 | >10 |
| 46 | >30 |
| 46 | >100 |
| 46 | >100 |
| 47 | <1 |
| 47 | <1 |
| 47 | >100 |
| 47 | 9.2 |
| 47 | 7 |
| 47 | 1.3 |
| 47 | 8 |
| 47 | 10 |
| 47 | 8 |
| 47 | 9 |
| 47 | 20 |
| 47 | 5 |
| 47 | <1 |
| 47 | 1 |
| 47 | <1 |
| 47 | 5 |
| 47 | <1 |
| 47 | 2 |
| 47 | >100 |

TABLE 14-continued

Mitogen Activated Protein Kinase (MAPK) Assay

| Example | IC$_{50}$($\mu$M) |
|---|---|
| 47 | >100 |
| 48 | 10 |
| 49 | >100 |
| 49 | >100 |
| 50 | >100 |
| 61 | >100 |
| 62 | 2 |
| 62 | 20 |
| 63 | >100 |
| 64 | >100 |
| 64 | 3 |
| 65 | 40 |
| 76 | <1 |
| 81 | 0.1 |
| 82 | 5.5 |
| 83 | 1.8 |
| 83 | 25 |
| 84 | <1 |
| 84 | <1 |
| 85 | <1 |
| 85 | <1 |
| 85 | 0.2 |
| 86 | 1.8 |
| 86 | 2 |
| 87 | <1 |
| 87 | <1 |
| 87 | 2 |
| 87 | 30 |
| 88 | <10 |
| 88 | >50 |
| 89 | 2.5 |
| 89 | 4 |
| 89 | >50 |
| 89 | 2 |
| 99 | 40 |
| 100 | 20 |
| 101 | 20 |
| 105 | >100 |
| 108 | >100 |
| 110 | 40 |
| 111 | 100 |
| 112 | >100 |
| 117 | 40 |
| 117 | 28 |
| 125 | >100 |
| 126 | >100 |
| 127 | 6 |
| 129 | 60 |
| 130 | >100 |
| 130 | >100 |
| 130 | >100 |
| 131 | >100 |
| 131 | >100 |
| 132 | >100 |
| 133 | >100 |
| 134 | >100 |
| 134 | 80 |
| 135 | 10 |
| 135 | 30 |
| 135 | >100 |
| 136 | 70 |
| 136 | >100 |
| 136 | >100 |
| 138 | 2.3 |
| 138 | 38 |
| 139 | 35 |
| 140 | >100 |
| 141 | 35 |
| 143 | 40 |
| 144 | 40 |
| 145 | 35 |
| 146 | 6 |
| 147 | 80 |
| 149 | 2 |
| 149 | 4 |
| 150 | >100 |
| 150 | >100 |
| 152 | <1 |
| 152 | 40 |
| 153 | >100 |
| 154 | 20 |
| 155 | 3 |
| 155 | <1 |
| 156 | >100 |
| 157 | 90 |
| 158 | <1 |
| 158 | <1 |
| 158 | <1 |
| 158 | 0.3 |
| 159 | >100 |
| 160 | 30 |
| 161 | 55 |
| 162 | 35 |
| 163 | >100 |
| 164 | >100 |
| 165 | >100 |
| 166 | >100 |
| 167 | >100 |
| 168 | 80 |
| 169 | >100 |
| 170 | >100 |
| 171 | 100 |
| 172 | 90 |
| 173 | 8 |
| 174 | 2.5 |
| 176 | >100 |
| 177 | 40 |
| 186 | 3 |
| 186 | 7 |
| 186 | 2.5 |
| 187 | >100 |
| 188 | <1 |
| 188 | 50 |
| 188 | 30 |
| 189 | 50 |
| 190 | 12 |
| 191 | 40 |
| 191 | >100 |
| 192 | >100 |
| 192 | >100 |
| 193 | 50 |
| 194 | >100 |
| 197 | 35 |
| 198 | 15 |
| 198 | 7 |
| 200 | >100 |
| 203 | <1 |
| 203 | <1 |
| 203 | 0.8 |
| 204 | 35 |
| 205 | >100 |
| 208 | 13 |
| 209 | 9 |
| 229 | <1 |
| 229 | <1 |
| 232 | >100 |
| 232 | 45 |
| 232 | >100 |
| 233 | 80 |
| 234 | >100 |
| 238 | >100 |
| 239 | >100 |
| 240 | 10 |
| 241 | >100 |
| 242 | 10 |
| 243 | >100 |
| 244 | >100 |
| 246 | 35 |
| 248 | 8 |
| 249 | 15 |

TABLE 14-continued

Mitogen Activated Protein Kinase (MAPK) Assay

| Example | IC$_{50}$($\mu$M) |
|---|---|
| 250 | 10 |
| 252 | 100 |
| 254 | <1 |
| 254 | <1 |
| 254 | 9 |
| 254 | <0.5 |
| 255 | <1 |
| 255 | <1 |
| 255 | 0.2 |
| 255 | 10 |
| 255 | <1 |
| 255 | 2 |
| 255 | 10 |
| 255 | 0.2 |
| 256 | 95 |
| 256 | 3 |
| 257 | >100 |
| 258 | 4 |
| 258 | 1 |
| 258 | <1 |
| 259 | 3 |
| 259 | >50 |
| 259 | >100 |
| 259 | >100 |
| 260 | 55 |
| 261 | <1 |
| 261 | <1 |
| 261 | <1 |
| 261 | 5 |
| 262 | 4 |
| 262 | 1.2 |
| 263 | 80 |
| 264 | 3 |
| 264 | 1 |
| 264 | 3 |
| 264 | 8 |
| 265 | 20 |
| 266 | >100 |
| 268 | 15 |
| 269 | 5 |
| 269 | <1 |
| 269 | 3 |
| 269 | 8 |
| 270 | >100 |
| 270 | >100 |
| 275 | >100 |
| 276 | >100 |
| 277 | >100 |
| 278 | >100 |
| 279 | >100 |
| 280 | >100 |
| 281 | 2.5 |
| 281 | 2.5 |
| 282 | >100 |
| 282 | >100 |
| 283 | >100 |
| 284 | 4 |
| 288 | 16 |
| 290 | 3 |
| 291 | >100 |
| 292 | >100 |
| 293 | >100 |
| 294 | 9 |
| 295 | 50 |
| 296 | 3.5 |
| 298 | <1 |
| 299 | >100 |
| 300 | 20 |
| 301 | 12 |
| 303 | >100 |
| 305 | >100 |
| 311 | 2 |
| 311 | 70 |
| 311 | 2.5 |
| 312 | >100 |

TABLE 14-continued

Mitogen Activated Protein Kinase (MAPK) Assay

| Example | IC$_{50}$($\mu$M) |
|---|---|
| 313 | >100 |
| 318 | 70 |
| 319 | <1 |
| 319 | <1 |
| 323 | 15 |
| 324 | 100 |
| 325 | >100 |
| 326 | 35 |
| 327 | 10 |
| 327 | 3 |
| 327 | >100 |
| 328 | >100 |
| 329 | >100 |
| 330 | >100 |
| 331 | >100 |
| 332 | 25 |
| 332 | <50 |
| 333 | 10 |
| 339 | 65 |
| 339 | 50 |
| 340 | >100 |
| 340 | >100 |
| 341 | >100 |
| 342 | >100 |
| 343 | 60 |
| 344 | >100 |
| 345 | >100 |
| 348 | >100 |
| 348 | 80 |
| 349 | >100 |
| 349 | >100 |
| 351 | 32 |
| 353 | 40 |
| 354 | >100 |
| 355 | 45 |
| 356 | >100 |
| 357 | >100 |
| 358 | 18 |
| 359 | >100 |
| 362 | >100 |
| 363 | 25 |
| 364 | >100 |
| 365 | >100 |
| 366 | <1 |
| 366 | 10 |
| 366 | 4 |
| 366 | 3 |
| 366 | 50 |
| 366 | 4 |
| 374 | <1 |
| 374 | 2 |
| 377 | >100 |
| 379 | 40 |
| 380 | >100 |
| 381 | >100 |
| 382 | >100 |
| 383 | >100 |
| 384 | >100 |
| 385 | 90 |
| 386 | >100 |
| 387 | >100 |
| 388 | 25 |
| 388 | 50 |
| 389 | >100 |
| 390 | >100 |
| 391 | >100 |
| 392 | 40 |
| 393 | 40 |
| 394 | >100 |
| 395 | 15 |
| 396 | 50 |

Based on the results obtained for representative compounds of this invention, the compounds of this invention are antineoplastic agents which are useful in treating, inhibiting the growth of, or eradicating neoplasms. In particular, the compounds of this invention are useful in treating, inhibiting the growth of, or eradicating neoplasms that express EGFR such as those of the breast, kidney, bladder, mouth, larynx, esophagus, stomach, colon, ovary, or lung. In addition, the compounds of this invention are useful in treating, inhibiting the growth of, or eradicating neoplasms of the breast that express the receptor protein produced by the erbB2 (Her2) oncogene.

The compounds of this invention may formulated neat or may be combined with one or more pharmaceutically acceptable carriers for administration. For example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solution or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 1000 mg/kg of animal body weight, optionally given in divided doses two to four times a day, or in sustained release form. For most large mammals the total daily dosage is from about 1 to 1000 mg, preferably from about 2 to 500 mg. Dosage forms suitable for internal use comprise from about 0.5 to 1000 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The compounds of this invention may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred. In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the treatment of cancer, the compounds of this invention can be administered in combination with other antitumor substances or with radiation therapy. These other substances or radiation treatments can be given at the same or at different times as the compounds of this invention. These combined therapies may effect synergy and result in improved efficacy. For example, the compounds of this invention can be used in combination with mitotic inhibitors such as taxol or vinblastine, alkylating agents such as cisplatin or cyclophosamide, antimetabolites such as 5-fluorouracil or hydroxyurea, DNA intercalators such as adriamycin or bleomycin, topoisomerase inhibitors such as etoposide or camptothecin, and antiestrogens such as tamoxifen.

The preparation of representative examples of the compounds of this invention is described below.

EXAMPLE 1

1,4-Dihydro-7-methoxy-4-oxo-3-quinolinecarbonitrile

A mixture of 30.2 g (245.2 mmol) of 3-methoxy aniline and 41.5 g (245.2 mmol) of ethyl(ethoxymethylene) cyanoacetate was heated in the absence of solvent to 140° C. for 30 minutes. To the resulting oil was added 1200 ml of Dowtherm. The solution was refluxed with stirring under nitrogen for 22 hours. The mixture was cooled to room temperature and solid was collected and washed with hexanes. The solid was recrystallized from acetic acid to give 17 g of 1,4-dihydro-7-methoxy-4-oxo-3-quinolinecarbonitrile: mass spectrum (electrospray, m/e): M+H 200.9.

EXAMPLE 2

4-Chloro-7-methoxy -3-quinolinecarbonitrile

A mixture of 4.0 g (20 mmol) of 1,4-dihydro-7-methoxy-4-oxo-3-quinolinecarbonitrile and 8.3 g (40 mmol) of phosphorous pentachloride was heated at 165° C. for 3 hours. The mixture was diluted with hexanes and the solid was collected. The solid was mixed with brine and dilute sodium hydroxide solution and extracted several times with a mixture of tetrahydrofuran and ethyl acetate. The solution was dried over magnesium sulfate and filtered through a pad of silica gel giving 3.7 g of 4-chloro-7-methoxy-3-quinolinecarbonitrile as a white solid: mass spectrum (electrospray, m/e): M+H 218.9.

EXAMPLE 3

4-[(3-Bromophenyl)amino]-7-methoxy -3-quinolinecarbonitrile

A solution of 2.97 g (13.6 mmol) of 4-chloro-7-methoxy-3-quinolinecarbonitrile and 4.67 g (27.2 mmol) of 3-bromo aniline in 76 ml of methoxyethanol was refluxed under nitrogen for 5 hours. The solution was cooled and diluted with ether. Solid was collected and washed with ether. The solid was stirred with a hot mixture of ethyl acetate and sodium bicarbonate solution. The organic layer was separated and dried over magnesium sulfate. Solvent was removed and the residue was recrystallized from a chloroform-ethyl acetate mixture giving 1.6 g of 4-[(3-bromophenyl)amino]-7-methoxy -3-quinolinecarbonitrile as a white solid: mass spectrum (electrospray, m/e): M+H 354.1, 356.1.

EXAMPLE 4

1,4-Dihydro-7-methoxy-6-nitro-4-oxo-3-quinolinecarbonitrile

To a suspension of 10 g (49.6 mmol) of 1,4-dihydro-7-methoxy-4-oxo-3-quinolinecarbonitrile in 160 ml of trifluroacetic anhydride was added 6 g (74.9 mmol) of ammonium nitrate over a period of 3 hours. The mixture was stirred an additional two hours. Excess anhydride was removed at reduced pressure at 45° C. The residue was stirred with 500 ml of water. The solid was collected and washed with water. The solid was dissolved in 1000 ml of boiling acetic acid and the solution was treated with decolorizing charcoal. The mixture was filtered and concentrated to a volume of 300 ml. Cooling gave a solid which was collected giving 5.4 g of 1,4-dihydro-7-methoxy-6-nitro-4-oxo-3-quinolinecarbonitrile as a brown solid: mass spectrum (electrospray, m/e): M+H 246.

EXAMPLE 5

4-Chloro-7-methoxy-6-nitro -3-quinolinecarbonitrile

A mixture of 5.3 g (21.6 mmol) of 1,4-dihydro-7-methoxy-6-nitro-4-oxo-3-quinolinecarbonitrile and 9 g (43.2 mmol) of phosphorous pentachloride was heated at 165° C. for 2 hours. The mixture was diluted with hexanes and the solid was collected. The solid was dissolved in 700 ml ethyl acetate and washed with cold dilute sodium hydroxide solution. The solution was dried over magnesium sulfate and filtered through a pad of silica gel giving 5.2 g of 4-chloro-7-methoxy-6-nitro-3-quinolinecarbonitrile as a tan solid.

EXAMPLE 6

4-[(3-Bromophenyl)amino]-7-methoxy-6-nitro -3-quinolinecarbonitrile

A solution of 5.2 g (19.7 mmol) of 4chloro-7-methoxy-6-nitro-3-quinolinecarbonitrile and 3.7 g (21.7 mmol) of 3-bromo aniline in 130 ml of methoxyethanol was refluxed under nitrogen for 4 hours. The reaction mixture was poured into dilute sodium bicarbonate solution. Solid was collected and washed with water and dried in air. The solid was chromatographed on silica gel eluting with chloroform-ethyl acetate 9:1. Solvent was removed from product fractions giving 1.2 g of 4-[(3-bromophenyl)amino]-7-methoxy-6-nitro-3-quinolinecarbonitrile as a yellow solid: mass spectrum (electrospray, m/e): M+H 399.0, 402.0.

EXAMPLE 7

6-Amino-4-[(3-bromophenyl)amino]-7-methoxy -3-quinolinecarbonitrile

A mixture of 2.05 g (5.1 mmol) of 4-[(3-bromophenyl) amino]-7-methoxy-6-nitro -3-quinolinecarbonitrile, 1.37 g (25.7 mmol) of ammonium chloride, and 0.86 g (15.4 mmol) of powdered iron was stirred at reflux in 26 ml water and 26 ml methanol for 2 hours. The mixture was diluted with ethyl acetate and the hot mixture was filtered. The organic layer was separated from the filtrate and dried over magnesium sulfate. The solvent was removed and the residue was chromatographed on silica gel eluting with mixtures of chloroform and ethyl acetate. Product fractions were combined to give 1.3 g of 6-amino-4-[(3-bromophenyl)amino]-7-methoxy -3-quinolinecarbonitrile as a yellow solid: mass spectrum (electrospray, m/e): M+H 369.1, 371.1.

EXAMPLE 8

N-[4-[(3-Bromophenyl)amino]-3-cyano-7-methoxy -6-quinolinyl]-2-butynamide

To a solution of 1.44 g (17.14 mmol) of 2-butynoic acid and 2.26 g (16.5 mmol) of isobutyl chloroformate in 30 ml of tetrahydrofuran at 0° C., with stirring , was added 3. 1 g (3.4 mmol) of N-methyl morpholine. This solution of the mixed anhydride was added to a stirred solution of 1.13 g (3.06 mmol) of 6-amino-4-[(3-bromophenyl)amino]-7-methoxy-3-quinolinecarbonitrile in 30 ml tetrahydrofuran in three portions over a 24 hour period. The solvent was removed. The residue was stirred with dilute sodium bicarbonate solution. Solid was collected and washed with water and ether. This was recrystallized from 1-butanol. The resulting solid was taken up in hot tetrahydrofuran and filtered through silica gel. The filtrate was concentrated and diluted with hexanes to give 0.71 g of N-[4-[(3-bromophenyl)amino]-3-cyano-7-methoxy -6-quinolinyl]-2-butynamide as a yellow powder: mass spectrum (electrospray, m/e): M+H 437.1,438.1.

EXAMPLE 9

N-[4-[(3-Bromophenyl)amino]-3-cyano-7-methoxy -6-quinolinyl]-2-propenamide

To a solution of 1.5 g (4.06 mmol) of 6-Amino-4-[(3-bromophenyl)amino]-7-methoxy-3-quinolinecarbonitrile and 0.45 ml of N-methylmorpholine in 30 ml of tetrahydrofuran was added at 0° C., under nitrogen, with stirring, 0.42 g (4.7 mmol) of acryloyl chloride of a 15 minute period. After 1 hour at 0° C., the solution was diluted with 200 ml ethyl acetate. The mixture was washed with saturated sodium bicarbonate solution and then dried over magnesium sulfate. The solvent was removed. The residue was chromatographed on silica gel eluted with chloroform-ethyl acetate mixtures to give 0.5 g of the tide compound as a light yellow solid powder: mass spectrum (electrospray, m/e): M+H 423.1,425.1

EXAMPLE 10

2-Cyano-3-(4-nitrophenylamino)acrylic Acid Ethyl Ester

4-Nitroaniline (60.0 g, 0.435 mol) and ethyl (ethoxymethylene) cyanoacetate (73.5 g, 0.435 mol) were mixed mechanically in a flask. The mixture was heated at 100° C. for 0.5 h after it had melted and resolidified. A 114 g portion of the crude product was recrystallized from dimethylformamide to give 44.2 g of yellow crystals; mp 227–228.5° C.

EXAMPLE 11

1,4-Dihydroquinoline-6-Nitro-4-oxo-3-carbonitrile

A slurry of 25.0 g (95.8 mmol) of 2-cyano-3-(4-nitrophenylamino)acrylic acid ethyl ester in 1.0 L of Dowtherm A was heated at 260° C. under N₂ for 12.5 h. The cooled reaction was poured into 1.5 L of hexane. The product was collected, washed with hexane and hot ethanol and dried in vacuo. There was obtained 18.7 g of brown solid. An analytical sample was obtained by recrystallization from dimethylformamide/-ethanol: mass spectrum (electrospray, m/e): M+H 216.

EXAMPLE 12

4-Chloro-6-nitro-3-quinolinecarbonitrile

A mixture of 31.3 g (0.147 mol) of 6-nitro-4-oxo-1,4-dihydro-3-quinolinecarbonitrile and 160 mL of phosphorous oxychloride was refluxed for 5.5 h. The phosphorous oxychloride was removed in vacuo and the residue was poured over ice and neutralized with sodium bicarbonate. The product was collected, washed with water and dried in vacuo (50° C.). There was obtained 33.5 g of tan solid; solid: mass spectrum (electrospray, m/e): M+H 234.

EXAMPLE 13

4-[(3-Bromophenyl)amino]-6-nitro-3-quinolinecarbonitrile

A mixture of 17.0 g (73.1 mmol) of 4-chloro-6-nitro-3-quinolinecarbonitrile and 15.1 g (87.7 mmol) of 3-bromoaniline in 425 mL of ethanol was refluxed for 5 h. Saturated sodium bicarbonate was added and then all volatile material was removed in vacuo. The residue was slurried with hexane and the product was collected and washed with hexane. The crude product was washed with water and dried in vacuo(60° C.). There was obtained 22.5 g of yellow solid. An analytical sample was obtained by recrystallization from ethyl acetate; mp 258–259° C.

Example 14

6-Amino-4-[(3-bromophenyl)amino]-3-quinolinecarbonitrile

A mixture of 4.00 g (10.8 mmol) of 4-[(3-bromophenyl)amino]-6-nitro-3-quinolinecarbonitrile and 12.2 g (54.2 mmol) of SnCl₂ dihydrate in 160 mL of ethanol was refluxed under N₂ for 1.3 h. After cooling to 25° C., ice water and sodium bicarbonate were added and the mixture was stirred for 2 h. Extraction with chloroform, treatment with Darco, drying (magnesium sulfate) and solvent removal gave 3.9 g of brown crystals: mass spectrum (electrospray, m/e): M+H 339.

EXAMPLE 15

N-[4-[(3-Bromophenyl)amino]-3-cyano-6-quinolinyl]-2-butynamide

Isobutyl chloroformate(0.788 g, 5.75 mmol) and N-methylmorpholine(0.581 g, 5.75 mmol) were added to an ice cold solution of 0.485 g (5.75 mmol) of 2-butynoic acid in 20 mL of tetrahydrofuran under N₂. After stirring for 10 min, a solution of 1.50 g (4.42 mmol) of 6-amino-4-[(3-bromophenyl)amino]-3-quinolinecarbonitrile in 10 mL of tetrahydrofuran was added and the mixture was stirred overnight at 25° C. A second equivalent of preformed mixed anhydride was then added. After 6 h, the reaction was poured into saturated sodium bicarbonate and brine. The product was collected and washed with hot ethyl acetate and ethanol and dried in vacuo to give 0.638 g of yellow solid; mp 283–285° C.(dec).

EXAMPLE 16

N-[4-[(3-Bromophenyl)amino]-3-cyano-6-quinolinyl]acetamide

Triethylamine (0.359 g, 3.55 mmol) and acetyl chloride (0.277 mg, 3.55 mmol) were added to an ice cold solution of 1.00 g (2.96 mmol) of 6-amino-4-[(3-bromophenyl)-amino]-3-quinolinecarbonitrile in 8 mL of methylene chloride and 6 mL of tetrahydrofuran under N₂. After stirring overnight at 25° C., volatile material was removed, and the residue was slurried with water and collected. Recrystallization from ethanol gave 0.543 g of brown solid; mp 258–261° C.(dec).

EXAMPLE 17

N-[4-[(3-Bromophenyl)amino]-3-cyano-6-quinolinyl]butynamide

Triethylamine (0.359 g, 3.55 mmol) and butyryl chloride (0.380 g, 3.55 mmol) were added to an ice cold solution of 1.00 g (2.96 mmol) of 6-amino-4-[(3-bromophenyl)amino]-3-quinolinecarbonitrile in 12 mL of tetrahydrofuran under N₂. After stirring overnight at 25° C., volatile material was removed, and the residue was slurried with water and collected. The residue was washed with boiling methanol and dried in vacuo to give 0.773 g of brown powder; mp 276–277° C.(dec).

EXAMPLE 18

N-[4-[(3-Bromophenyl)amino]-3-cyano-6-quinolinyl]-2-propenamide

Triethylamine (0.359 g, 3.55 mmol) and acryloyl chloride (0.321 g, 3.55 mmol) were added to an ice cold solution of 1.00 g (2.96 mmol) of 6-amino-4-[(3-bromophenyl)amino]-3-quinolinecarbonitrile in 12 mL of tetrahydrofuran under N₂. After stirring overnight at 25° C., volatile material was removed and the residue was slurried with water and collected. Recrystallization from ethanol gave 0.580 g of brown solid: mass spectrum (electrospray, m/e): M+H 393, 395.

EXAMPLE 19

N-[4-[(3-Bromophenyl)amino]-3-cyano-6-quinolinyl]-2-chloroacetamide

Triethylamine(0.359 g, 3.55 mmol) and chloroacetyl chloride (0.402 g, 3.55 mmol) were added to an ice cold solution of 1.00 g (2.96 mmol) of 6-amino-4-[(3 -bromophenyl)amino]-3-quinolinecarbonitrile in 12 mL of tetrahydrofuran under N₂. After stirring overnight at 25° C., volatile material was removed and the residue was slurried in water and collected. Recrystallization from methanol gave 0.540 g of tan solid: mass spectrum (electrospray, m/e): M+H 415, 417.

EXAMPLE 20

4-[(3,4-Dibromophenyl)amino]-6-nitro-3-quinolinecarbonitrile

A mixture of 6.20 g (26.6 mmol)of 4-chloro-6-nitro-3-quinolinecarbonitrile and 8.00 g (31.9 mmol) of 3,4-dibromoaniline in 160 mL of ethanol was refluxed under N₂ for 5 h. Saturated sodium bicarbonate was added and volatile material was removed. The residue was slurried with hexane, collected, washed with hexane and water and dried.

The insoluble material was repeatedly extracted with boiling ethyl acetate and the solution was then filtered through silica gel. The solvent was removed to give 3.80 g of green solid: mass spectrum (electrospray, m/e): M+H 449.

EXAMPLE 21

6-Amino-4-[(3,4-dibromophenyl)amino]-3-quinolinecarbonitrile

A mixture of 4.90 g (10.9 mmol) of 4-[(3,4-dibromophenyl)amino]-6-nitro-3-quinolinecarbonitrile and 12.4 g (54.7 mmol) of $SnCl_2$ dihydrate in 200 mL of ethanol was refluxed under $N_2$ for 1.5 h. After cooling to 25° C., the reaction was diluted with ice water, neutralized with sodium bicarbonate and stirred for 2 h. This solution was then extracted with chloroform, treated with Darco, dried (magnesium sulfate) and evaporated. After drying in vacuo (40° C.), there was obtained 1.25 g of brown solid: mass spectrum (electrospray, m/e): M+H 417, 419, 421.

EXAMPLE 22

N-[4-[(3,4-dibromophenyl)amino]-3-cyano-6-quinolinyl]-2-butynamide

Isobutyl chloroformate (0.984 g, 7.18 mmol) and N-methylmorpholine (0.725 g, 7.18 mmol) were added to an ice cold solution of 0.604 g (7.18 mmol) of 2-butynoic acid in 25 mL of tetrahydrofuran. After 10 min, a solution of 1.20 g (2.87 mmol) of 6-amino-4-[(3,4-dibromophenyl)amino]-3-quinolinecarbonitrile in 12 mL of tetrahydrofuran was added dropwise. After stirring overnight at 25° C., volatile material was removed and the residue was slurried in water and filtered. The crude product was washed with boiling EtOAC and ethanol and dried in vacuo(50° C.) to give 0.651 g of brown solid: mass spectrum (electrospray, m/e): M+H 485.

EXAMPLE 23

6-Nitro-4-[(3-trifluoromethylphenyl)amino]-3quinolinecarbonitrile

A mixture of 10.6 g (45.7 mmol) of 4-chloro-6-nitro-3-quinolinecarbonitrile and 8.82 g (54.8 mmol) of 3-(trifluoromethyl)aniline in 270 mL of ethanol was refluxed under $N_2$ for 5 h. The reaction was diluted with ethanol, neutralized with said sodium bicarbonate and evaporated. The residue was slurried with hexane, collected, washed with hexane and water and dried in vacuo(60° C.) to give 10.9 g of yellow solid. A 2.00 g sample was recrystallized from ethanol to give 1.20 g of bright yellow solid; mp 260–261° C.

EXAMPLE 24

6-Amino-4-[(3-trifluoromethylphenyl)amino]-3-quinolinecarbonitrile

A slurry of 6.00 g(16.8 mmol) of 6-nitro-4-[(3-trifluoromethylphenyl)amino]-3-quinolinecarbonitrile and 18.9 g (83.3 mmol) of $SnCl_2$ dihydrate in 240 mL of ethanol was refluxed under $N_2$ for 1 h. After cooling to 25° C., the reaction was diluted with ice water, neutralized with sodium bicarbonate and stirred for 2 h. The product was extracted with chloroform, treated with Darco, dried(magnesium sulfate) and evaporated. The residue was filtered through silica gel(10% methanol in chloroform), evaporated and dried in vacuo(40° C.) to give 4.87 g of brown solid: mass spectrum (electrospray, m/e): M+H 329.

Example 25

N-[4-[(3-Trifluoromethylphenyl)amino]-3-cyano-6-quinolinyl]-2-butynamide

Isobutyl chloroformate (1.56 g, 11.4 mmol) and N-methylmorpholine (1.15 g, 11.4 mmol) were added to an ice cold solution of 0.961 g (11.4 mmol) of 2-butynoic acid in 40 mL of tetrahydrofuran under $N_2$. After stirring for 10 min, a solution of 1.50 g (4.57 mmol) of 6-amino-4-[(3-trifluoromethylphenyl)amino]-3-quinolinecarbonitrile in 12 mL of tetrahydrofuran was added dropwise. After stirring at 25° C. overnight, volatile material was removed and the residue was slurried in water and filtered. The crude product was washed 3 times with small portions of hot ethyl acetate and then dried in vacuo (45° C.) to give 0.831 g of yellow solid: mass spectrum (electrospray, m/e): M+H 395.

EXAMPLE 26

3-Carbethoxy-4-hydroxy-6,7-dimethoxyquinoline

A mixture of 30.6 g of 4-aminoveratrole and 43.2 g of diethyl ethoxymethylenemalonate was heated at 100 for 2 h and at 165° C. for 0.75 h. The intermediate thus obtained was dissolved in 600 ml of diphenyl ether, and the resulting solution was heated at reflux temperature for 2 h, cooled, and diluted with hexane. The resulting solid was filtered, washed with hexane followed by ether, and dried to provide the tide compound as a brown solid, mp 275–285° C.

EXAMPLE 27

3-Carbethoxy-4-chloro-6,7-dimethoxylquinoline

A mixture of 28.8 g of 3-carbethoxy-4-hydroxy-6,7-dimethoxyquinoline and 16.6 ml of phosphorous oxychloride was stirred at 1 10° C. for 30 min, cooled to 0° C., and treated with a mixture of ice and ammonium hydroxide. The resulting grey solid was filtered, washed with water and ether, and dried, mp 147–150° C.

EXAMPLE 28

4-[(3-Bromophenyl)amino]-6,7-dimethoxy-3-quinolinecarboxylic Acid, Ethyl Ester

A mixture of 14.8 g of 3-carbethoxy-4-chloro-6,7-dimethoxylquinoline, 9.46 g of 3-bromoaniline, 4.05 ml of pyridine, and 150 ml of ethanol was refluxed for 30 min, evaporated to remove ethanol, and partitioned with dichloromethane-aq sodium bicarbonate. The organic layer was washed with water, dried, and concentrated. The residue was recrystallized from ethanol to give a white solid, mp 155–158° C.

EXAMPLE 29

4-[(3-Bromophenyl)amino]-6,7-dimethoxy-3-quinolinecarboxylic Acid

A mixture of 13 g of 4-[(3-bromophenyl)amino]-3-quinolinecarboxylic acid, ethyl ester, 15 ml of 10 N sodium hydroxide, and 300 ml of ethanol was refluxed for 2 h. After evaporation of most ethanol, the residue was diluted with water and acidified with sodium dihydrogen phosphate to pH 7. The resulting white solid was filtered, washed with water, and dried, mp 282–285° C.

EXAMPLE 30

4-[(3-Bromophenyl)amino]-6,7-dimethoxy-3-quinolinecarboxamide

A mixture of 4.03 g of 4-[(3-bromophenyl)amino]-6,7-dimethoxy-3-quinolinecarboxylic acid, 3.24 g of carbonyldiimiazole, and 100 ml of dimethylformamide was heated at 55 for 30 m, cooled to 0° C., and saturated with ammonia gas. After warming to 25 the resulting solution was stirred for 45 m, heated at 50, and evaporated to remove dimethylformamide. The residue was stirred with water, and the resulting solid was filtered, washed with water, and dried. Recrystallization from acetone gave a grey solid, mp 239–242° C.

EXAMPLE 31

4-[(3-Bromophenyl)amino]-6,7-dimethoxy-3-quinolinecarbonitrile

To a stirred mixture of 3.02 g of 4-[(3-bromophenyl)amino]-6,7-dimethoxy-3-quinolinecarboxamide, 2.43 ml of pyridine, and 22.5 ml of dichloromethane at 0° C. was added 3.18 ml of trifluoroacetic anhydride during 3 min. The reaction mixture was warmed to 25° C., stirred for 60 min, and concentrated. The residue was dissolved in 38 ml of methanol. The resulting solution was treated with 15 ml of 5 N NaOH at 25° C. After 5 m the solution was acidified with carbon dioxide and evaporated free of methanol. The residue was partitioned with dichloromethane-water. The organic layer was washed with water, dried, and evaporated to give a white solid. Recrystallization from ethyl acetate-hexane gave mp 224–228° C.

EXAMPLE 32

Ethyl 2-cyano-3-(3,4-dimethoxyphenylamino)acrylate

A mixture of 7.66 g of 4-aminoveratrole, 8.49 g of ethyl ethoxymethylenecyanoacetate, and 20 ml of toluene was heated at 100° C. for 90 min. The toluene was evaporated to give a solid, mp 150–155° C.

EXAMPLE 33

1,4-Dihydro-6,7-dimethoxy-4-oxo-3-quinolinecarbonitrile

A mixture of 40 g of ethyl 2-cyano-3-(3,4-dimethoxyphenylamino)acrylate and 1.2 L of Dowtherm® A was refluxed for 10 h, cooled, and diluted with hexane. The resulting solid was filtered, washed with hexane followed by dichloromethane, and dried; mp 330–350° C. (dec).

EXAMPLE 34

4-Chloro-6,7-dimethoxy-3-quinolinecarbonitrile

A stirred mixture of 20 g of 1,4-dihydro-6,7-dimethoxy-4-oxo-3-quinolinecarbonitrile and 87 ml of phosphorous oxychloride was refluxed for 2 h, cooled, and evaporated free of volatile matter. The residue was stirred at 0° C. with dichloromethane-water as solid sodium carbonate was added until the aqueous layer was pH 8. The organic layer was separated, washed with water, dried and concentrated. Recrystallization from dichloromethane gave a solid, mp 220–223° C.

EXAMPLE 35

4-[(3-Fluorophenyl)amino]-6,7-dimethoxy-3-quinolinecarbonitrile

A mixture of 1.00 g of 4-chloro-6,7-dimethoxy-3-quinolinecarbonitrile, 0.89 g of 3-fluoroaniline, 0.32 ml of pyridine, and 12 ml of ethoxyethanol was stirred at reflux temperature for 4 h. The mixture was cooled and partitioned with dichloromethane and aqueous sodium bicarbonate. The organic layer was washed with water, dried and evaporated. The residue was recrystallized from ethyl acetate to give a solid, mp 226–230° C.

EXAMPLE 36

Methyl 2-(dimethylaminomethyleneamino)benzoate

To a stirred solution of 7.56 g of methyl anthranilate in 50 ml of dimethylformamide at 0° C. was added 5.6 ml of phosphorous oxychloride during 15 m. The mixture was heated at 55 for 45 m, cooled to 0, and diluted with dichloromethane. The mixture was basified at 0° C. by slow addition of cold 1N NaOH to pH 9. The dichloromethane layer was separated, washed with water, dried and concentrated to an oil.

EXAMPLE 37

1,4-Dihydro-4oxo-3-quinolinecarbonitrile

A stirred mixture of 1.03 g of methyl 2-(dimethylaminomethyleneamino)benzoate, 0.54 g of sodium methoxide, 1.04 ml of acetonitrile, and 10 ml of toluene was refluxed for 18 h. The mixture was cooled, treated with water, and brought to pH 3 by addition of dilute HCl. The resulting solid was extracted with ethyl acetate. The extract was washed with water, dried and evaporated. The residue was recrystallized from ethanol to give a solid, mp 290–300° C.

EXAMPLE 38

4-(Cyclohexyamino)-6,7-dimethoxy-3-quinolinecarbonitrile

A solution of 1.24 g (5 mmole) of 4-chloro-6,7-dimethoxy-3-quinolinecarbonitrile 1.14 ml (0.99 g; 10 mmole) of cyclohexylamine, and 0.4 ml (0.39 g) of pyridine in 10 ml of methyl celluosolve was refluxed in an oil bath at 148° C. for 3 hours. The reaction was poured into 25 ml of saturated aqueous sodium bicarbonate, and the resulting solid was filtered. This solid was dissolved in methylene chloride, and the solution was passed through Magnesol. Hexanes were added to the filtrate, and this solution was evaporated on a hot plate until crystals formed. Cooling gave 1.54 g of 4-(cyclohexyamino)-6,7-dimethoxy-3-quinolinecarbonitrile melting at 193–195° C.: mass spectrum (electrospray, m/e): M+H 312.1.

EXAMPLE 39

4-[(3-Bromophenyl)amino]-6,7-dihydroxy-3-quinolinecarbonitrile 5.11 g of of 4-[(3-bromophenyl)amino]-6,7-dimethoxy-3-quinolinecarbonitrile and 30.74 g of pyridine hydrochloride were intimately mixed and then heated under nitrogen at 207° C. for an hour. On cooling the reaction was treated with about 100 ml of water and the solid was filtered. This solid was digested with methyl cellusolve and washed with ether to give 3.00 g of 4-[(3-bromophenyl)amino]-6,7-dihydroxy-3-quinolinecarbonitrile: mass spectrum (electrospray, m/e): M+H 356, 358.

EXAMPLE 40

8-[(3-Bromophenyl)amino]-[1,3]-dioxolo[4.5-g]quinoline-7-carbonitrile

A mixture of 2.17 g (6.09 mmole) of 4-[(3-bromophenyl)amino]-6,7-dihydroxy-3-quinolinecarbonitrile, 0.59 ml (1.18 g; 9.14 mmole) of bromochloromethane and 2.98 g (9.14 mmole) of cesium carbonate in 20 ml of N,N-dimethylformamide was heated and stirred for 2 hours in an oil bath at 111° C. The reaction was poured into 75 ml of water and extracted with four 50 ml portions of methylene chloride. The combined methylene chloride extracts were washed with several portions of water. This solution was taken to an oil in vacuo and this was dissolved in ethyl acetate. This solution was washed repeatedly with water, then with brine. The solution was dried over anhydrous magnesium sulfate, and taken to a solid in vacuo to give 0.95 g of 8-[(3-bromophenyl)amino]-[1,3]-dioxolo[4,5-g] quinoline-7-carbonitrile, m.p. 201–205° C.: mass spectrum (electrospray, m/e): M+H 368.1, 370.1.

EXAMPLE 41

4-[(3-Chlorophenyl)amino]-6.7-dimethoxy-3-quinolinecarbonitrile

A mixture of 0.5 g of 4-chloro-6,7-dimethoxy-3-quinolinecarbonitrile, 0.51 g of 3-chloroaniline, 0.16 ml of pyridine, and 6 ml of ethoxyethanol was stirred under nitrogen, at reflux temperature for 6 h. The mixture was cooled and partitioned with dichloromethane and aqueous sodium bicarbonate. The organic layer was washed with water, dried and evaporated. The residue was recrystallized from ethyl acetate-hexanes to give 0.37 g of 4-[(3-chlorophenyl)amino]-6,7-dimethoxy-3-quinolinecarbonitrile as a solid, mp 214–217° C.

EXAMPLE 42

4-[(3-Trifluoromethylphenyl)amino]-6.7-dimethoxy-3-quinolinecarbonitrile

A mixture of 1.24 g of 4-chloro-6,7-dimethoxy-3-quinolinecarbonitrile, 1.61 g of 3-trifluoromethylaniline, 0.4 ml of pyridine, and 15 ml of ethoxyethanol was stirred, under nitrogen, at reflux temperature for 5 h. The mixture was cooled and partitioned with dichloromethane and aqueous sodium bicarbonate. The organic layer was washed with water, dried and evaporated. The residue was recrystallized from ethyl acetate-hexanes to give 1.34 g of 4-[(3-trifluoromethylphenyl)amino]-6,7-dimethoxy-3-quinolinecarbonitrile as a solid, mp 190–193° C.

EXAMPLE 43

4-[(3.4-Dimethoxyphenyl)amino]-6,7-dimethoxy-3-quinolinecarbonitrile

A mixture of 1.0 g of 4-chloro-6,7-dimethoxy-3-quinolinecarbonitrile, 1.22 g of 3,4-dimethoxyaniline, 0.32 ml of pyridine, and 12 ml of ethoxyethanol was stirred, under nitrogen, at reflux temperature for 5 h. The mixture was cooled and partitioned with dichloromethane and aqueous sodium bicarbonate. The organic layer was washed with water, dried and evaporated. The residue was recrystalized from ethyl acetate to give 0.96 g of 4-[(3,4-dimethoxyphenyl)amino]-6,7-dimethoxy-3-quinolinecarbonitrile as a solid, mp 230–240° C.

EXAMPLE 44

4-[(Methylphenyl)amino]-6,7-dimethoxy-3-quinolinecarbonitrile

A mixture of 0.86 g of 4-chloro-6,7-dimethoxy-3-quinolinecarbonitrile, 0.86 g of N-methylaniline, 0.32 ml of pyridine, and 12 ml of ethoxyethanol was stirred, under nitrogen, at reflux temperature for 24 h. The mixture was cooled and partitioned with dichloromethane and aqueous sodium bicarbonate. The organic layer was washed with water, dried and evaporated. The residue was recrystallized from ethyl acetate-hexanes to give 0.54 g of 4-[(methylphenyl)amino]-6,7-dimethoxy-3-quinolinecarbonitrile as a solid, mp 137–141° C.

EXAMPLE 45

4-[(3-Cyanophenyl)amino]-6,7-dimethoxy-3-quinolinecarbonitrile

A mixture of 0.5 g of 4-chloro-6,7-dimethoxy-3-quinolinecarbonitrile, 0.47 g of 3-aminobenzonitrile, 0.16 ml of pyridine, and 12 ml of ethoxyethanol was stirred, under nitrogen, at reflux temperature for 22 h. The mixture was cooled and partitioned with dichloromethane and aqueous sodium bicarbonate. The organic layer was washed with water, dried and evaporated. The residue was recrystallized from ethyl acetate-hexanes to give 0.59 g of 4-[(3-cyanophenyl)amino]-6,7-dimethoxy-3-quinolinecarbonitrile as a solid, mp 285–288° C.

EXAMPLE 46

4-[(4-Fluorophenyl)amino]-6,7-dimethoxy-3-quinolinecarbonitrile

A mixture of 0.5 g of 4-chloro-6,7-dimethoxy-3-quinolinecarbonitrile, 0.44 g of 4-fluoroaniline, 0.16 ml of pyridine, and 6 ml of ethoxyethanol was stirred, under nitrogen, at reflux temperature for 4 h. The mixture was cooled and partitioned with dichloromethane and aqueous sodium bicarbonate. The organic layer was washed with water, dried and evaporated. The residue was recrystallized from ethyl acetate to give 0.59 g of 4-[(4-fluorophenyl) amino]-6,7-dimethoxy-3-quinolinecarbonitrile as a solid, mp 282–285° C.

EXAMPLE 47

4-[(3-Bromophenyl)amino]-6,7-diethoxy-3-quinolinecarbonitrile

A mixture of 0.36 g of 4-[(3-bromophenyl)amino]-6,7-dihydroxy-3-quinolinecarbonitrile, 0.32 ml of ethyl iodide and 0.55 g of potassium carbonate in 4 ml of dimethylsulfoxide was stirred for 3 hours in an oil bath with heating. Most of the solvent was removed at reduced pressure. The mixture was mixed with ethyl acetate and water. The organic layer was washed with water and dried over magnesium sulfate. Solvent was removed to give 0.23 g of 4-[(3-bromophenyl)amino]-6,7-diethoxy-3-quinolinecarbonitrile which after recrystallization from ethyl acetate gave mp=173–175° C.

EXAMPLE 48

4-[(3-(hydroxymethyl)phenyl)amino]-6,7-dimethoxy-3-quinolinecarbonitrile

A mixture of 1.0 g of 4-chloro-6,7-dimethoxy-3-quinolinecarbonitrile, 0.98 g of 3-aminobenzyl alcohol, 0.32 ml of pyridine, and 12 ml of ethoxyethanol was stirred, under nitrogen, at reflux temperature for 3 h. The mixture was cooled and partitioned with dichloromethane and aqueous sodium bicarbonate. The organic layer was washed with water, dried and evaporated. The residue was washed with hot methanol to give 1.16 g of 4-[(3-(hydroxymethyl) phenyl)amino]-6,7-dimethoxy-3-quinolinecarbonitrile as a solid, mp 250–255° C.

EXAMPLE 49

4-(3-Bromophenoxy)-6,7-dimethoxy-3-quinolinecarbonitrile

A mixture of 0.16 g of 88% KOH and 1.73 g of 3-bromophenol at 50° C. was treated with 0.50 g of 4-chloro-6,7-dimethoxy-3-quinolinecarbonitrile. The resulting mixture was heated to 170° C. during 30 min, cooled, and treated at 0° C. with 40 ml of 0.1N NaOH. The solid which resulted was filtered, washed with water, and dissolved in methylene chloride. The solution was washed with 0.5 N NaOH and water, dried, and concentrated. The resulting solid was recrystallized from methylene chloride-hexane to give 4-(3-bromophenoxy)-6,7-dimethoxy-3-quinolinecarbonitrile as a white solid, mp187–190° C.

EXAMPLE 50

4-[(4-Bromophenyl)sulfanyl]-6,7-dimethoxy-3-quinolinecarbonitrile

To 1.89 g of 4-bromothiophenol at 25 under argon was added 0.16 g of 88% KOH. The resulting mixture was heated at 85° C. for 15 minutes, treated with 0.50 g of 4-chloro-6,7-dimethoxy-3-quinolinecarbonitrile, and heated at 140° C. for 1 hour and 160° C. for 15 minutes. The mixture was cooled and stirred at 0° C. with 40 ml of 0.1 N NaOH. The resulting solid was filtered, washed with water, and dissolved in methylene chloride. The solution was washed with 0.2 N NaOH and water, dried, and concentrated. The residue which resulted was recrystallized from ethyl acetate to give 4-[(3-bromophenyl)sulfanyl]-6,7-dimethoxy-3-quinolinecarbonitrile as a an off-white solid, mp 173–175° C.

EXAMPLE 51

N-[4-[(3-Bromophenyl)amino]-3-cyano -6-quinolinyl]-3(E)-chloro-2-propenamide and

EXAMPLE 52

N-[4-[(3-Bromophenyl)amino]-3-cyano -6-quinolinyl]-3(Z)-chloro-2-propenamide

A mixture of 3 g (28.2 mmol) of cis-3-chloro acrylic acid and 3.3 ml (37.5 mmol) of oxalyl chloride in 30 ml of methylene chloride containing one drop of dimethylformamide was stirred for 2.5 hours. The solvent was removed to give the acid chloride as a mixture of cis and trans isomers.

To a solution of 0.5 g (1.5 mmol) of 6-amino-4[(3-bromophenyl)amino]-3-quinolinecarbonitrile and 0.24 g (1.8 mmol) of N,N-diisopropylethylamine in 5 ml tetrahydrofuran was added at 0° C., under nitrogen, with stirring, 0.21 g (1.7 mmol) of 3-chloro acryloyl chloride isomer mixture over a 4 minute period. After 40 min at 0° C., the solution was diluted with ether. The solid was collected and dissolved in a mixture of tetrahydrofuran and ethyl acetate. The mixture was washed with brine and then dried over magnesium sulfate. The solvent was removed. The residue was chromatographed on silica gel eluted with chloroform-ethyl acetate. Two products were obtained. The less polar product is N-[4-[(3-bromophenyl)amino]-3-cyano-6-quinolinyl]-3(E)-chloro-2-propenamide: mass spectrum (electrospray, m/e): M+H 424.9,427.0. The more polar product is N-[4-[(3-bromophenyl)amino]-3-cyano-6-quinolinyl]-3(Z)-chloro-2-propenamide: mass spectrum (electrospray, m/e): M+H 425.0,427.0.

EXAMPLE 53

N-[4-[(3-Bromophenyl)amino]-3-cyano-6-quinolinyl]-2-methyl-2-propenamide

To a solution of 0.5 g (1.48 mmol) of 6-amino-4-[(3-bromophenyl)amino]-3-quinolinecarbonitrile and 0.194 g (1.92 mmol) of triethylamine in 6 ml tetrahydrofuran was added at 0° C., under nitrogen, with stirring, 0.21 g (1.92 mmol) of 2-methyl acryloyl chloride over a 10 minute period. The solution was stirred at room temperature overnight. The mixture was poured into water. The solid was collected and air dried. The solid was washed with bioling ethyl acetate and air dried giving 0.32 g of N-[4-[(3-bromophenyl)amino]-3-cyano -6-quinolinyl]-2-methyl-2-propenamide : mass spectrum (electrospray, m/e): M+H 407, 409.

EXAMPLE 54

N-[4-[(3,4-Dibromophenyl)amino]-3-cyano-6-quinolinyl]-2-propenamide

To a solution of 0.75 g (1.79 mmol) of 6-amino-4-[(3,4-dibromophenyl)amino]-3-quinolinecarbonitrile and 0.22 g (2.15 mmol) of triethylamine in 10 mL of tetrahydrofuran was added dropwise 0.195 g (2.15 mmol) of acryloyl chloride. After stirring overnight at 25° C., volatile material was removed and the residue was slurried in water and solid was collected. The crude product was washed with boiling ethyl acetate dried in vacuo (50° C.) to give 0.609 g of brown solid: high resolution mass spectrum (m/e): 470.9457.

EXAMPLE 55

N-[4-[(5-bromo-3-pyridinyl)amino]-6,7-dimethoxy-3-quinolinecarbonitrile

A mixture of 249 mg (1 mmole) of 3-cyano-4-chloro-6,7-dimethoxy quinoline, 346 mg (2 mmoles) of 3-amino-5-bromo pyridine and 20 mg (about 0.1 mmole) of p-toluenesulfonic acid monohydrate in 5 ml of 2-methoxy ethanol was stirred and refluxed in an oil bath at 153° C. for 7 hours. On cooling overnight to room temperature, the solid was filtered and washed with ethanol, then with ether to give 287 mg (74.5%) of N-[4-[(5-bromo-3—pyridinyl)amino]-6,7-dimethoxy-3-quinolinecarbonitrile, which melted at 272–275° C. mass spectrum (electrospray, m/e) M+H= 384.9, 386.8.

EXAMPLE 56

4-[(3-Bromophenyl)amino]-6,7-bis (methoxymethoxy)-3-quinolinecarbonitrile

A mixture of 0.36 g of 4-[(3-bromophenyl)amino]-6,7-dihydroxy-3-quinolinecarbonitrile, 0.30 ml of 2-chloromethyl methyl ether and 0.55 g of potassium carbonate in 4 ml of dimethylformamide was stirred for 6 hours at 0° C. Most of the solvent was removed at reduced pressure. The mixture was mixed with ethyl acetate and water and the pH was adjusted to 8 with dilute hydrochloric acid. The organic layer was washed with water and dried over magnesium sulfate. Solvent was removed to give 4-[(3-bromophenyl)amino]-6,7-bis(methoxymethoxy)-3-quinolinecarbonitrile which was purified by column chromatography on silica gel.: mass spectrum (electrospray, m/e): M+H 356, 358.

EXAMPLE 57

N-[4-[(3-Bromophenyl)amino]-3-cyano-6-quinolinyl]-4-hydroxy-2-butynamide

Isobutyl chloroformate(0.214 g, 1.57 mmol) and N-methylmorpholine(0.190 g, 1.88 mmol) were added to an ice cold solution of 0.336 g (1.57 mmol) of 4(tert-butyl-dimethyl-silanyloxy)-2-butynoic acid in 15 mL of tetrahydrofuran under $N_2$. After stirring for 30 min, it was transferred to an additional funnel plugged with a glass wool and added dropwise to a solution of 0.4 g (1.18 mmol) of 6-amino-4-[(3-bromophenyl)amino]-3-quinolinecarbonitrile in 3 mL of tetrahydrofuran and 1.5 ml of pyridine. The mixture was stirred at 25° C. for 1 h. The reaction solution was poured into ethyl acetate and washed with saturated sodium bicarbonate and brine. The product was collected and purified by flash column chromatography (60% ethyl acetate in hexane) to give 0.220 g of N-[4-[(3-Bromophenyl)amino]-3-cyano-6-quinolinyl]-4-(tert-butyl-dimethyl-silanyloxy)-2-butynamide as a yellow solid (35%); ESMS m/z 535.1 (M+H$^+$); mp ° C.(dec).

N-[4-[(3-Bromophenyl)amino]-3-cyano-6-quinolinyl]-4-(tert-butyl-dimethyl-silanyloxy)-2-butynamide (0.120 g, 0.224 mmol) was dissolved in a 25 ml solution (acetic acid:tetrahydrofuran:water=3:1:1) and stirred overnight at 25° C. The reaction was poured into ethyl acetate and washed with saturated sodium bicarbonate and brine. The product was collected, washed with ethyl acetate, and dried in vacuo to give 0.085 g of yellow solid (90%); ESMS m/z 421.2 (M+H$^+$); mp 253–254° C.(dec).

EXAMPLE 58

N-[4-[(3-Bromophenyl)amino]-3-cyano-6-quinolinyl]-4-morpholino-2-butynamide

Isobutyl chloroformate(0.161 g, 1.18 mmol) and N-methylmorpholine(0.150 g, 1.48 mmol) were added to an ice cold solution of 0.250 g (1.48 mmol) of 4-morpholino-2-butynoic acid in 10 mL of tetrahydrofuran under $N_2$. After stirring for 30 min, a solution of 0.250 g (0.74 mmol) of 6-amino-4-[(3-bromophenyl)amino]-3-quinolinecarbonitrile in 8 mL of pyridine was added and the mixture was stirred at 0° C. for 2 h. The reaction was quenched with ice water and then poured into saturated sodium bicarbonate and brine. The product was collected, washed with ethyl acetate, and dried in vacuo to give 0.096 g (27%) of yellow solid; ESMS m/z 490.1 (M+H$^+$); mp 112–115° C.

EXAMPLE 59

N-[4-[(3-Bromophenyl)amino]-3-cyano-6-quinolinyl]-4-dimethylamino-2-butynamide Isobutyl chloroformate(0.260 g, 1.91 mmol) and N-methylmorpholine(0.594 g, 5.88 mmol) were added to an ice cold solution of 0.370 g (2.94 mmol) of 4-dimethylamino-2-butynoic acid in 50 mL of tetrahydrofuran under $N_2$. After stirring for 30 min, a solution of 0.500 g (01.47 mmol) of 6-amino-4-[(3-bromophenyl)amino]-3-quinolinecarbonitrile in 10 mL of pyridine was added and the mixture was stirred at 0° C. for 2 h. The reaction was quenched with ice water, and then poured into saturated sodium bicarbonate and brine. The product was collected, washed with ethyl acetate, and dried in vacuo to give 0.144 g (21%) of yellow solid; ESMS m/z 448.0 (M+H$^+$); mp 114–118° C.

EXAMPLE 60

N-[4-[(3-Bromophenyl)amino]-3-cyano-6-quinolinyl]-4-methoxy-2-butynamide

Isobutyl chloroformate(0.410 g, 3.0 mmol) and N-methylmorpholine(0.910 g, 9.0 mmol) were added to an ice cold solution of 0.680 g (6.0 mmol) of 4-methoxy-2-butynoic acid in 20 mL of tetrahydrofuran under $N_2$. After stirring for 30 min, a solution of 0.500 g (01.47 mmol) of 6-amino-4-[(3-bromophenyl)amino]-3-quinolinecarbonitrile in 10 mL of pyridine was added and the mixture was stirred at 0° C. for 2 h. The reaction was quenched with ice water, and then poured into saturated sodium bicarbonate and brine. The product was collected, washed with ethyl acetate, and dried in vacuo to give 0.200 g (35%) of yellow solid; ESMS m/z 435.1 (M+H$^+$); mp 198–202° C.(dec).

EXAMPLE 61

4-(3-Bromophenylmethylamino)-6,7-diethoxy-3-quinolinecarbonitrile

A stirred mixture of 4-chloro-6,7-diethoxy-3-quinolinecarbonitrile (0.69 g, 2.5 mmol), 3-bromobenzylamine (0.78 g, 3.5 mmol), diisopropylethyl amine (1.05 ml, 6.0 mmol), and 7.5 ml of ethoxyethanol was refluxed for 4 h, cooled, and stirred with a mixture of hexane and water containing 0.4 g of potassium carbonate for 3 h. The resulting solid was filtered, washed with water, and dried. Recrystallization from acetone-hexane gave 0.73 g of off-white solid, mp 156–159° C.

EXAMPLE 62

4(3-Phenylmethylamino)-6,7-diethoxy-3-quinolinecarbonitrile

In the manner of Example 61 reaction of 4-chloro-6,7-diethoxy-3-quinolinecarbonitrile with benzylamine gave the title compound as an off-white solid, mp 150–153° C.

EXAMPLE 63

4-(3,4-Dimethoxyphenylmethylamino)-6,7-diethoxy-3quinolinecarbonitrile

In the manner of Example 61 reaction of 4-chloro-6,7-diethoxy-3-quinolinecarbonitrile with 3,4-dimethoxybenzylamine gave the title compound as a tan solid, mp 200–204° C.

EXAMPLE 64

4-(3,4-Dichlorophenylmethylamino)-6,7-diethoxy-3-quinolinecarbonitrile

In the manner of Example 61 reaction of 4-chloro-6,7-diethoxy-3-quinolinecarbonitrile with 3,4-dichlorobenzylamine gave the tide compound as a tan solid, mp 163–165° C.

EXAMPLE 65

4-Methoxy-but-2-enoic acid [4-(3-bromo-phenylamino)-3-cyano-quinolin-6-yl]-amide To a solution of 1.0 g (2.95 mmol) of of 6-amino-4-[(3-bromophenyl)amino]-3-quinolinecarbonitrile and 0.57 g (4.42 mmol) of diisopropylethyl amine at 0° C. with stirring was added 0.43 g (3.24 mmol) of 4-methoxycrotonyl chloride. After 1.5 hr at 0° C., the mixture was poured into a saturated solution of sodium bicarbonate and then extracted with ethyl acetate. The organic solution was dried over magnesium sulfate and the sovent was removed. The residue was recrystallized from 1-butanol giving 1.3 g of 4-Methoxy-but-2-enoic acid [4-(3-bromo-phenylamino)-3-cyano-quinolin-6-yl]-amide as a yellow solid: mass spectrum (electrospray, m/e,): M+H 436.4, 438.9.

EXAMPLE 66

4-(3-Chloro-propoxy)-5-methoxy -benzoic acid methyl ester

A mixture of 102.4 g (411.7 mmol) of 3-chloropropyl p-toluene sulfonate, 75 g (411.7 mmol) of 4-hydroxy-5-methoxy -benzoic acid methyl ester, 75.7 g (547.5 mmol) of potassium carbonate, and 1.66 g (4.1 mmol) of methyl-tricapryl ammonium chloride in 900 ml of acetone was stirred rapidly at reflux for 18 hr. The mixture was filtered and the solvent was removed giving 106 g of the tile compound after recrystallization from a chloroform-hexane mixture.

EXAMPLE 67

4-(2-Chloro-ethoxy)-5-methoxy -benzoic acid methyl ester

By using an identical method as above 77 g of 4-hydroxy-5-methoxy-benzoic acid methyl ester, 99.2 g of 2-chloroethyl p-toluene sulfonate, 77.7 g of potassium carbonate, and 1.7 g (4.1 mmol) of methyl-tricapryl ammonium chloride was converted to 91.6 g of the tide compound: mass spectrum (electrospray, m/e,): M+H 245.0

EXAMPLE 68

4-(3-Chloro-propoxy)-5-methoxy-2-nitro-benzoic acid methyl ester

To a solution of 100 g (386.5 mmol) 4(3-chloro-propoxy)-5-methoxy -benzoic acid methyl ester in 300 ml acetic acid was added dropwise 100 ml of 70% nitric acid. The mixture was heated to 50° C. for 1 hr and then poured into ice water. The mixture was extracted with chloroform. The organic solution was washed with dilute sodium hydroxide and then dried over magnesium sulfate. The solvent was removed. Ether was added an the mixture was stirred until solid was deposited. The solid was collected by filtration giving 98 g of 4-(3-Chloro-propoxy)-5-methoxy-2-nitro-benzoic acid methyl ester as white crystals: mass spectrum (electrospray, m/e,): M+H 303.8; 2M+NH$_4$ 623.9.

EXAMPLE 69

4-(2-Chloro-ethoxy)-5-methoxy-2-nitro-benzoic acid methyl ester

By using an identical method as above 85 g of 4-(2-Chloro-ethoxy)-5-methoxy-benzoic acid methyl ester was nitrated to give 72 g of the title compound: mass spectrum (electrospray, m/e,): 2M+NH$_4$ 595.89

EXAMPLE 70

2-Amino-4-(3-chloro-propoxy)-5-methoxy-benzoic acid methyl ester

A mixture of 91 g (299.6 mmol) of 4-(3-chloro-propoxy)-5-methoxy-2-nitro-benzoic acid methyl ester and 55.2 g (988.8 mmol) of iron was mechanically stirred at reflux in a mixture containing 60.1 g ammonium chloride, 500 ml water, and 1300 ml methanol for 5.5 hr. The mixture was concentrated and mixed with ethyl acetate. The organic solution was washed with water and saturated sodium bicarbonate. The solution was dried over magnesium sulfate and filtered through a short column of silica gel. The solvent was removed and the residue mixed with 300 ml of ether-hexane 2:1. After standing 73.9 g of the title compound was obtained as a pink solid: mass spectrum (electrospray, m/e): 2M−HCl+H 511.0; M+H 273.8

EXAMPLE 71

2-Amino-4-(2-chloro-ethoxy)-5-methoxy-benzoic acid methyl ester

A mixture of 68.2 g (235.4 mmol) of 4-(2-chloro-ethoxy)-5-methoxy-2-nitro-benzoic acid methyl ester and 52.6 g (941.8 mmol) of iron was mechanically stirred at reflux in a mixture containing 62.9 g ammonium chloride, 393 ml water, and 1021 ml methanol for 15 hr. The mixture was concentrated and mixed with ethyl acetate. The organic solution was washed with water and saturated sodium bicarbonate. The solution was dried over magnesium sulfate and filtered through a short column of silica gel. The solution was concentrated to 200 ml and diluted with 250 of hot hexane. After standing 47.7 g of the tide compound was obtained as a solid: mass spectrum (electrospray, m/e) M+H 259.8.

EXAMPLE 72

7-(2-Chloro-ethoxy)-4-hydroxy-6-methoxy-quinoline-3-carbonitrile

A mixture of 25 g (96.3 mmol) of 2-amino-4-(2-chloro-ethoxy)-5-methoxy-benzoic acid methyl ester and 17.2 g (144.4 mmol) of dimethyformamide dimethyacetal was heated to reflux for 1.5 hr. Excess reagents were removed at reduced pressure leaving 30.3 g of a residue which was dissolved in 350 ml of tetrahydrofuran. In a separate flask, to a stirred solution of 80.9 ml of 2.5M n-butyl lithium in hexane in 300 ml of tetrahydrofuran at −78° C. was added dropwise 8.3 g (202.1 mmol) of acetonitrile over 40 min. After 30 min, the above solution of amidine was added dropwise over 45 min at −78° C. After 1 hr, 27.5 ml of acetic acid was added and the mixture was allow to warm to room temperature. The solvent was removed and water was added. Solid was collected by filtration and washed with water and ether. After drying in vacumn, 18.5 g of the tide compound was obtained as a tan powder: mass spectrum (electrospray, m/e) M+H 278.8.

EXAMPLE 73

7-(3-Chloro-propoxy)-4-hydroxy-6-methoxy-quinoline-3-carbonitrile

By using the above method, starting with 6.01 g of the corresponding amidine, 1.58 g of acetonitrile, and 15.35 ml of n-butyl lithium solution, 3.7 g of the tide compound was obtained as a tan powder: mass spectrum (electrospray, m/e) M+H 292.8; 2M+H 584.2

EXAMPLE 74

7-(3-Chloro-propoxy)-4-chloro-6-methoxy-quinoline-3-carbonitrile

A mixture of 3.5 g (12 mmol) of 7-(3-chloro-propoxy)-4-hydroxy-6-methoxy-quinoline-3-carbonitrile and 28 ml of phosphorous oxychloride was refluxed for 1.5 hr. Excess reagent was removed at reduced pressure. The residue was mixed with ice cold dilute sodium hydroxide and ethyl acetate. The mixture was extracted with a combination of ethyl acetate and tetrahydrofuran. The combined extracts were washed with a saturated solution of sodium bicarbonate, dried over magnesium sulfate, and filter through a short column of silica gel. Solvents were removed giving 3.2 g of the title compound as a pink solid that is used with additional purification.

EXAMPLE 75

7-(3-Chloro-ethoxy)-4-chloro-6-methoxy-quinoline-3-carbonitrile

A solution of 8 g (28.7 mmol) of 7-(3-chloro-ethoxy)-4-hydroxy-6-methoxy-quinoline-3-carbonitrile and 18.2 g (143.5 mmol) of oxalyl chloride in 80 ml of methylene chloride containing 0.26 g of dimethylformamide was stirred at reflux for 2.5 hr. The solvent was removed. The residue was mixed with cold dilute sodium hydroxide and extracted several time with ethyl acetate and tetrahydrofuran. The combined extracts were dried over magnesium sulfate and the solution was passed through a short silica gel column. The solvents were removed giving 6.0 g of the title compound as an off-white solid that is used without additional purification.

EXAMPLE 76

4-(4-Chloro-2-fluoro-phenylamino)-7-(3-chloro-propoxy)-6-methoxy-quinoline-3-carbonitrile A mixture of 3.1 g (9.96 mmol) of 7-(3-Chloro-propoxy)-4-chloro-6-methoxy-quinoline-3-carbonitrile, 1.6 g (10.96 mmol) of 4-chloro-2-fluoro-aniline, and 1.2 g (10 mmol) of pyridine hydrochloride in 31 ml of 2-ethoxyethanol was stirred at reflux for 1.5 hr. The mixture was poured into saturated sodium bicarbonate solution and extracted with ethyl acetate. The organic solution was dried and solvent was removed. The residue was purified on a silica gel column eluting with chloroform-ether mixtures to give 2.88 g of the title compound as an off-white solid powder: mass spectrum (electrospray, m/e) M+H 419.7.

EXAMPLE 77

7-(2-Chloro-ethoxy)-4-(3-hydroxy-4-methyl-phenylamino)-6-methoxy-quinoline-3-carbonitrile By using the above method, starting with 3 g of 7-(2-chloro-ethoxy)-4-chloro-6-methoxy-quinoline-3-carbonitrile, 1.37 g of 3-hydroxy-4-methyl-aniline, and 1.2 g of pyridine hydrochloride in 31 ml of 2-ethoxyethanol, 2.6 g of the title compound was obtained as a crystalline solid: mass spectrum (electrospray, m/e) M+H 383.9.

EXAMPLE 78

4-(4-Chloro-2-fluoro-5-hydroxy-phenylamino)-7-(3-chloro-propoxy)-6-methoxy-quinoline-3-carbonitrile By using the above method, starting with 3 g of 7-(3-chloro-propoxy)-4-chloro-6-methoxy-quinoline-3-carbonitrile, 2.35 g of the methyl carbonate of 4chloro-2-fluoro-5-hydroxy-aniline, and 1.1 g of pyridine hydrochloride in 30 ml of 2-ethoxyethanol, 1.7 g of the title compound was obtained as a crystalline solid: mass spectrum (electrospray, m/e) M+H 435.8, 437.8.

EXAMPLE 79

4-(4-Chloro-2-fluoro-5-hydroxy-phenylamino)-7-(2-chloro-ethoxy)-6-methoxy-quinoline-3-carbonitrile By using the above method, starting with 3 g of 7-(2-chloro-ethoxy)-4-chloro-6-methoxy-quinoline-3-carbonitrile, 2.46 g of the methyl carbonate of 4-chloro-2-fluoro-5-hydroxy-aniline, and 1.18 g of pyridine hydrochloride in 31 ml of 2-ethoxyethanol, 2.2 g of the title compound was obtained as a tan solid: mass spectrum (electrospray, m/e) M+H 421.9.

EXAMPLE 80

4-(4-Chloro-2-fluoro-phenylamino)-7-(3-dimethylamino-propoxy)-6-methoxy-quinoline-3-carbonitrile A mixture of 1 g (2.38 mmol) of 4-(4-Chloro-2-fluoro-phenylamino)-7-(3-chloro-propoxy)-6-methoxy-quinoline-3-carbonitrile and 0.07 g of sodium iodide in 17.85 ml of 2M dimethylamine in tetrahydrofuran was placed in a sealed tube and heated to 125° C. for 3.5 hr. The solvent was removed and the residue was mixed with warm ethyl acetate and saturated sodium bicarbonate solution. The organic layer was separated and dried over magnesium sulfate. Solvent was removed and ether was added. One standing, the crystals were deposited giving 0.93 g of the tide compound as a white solid: mass spectrum (electrospray, m/e) M+H 428.9.

EXAMPLE 81

4-(4-Chloro-2-fluoro-phenylamino)-6-methoxy-7-(3-morpholin-4-yl-propoxy)-quinoline-3-carbonitrile A mixture of 1 g (2.38 mmol) of 4-(4-Chloro-2-fluoro-phenylamino)-7-(3-chloro-propoxy)-6-methoxy-quinoline-3-carbonitrile, 3.1 g (35.7 mmol) of morpholine, and 0.07 g of sodium iodide in 20 ml ethylene glycol dimethyl ether refluxed for 7 hr. The solvent was removed and the residue was mixed with warm ethyl acetate and saturated sodium bicarbonate solution. The organic layer was separated and dried over magnesium sulfate. Solvent was removed and ether-hexane was added. One standing, the crystals were deposited giving 1.1 g of the title compound as a off-white solid: mass spectrum (electrospray, m/e) M+H 470.9.

EXAMPLE 82

7-(2-Dimethylamino-ethoxy)-4-(3-hydroxy-4-methyl-phenylamino)-6-methoxy-quinoline-3-carbonitrile A mixture of 1 g (2.38 mmol) of 7-(2-chloro-ethoxy)-4-(3-hydroxy-4-methyl-phenylamino)-6-methoxy-quinoline-3-carbonitrile and 0.078 g of sodium iodide in 19.5 ml of 2M dimethylamine in tetrahydrofuran was placed in a sealed tube and heated to 125° C. for 14 hr. The solvent was removed and the residue was mixed with warm ethyl acetate and saturated sodium bicarbonate solution. The organic layer was separated and dried over magnesium sulfate. Solvent was removed and the residue was chromatographed on silica gel eluting with ethyl acetate-methanol-triethylamine 70:30:2.5 giving 0.89 g of the tide compound as a light yellow solid: mass spectrum (electrospray, m/e) M+H 393.0; (M+2H)$^{+2}$ 196.9.

EXAMPLE 83

4-(3-Hydroxy-4-methyl-phenylamino)-6-methoxy-7-(2-morpholin-4-yl-ethoxy)-quinoline-3-carbonitrile A mixture of 1 g (2.38 mmol) of 7-(2-chloro-ethoxy)-4-(3-hydroxy-4-methyl-phenylamino)-6-methoxy-quinoline-3-carbonitrile, 3.4 g (39 mmol) of morpholine, and 0.08 g of sodium iodide in 22 ml ethylene glycol dimethyl ether refluxed for 34 hr. The solvent was removed and the residue was mixed with warm ethyl acetate and saturated sodium bicarbonate solution. The organic layer was separated and dried over magnesium sulfate. Solvent was removed and the residue was chromatographed on silica gel eluting with ethyl acetate-methanol-triethylamine 70:30:2.5 giving 1.05 of the title compound as a light orange solid: mass spectrum (electrospray, m/e) M+H 435.0; (M+2H)$^{+2}$ 218.0.

EXAMPLE 84

4-(4-Chloro-2-fluoro-5-hydroxy-phenylamino)-7-(3-dimethylamino-propoxy)-6-methoxy-quinoline-3-carbonitrile A mixture of 0.8 g (1.83 mmol) of 4-(4-chloro-2-fluoro-5-hydroxy-phenylamino)-7-(3-chloro-propoxy)-6-methoxy-quinoline-3-carbonitrile and 0.055 g of sodium iodide in 15.6 ml of 2M dimethylamine in tetrahydrofuran was placed in a sealed tube and heated to 125° C. for 2.5 hr. The solvent was removed and the residue was mixed with warm ethyl acetate and saturated sodium bicarbonate solution. The organic layer was separated and dried over magnesium sulfate. Solvent was removed and the residue was treated with with ethyl acetate-ether depositing a solid and giving 0.51 g of the title compound as a off-white solid: mass spectrum (electrospray, m/e) M+H 445.0; (M+2H)$^{+2}$ 243.4.

EXAMPLE 85

4-(4-Chloro-2-fluoro-5-hydroxy-phenylamino)-6-methoxy-7-(3-morpholin-4yl-propoxy)-quinoline-3-carbonitrile A mixture of 0.8 g (1.83 mmol) of 4-(4-chloro-2-fluoro-5-hydroxy-phenylamino)-7-(3-chloro-propoxy)-6-methoxy-quinoline-3-carbonitrile, 2.4 g (27.5 mmol) of morpholine, and 0.11 g of sodium iodide in 15 ml ethylene glycol dimethyl ether refluxed for 7 hr. The solvent was removed and the residue was mixed with warm ethyl acetate and saturated sodium bicarbonate solution. The organic layer was separated and dried over magnesium sulfate. Solvent was removed and the residue was recrystallized from ethyl acetate-carbon tetrachloride giving 0.63 of the title compound as a light tan solid: mass spectrum (electrospray, m/e) M+H 487.0; (M+2H)hu +2 243.9.

EXAMPLE 86

4-(4-Chloro-2-fluoro-5-hydroxy-phenylamino)-7-(2-dimethylamino-ethoxy)-6-methoxy-quinoline-3-carbonitrile A mixture of 0.8 g (1.83 mmol) of 4-(4-chloro-2-fluoro-5-hydroxy-phenylamino)-7-(2-chloro-ethoxy)-6-methoxy-quinoline-3-carbonitrile and 0.11 g of sodium iodide in 16.1 ml of 2M dimethylamine in tetrahydrofuran was placed in a sealed tube and heated to 135° C. for 14 hr. The solvent was removed and the residue was mixed with warm ethyl acetate and saturated sodium bicarbonate solution. The organic layer was separated and dried over magnesium sulfate. Solvent was removed and the residue was chromatographed on silica gel eluting with ethyl acetate-methanol-triethylamine 60:40:3 giving 0.41 g of the title compound as a tan solid: mass spectrum (electrospray, m/e) M+H 430.9; (M+2H)$^{+2}$ 216.0.

EXAMPLE 87

4-(4-Chloro-2-fluoro-5-hydroxy-phenylamino)-6-methoxy-7-(2-morpholin-4-yl-ethoxy)-quinoline-3-carbonitrile A mixture of 0.8 g (1.83 mmol) of 4-(4-chloro-2-fluoro-5-hydroxy-phenylamino)-7-(2-chloro-ethoxy)-6-methoxy-quinoline-3-carbonitrile, 2.4 g (27.5 mmol) of morpholine, and 0.11 g of sodium iodide in 15 ml ethylene glycol dimethyl ether heated in a sealed tube at 135° C. for 12 hr. The solvent was removed and the residue was mixed with warm ethyl acetate and saturated sodium bicarbonate solution. The organic layer was separated and dried over magnesium sulfate. Solvent was removed and the residue was chromatographed on silica gel eluting with ethyl acetate-methanol-triethylamine 70:30:1 giving 0.43 g of the title compound as a tan solid: mass spectrum (electrospray, m/e) M+H 470.0; (M+2H)$^{+2}$ 237.0.

EXAMPLE 88

N-[3-Cyano-4-(3-fluorophenylamino)quinolin-6-yl]acrylamide

A solution of 1.00 g (3.60 mmol) of 6-amino-4-(3-fluorophenylamino)quinoline-3-carbonitrile in 12 mL of THF under N$_2$ was chilled in ice. Triethylamine (0.436 g, 4.32 mmol) was added followed by 0.393 g (4.32 mmol) of acryloyl chloride and the reaction was stirred at 25° C. overnight. The solvent was removed and the residue was slurried with water and filtered. The crude product was washed with water, dried, washed with hot ethyl acetate and dried in vacuo (50° C.). This yielded 0.862 g of N-[3-cyano-4-(3-fluorophenylamino)quinolin-6-yl]acrylamide as a brown solid: mass spectrum (electrospray, m/e): M+H 333.1.

EXAMPLE 89

6,7-Dimethoxy-4-(3-nitrophenylamino)quinoline-3-carbonitrile

A solution of 0.500 g (2.00 mmol) of 4-chloro-6,7-dimethoxy-3-quinolinecarbonitrile and 0.332 g (2.41 mmol) of 3-nitroaniline in 6 mL of methyl cellosolve was refluxed under N$_2$ for 8 hr. Methanol was added, followed by satd NaHCO$_3$ (pH 8) and volatile material was removed. The residue was slurried with water, collected by filtration and dried. Recrystallization from ethanol gave 0.480 g of 6,7-dimethoxy-4-(3-nitrophenylamino)quinoline-3-carbonitrile as yellow crystals: mass spectrum (electrospray, m/e): M+H 351.0.

EXAMPLE 90

4(3-Bromophenylamino)-6-ethoxy-7-methoxyquinoline-3-carbonitrile

A mixture of 1.00 g (3.82 mmol) of 4-chloro-6-ethoxy-7-methoxyquinoline-3-carbonitrile and 0.788 g (4.58 mmol)

of 3-bromoaniline in 20 mL of ethanol was refluxed under $N_2$ for 7 h. Saturated $NaHCO_3$ was added, volatile material was removed and the residue was azeotroped with ethanol. The crude product was slurried with hexane, filtered, washed with water and dried. Recrystallization from ethanol gave 1.31 g of 4(3-bromophenylamino)-6-ethoxy-7-methoxyquinoline-3-carbonitrile as tan crystals: mass spectrum (electrospray, m/e): M+H 397.9, 399.8.

EXAMPLE 91

4-Chloro-6-ethoxy-7-methoxyquinoline-3-carbonitrile

A mixture of 7.95 g (32.6 mmol) of 6-ethoxy-7-methoxy-4-oxo-1,4-dihydroquinoline-3-carbonitrile and 50 mL of phosphorous oxychloride was refluxed for 3 h 40 min. The phosphorous oxychloride was removed in vacuo and the residue was slurried with ice water. Solid $NaHCO_3$ was added (pH8) and the product was collected by filtration, washed well with water and dried in vacuo (40° C.). The yield was 7.75 g of 4-chloro-6-ethoxy-7-methoxyquinoline-3-carbonitrile as a tan solid: mass spectrum (electrospray, m/e): M+H 262.8, 264.8.

EXAMPLE 92

6-Ethoxy-7-methoxy-4-oxo-1,4-dihydroquinoline-3-carbonitrile

A solution of 10.2 g (45.3 mmol) of methyl 2-amino-5-ethoxy-4-methoxy benzoate and 10.8 g (90.7 mmol) of dimethylformamide dimethyl acetal in 50 mL of dimethylformamide was refluxed for 3 h. Volatile material was removed and the residue was azeotroped with toluene and dried in vacuo to give the formamidine as a purple syrup. n-Butyllithium (100 mmol) in hexane was diluted with 60 mL of tetrahydrofuran at −78° C. A solution of 4.18 g (102 mmol) of acetonitrile in 80 mL of tetrahydrofuran was added over 15 min and the solution was stirred for 20 min. The crude formamidine was dissolved in 80 mL of tetrahydrofuran and added dropwise to the cold solution over 0.5 h. After stirring for 2 h, the reaction was quenched at −78° C. with 13 mL of acetic acid. It was allowed to warm to room temperature and volatile material was removed in vacuo. The residue was slurried with water and the crude product was collected by filtration washed with water and dried. This material was then washed with chloroform and dried to give 7.95 g of 6-ethoxy-7-methoxy-4-oxo-1,4-dihydroquinoline-3-carbonitrile as yellow crystals: mass spectrum (electrospray, m/e): M−H 243.2.

EXAMPLE 93

Methyl 2-Amino-5-ethoxy-4-methoxybenzoate

Mixture of 17.0 g (66.7 mmol) of methyl 5-ethoxy-4-methoxy-2-nitrobenzoate, 13.1 g (233 mmol) of powdered iron and 17.7 g (334 mmol) of ammonium chloride in 95 mL of water and 245 mL of methanol was refluxed for 4.5 h. An additional 13.1 g of iron was added followed by refluxing for 2.5 h. Then an additional 13.1 g of iron and 17.7 g of ammonium chloride was added and refluxing was continued for 12 h. The reaction was filtered through Celite and methanol was removed from the filtrate. The filtrate was extracted with chloroform and the extracts were treated with Darco, evaporated and dried in vacuo (50° C.).The yield was 11.0 g of methyl 2-amino-5-ethoxy-4-methoxybenzoate as tan crystals: mass spectrum (electrospray, m/e): M+H 225.9.

EXAMPLE 94

Methyl 5-Ethoxy-4-methoxy-2-nitrobenzoate

A mixture of 15.0 g (74.1 mmol) of methyl 3-ethoxy-4-methoxybenzoate in 45 mL of acetic acid was treated with 15 mL of conc nitric acid dropwise over 12 min. The reaction was kept at 55° C. for 45 min, cooled to 25° C. and poured into ice water. The product was extracted into methylene chloride and the extracts were washed with water and $\mu$l sodium hydroxide, dried and evaporated. The yield was 17.8 g of methyl 5-ethoxy-4-methoxy-2-nitrobenzoate as yellow crystals: mass spectrum (electrospray, m/e): M+H 256.0.

EXAMPLE 95

Methyl 3-Ethoxy-4-methoxybenzoate

A mixture of 24.3 g (134 mmol) of methyl 3-hydroxy-4-methoxybenzoate, 36.8 g (267 mmol) of anhyd potassium carbonate and 31.4 g (201 mmol) of ethyl iodide in 500 mL of dimethylformamide was stirred at 100° C. for 5.5 h. An additional amount of ethyl iodide (31.4 g) and potassium carbonate (18.4 g) was added and heating was continued for 2 h more. The reaction was filtered and volatile material was removed from the filtrate in vacuo. The residue was slurried with water and filtered to collect the product which was washed with water and dried. Recrystallization from heptane gave 15.6 g of methyl 3-ethoxy-4-methoxybenzoate as white crystals: mass spectrum (electrospray, m/e): M+H 210.9.

EXAMPLE 96

Methyl 3-Hydroxy-4-methoxybenzoate

A solution of 30.8 g (183 mmol) of 3-hydroxy-4-methoxybenzoic acid and 6 mL of conc sulfuric acid in 600 mL of methanol was refluxed overnight. Most of the solvent was removed and the remaining solution was poured into 600 mL of water containing 25 g of sodium bicarbonate. The product was extracted into ether, treated with Darco, dried and evaporated. The yield was 31.8 g of methyl 3-hydroxy-4-methoxybenzoate as pale yellow crystals.

EXAMPLE 97

6-Ethoxy-4-(3-hydroxy-4-methylphenylamino)-7-methoxyquinoline-3-carbonitrile

A mixture of 1.00 g (3.82 mmol) of 4-chloro-6-ethoxy-7-methoxyquinoline-3-carbonitrile and 0.563 g (4.58 mmol) of 3-hydroxy-4-methylaniline in 20 mL of ethanol was refluxed under $N_2$ for 8 h. Saturated $NaHCO_3$ was added, volatile material was removed and the residue was azeotroped with ethanol. The crude product was slurried with hexane, filtered, washed with water and cold ethanol and dried. Recrystallization from ethanol gave 0.632 g of 6-ethoxy-4-(3-hydroxy-4-methylphenylamino)-7-methoxyquinoline-3-carbonitrile as light yellow crystals: mass spectrum (electrospray, m/e): M+H 349.9.

EXAMPLE 98

4-Bromo-but-2-enoic acid [4-(3-bromo-phenylamino)-3-cyano-quinolin-6-yl]-amide

A solution of 1.65 grams (0.01 mole) of 4-bromo crotonic acid (Giza Braun, J. Am. Chem. Soc. 52, 3167 1930) in 15 ml of dichloromethane was treated with 1.74 ml (0.02 moles) of oxalyl chloride and 1 drop of N,N-dimethylformamide. After an hour the solvents were removed on the rotary evaporator. The residual oil was taken up in ml of tetrahydrofuran, and 3.39 grams of 6-Amino-4-(3-bromo-phenylamino)-quinoline-3-carbonitrile in 25 ml of tetrahydrofuran was added dropwise. This was followed by the dropwise addition of 1.92 ml (0.011 moles) of diisopropylethylamine. After the addition of 25 ml of water and 50 ml of ethyl acetate, the layers were separated. The organic layer was dried over anhydrous sodium sulfate, and taken to a solid in vacuo. This solid was digested for an hour with refluxing ethyl acetate then filtered from the ethyl acetate while still hot. Thus was obtained 3.31 grams (68%) of 4-bromo-but-2-enoic acid [4-(3-bromo-phenylamino)-3-cyano-quinolin-6-yl]-amide.

EXAMPLE 99

4-Dimethylamino-but-2-enoic acid [4-(3-bromo-phenylamino)-3-cyano-quinolin-6-yl]-amide Fifteen milliters of a 2 molar solution of dimethylamine in tetrahydrofuran was cooled in an ice bath and a solution of 729 mg (1.5 mmoles) of 4-bromo-but-2-enoic acid [4-(3-bromo-phenylamino)-3-cyano-quinolin-6-yl]-amide in 5 ml of N,N-dimethylformamide was added dropwise. Stirring and cooling were continued for 2 hours. Then 25 ml of water and 15 ml of ethyl acetate were added. The layers were separated and the organic layer was extracted with an addition 25 ml of water. The combined aqueous layers were extracted with 2–25 ml portions of 1:1 tetrahydrofuran-ethyl acetate. The combined organic layers were absorbed onto silica gel and chromatographed on silica gel. The column was eluted with a gradient of 1:19 to 1:4 methanol-methylene chloride. Obtained was 381 mg (56%) of 4-Dimethylamino-but-2-enoic acid [4-(3-bromo-phenylamino)-3-cyano-quinolin-6-yl]-amide which melted at 209–211 deg.: mass spectrum (electrospray, m/e): M+H 225.5, 226.2.

EXAMPLE 100

4-Diethylamino-but-2-enoic acid [4-(3-bromo-phenylamino)-3-cyano-quinolin-6-yl]-amide A solution of 3.15 ml (30 mmoles) of diethylamine in 15 ml of tetrahydrofuran was cooled in an ice bath and a solution of 729 mg (1.5 mmoles) of 4-bromo-but-2-enoic acid [4-(3-bromo-phenylamino)-3-cyano-quinolin-6-yl]-amide in 5 ml of N, N-di-methylformamide was added dropwise. Stirring and cooling were continued for 2 hours. Then 25 ml of water and 15 ml of ethyl acetate were added. The layers were separated and aqueous layer was extracted with 2–15 ml portions of 1:1 tetrahydrofuran-ethyl acetate. The combined organic layers were absorbed onto silica gel and chromatographed on silica gel. The column was eluted with a gradient of 1:19 to 1:4 methanol-methylene chloride to give 367 mg (51%) of 4-Diethylamino-but-2-enoic acid [4-(3-bromo-phenylamino)-3-cyano-quinolin-6-yl]-amide. The compound melted at 141–145 deg: mass spectrum (electrospray, m/e): M+H 478.0,480.0.

EXAMPLE 101

4-Methylamino-but-2-enoic acid [4(3-bromo-phenylamino)-3-cyano-quinolin-6-yl]-amide Fifteen milliliters of a 2 molar solution of methylamine in tetrahydrofuran was cooled in an ice bath and a solution of 729 mg (1.5 mmoles) of 4-bromo-but-2-enoic acid [4-(3-bromo-phenylamino)-3-cyano-quinolin-6-yl]-amide in 5 ml of N, N-dimethylformamide was added dropwise. Stirring and cooling were continued for 2 hours. Then 25 ml of water and 15 ml of ethyl acetate were added. The layers were separated aqueous layer was extracted with 2–15 ml portions of 1:1 tetrahydrofuran-ethyl acetate. The combined organic layers were absorbed onto silica gel and chromatographed on silica gel. The column was eluted with a gradient of 1:19 to 1:1 methanol-methylene chloride. Obtained was 210 mg (32%) of 4-Methylamino-but-2-enoic acid [4-(3-bromo-phenylamino)-3-cyano-quinolin-6-yl]-amide which slowly went to a tar in the range of 194–202 deg.: mass spectrum (electrospray, m/e): M+H 437.9; M+2H 219.5.

EXAMPLE 102

2-Cyano-3-(2-methyl-4-nitrophenyl)acrylic Acid Ethyl Ester

A mixture of 2-methyl-4-nitroaniline (38.0 g, 250 mmol), ethyl (ethoxymethylene)-cyanoacetate (50.8 g, 300 mmol), and 200 ml of toluene was refluxed for 24 h, cooled, diluted with 1:1 ether-hexane, and filtered. The resulting white solid was washed with hexane-ether and dried to give 63.9 g, mp 180–210° C.

EXAMPLE 103

1,4-Dihydroquinoline-8-methyl-6-nitro-3-carbonitrile

A stirred mixture of 64 g (230 mmol) of 2-cyano-3-(2-methyl-4-nitrophenyl)acrylic acid ethyl ester and 1.5 L of Dowtherm A was heated at 260° C. for 12 h, cooled, diluted with hexane, and filtered. The grey solid thus obtained was washed with hexane and dried to give 51.5 g, mp 295–305° C.

EXAMPLE 104

4-Chloro-8-methyl-6-nitro-3-quinolinecarbonitrile

A stirred mixture of 1,4-dihydroquinoline-8-methyl-6-nitro-3-carbonitrile (47 g, 200 mmol) and 200 ml of phosphorous oxychloride was refluxed for 4 h. The phosphorous oxychloride was removed in vacuo, and the residue was stirred with methylene chloride at 0° C. and treated with a slurry of ice and sodium carbonate. The organic layer was separated and washed with water. The solution was dried and concentrated to a volume of 700 ml. The product was precipitated by the addition of hexane and cooling to 0° C. The white solid was filtered off and dried to give 41.6 g, mp 210–212° C.

EXAMPLE 105

4-[(3-Bromophenyl)amino]-8-methyl-6-nitro-3-quinolinecarbonitrile

A stirred mixture of 4-chloro-8-methyl-6-nitro-3-quinolinecarbonitrile (14.8 g, 60 mmol), 3-bromoaniline (12.4 g, 72 mmol), pyridine hydrochloride (6.93 g, 60 mmol), and 180 ml of ethoxyethanol was refluxed for 1.5 h, cooled, poured into a stirred mixture of water and an amount of sodium carbonate to give a H of 8–9. The resulting yellow solid was filtered, washed with water, dried, digested in boiling ether, filtered, and dried to give 22.6 g, mp 263–267° C.

EXAMPLE 106

4-[(3-Bromophenyl)-N-acetylamino]-8-methyl-6-nitro-3-quinolinecarbonitrile

A stirred mixture of 4-[(3-bromophenyl)amino]-8-methyl-6-nitro-3-quinolinecarbonitrile (15.3 g, 40 mmol), 0.37 g (3 mmol) of dimethylaminopyridine, 40 ml of acetic anhydride, and 80 ml of pyridine was refluxed for 3 h and concentrated at 50° C. under vacuum. The residue was stirred with methylene chloride and 0.1 N HCl. After filtration through Celite, the organic layer was washed with water, dried and concentrated. The residue was subjected to chromatography on silica gel with 1% acetic acid in methylene chloride to give 11.2 g of an amber glass, NMR (CDCl$_3$) δ 2.29 (N-acetyl group).

EXAMPLE 107

8-Bromomethyl-4-(3-bromophenyl)-N-aceylamino]-6-nitro-a-quinolinecarbonitrile

A stirred mixture of 4-[(3-bromophenyl)-N-acetylamino]-8-methyl-6-nitro-3-quinolinecarbonitrile (10.6 g, 25 mmol), N-bromosuccinimide (6.68 g, 37.5 mmol), 0.30 g of dibenzoyl peroxide, and 200 ml of carbon tetrachloride was refluxed for 2 h, treated with an additional 0.30 g of dibenzoyl peroxide, and refluxed an additional 2.5 h, cooled, diluted with methylene chloride, and stirred with aqueous sodium bisulfite. The organic layer was separated and washed successively with water, sodium bicarbonate solution, and water. The solution was dried and evaporated to give 15 g of a white foam, NMR (CDCl$_3$) δ 5.19 (dd, CH$_2$Br).

EXAMPLE 108

4-[(3-Bromophenyl)amino]-8-dimethylaminomethyl-6-nitro-3-quinolinecarbonitrile

To a stirred solution of dimethylamine in THF (2.0 M; 115 ml; 230 mmol) at 0° C. was added a solution of 8-bromomethyl 4[(3-bromophenyl)-N-acetylamino]--6-nitro-3-quinolinecarbonitrile (11.6 g, 23 mmol) in 115 ml of THF during 15 m. After warming to 25° C. the mixture was stirred for 2 h. The THF was evaporated off, and the residue was refluxed in 230 ml of methanol with 12.7 g (92 mmol) of potassium carbonate for 1 h. The mixture was cooled, saturated with CO$_2$, and concentrated. The residue was partitioned with methylene chloride and water. The organic layer was washed with water, dried, and concentrated. The residue was subjected to chromatography on silica gel with methylene chloride-ethyl acetate-methanol-triethylamine to give 6.0 g yellow solid, mp 223–226° C.

EXAMPLE 109

6-Amino-4-[(3-bromophenyl)amino]-8-dimethylaminomethyl-3-quinolinecarbonitrile

A stirred mixture of 4-[(3-bromophenyl)amino]-8-dimethylaminomethyl-6-nitro-3-quinolinecarbonitrile (5.98 g, 14.1 mmol), iron powder (2.76 g, 49 mg-atoms), acetic acid (5.67 ml, 99 mmol), and 70 ml of methanol was refluxed for 2 h and then evaporated to remove methanol. The residue was stirred with water for 10 m, and the orange solid was filtered off and washed with 2% acetic acid. The total filtrate was basified to pH 10 with 5 N sodium hydroxide. The resulting precipitate was extracted with methylene chloride. The extract was washed with water, dried, and concentrated. The residue was subjected to chromatography on silica gel with ethyl acetate-methanol-triethylamine to give 3.34 g of amber solid; mass spectrum (electrospray, m/e) M+H 396.2, 398.1.

EXAMPLE 110

N-{4-[(3-Bromophenyl)amino]-3-cyano-8-dimethylaminomethyl-6-quinolinyl}-2-butynamide To a stirred mixture of 2-butynoic acid (0.42 g, 5.0 mmol) and N-methylmorpholine (0.66 ml, 6.0 mmol) in 4.0 ml of THF at 0° C. was added i-butyl chloroformate (0.52 ml, 4.0 mmol)during 10 m. After 10 m a solution of 6-amino-4-[(3-bromophenyl)amino]-8-dimethylaminomethyl-3-quinolinecarbonitrile (0.79 g, 2.0 mmol) in 4.0 ml of THF was added during 60 s. The mixture was warmed to 25° C., stirred for 2 h, and diluted with water. The $_p$H was adjusted to 9–10 with potassium carbonate, and the resulting solid was filtered off, washed with water, stirred with methylene chloride, and filtered. The latter filtrate was concentrated to give a solid which was subjected to chromatography on silica gel with methylene chloride-ethyl acetate-methanol-triethylamine to give an amber solid; mass spectrum (electrospray, m/e) M+H 462, 464.

EXAMPLE 111

N-{4-[(3-Bromophenyl)amino]-3-cyano-8-dimethylaminomethyl-6-quinolinyl}-2-propenamide To a stirred solution of 6-amino-4-[(3-bromophenyl)amino]-8-dimethylaminomethyl-3-quinolinecarbonitrile (0.20 g, 0.50 mmol) and N,N-diisopropylethylamine (0.13 ml, 0.75 mmol) in 3.4 ml of THF at 0° C. was added acryloyl chloride (0.045 ml, 0.55 mmol) during 5 m. After stirring for 3 h at 0° C. the mixture was diluted with sodium bicarbonate solution. The resulting solid was filtered off, washed with water, dried, and subjected to chromatography on silica gel with methylene chloride-ethyl acetate-methanol-triethylamine to give a yellow solid; mass spectrum (electrospray, m/e) M+H 449.9, 452.0.

EXAMPLE 112

N-{4-[(3-Bromophenyl)amino]-3-cyano-8-dimethylaminomethyl-6-quinolinyl}acetamide To a stirred mixture of 6-amino-4-[(3-bromophenyl) amino]-8-dimethylaminomethyl-3-quinolinecarbonitrile (0.20 g, 0.50 mmol) and 1.5 ml of acetic acid at 25° C. was added 0.14 ml (1.5 mmol) of acetic anhydride. After 60 m volatile matter was evaporated off under vacuum. The residue was stirred with sodium bicarbonate solution. The resulting solid was filtered off, washed with water, dried, and recrystallized from isopropanol-hexane to give a light yellow solid, mp 162–167° C.

EXAMPLE 113

N'-[2-Carbethoxy-4,5-bis(2-methoxyethoxy)phenyl]-N,N-dimethylformamidine

To a stirred solution of 15.7 g (50 mmol) of ethyl 2-amino-4,5-bis(2-methoxyethoxy)-benzoate (Pfizer patent WO 96130347) in 50 ml of DMF at 0° C. was added phosphorous oxychloride (5.6 ml, 60 mmol) during 15 m. The resulting solution was heated at 55° C. for 45 m, cooled, diluted with methylene chloride, and treated at 0° C. with 200 ml of N/i sodium hydroxide during 2 m. The organic layer was separated and washed at 0° C. with water. The solution was dried and evaporated with added toluene present to give 18.4 g of amber oil; NMR (CDCl$_3$) δ 3.02 (s, Me$_2$N).

EXAMPLE 114

1,4-Dihydroquinoline-5,6-bis(2-methoxyethoxy)-3-carbonitrile

To a stirred solution of n-butylllithium (44 ml of 2.5 M in hexane; 110 mmol) in 65 ml of THF at −78° C. was added a solution of acetonitrile (5.85 ml, 112 mmol) in 110 ml of THF during 10 m. After stirring at −78° C. for 15 m, the mixture was treated with a solution of N'-[2-carbethoxy-4, 5-bis(2-methoxyethoxy)phenyl]-N,N-dimethylformamidine in 75 ml of THF during 20 m. After 30 m at −78° C. the stirred mixture was treated with acetic acid (14.3 ml, 250 mmol). The mixture was warmed to 25° C. and stirred for 2 h. The mixture was evaporated to dryness, and diluted with water. The resulting white solid was filtered, washed with water, and dried to give 10.7 g; mass spectrum (electrospray, m/e) M+H 319.2.

EXAMPLE 115

4-Chloro-5,6-bis(2-methoxyethoxy)-3-quinolinecarbonitrile

A stirred mixture of 1,4-dihydroquinoline-5,6-bis(2-methoxyethoxy)-3-carbonitrile 9.68 g, 30.4 mmol) and 30 ml of phosphorous oxychloride was refluxed for 1.5 h. The resulting solution was concentrated under vacuum, and the residue was stirred with methylene chloride at 0° C. as ice-water and sodium carbonate were added until pH of mixture was 8–9. The organic layer was separated, washed with water, dried and concentrated to give a tan solid; mass spectrum (electrospray, m/e) M+H 337.1, 339.1.

EXAMPLE 116

4-[(3-Ethynylphenyl)amino]-5,6-bis(2-methoxyethoxy)-3-quinolinecarbonitrile

A stirred mixture of 4-Chloro-5,6-bis(2-methoxyethoxy)-3-quinolinecarbonitrile (2.52 g, 7.5 mmol), pyridine hydrochloride (0.87 g, 9.0 mmol), 3-ethynylaniline (1.06 g, 9.0 mmol), and ethoxyethanol (22 ml) was refluxed for 1.5 h, cooled, diluted with water containing potassium carbonate to give pH-9, and extracted with ethyl acetate. The extract was washed well with water, dried, and concentrated. The resulting solid was recrystallized from ethyl acetate to give an off-white solid, mp 150–153°.

EXAMPLE 117

4-[3-Dimethylaminophenyl)amino]-5,6-bis(2-methoxyethoxy)-3-quinolinecarbonitrile A stirred mixture of 4-Chloro-5,6-bis(2-methoxyethoxy)-3-quinolinecarbonitrile (0.67 g, 2.0 mmol), pyridine (0.39 ml, 4.8 mmol), 3-dimethylaminoaniline dihydrochloride (0.50 g, 2.4 mmol), and ethoxyethanol (6.0 ml) was refluxed for 2 h, cooled, and partitioned with ethyl acetate and water containing potassium carbonate to give ph-9–10. The organic layer was washed with water, dried and concentrated. The residue was chromatographed on silica gel with methylene chloride-ethyl acetate-methanol to give an amber glass; mass spectrum (electrospray, m/e) M+H 437.0.

EXAMPLE 118

4-[(3-Acetylphenyl)amino]-5,6-bis(2-methoxyethoxy)-3-quinolinecarbonitrile

In the manner of Example 116, 4-Chloro-5,6-bis(2-methoxyethoxy)-3-quinolinecarbonitrile was reacted with 3-aminoacetophenone to give the title compound; recrystallized from ethanol to give off-white solid, mp 250–253 (dec).

EXAMPLE 119

Methyl 4-methoxy-3-(3-morpholin-4-yl-propoxy)) benzoate

A stirred mixture of methyl isovanillate (22.6 g, 124 mmol), N-(3-chloropropyl)-morpholine (25.4 g, 155 mmol), potassium carbonate (18.8 g, 136 mmol), tetrabutylammonium iodide (0.92 g, 2.5 mmol), and 248 ml of 2-butanone was refluxed for 20 h. The 2-butanone was evaporated off, and the residue was stirred with water at 0° C. The resulting white solid was filtered off, washed successively with water and hexane, and dried; mp 90–94° C.

EXAMPLE 120

Methyl 4-methoxy-5-(3-morpholin-4-yl-propoxy))-2-nitrobenzoate

To a stirred solution of methyl 4-methoxy-3-(3-morpholin-4-yl-propoxy))benzoate (30.9 g, 100 mmol) in 100 ml of acetic acid at 25° C. was added 50 ml of 70% nitric acid during 30 m. The solution was heated to 45° C. at which point the reaction started and was self-sustaining at that temperature. After a total of 1.5 h at 45–50° C. the mixture was cooled to 0° C., treated with ice-water and 240 g (1.75 mol) of potassium carbonate, and extracted with ethyl acetate. The extract was washed with water, dried, and concentrated to give a yellow solid, mp 78–82° C.

EXAMPLE 121

Methyl 2-amino-4-methoxy-5-(3-morpholin-4-yl-propoxy))benzoate

A solution of methyl 4-methoxy-3-(3-morpholin-4-yl-propoxy))-2-nitrobenzoate (32.5 g, 91.7 mmol) in 110 ml of methanol and 220 ml of ethyl acetate was hydrogenated at 55 psi in the presence of 2.0 g of 10% Pd on carbon catalyst at 25° C. After 4 h the mixture was filtered, and the filtrate was evaporated to dryness. The residue was recrystallized from acetone-hexane to give a tan solid, mp 78–82° C.

EXAMPLE 122

Ethyl 2-(dimethylaminomethyleneamino)-4-methoxy-5-(3-morpholin-4-yl-propoxy))benzoate A mixture of methyl 2-amino-4-methoxy-5-(3-morpholin-4yl-propoxy))benzoate (6.49 g, 20 mmol) and dimethylformamide dimethyl acetal (4.25 ml, 30 mmol) was heated at 100° C. for 1.5 h. All volatile materials were evaporated off directly at 70° C. to give a syrup; mass spectrum (electrospray, m/e) M+H 380.5.

EXAMPLE 123

1,4-Dihydroquinoline-7-methoxy-6-(3-morpholin-4-yl-propoxy))-4-oxo-3-carbonitrile To a stirred solution of n-butyllithium (17.6 ml of 2.5 M in hexane; 44 mmol) in 26 ml of THF at −78° C. was added a solution of acetonitrile (1.85 ml, 45 mmol) in 44 ml of THF during 10 m. After stirring at −78° C. for 15 m, the mixture was treated with a solution of ethyl 2-(dimethylaminomethyleneamino)-4-methoxy-5-(3-morpholin-4-yl-propoxy))benzoate (7.6 g, 20 mmol) in 30 ml of THF during 20 m. After 90 m at −78° C. the mixture was treated with carbon dioxide while warming slowly to 25° C. and then evaporated to dryness. The residue was partitioned with n-butanol (200 ml) and half-saturated NaCl solution (40 ml). The organic layer was separated, washed with saturated NaCl solution, and evaporated to dryness. The resulting solid was triturated successively with boiling acetone and methanol, filtered, and dried to give a tan solid, mp 255–260° C.

EXAMPLE 124

4-Chloro-7-methoxy-6-(3-morpholin-4-yl-propoxy))-3-quinolinecarbonitrile

A stirred mixture of 1,4-Dihydroquinoline-7-methoxy-6-(3-morpholin-4-yl-propoxy))-4-oxo-3-carbonitrile (4.75 g, 13.8 mmol), 0.10 ml of DMF, and 55 ml of thionyl chloride was refluxed for 3 h. Volatile matter was removed by evaporation at 30° C., and the residue was stirred at 0° C. with a mixture of methylene chloride and water containing potassium carbonate to give pH 9–10. The organic layer was separated, washed with water, dried and concentrated to give a brown solid; mass spectrum (electrospray, m/e) M+H 362.4, 364.4.

EXAMPLE 125

4-[(3-Chloro-4-fluorophenyl)amino]-7-methoxy-6-(3-morpholin-4-yl-propoxy))-3-quinolinecarbonitrile A stirred mixture of 4chloro-7-methoxy-6-(3-morpholin-4-yl-propoxy))-3-quinolinecarbonitrile (1.8 g, 5.0 mmol), 3-chloro-fluoroaniline (0.87 g, 6.0 mmol), pyridine hydrochloride (1.15 g, 10 mmol), and 15 ml of ethoxyethanol was refluxed for 2 h, cooled, and stirred with hexane and water containing potassium carbonate to give pH 10. The resulting brown solid was filtered off, washed with water and hexane, and dried. Recrystallization from ethanol gave an off-white solid, mp 240–244° C.

EXAMPLE 126

4-[(3-Bromophenyl)amino]-7-methoxy-6-(3-morpholin-4-yl-propoxy))-3-quinolinecarbonitrile In the manner of Example 125, 4-chloro-7-methoxy-6-(3-morpholin-4-yl-propoxy))-3-quinolinecarbonitrile was reacted with 3-bromoaniline to give the title compound; recrystallized from methanol to give an off-white solid, mp 208–212° C.

EXAMPLE 127

4-[(4-Chloro-2-fluorophenyl)amino]-7-methoxy-6-(3-morpholin-4-yl-propoxy))-3-quinolinecarbonitrile In the manner of Example 125, 4-chloro-7-methoxy-6-(3-morpholin-4-yl-propoxy))-3-quinolinecarbonitrile was reacted with 4-chloro-2-fluoroaniline to give the title compound; recrystallized from methanol to give an off-white solid, mp 207–212° C.

EXAMPLE 128

4-[(3-Hydroxy-4-methylphenyl)amino]-7-methoxy-6-(3-morpholin-4-yl-propoxy))-3-quinolinecarbonitrile In the manner of Example 125, 4-chloro-7-methoxy-6-(3-morpholin-4-yl-propoxy))-3-quinolinecarbonitrile was reacted with 3-hydroxy-4-methylaniline to give the tide compound; recrystallized from ethyl acetate to give an amber solid, mp 222–227° C. (dec).

EXAMPLE 129

N-{3-Cyano-4-[(3-iodophenyl)amino]-6-quinolinyl}-2-propenamide

Dissolved 500 mg (1.29 mmol) 6-amino-4-[(3-iodophenyl)amino]-3-quinolinecarbonitrile in 1.0 ml of DMF and added 6 ml THF. Chilled to 0° C. under $N_2$ and added 200 µl (1.43 mmol) triethyl amine and 120 µl (1.44 mmol) acryloyl chloride. Removed ice bath at 15 minutes. At 1.5 hours stripped solvent. Slurried residue with water and dilute sodium bicarbonate. Collected, washed with water, air dried. Boiled solids in ethyl acetate. Filtered off solids, removed solvent of the filtrate, and dried in vacuo, giving 391 mg of orange-brown solid: mass spectrum (electrospray m/e): M+H=441.1.

EXAMPLE 130

6-Amino-4-[(3-iodophenyl)amino]-3-quinolinecarbonitrile

A mixture of 6.70 g (16.1 mmol) 4-[(3-iodophenyl)amino]-6-nitro-3-quinolinecarbonitrile, 300 ml ethanol, and 18.2 g (80.5 mmol) $SnCl_2$ dihydrate was heated to reflux under $N_2$. Removed heat at 2 hours, added ice water. Added sodium bicarbonate until pH was basic, forming a thick yellow mixture. Stirred for 2.5 hours. Extracted with chloroform, stirred organic portion with Darco and filtered through magnesium sulfate. Stripped solvent and dried in vacuo, giving 3.48 g of yellow-brown solid: mass spectrum (electrospray m/e): M+H=387.0.

EXAMPLE 131

4-[(3-Iodophenyl)amino]-6-nitro-3-quinolinecarbonitrile

A mixture of 3.10 ml (25.7 mmol) 3-iodoaniline, 200 ml ethanol, and 5.00 g (21.4 mmol) 4-chloro-6-nitro-3-quinolinecarbonitrile was heated to reflux under $N_2$ for 3.5 hours. Cooled and made basic with a saturated sodium bicarbonate. Stripped solvents and azeotroped with ethanol. Slurried residue with hexane and collected. Air dried, washed solids with water, and dried in vacuo. Dissolved solids in 400 ml ethyl acetate, stirred with Darco, filtered and removed solvent. Dried solids in vacuo to give 7.38 g of yellow solid: mass spectrum (electrospray m/e): M+H=417.0.

EXAMPLE 132

N-{3-Cyano-[(3-methylphenyl)amino]-6-quinolinyl}-2-butynamide

Dissolved 597 mg (7.10 mmol) 2-butynoic acid in 25 ml THF under $N_2$ and chilled to 0° C. Added 950 µl (7.30 mmol) isobutyl chloroformate and 780 µl (7.10 mmol) N-methylmorpholine and stirred for 10 minutes. Added dropwise a solution of 778 mg (2.84 mmol 6-amino-4-[(3-methylphenyl)amino]-3-quinolinecarbonitrile, stirred for 15 minutes at 0° C. and then at 25° C. overnight. Stripped solvent and slurried residue with water, drying the gummy solid in vacuo briefly. Boiled solid in ethyl acetate and collected. Recrystallized from DMF, using ethanol to crash out the product, and dried in vacuo, giving 401 mg of yellow-brown solid: mass spectrum (electrospray m/e): M+H=341.2.

EXAMPLE 133

6-Amino-4-[(3-methylphenyl)amino]-3-quinolinecarbonitrile

Added 253 mg 10% palladium on carbon to a round bottom flask under $N_2$ and covered catalyst with 140 ml ethanol. To this added 2.49 g (8.18 mmol) 6-nitro-4-[(3-methylphenyl)amino]-3-quinolinecarbonitrile and 640 µl (20.4 mmol) anhydrous hydrazine. The mixture was heated to reflux for 2 hours 15 minutes and filtered hot through celite. Stripped solvent and dried in vacuo, giving 2.455 g of yellow solid: mass spectrum (electrospray m/e): M+H=275.2.

EXAMPLE 134

6-Nitro-4-[(3-methylphenyl)amino]-3-quinolinecarbonitrile

A mixture of 5.00 g (21.5 mmol) 4-chloro-6-nitro-3-quinolinecarbonitrile, 200 ml ethanol, and 2.75 ml (25.7 mmol) 3-toluidine was heated to reflux for 4.5 hours. Cooled and added a saturated sodium bicarbonate until pH was basic. Stripped solvents and azeotroped with ethanol. Slurried with hexane, collected, and air dried. Washed with water and dried in vacuo. Boiled in ethyl acetate, stirred with Darco and filtered. Stripped solvent and dried in vacuo to give 4.82 g of yellow-orange solid: mass spectrum (electrospray m/e): M+H=305.2.

EXAMPLE 135

N-{4-[(3-Chlorophenyl)amino]-3-cyano-6-quinolinyl}-2-propenamide

Dissolved 430 mg (1.46 mmol) 6-amino-4-[(3-chlorophenyl)amino]-3-quinolinecarbonitrile in 4 ml DMF, added 10 ml THF and chilled to 0° C. under $N_2$. Added 224 μl (1.60 mmol) triethylamine and 133 μl (1.60 mmol) acryloyl chloride. Removed ice bath at 15 minutes, reaction complete at this time, but stirred overnight at 25° C. Stripped solvent, added a dilute sodium bicarbonate to the residue and collected solids. Washed with water and dried in vacuo. Boiled in ethyl acetate, collected solids and dried in vacuo, giving 200 mg of orange solid: mass spectrum (electrospray m/e): M+H=349.0, 351.0.

EXAMPLE 136

6-Amino-4-[(3-chlorophenyl)amino]-3-quinolinecarbonitrile

A mixture of 6.30 g (19.4 mmol) 4-[(3-chlorophenyl)amino]-6-nitro-3-quinolinecarbonitrile, 300 ml ethanol, and 21.9 g (97 mmol) $SnCl_2$ dihydrate were heated to reflux under $N_2$. Removed heat at 2.5 hours, added ice water and made basic with sodium bicarbonate. Stirred for 2 hours and extracted with chloroform. Dried organic layer with sodium sulfate, filtered, stripped solvent and dried residue in vacuo, giving 5.74 g of yellow-brown solid: mass spectrum (electrospray m/e): M+H=295.1, 297.1.

EXAMPLE 137

4-[(3-Chlorophenyl)amino]-6-nitro-3-quinolinecarbonitrile

A mixture of 10.0 g (42.9 mmol)) 4-chloro-6-nitro-3-quinolinecarbonitrile, 260 ml ethanol, and 5.40 ml 3-chloroaniline was heated to reflux under $N_2$. Removed heat at 4 hours, cooled to 25° C. and added saturated sodium bicarbonate until the pH was basic. Stripped solvents and azeotroped with ethanol. Slurried residue with hexane, collected solid, and air dried. Washed solids with water and dried in vacuo. Dissolved in boiling ethyl acetate, stirred with Darco, and filtered. Stripped solvent and dried residue in vacuo, giving 6.5 g of yellow solid: mass spectrum (electrospray m/e): M+H=325.0, 327.0.

EXAMPLE 138

N-{3-Cyano-4-[(3-methoxyphenyl)amino]-6-quinolinyl}-2-propenamide

Dissolved 500 mg (1.72 mmol) 6-amino-4-[(3-methoxyphenyl)amino]-3-quinolinecarbonitrile in 2 ml hot DMF, added 6 ml THF, and chilled to 0° C. Added 264 μl (1.90 mmol) triethylamine and 158 μl (1.90 mmol) acryloyl chloride. Removed ice bath at 15 minutes. Stripped solvent at 2 hours. Washed residue with dilute sodium bicarbonate, collected solids, washed with water, and air dried. Boiled solids in ethyl acetate, collected and dried in vacuo, giving 288 mg of yellow-orange solid: mass spectrum (electrospray m/e): M+H=345.2.

EXAMPLE 139

N-{3-Cyano-4-[(3-methoxyphenyl)amino]-6-quinolinyl}-2-butynamide

Dissolved 362 mg (4.31 mmol) acid in 20 ml THF under $N_2$ and chilled to 0° C. Added 560 μl (4.30 mmol) isobutyl chloroformate and 475 μl (4.31 mmol) N-methylmorpholine and stirred for 10 minutes. Dissolved 500 mg (1.72 mmol) 6-amino-4-[(3-methoxyphenyl)amino]-3-quinolinecarbonitrile in 2 ml hot DMF and added 10 ml THF. Added this to the mixed anhydride dropwise, stirred for 15 minutes at 0° C. and at 25° C. overnight. Stripped solvent, slurried residue with water, collected solids, and air dried. Recrystallized from ethyl acetate and dried in vacuo, giving 270 mg of yellow solid: mass spectrum (electrospray m/e): M+H=357.1.

EXAMPLE 140

N-{3-cyano-4-[(3-methoxyphenyl)amino]-6-quinolinyl}-4-piperidino-2-butynamide Partially dissolved 1.21 (7.22 mmol) 4-piperidino-2-butynoic acid in 100 ml THF and chilled to 0° C. under $N_2$. Added 955 μl (8.67 mmol) N-methylmorpholine and 750 μl (5.78 mmol) isobutyl chloroformate. Stirred for 40 minutes and added a solution of 840 mg (2.89 mmol) 6-amino-4-[(3-methoxyphenyl)amino]-3-quinolinecarbonitrile dissolved in 10 ml hot pyridine. At 2 hours, poured into ice water and made basic with saturated sodium bicarbonate. Extracted with ethyl acetate, dried with sodium sulfate, and stripped down to a small volume, which was loaded onto a column of silica gel. Eluted with 10% methanol/ethyl acetate, stripped solvent of desired fractions, and dried in vacuo, giving 970 mg of green solid: mass spectrum (electrospray m/e): M+H=440.1.

EXAMPLE 141

6-Amino-4-[(3-methoxyphenyl)amino]-3-quinolinecarbonitrile 325 mg of 10% palladium on carbon was added to a round bottom flask under $N_2$ and covered with 165 ml ethanol. Added 3.29 g (10.3 mmol) 4-[(3-methoxyphenyl)-amino]-6-nitro-3-quinolinecarbonitrile and 800μl anhydrous hydrazine and heated mixture to reflux. At 1.5 hours, filtered hot through celite, stripped solvent and dried in vacuo, giving 2.876 g of yellow solid: mass spectrum (electrospray m/e): M+H=291.2.

EXAMPLE 142

4-[(3-methoxyphenyl)amino]-6-nitro-3-quinolinecarbonitrile

A mixture of 5.00 g (21.5 mmol) 4-chloro-6-nitro-3-quinolinecarbonitrile, 200 ml ethanol, and 3.0 ml (26.0 mmol) m-anisidine was heated to reflux under $N_2$. Removed heat at 4.5 hours and made basic with saturated sodium bicarbonate. Stripped solvents and azeotroped with ethanol. Slurried with hexane and collected crystals. Washed with water, dried in vacuo. Dissolved 5.94 g of crude product in 320 ml boiling ethyl acetate, stirred with Darco, filtered, stripped solvent, and dried in vacuo, giving about 5 g of yellow-orange solid: mass spectrum (electrospray m/e): M+H=291.1.

EXAMPLE 143

N-{4-[(3-Chloro-4-fluoro-phenyl)amino]-3-cyano-6-quinolinyl}-2-butynamide

Dissolved 336 mg (4.00 mmol) 2-butynoic acid in 20 ml of THF and chilled to 0° C. under $N_2$. Added 520 μl (4.00 mmol) isobutyl chloroformate and 440 μl (4.00 mmol) N-methylmorpholine and stirred for 10 minutes. Added a solution of 500 mg (1.60 mmol) 6-amino-4-[(3-chloro-4-fluorophenyl)amino]-3-quinolinecarbonitrile, stirred for minutes at 0° C. and then at 25° C. overnight. Stripped solvent, washed with water, collected and dried in vacuo. Recrystallized from ethyl acetate, giving 148 mg of a yellow solid: mass spectrum (electrospray m/e): M+H=379.1, 381.1.

EXAMPLE 144

N-{4-[(3-Chloro-4-fluorophenyl)amino]-3-cyano-6quinolinyl}-2-propenamide

Dissolved 1.00 g (3.20 mmol) 6-amino-4-[(3-chloro-4-fluorophenyl)amino]-3-quinolinecarbonitrile in 2 ml hot DMF, added 12 ml THF and chilled to 0° C. under $N_2$. Added 490 μl (3.52 mmol) triethyl amine and 295 μl (3.52 mmol) acryloyl chloride. Removed ice bath at 15 minutes, and at 1.5 hours stripped solvent. Slurried residue with a dilute sodium bicarbonate, collected solids, and washed with water. Recrystallized from ethyl acetate, giving 215 mg of yellow solid: mass spectrum (electrospray m/e): M+H= 367.1, 369.1.

EXAMPLE 145

N-{4-[(3-Chloro-4-fluorophenyl)amino]-3-cyano-6-quinolinyl}-4-dimethylamino-2-butenamide Dissolved 1.50 g (4.80 mmol) 6-amino-4-[(3-chloro-4-fluorophenyl)amino]-3-quinolinecarbonitrile in 50 ml THF, added 836 μl (4.80 mmol) N,N-diisopropylethylamine, and chilled to 0° C. under $N_2$. Added 500 μl (4.80 mmol) 4-bromo-but-2-enoyl chloride and after 1 hour dropwise added the mixture to 10 ml of a 2M solution (19 mmol) of dimethylamine in THF cooled to −78° C. At 2 hours, added 5 ml (9.5 mmol) more of dimethyl amine solution and warmed to 25° C. After 1 hour, poured onto a cold solution of sodium bicarbonate. Extracted with ethyl acetate, dried organics with brine and sodium sulfate, reduced to small volume and loaded onto a column of silica gel. Eluted with 70% methanol/ethyl acetate, stripped solvent of desired fractions and dried in vacuo, giving 427 mg of yellow solid: mass spectrum (electrospray m/e): M+H=424.0, 426.0.

EXAMPLE 146

N-{4-[(3-Chloro-4-fluorophenyl)amino]-3-cyano-6-quinolinyl}-4-diethylamino-2-butenamide Added 500 μl (4.80 mmol) 4-bromo-but-2-enoyl chloride to a solution of 1.50 g (4.80 mmol) ) 6-amino-4-[(3-chloro-4-fluorophenyl)amino]-3-quinolinecarbonitrile and 836 μl (4.80 mmol) N,N-diisopropylethylamine in 50 ml ThF at 0° C. under $N_2$. At 1 hour added the mixture dropwise to 1.26 ml (24 mmol) diethylamine in 11 ml THF chilled to −78° C. Removed dry ice bath after complete addition, and at 2 hours, 45 minutes poured onto a mixture of ice and saturated sodium bicarbonate. Extracted with ethyl acetate, dried organic layer with brine and sodium sulfate, and stripped solvent. Loaded compound onto a column of silica gel, eluted with 35% methanol/ethyl acetate, stripped solvent from desired fractions, and dried in vacuo, giving 292 mg of yellow-orange solid: mass spectrum (electrospray m/e): M+H=452.4, 454.4.

EXAMPLE 147

N-{4-[(3-Chloro-4-fluorophenyl)amino]-3-cyano-6-quinolinyl}-4-morpholino-2-butenamide Added 500 μl (4.80 mmol) 4-bromo-but-2-enoyl chloride to a solution of 1.50 g (4.80 mmol) 6-amino-4-[(3-chloro-4-fluorophenyl)amino]-3-quinolinecarbonitrile and 836 μl (4.80 mmol) N,N-diisopropylethylamine in 50 ml THF at 0° C. under $N_2$. At 1 hour added the mixture dropwise to 2.09 ml (24 mmol) morpholine in 10 ml THF at 0° C. Removed ice bath upon complete addition and at 3 hours, poured reaction onto a mixture of ice and saturated sodium bicarbonate. Extracted with ethyl acetate, dried organic layer with brine and sodium sulfate, and stripped solvent. Loaded compound onto a column of silica gel, eluted with 12% methanol/ethyl acetate, stripped solvent from desired fractions, and dried in vacuo, giving 798 mg of yellow solid: mass spectrum (electrospray m/e): M+H=466.4, 468.4.

EXAMPLE 148

N-{4-[(3-chloro-4-fluorophenyl)amino]-3-cyano-6-quinolinyl}-2-morpholin-4-ylmethyl-2-propenamide Partially dissolved 1.37 g (8.00 mmol) 2-morpholin-4ylmethyl-2-propenoic acid in 50 ml ThF and chilled to 0° C. under $N_2$. Added 1.06 ml (9.6 mmol) N-methylmorpholine and 833 μl (6.4 mmol) isobutyl chloroformate. Stirred at 0° C. for 1 hour and added a solution of 1.00 g (3.20 mmol) 6-amino-4-[(3-chloro-4-fluorophenyl)-amino]-3-quinolinecarbonitrile in 5 ml pyridine. Stirred overnight at 25° C. Poured onto a mixture of ice and saturated sodium bicarbonate, extracted with ethyl acetate, dried organic layer with brine and sodium sulfate, and stripped solvent to a small volume. Loaded onto a column of silica gel, eluted with 1% methanol/ethyl acetate, stripped solvent from desired fractions and dried under vacuum, giving 139 mg of yellow-orange solid: mass spectrum (electrospray m/e): M+H=465.8, 468.0.

EXAMPLE 149

6-Amino-4-[(3-chloro-4-fluorophenyl)amino]-3-quinolinecarbonitrile

A mixture of 5.360 g (15.6 mmol) 4-[(3-chloro-4-fluorophenyl)amino]-6-nitro-3-quinolinecarbonitrile, 250 ml ethanol, and 17.67 g (78.2 mmol) $SnCl_2$ dihydrate was heated to reflux under $N_2$. Removed heat at 1.5 hours and added ice water. Made basic with sodium bicarbonate. Stirred for 2 hours extracted with chloroform. Added brine to the separatory funnel to help separate layers. Stirred organic layer with Darco and dried with sodium sulfate. Filtered, stripped solvent and dried in vacuo, giving 4.460 g of yellow-brown solid: mass spectrum (electrospray m/e): M+H=312.9, 315.0.

EXAMPLE 150

4-[(3-chloro-4-fluorophenyl)amino]-6-nitro-3-quinolinecarbonitrile

A mixture of 5.00 g (21.5 mmol) 4-chloro-6-nitro-3-quinolinecarbonitrile, 200 ml ethanol, and 3.75 g (25.8 mmol) 3-chloro-4-fluoroaniline was heated to reflux under $N_2$. Removed heat at 3.5 hours and added a solution of saturated sodium bicarbonate until mixture was basic. Stripped solvents and azeotroped with ethanol. Slurried residue with hexane, collected solids, washed with water and dried in vacuo. Dissolved solids in 250 ml boiling ethyl acetate, stirred with Darco, and filtered. Stripped solvent and dried in vacuo, giving 6.036 g of yellow solid: mass spectrum (electrospray m/e): M+H=343.1, 345.1.

EXAMPLE 151

N-{4-[(4-Bromophenyl)amino]-3-cyano-6-quinolinyl}-2-propenamide

Dissolved 500 mg (1.47 mmol) 6-amino-4-[(4-bromophenyl)amino]-3-quinolinecarbonitrile in 1 ml hot DMF, added 6 ml THF and chilled to 0° C. under $N_2$. Added 226 μl (1.62 mmol) triethylamine and 135 μl (1.62 mmol) acryloyl chloride. Removed ice bath at 15 minutes. At 1.5 hours, stripped solvent, slurried residue in dilute sodium bicarbonate, collected solids, and dried in vacuo. Boiled solids in ethyl acetate, collected, and dried in vacuo, giving 194 mg of yellow-orange solid: mass spectrum (electrospray m/e): M+H=393.1, 395.1.

EXAMPLE 152

6-Amino-4-[(4-bromophenyl)amino]-3-quinolinecarbonitrile

A mixture of 3.10 g (8.40 mmol) 4-[(4-bromophenyl) amino]-6-nitro-3-quinolinecarbonitrile, 155 ml ethanol, and 9.47 g (42.0 mmol) $SnCl_2$ dihydrate was heated to reflux under $N_2$. After 4 hours, removed heat and added ice water. Made basic with sodium bicarbonate and stirred for 2 hours. With mixture still basic, extracted with chloroform, stirred organic layer with Darco and dried with sodium sulfate. Filtered, stripped solvent and dried in vacuo, giving 2.265 g of brown-yellow solid: mass spectrum (electrospray m/e): M+H=339.0, 341.0.

EXAMPLE 153

4-[(4-Bromophenyl)amino]-6-nitro-3-quinolinecarbonitrile

A mixture of 5.00 g (21.5 mmol) 4-chloro-6-nitro-3-quinolinecarbonitrile, 200 ml ethanol, and 4.42 g (25.8 mmol) p-bromoaniline was heated to reflux under $N_2$ for 3 hours. Removed heat and added saturated sodium bicarbonate until basic. Stripped solvents and azeotroped with ethanol. Slurried residue with hexane, collected solids, and air dried. Washed with water and dried in vacuo. Boiled in 1.4 liters ethyl acetate, and without completely dissolving all solids, stirred with Darco, and filtered. Stripped solvent and dried in vacuo, giving 3.524 g of yellow solid: mass spectrum (electrospray m/e): M+H=369, 370.9.

EXAMPLE 154

N-{3-Cyano-4-[(3,4-difluorophenyl)amino]-6-quinolinyl}-2-propenamide

Dissolved 1.00 g (3.37 mmol) 6-amino-4-[(3,4-difluorophenyl)amino]-3-quinolinecarbonitrile in 2 ml DMF, added 12 ml THF, and chilled to 0° C. under $N_2$. Added 517 μl (3.71 mmol) triethylamine and 310 μl (3.72 mmol) acryloyl chloride. Removed ice bath a 15 minutes. At 3.5 hours stripped solvent and slurried residue with dilute sodium bicarbonate. Collected solids, washed with water, and air dried. Boiled in ethyl acetate, collected solids and dried in vacuo, giving 332 mg of yellow solid: mass spectrum (electrospray m/e): M+H=351.1.

EXAMPLE 155

6-Amino-4-[(3,4-difluorophenyl)amino]-3-quinolinecarbonitrile

A mixture of 4.53 g (13.9 mmol) 4-[(3,4-difluorophenyl) amino]-6-nitro-3-quinolinecarbonitrile, 200 ml ethanol and 15.72 g (69.4 mmol) $SnCl_2$ dihydrate was heated to reflux under $N_2$. Removed heat at 1.5 hours, added ice water and made basic with sodium bicarbonate. Stirred for 2 hours and extracted with chloroform. Stirred organic layer with Darco, dried with sodium sulfate and filtered. Stripped solvent and dried in vacuo, giving 3.660 g of yellow-green solid: mass spectrum (electrospray m/e): M+H=297.1.

EXAMPLE 156

4-[(3,4-Difluorophenyl)amino]-6-nitro-3-quinolinecarbonitrile

A mixture of 5.00 g (21.5 mmol) 4-chloro-6-nitro-3-quinolinecarbonitrile, 250 ml ethanol and 2.55 ml (25.8 mmol) 3,4-difluoroaniline was heated to reflux under $N_2$. Removed heat at 3.5 hours and made basic with saturated sodium bicarbonate. Stripped solvents and azeotroped with ethanol. Slurried residue with hexane, collected solids and air dried. Washed with water and dried in vacuo. Dissolved in ethyl acetate, stirred with Darco, filtered, stripped solvent and dried in vacuo, giving 5.02 g of yellow solid: mass spectrum (electrospray m/e): M+H=327.1.

EXAMPLE 157

N-{4-[(3-Chloro-4-thiophenoxyphenyl)amino]-3-cyano-6quinolinyl}-2-butynamide

Dissolved 314 mg (3.72 mmol) 2-butynoic acid in 40 ml THF under $N_2$. Chilled to 0° and added 409 μl (3.72 mmol) N-methylmorpholine and 485 μl (3.72 mmol) isobutyl chloroformate and stirred for 10 minutes. Added dropwise a solution that was prepared by dissolving 1.00 g (2.48 mmol) 6-amino-4-[(3-chloro-4-thiophenoxyphenyl)amino]-3-quinolinecarbonitrile in 2.0 ml hot DMF and adding 20 ml THF. Stirred mixture for minutes at 0° and 25° C. overnight. To drive reaction to completion, added 1.24 mmol of the mixed anhydride (104 mg acid, 136 μl NMM, and 161 μl isobutyl chloroformate) in 15 ml THF. Stirred overnight. Stripped solvent, dried in vacuo. Recrystallized from ethyl acetate, dried in vacuo, giving 284 mg of yellow-orange solid: mass spectrum (electrospray m/e): M+H=469.2, 471.2.

EXAMPLE 158

6-Amino-4-[(3-chloro-4thiophenoxyphenyl)amino]-3-quinolinecarbonitrile

A mixture of 6.753 g (15.6 mmol) 4-[(3-chloro-4thiophenoxyphenyl)amino]-6-nitro-3-quinolinecarbonitrile, 250 ml ethanol, and 17.66 g (78.0 mmol) $SnCl_2$ dihydrate was heated to reflux under $N_2$.

Removed heat at 2 hours, added large volume of ice water, and made basic with sodium bicarbonate. Stirred for 2 hours and with mixture still basic, extracted with chloroform. Stirred organic layer with Darco, dried with sodium sulfate, filtered, stripped solvent and dried in vacuo, giving 5.996 g of yellow-brown solid: mass spectrum (electrospray m/e): M+H=403.1, 405.1.

EXAMPLE 159

4-[(3-Chloro-4thiophenoxyphenyl)amino]-6-nitro-3-quinolinecarbonitrile

A mixture of 5.00 g (21.5 mmol) 4-chloro-6-nitro-3-quinolinecarbonitrile, 250 ml ethanol, and 6.07 g (25.6 mmol) 3-chloro-4-thiophenoxyaniline was heated to reflux under $N_2$. Removed heat at about 8 hours, made basic with saturated sodium bicarbonate, stripped solvents and azeotroped with ethanol. Slurried residue with hexane and collected solids. Washed with water and dried in vacuo. Dissolved nearly completely in 400 ml ethyl acetate, stirred with Darco and filtered. Stripped solvent and boiled in hexane to remove last of the excess aniline. Dried in vacuo, giving 6.90 g of red solid: mass spectrum (electrospray m/e): M+H=433.1, 435.1.

EXAMPLE 160

N-{3-Cyano-4-[(3-cyanophenyl)amino]-6-quinolinyl}-2-propenamide

Dissolved 729 mg (2.56 mmol) 6-amino-4[(3-cyanophenyl)amino]-3-quinolinecarbonitrile in 2 ml hot DMF, added 12 ml THF and cooled to 0° C. under $N_2$. Added 392 µl (2.81 mmol) triethylamine and 234 g (2.81 mmol) acryloyl chloride. Removed ice bath after 15 minutes and stripped solvent at 2 hours. Washed residue with water and collected solids. Recrystallized from ethyl acetate and dried in vacuo, giving 318 mg of yellow solid: mass spectrum (electrospray m/e): M+H=340.1.

EXAMPLE 161

N-{3-Cyano-4-[(3-cyanophenyl)amino]-6-quinolinyl}-4-piperidino-2-butynamide

Partially dissolved 1.46 g (8.75 mmol) 4-piperidino-2-butynoic acid in 100 ml THF and chilled to 0° C. under $N_2$. Added 1.16 ml (10.5 mmol) N-methylmorpholine and 911 µl (7.00 mmol) isobutyl chloroformate and stirred for 30 minutes. Added a solution of 1.00 g (3.50 mmol) 6-amino-4-[(3-cyanophenyl)amino]-3-quinolinecarbonitrile in 8 ml pyridine. At 3.5 hours poured onto ice bath and made basic with saturated sodium bicarbonate. Extracted with ethyl acetate, dried organic layers with magnesium sulfate, filtered, and reduced solvent to a small volume. Loaded compound onto a column of silica gel and eluted with 7% methanol/ethyl acetate. Stripped solvent from desired fractions and dried in vacuo, giving 1.008 g of off-white solid: mass spectrum (electrospray m/e): 435.0.

EXAMPLE 162

6-Amino-4-[(3-cyanophenyl)amino]-3-quinolinecarbonitrile

Added 100 mg of 10% palladium on carbon to a round bottom flask under $N_2$ and covered with 50 ml ethanol. Added 1.00 g (3.17 mmol) 4-[(3-cyanophenyl)amino]-6-nitro-3-quinolinecarbonitrile and 250 µl (7.39 mmol) anhydrous hydrazine and heated to reflux. Removed heat at 2 hours and filtered hot through celite. Stripped solvent and dried in vacuo, giving 887 mg of yellow solid: mass spectrum (electrospray m/e): M+H=286.2.

EXAMPLE 163

4-[(3-Cyanophenyl)amino]-6-nitro-3-quinolinecarbonitrile

A mixture of 5.00 g (21.5 mmol) 4-chloro-6-nitro-3-quinolinecarbonitrile, 200 ml ethanol, and 3.04 g (25.8 mmol) 3-aminobenzonitrile was heated to reflux. Removed heat at 3.5 hours and made basic with saturated sodium bicarbonate. Stripped solvents and air dried. Slurried residue with hexane and collected solids. Washed with water and dried in vacuo. Boiled in large volume ethyl acetate, collected solids and dried in vacuo, giving 5.15 g of yellow-brown solid: mass spectrum (electrospray m/e): 316.0.

EXAMPLE 164

N-{3-Cyano-4-[(3-ethynylphenyl)amino]-6-quinolinyl}-2-butynamide

Dissolved 370 mg (4.40 mmol) 2-butynoic acid in 20 ml THF under $N_2$ and chilled to 0° C. Added 484 1 (4.40 mmol) N-methylmorpholine and 572 µl (4.40 mmol) isobutyl chloroformate and stirred for 10 minutes. Added a solution of 500 mg (1.76 mmol) 6-amino-4-[(3-ethynylphenyl)amino]-quinoline-3-carbonitrile in 1 ml DMF and ml THF. Removed ice bath at 15 minutes and stirred overnight at 25° C. Stripped solvent, slurried residue with water, collected solids, and dried in vacuo. Boiled in ethyl acetate, collected solids and dried in vacuo, giving 494 mg of yellow solid: mass spectrum (electrospray m/e): M+H=350.9.

EXAMPLE 165

N-{3-Cyano-4-[(3-ethynylphenyl)amino]-6-quinolinyl}-2-propenamide

Dissolved 1.00 g (3.52 mmol) 6-amino-4-[(3-ethynylphenyl)amino)-3-quinolinecarbonitrile in 2 ml hot DMF, added 12 ml THF and chilled to 0° C. under $N_2$. Added 539 µl (3.87 mmol) triethylamine and 322 µl (3.87 mmol) acryloyl chloride. Removed ice bath at 15 minutes and stripped solvent at 1.5 hours. Slurried residue in water, collected solids and air dried overnight. Recrystallized from ethyl acetate, dried in vacuo, giving 302 mg of orange solid: mass spectrum (electrospray m/e): 339.1.

EXAMPLE 166

N-{3-cyano-4-[(3-ethynylphenyl)amino]-6-quinolinyl}-4piperidino-2-butynamide

Partially dissolved 1.03 g (6.16 mmol) 4-piperidino-2-butynoic acid in 70 ml THF and chilled to 0° under $N_2$. Added 812 µl (7.38 mmol) N-methylmorpholine and 640 µl (4.92 mmol) isobutyl chloroformate. After 0.5 hour stirring, added a solution of 700 mg (2.46 mmol) 6-amino-4-[(3-ethynylphenyl)amino)-3-quinolinecarbonitrile dissolved in 5 ml pyridine. At I hours poured onto ice bath and made basic with a saturated solution of sodium bicarbonate. Extracted with ethyl acetate, dried organics with sodium sulfate, reduced to a small volume and loaded onto a column of silica gel. Eluted with 8% methanol in ethyl acetate. Stripped solvent of desired fractions and dried in vacuo, giving 641 mg of yellow-orange solid: mass spectrum (electrospray m/e): M+H=434.2.

EXAMPLE 167

6-Amino-4-(3-ethynylphenyl)amino)-3-quinolinecarbonitrile

A mixture of 2.00 g (6.36 mmol) 4-[(3-ethynylphenyl)amino]-6-nitro-3-quinolinecarbonitrile, 100 ml ethanol, and 7.19 g (31.8 mmol) SnCl, dehydrate was heated to reflux under $N_2$. Removed heat at 3.5 hours and added ice water. Made basic with sodium bicarbonate and stirred for 2 hours. Extracted with chloroform, stirred organic layer with Darco, dried with sodium sulfate, filtered, stripped solvent, and dried in vacuo, giving 1.737 g of yellow-brown solid: mass spectrum (electrospray m/e): M+H=285.2.

EXAMPLE 168

4-[(3-Ethynylphenyl)amino]-6-nitro-3-quinolinecarbonitrile

A mixture of 5.00 g (21.5 mmol) 4-chloro-6-nitro-3-quinolinecarbonitrile, 200 ml ethanol, and 3.82 g (32.6 mmol) 3-ethynylaniline was heated to reflux under $N_2$. Removed heat at 3.5 hours and added a solution of saturated sodium bicarbonate until basic. Stripped solvents and azeotroped with ethanol. Slurried residue with hexane and collected solids. Washed with water and dried in vacuo. Dissolved in ethyl acetate, stirred with Darco, filtered, stripped solvent and dried in vacuo, giving 4.544 g of yellow solid: mass spectrum (electrospray m/e): M+H=315.1.

EXAMPLE 169

N-{4-[(3-Bromophenyl)amino]-3-cyano-6-quinolinyl}-4-piperidino-2-butynamide

Partially dissolved 1.23 g (7.37 mmol) 4-piperidino-2-butynoic acid in 40 ml THF and chilled to 0° C. under $N_2$. Added 973 µl (8.4 mmol) N-methylmorpholine and 768 µl (5.9 mmol) isobutyl chloroformate. Stirred 10 minutes and added a solution of 1.00 g (2.95 mmol) 6-amino-4-[(3-bromophenyl)amino]-3-quinolinecarbonitrile in 2 ml DMF and 10 ml THF. Removed ice bath at 15 minutes and at 5 hours added 2.95 mmol more of mixed anhydride (0.493 g acid, 487 µl NMM, and 384 µl isobutyl chloroformate), stirred overnight at 25° C. Stripped solvent, slurried residue with water, and collected solids. Boiled in ethyl acetate and collected. Dissolved in 20% methanol/chloroform and coated 5 g of silica gel. Flash chromatographed with 20% methanol/ethyl acetate, stripped solvent of desired fractions and dried in vacuo, giving 122 mg of brown solid: mass spectrum (electrospray m/e): M+H=488.0, 489.9.

EXAMPLE 170

N-{4-[(3-Bromophenyl)amino]-3-cyano-6-quinolinyl}-4-dipropylamino-2-butynamide Partially dissolved 1.28 g (7.0 mmol) 4-dipropylamino-2-butynoic acid in 100 ml THF and chilled to 0° C. under $N_2$. Added 974 µl (8.85 mmol) N-methylmorpholine 768 µl (5.90 mmol) isobutyl chloroformate and stirred for 30 minutes. Added a solution of 1.00 g (2.95 mmol) ) 6-amino-4-[(3-bromophenyl)amino]-3-quinolinecarbonitrile in 8 ml pyridine. At two hours, quenched with ice water and extracted with ethyl acetate. Dried organic layer with magnesium sulfate, reduced solvent to a small volume and loaded onto a column of silica gel. Eluted with ethyl acetate, stripped solvent from desired fractions and dried in vacuo, giving 764 mg of yellow solid: mass spectrum (electrospray m/e): M+H=504, 506.4.

EXAMPLE 171

N-{4-[(3-Bromophenyl)amino]-3-cyano-6-quinolinyl}-2-morpholin-4-ylmethyl-2-propenamide Partially dissolved 1.26 g (7.37 mmol) 2-morpholin-4-ylmethyl-2-propenoic acid in 40 ml THF and chilled to 0° C. under $N_2$. Added 810 µl (7.37 mmol) N-methylmorpholine and 950 µl (7.37 mmol) isobutyl chloroformate. After stirring 10 minutes, added a solution of 1.00 g (2.95 mmol) 6-amino-4-[(3-bromophenyl)amino]-3-quinolinecarbonitrile in 2.5 ml DMF and 20 ml THF. Stripped solvent at 2 hours, slurried residue with water, collected solids, and dried in vacuo. Recrystallized from ethyl acetate and dried in vacuo, giving 334 mg of yellow-orange solid: mass spectrum (electrospray m/e): M+H=492, 494.3.

EXAMPLE 172

N-{4-[(3-Bromo-4-fluorophenyl)amino]-3-cyano-6-quinolinyl}-4-dimethylamino-2-butenamide Made 2.25 mmol of 5-bromo-but-2-enoyl chloride by mixing 386 µl (2.25 mmol) trimethylsilyl 4-bromo-but-2-enoate, 10 ml methylene chloride, 294 µl (3.38 mmol) oxalyl chloride, and 2 drops of DMF. After bubbling had subsided, removed solvent and dissolved in 10 ml THF. This solution was added to a mixture of 800 mg (2.25 mmol) 6-amino-4-[(3-bromo-4-fluorophenyl)amino]-3-quinolinecarbonitrile, 50 ml THF, and 392 µl (2.25 mmol) N,N-diisopropylethylamine chilled to 0° C. under $N_2$. At 1 hour, added dropwise to a solution of 5.62 ml of 2.0M dimethyl amine in THF (11.2 mmol) at −78° C. Removed dry ice bath after complete addition. After 2 hours, poured into a cold solution of sodium bicarbonate, extracted with ethyl acetate, dried organic layer with sodium sulfate and reduced solvent to a small volume. Loaded onto a column of silica gel and eluted with 50% methanol/ethyl acetate. Stripped solvent of desired fractions and dried in vacuo, giving 386 mg of yellow solid: mass spectrum (electrospray m/e): M+H=467.9, 469.9.

EXAMPLE 173

N-{4-[(3-Bromo-4fluorophenyl)amino]-3-cyano-6-quinolinyl}-4-diethylamino-2-butenamide Made 2.25 mmol of 5-bromo-but-2-enoyl chloride by mixing 386 µl (2.25 mmol) trimethylsilyl 4-bromo-but-2-enoate, 10 ml methylene chloride, 294 µl (3.38 mmol) oxalyl chloride, and 2 drops of DMF. After bubbling had subsided, removed solvent and dissolved in 10 ml THF. This solution was added to a mixture of 800 mg (2.25 mmol) 6-amino-4-[(3-bromo-4-fluorophenyl)amino]-3-quinolinecarbonitrile, 50 ml THF, 3 ml DMF (failed to dissolve amine) and 392 µl (2.25 mmol) N,N-diisopropylethylamine chilled to 0° C. under $N_2$. Removed ice bath at 20 minutes. At 1 hour added dropwise to a solution of 1.2 ml (11.2 mmol) diethylamine in 4.4 ml THF chilled to −78° C. Removed dry ice bath after complete addition and stirred for 3 hours. Poured into a mixture of ice and saturated sodium bicarbonate, extracted with ethyl acetate, dried organic layer with sodium sulfate and reduced solvent to a small volume. Loaded compound onto a column of silica gel, eluted with 30% methanol/ethyl acetate, stripped solvent from desired fractions and dried in vacuo, giving 321 mg of yellow-brown solid: mass spectrum (electrospray m/e): M+H=496.0, 497.9.

EXAMPLE 174

N-{4-[(3-Bromo-4-fluorophenyl)amino]-3-cyano-6-quinolinyl}-4-morpholino-2-butenamide Made 2.25 mmol of 5-bromo-but-2-enoyl chloride by mixing 386 µl (2.25 mmol) trimethylsilyl 4-bromo-but-2-enoate, 10 ml methylene chloride, 294 µl (3.38 mmol) oxalyl chloride, and 2 drops of DMF. After bubbling had subsided, removed solvent and dissolved in 10 ml THF. This solution was added to a mixture of 800 mg (2.25 mmol) 6-amino-4-[(3-bromo-4-fluorophenyl)amino]-3-quinolinecarbonitrile, 50 ml THF, and 392 µl (2.25 mmol) N,N-diisopropylethylamine chilled to 0° C. under $N_2$. At 1 hour, added the mixture dropwise to a solution of 1 ml (11.2 mmol) morpholine in 4.5 ml THF chilled to 0° C. After complete addition, removed the ice bath, and at 2 hours poured onto a mixture of ice and saturated sodium bicarbonate. Extracted with ethyl acetate, dried organic layer with sodium sulfate and reduced solvent to a small volume. Loaded onto a column of silica gel, eluted with 12% methanol/ethyl acetate, stripped solvent from desired fractions and dried in vacuo, giving 369 mg of yellow solid: mass spectrum (electrospray m/e): M+H=509.9, 511.9.

Example 175

N-{4-[(3-Bromo-4-fluorophenyl)amino]-3-cyano-7-methoxy-6-quinolinyl}-4-morpholino-2-butenamide Made 2.07 mmol of 5-bromo-but-2-enoyl chloride by mixing 363 µl (2.07 mmol) trimethylsilyl 4-bromo-but-2-enoate, 8 ml methylene chloride, 270 µl (3.10 mmol) oxalyl chloride and 2 drops of DMF. Removed solvent when bubbling subsided and dissolved in 10 ml THF. The acid chloride solution was added to a mixture of 800 mg A (2.07 mmol) 6-amino-4-[(3-bromo-4-fluorophenyl)amino]-7-methoxy-3-quinolinecarbonitrile, 50 ml THF, and 721 µl (4.14 mmol) N,N-diisopropylethylamine chilled to 0° C. under $N_2$. At 1.5 hours added this mixture to a solution of 900 g (10.4 mmol) morpholine in 4.3 ml THF at 0° C. Warmed to 25° C. after complete addition, and at 2 hours added 900 µl more morpholine. At 3 hours, poured onto a mixture of ice and saturated sodium bicarbonate, extracted with ethyl acetate, dried with sodium sulfate, and reduced solvent to a small volume. Loaded compound onto a column of silica gel, eluted with 12% methanol/ethyl acetate, stripped solvent from desired fractions, and dried in vacuo, giving 287 mg of orange-brown solid: mass spectrum (electrospray m/e): M+H=539.9, 541.9.

EXAMPLE 176

4-[(3-Bromophenyl)amino]-7-ethoxy-6-methoxy-3-quinolinecarbonitrile

A mixture of 500 mg (1.90 mmol) 4-chloro-7-ethoxy-6-methoxy-3-quinolinecarbonitrile, 20 ml ethanol, and 250 µl (2.28 mmol) 3-bromoaniline was heated to reflux under $N_2$. At 3 hours, added 103 µl (0.95 mmol) and 10 ml ethanol and refluxed overnight. Removed heat and made basic with saturated sodium bicarbonate. Stripped solvent, slurried residue with hexane, collected solids, and dried. Washed with water and dried in vacuo, giving 554 mg of tan solid: mass spectrum (electrospray m/e): M+H=398, 399.8.

EXAMPLE 177

7-Ethoxy-4-[(3-hydroxy-4-methylphenyl)amino]-6-methoxy-3-quinolinecarbonitrile

A mixture of 500 mg (1.90 mmol) 4chloro-7ethoxy-6-methoxy-3-quinolinecarbonitrile, 30 ml ethanol, and 281 mg (2.28 mmol) 3-hydroxy-4-methylaniline was heated to reflux under $N_2$ overnight. Removed heat and made basic with saturated sodium bicarbonate. Stripped solvents and slurried residue in hexane. Collected solids, washed with water, and dried in vacuo, giving 364 mg off-white solid: mass spectrum (electrospray m/e): M+H=349.9.

EXAMPLE 178

4-Chloro-7-ethoxy-6-methoxy-3-quinolinecarbonitrile

Mixed 122 mg (0.50 mmol) 7-ethoxy-1,4-dihydro-6-methoxy-4-oxo-3-quinolinecarbonitrile and 2.0 ml methylene chloride under $N_2$ and kept temperature near 25° C. Added 218 ill (2.5 mmol) oxalyl chloride and 10 µl (0.125 mmol) DMF. Stirred overnight, diluted with chloroform and stirred in saturated sodium bicarbonate until basic. Separated layers and dried organics with magnesium sulfate, stripped solvent and dried in vacuo, giving 117 mg of tan solid: mass spectrum (electrospray m/e): M+H=262.8, 264.8.

EXAMPLE 179

7-Ethoxy-1,4-dihydro-6-methoxy-4-oxo-3-quinolinecarbonitrile

Added 54.0 ml (135 mmol) n-butyl lithium to 150 ml THF and chilled to −78° C. under $N_2$. Added dropwise over 20 minutes 7.05 ml (135 mmol) acetonitrile in 200 ml THF. Stirred 15 minutes and added a solution of 17.99 g (64.2 mmol) methyl 4-ethoxy-5-methoxy-2-(dimethylaminomethyleneamino)benzoate in 150 ml THF dropwise over 20 minutes. Let stir for 0.5 hour at −78° C. Added 11.0 ml (193 mmol) acetic acid and warmed gradually to 25° C. After 2.5 hours, stripped solvent, slurried residue with water, collected solids and dried in vacuo, giving 13.025 g of yellow solid: mass spectrum (electrospray m/e): M+H=245.2.

EXAMPLE 180

Methyl 4-ethoxy-5-methoxy-2-(dimethylaminomethyleneamino)benzoate

A mixture of 15.056 g (66.9 mmol) methyl 2-amino-4-ethoxy-5-methoxybenzoate and 14.1 ml (100 mmol) N,N-dimethylformamide dimethylacetal was heated to 100° C. under $N_2$. At 4.5 hours added 4.7 ml (33.3 mmol) more DMF/DMA and removed heat at 5 hours. Stripped solvent, azeotroped with toluene, and dried in vacuo, giving 18.211 g of grey-brown solid: mass spectrum (electrospray m/e): M+H=281.3.

EXAMPLE 181

Methyl 2-amino-4-ethoxy-5-methoxybenzoate

A mixture of 24.110 g (94.5 mmol) methyl 4-ethoxy-5-methoxy-2-nitrobenzoate, 15.81 g (283 mmol) iron powder, 25.28 g (472 mmol) ammonium chloride, 135 ml water, and 350 ml methanol was heated to reflux under $N_2$. At both 3 and 5.5 hours added the same amount of iron and ammonium chloride. Removed heat at 6.5 hours, added ethyl acetate and saturated sodium bicarbonate, filtered through celite and separated layers. Washed organic layer with saturated sodium bicarbonate, dried with magnesium sulfate, stripped solvent, and dried in vacuo, giving 17.594 g of pink solid: mass spectrum (electrospray m/e): M+H=226.2.

EXAMPLE 182

Methyl 4-ethoxy-5-methoxy-2-nitrobenzoate

Dissolved 5.00 g (23.7 mmol) methyl 4-ethoxy-3-methoxybenzoate in 25 ml acetic acid under $N_2$ and added 6.1 ml (95.1 mmol) 69% nitric acid dropwise over 30 minutes. Heated to 50° C. for 1.5 hours and poured onto ice bath. Extracted with chloroform, washed with dilute sodium hydroxide solution and filtered through magnesium sulfate. Stripped solvent and dried in vacuo, giving 5.268 of off-white solid: mass spectrum (electrospray m/e): M+H=255.8.

EXAMPLE 183

Methyl 4-ethoxy-3-methoxybenzoate

A mixture of 25.0 g (137 mmol) methyl vanillate, 38.87 g (274 mmol) potassium carbonate, 500 ml DMF, and 16.5 ml (206 mmol) ethyl iodide was heated to 100° C. under $N_2$. At 2.5 hours, cooled and removed solids. Stripped solvent, and partitioned between water and methylene chloride. Stripped solvent and dried in vacuo, giving 25.85 g of white solid: mass spectrum (EI m/e): M=210.0.

EXAMPLE 184

N-[4-[(3-Chloro-4-fluorophenyl)amino]-3-cyano-6-quinolinyl]-4dimethylamino-(Z)-2-butenamide A mixture of 0.05 g (0.118 mmol) N-[4[(3-chloro-4-fluorophenyl)amino]-3-cyano-6-quinolinyl]-4-dimethylamino-2-butynamide and 6 mg of Lindlar catalyst in 10 mL of methanol was hydrogenated at room temperature overnight. The mixture was filtered through a pad of Celite. After the solvent was removed, the residue was purified by thin-layer chromatography eluted with 30% methanol in ethyl acetate. The product was dried to give 0.018 g (36%) pale yellow solid; HRMS m/z 423.1270 ($M^+$.).

EXAMPLE 185

N-[4-[(3-Chloro-4-fluorophenyl)amino]-3-cyano-6-quinolinyl]-4-methoxy-(Z)-2-butenamide A mixture of 0.05 g (0.1 18 mmol) N-[4[(3-chloro-4-fluorophenyl)amino]-3-cyano-6-quinolinyl]-4-methoxy-2-butynamide and 6 mg of Lindlar catalyst in 15 mL of methanol was hydrogenated at room temperature for 5.5 hrs. The mixture was filtered through a pad of Celite. The solvent was removed to give 0.05 g (99.7%) yellow solid; HRMS m/z 410.0928 ($M^+$.).

EXAMPLE 186

4-[[4-[(3-Bromophenyl)amino]-3-cyano-6-quinolinyl]-amino]-2-methylene-4-oxo-butanoic acid Itaconic anhydride (0.14 g, 1.25 mmol) was added portionwise to a solution of 0.1 g (0.30 mmol) of 6-amino-4-[(3-bromophenyl)amino]-3-quinolinecarbonitrile in 2 mL of ethyl acetate under $N_2$. After stirring at room temperature overnight, the reaction solution was added into ice water and hexane. The product was collected, washed with water, ether and hexane, and dried in vacuo to give 0.09 g (68%) of yellowish brown solid; ESMS m/z 451.2 ($M+H^+$).

EXAMPLE 187

N-[4-[(3-Bromophenyl)amino]-3-cyano-6-quinolinyl]-4diethylamino-2-butynamide

Isobutyl chloroformate (0.261 g, 1.91 mmol) was dropwise added into an ice cold solution of 4-diethylamino-2-butynoic acid (0.456 g, 2.94 mmol) and N-methylmorpholine (0.294 g, 2.94 mmol) in 50 mL of tetrahydrofuan under $N_2$. After stirring for 30 min, a solution of 0.5 g (1.47 mmol) of 6-amino-4-[(3-bromophenyl)amino]-3-quinolinecarbonitrile in 3 mL of pyridine was added dropwise and the mixture was stirred at 0° C. for 2 hr. The reaction was quenched with ice water, poured into saturated sodium bicarbonate and brine, and extracted with ethyl acetate. The ethyl acetate layer was concentrated and purified by thin-layer chromatography eluted with 15% methanol in ethyl acetate. The product was collected, and dried in vacuo to give 0.2 g (28.5%) of pale greenish yellow solid; ESMS m/z 476.2, 478.2 ($M+H^+$); mp 133–135° C.

EXAMPLE 188

N-[4-[(3-Bromophenyl)amino]-3-cyano-6-quinolinyl]-4-(N-ethylpiperazino)-2-butynamide Isobutyl chloroformate (0.785 g, 5.75 mmol) was dropwise added into an ice cold solution of 4-(N-ethylpiperazino)-2-butynoic acid (1.75 g, 8.85 mmol) and N-methylmorpholine (1.3453 g, 13.3 mmol) in 50 mL of tetrahydrofuan under $N_2$. After stirring for 30 min, a solution of 1.5 g (4.42 mmol) of 6-amino-4-[(3-bromophenyl)amino]-3-quinolinecarbonitrile in 10 mL of pyridine was added dropwise and the mixture was stirred at 0° C. for 2 hr. The reaction was quenched with ice water, poured into saturated sodium bicarbonate and brine, and extracted with ethyl acetate. The ethyl acetate layer was concentrated and purified by flash column chromatography. The product fractions were collected, and dried in vacuo to give 1.07 g (46%) of light brown solid; ESMS m/z 517.1, 519.1 ($M+H^+$); mp 161° C. (dec).

EXAMPLE 189

N-[4-[(3-Chloro-4-fluorophenyl)amino]-3-cyano-6-quinolinyl]-4-diethylamino-2-butynamide Isobutyl chloroformate (0.061 g, 0.448 mmol) was dropwise added into an ice cold solution of 4-diethylamino-2-butynoic acid (0.104 g, 0.672 mmol) and N-methylmorpholine (0.068 g, 0.672 mmol) in 10 mL of tetrahydrofuan under $N_2$. After stirring for 30 min, a solution of 0.1 g (0.32 mmol) of 6-amino-4-[(3-chloro-4-fluorophenyl)-amino]-3-quinolinecarbonitrile in 1.5 mL of pyridine was added dropwise and the mixture was stirred at 0° C. for 1.5 hr. The reaction was quenched with ice water, poured into saturated sodium bicarbonate and brine, and extracted with ethyl acetate. The ethyl acetate layer was concentrated and purified by thin-layer chromatography eluted with 15% methanol in ethyl acetate. The product was collected, and dried in vacuo to give 0.046 g (32%) of light brown solid; ESMS m/z 450.2, ($M+H^+$); mp 117–120° C.

EXAMPLE 190

N-[4-[(3-Bromophenyl)amino]-3-cyano-6-quinolinyl]-4-(N-methylpiperazino)-2-butynamide Isobutyl chloroformate (0.785 g, 5.75 mmol) was dropwise added into an ice cold solution of 4-(N-methylpiperazino)-2-butynoic acid (1.65 g, 8.85 mmol) and N-methylmorpholine (1.36 g, 13.3 mmol) in 10 mL of tetrahydrofuan under $N_2$. After stirring for 30 min, a solution of 1.5 g (4.42 mmol) of 6-amino-4-[(3-bromophenyl)amino]-3-quinolinecarbonitrile in 10 mL of pyridine was added dropwise and the mixture was stirred at 0° C. for 2 hr.

The reaction was quenched with ice water, poured into saturated sodium bicarbonate and brine, and extracted with ethyl acetate. The ethyl acetate layer was concentrated and purified by thin-layer chromatography eluted with 15% methanol in ethyl acetate. The product was collected, and dried in vacuo to give 0.37 (16%) of yellow solid; ESMS m/z 503, 505, (M+H$^+$); mp 190° C. (dec).

EXAMPLE 191

N-[4-[(3-Bromophenyl)amino]-3-cyano-6-quinolinyl]-4(N-isopropyl-N-methylamino)-2-butynamide Isobutyl chloroformate (0.785 g, 5.75 mmol) was dropwise added into an ice cold solution of 4-(N-isopropyl-N-methylamino)-2-butynoic acid (1.4 g, 8.84 mmol) and N-methylmorpholine (0.94 g, 9.3 mmol) in 80 mL of tetrahydrofuan under N$_2$. After stirring for 30 min, a solution of 1.5 g (4.42 mmol) of 6-amino-4-[(3-bromophenyl)-amino]-3-quinolinecarbonitrile in 15 mL of pyridine was added dropwise and the mixture was stirred at 0° C. for 2 hr. The reaction was quenched with ice water, poured into saturated sodium bicarbonate and brine, and extracted with ethyl acetate. The ethyl acetate layer was concentrated and purified by flash column chromatography. The product fractions were collected, and dried in vacuo to give 0.65 (31%) of reddish brown solid; ESMS m/z 476.0, 478.0 (M+H$^+$); mp 124–126° C.

EXAMPLE 192

N-[4-[(3-Bromophenyl)amino]-3-cyano-6-quinolinyl]-4-diisopropylamino-2-butynamide Isobutyl chloroformate (0.785 g, 5.75 mmol) was dropwise added into an ice cold solution of 4-diisopropylamino)-2-butynoic acid (1.65 g, 8.85 mmol) and N-methylmorpholine (0.94 g, 9.3 mmol) in 100 mL of tetrahydrofuan under N$_2$. After stirring for 30 min, a solution of 1.5 g (4.42 mmol) of 6-amino-4-[(3-bromophenyl)amino]-3-quinolinecarbonitrile in 15 mL of pyridine was added dropwise and the mixture was stirred at 0° C. for 2 hr. The reaction was quenched with ice water, poured into saturated sodium bicarbonate and brine, and extracted with ethyl acetate. The ethyl acetate layer was concentrated and purified by flash column chromatography. The product fractions were collected, and dried in vacuo to give 1.08 (48%) of light brown solid; ESMS m/z 504.1, 506.1 (M+H$^+$); mp 130° C. (dec).

EXAMPLE 193

N-[4-[(3-Chloro-4-fluorophenyl)amino]-3-cyano-6-quinolinyl]-4-dimethylamino-2-butynamide Isobutyl chloroformate (0.85 g, 6.2 mmol) was dropwise added into an ice cold solution of 4-dimethylamino-2-butynoic acid (1.85 g, 14.4 mmol) and N-methylmorpholine (1.5 g, 14.8 mmol) in 100 mL of tetrahydrofuan under N$_2$. After stirring for 30 min, a solution of 1.5 g (4.79 mmol) of 6-amino-4-[(3-chloro-4fluorophenyl)amino]-3-quinolinecarbonitrile in 15 mL of pyridine was added dropwise and the mixture was stirred at 0° C. for 2 hr. The reaction was quenched with ice water, poured into saturated sodium bicarbonate and brine, and extracted with ethyl acetate. The ethyl acetate layer was concentrated and purified by flash column chromatography. The product fractions were collected, and dried in vacuo to give 0.47 (23%) of reddish brown solid; ESMS m/z 422.0 (M+H$^+$); mp 225° C. (dec).

EXAMPLE 194

N-[4-[(3-Chloro-4-fluorophenyl)amino]-3-cyano-6-quinolinyl]-4-methoxy-2-butynamide Isobutyl chloroformate (0.85 g, 6.2 mmol) was dropwise added into an ice cold solution of 4-methoxy-2-butynoic acid (1.1 g, 9.6 mmol) and N-methylmorpholine (1.02 g, 10 mmol) in 100 mL of tetrahydrofuan under N$_2$. After stirring for 30 min, a solution of 1.5 g (4.79 mmol) of 6-amino-4-[(3-chloro-4-fluorophenyl)amino]-3-quinolinecarbonitrile in 15 mL of pyridine was added dropwise and the mixture was stirred at 0° C. for 3 hr. The reaction was quenched with ice water, poured into saturated sodium bicarbonate and brine, and extracted with ethyl acetate. The ethyl acetate layer was concentrated and purified by flash column chromatography. The product fractions were collected, and dried in vacuo to give 0.73 (37%) of light yellowish brown solid; ESMS m/z 409(M+H$^+$); mp 170–171).

EXAMPLE 195

4-[(3-Bromo-4-fluorophenyl)amino]-6-nitro-3-quinolinecarbonitrile

A mixture of 3.8 g (16.33 mmol) of 4-chloro-6-nitro-3-quinolinecarbonitrile and 3.7 g (20 mmol) of 3-bromo-4-fluoroaniline in 200 mL of ethanol was refluxed for 3hr. After the solvent was removed, the residue as dissolved in ethyl acetate and washed with sodium bicarbonate. The product was collected as a pale yellow solid, 6.5 g (71%); ESMS m/z 387.3, 389.2, mp 269–270° C. (dec).

EXAMPLE 196

6-amino-4-[(3-Bromo-4fluorophenyl)amino]-3-quinolinecarbonitrile

A mixture of 8 g (20.67 mmol) of 4-[(3-chloro-4-fluorophenyl)amino]-6-nitro-3-quinolinecarbonitrile, 4 g (72.35 mmol) of iron dust and 8.9 g (165.36 mmol) of ammonium chloride in 240 mL of methanol and water (2:1 ratio) was refluxed for 4 hr. The mixture was filtered hot and washed with methanol and water. The product precipitated from the filtrate upon cooling. The solid was collected and dried in vacuo to give 5.8 g (79%) yellowish brown solid; ESMS m/z 356.8, 358.8, mp 210–212° C.

EXAMPLE 197

N-[4-[(3-Bromo-4-fluorophenyl)amino]-3-cyano-6-quinolinyl]-4-dimethylamino-2-butynamide Isobutyl chloroformate (0.373 g, 2.73 mmol) was dropwise added into an ice cold solution of 4-dimethylamino-2-butynoic acid (0.8 g, 6.3 mmol) and N-methylmorpholine (0.658 g, 6.5 mmol) in 80 mL of tetrahydrofuan under N$_2$. After stirring for 30 min, a solution of 10.65 g (2.1 mmol) of 6-amino-4-[(3-bromo-4-fluorophenyl)-amino]-3-quinolinecarbonitrile in 10 mL of pyridine was added dropwise and the mixture was stirred at 0° C. for 2.5 hr. The reaction was quenched with ice water, poured into saturated sodium bicarbonate and brine, and extracted with ethyl acetate. The ethyl acetate layer was concentrated and purified by flash column chromatography. The product fractions were collected, and dried in vacuo to give 0.33 (33%) of yellow solid; ESMS m/z 465.9, 467.9(M+H$^+$); mp 228–231° C.

EXAMPLE 198

4-Dimethylamino-but-2-enoic acid [4-(3-bromo-phenylamino)-3-cyano-7-methoxy-quinolin-6-yl]-amide To a mixture of 1.9 g (5.1 mmol) of 4-[(3-bromophenyl)amino]-7-methoxy-6-amino-3-quinolinecarbonitrile and 5.3 ml (31 mmol) of Hunig's base in 110 ml of dry THF at 0° C., with stirring, was added a THF solution containing 5.7 g (31 mmol) of 4-bromo crotonyl chloride dropwise. The mixture was stirred for additional 0.5 hour after addition. 100 ml of saturated sodium chloride solution was added to the reaction mixture, then it was extracted with ethyl acetate. The ethyl acetate solution was dried over sodium sulfate and then was added to 40 ml of dimethyl amine solution (2.0 M in THF) at 0° C. dropwise. The solution was stirred an additional 0.5 hour. The mixture was poured into diluted sodium bicarbonate solution. The organic layer was separated and dried over sodium sulfate. Chromatography gave 1.4 g of beige solid: mass spectrum (electrospray, m/e): M+H 480.0 and 481.9.

EXAMPLE 199

4-Diethylamino-but-2-enoic acid [4-(3-bromo-phenylamino)-3-cyano-7-methoxy-quinolin-6-yl]-amide To a mixture of 0.5 g (1.36 mmol) of 4-[(3-bromophenyl)amino]-7-methoxy-6-amino-3-quinolinecarbonitrile and 0.48 ml (2.7 mmol) of Hunig's base in 50 ml of dry THF at 0° C., with stirring, was added a THF solution containing 0.50 g (2.7 mmol) of 4-bromo crotonyl chloride dropwise. The mixture was stirred for additional 0.5 hour after addition and then was added to a solution of 4.2 ml (40.8 mmol) diethyl amine in 50 ml of THF at 0° C. dropwise. The solution was stirred for an additional 0.5 hour. The mixture was poured into diluted sodium bicarbonate solution. The organic layer was separated and dried over sodium sulfate. Chromatography gave 0.2 g of white solid: mass spectrum (electrospray, m/e): M+H 508.1 and 510.8.

EXAMPLE 200

4-Morpholin-4-yl-but-2-enoic acid [4-(3-bromo-phenylamino)-3-cyano-7-methoxy-quinolin-6-yl]-amide To a mixture of 0.69 g (1.87 mmol) of 4-[(3-Bromophenyl)amino]-7-methoxy-6-amino-3-quinolinecarbonitrile and 0.98 ml (5.6 mmol) of Hunig's base in 50 ml of dry THF at 0° C., with stirring, was added a THF solution containing 0.86 g (5 mmol) of 4-bromocrotonyl chloride dropwise. The mixture was stirred for a additional 0.5 hour and then was added to a solution of 4.89 ml (56 mmol) morpholine in 50 ml THF at 0° C. dropwise. The solution was stirred an additional 0.5 hour and then the mixture was poured into diluted sodium bicarbonate solution. The organic layer was separated and dried over sodium sulfate. The residue was chromatographed to give 0.38 g of grey solid: mass spectrum (electrospray, m/e): M+H 521.9 and 523.8.

EXAMPLE 201

4-(3-Chloro-4-fluoro-phenylamino)-7-methoxy-6-nitro-quinoline-3-carbonitrile

A mixture of 4.4 g (16.7 mmol) of 4-chloro-7-methoxy-nitro-3-quinolinecarbonitrile and 2.67 g (18.3 mmol) of 3-chloro-4-fluoro aniline in 110 ml of methoxyethanol was refluxed under nitrogen for 4 hours. The reaction mixture was diluted with ethyl acetate and wash with sodium bicarbonate solution and sodium chloride solution. The organic layer was dried over sodium sulfate and then the solvent was removed under vacuum. The residue was chromatographed on silica gel eluting with mixture of ethyl acetate and methanol to give 3 g yellow solid: mass spectrum (electrospray, m/e): 372.9.

EXAMPLE 202

6-Amino-4-(3-chloro-4-fluoro-phenylamino)-7-methoxy-quinoline-3-carbonitrile

A mixture of 4.88 g (13 mmol) of 4-[(3-chloro-4-fluorophenyl)amino]-7-methoxy-6-nitro-quinoline-3-carbonitrile, 5.2 g (97.5 mmol) of ammonium chloride, and 3.3 g (58.5 mmol) iron was stirred at reflux in 60 ml of water and 60 ml of methanol for 4.5 hours. The mixture was diluted with 500 ml of hot ethyl acetate and the hot mixture was filtered. The filtration was washed with saturated sodium chloride solution and then the organic layer was dried over sodium sulfate. The solvent was removed and the residue was chromatographed on silica gel eluting with mixture of ethyl acetate and methanol to give 3.38 g of yellow solid: mass spectrum (electrospray, m/e): M+H 343.4.

EXAMPLE 203

4-Dimethylamino-but-2-enoic acid [4-(3-chloro-4-fluoro-phenylamino)-3-cyano-7-methoxy-quinolin-6-yl]-amide To a mixture of 1.08 g (3.1 mmol) of 4-[(3-chloro-4-fluorophenyl)amino]-7-methoxy-6-amino-quinoline-3-carbonitrile and 1.7 ml (9.7 mmol) of Hunig's base in 30 ml of dry THF at 0° C., with stirring, was added a THF solution containing 1.99 g (9.3 mmol) of 4-bromo crotonyl chloride dropwise. The mixture was stirred for additional 0.5 hour at 0° C. under nitrogen. 50 ml of saturated sodium chloride solution was introduced to the reaction mixture, then it was extracted with ethyl acetate. The ethyl acetate solution was separated and dried over sodium sulfate and then it was added to 31 ml of dimethyl amine solution (2.0 M in THF) at 0° C. dropwise. After addition, the solution was stirred for another hour at room temperature. The mixture was poured into diluted sodium bicarbonate solution. The organic layer was separated and the residue was chromatographed to give 0.86 grams of white solid: mass spectrum (electrospray, m/e):

EXAMPLE 204

4-Diethylamino-but-2-enoic acid [4-(3-chloro-4-fluoro-phenylamino)-3-cyano-7-methoxy-quinolin-6-yl]-amide To a mixture of 1.1 g (3.2 mmol) of 4-[3-chloro-4-fluorophenyl)amino]-7-methoxy-6-amino-3-quinolinecarbonitrile and 2.24 ml (12.8 mmol) of Hunig's base in 40 ml of dry THF at 0° C., with stirring, was added a THF solution containing 2.34 g (12.8 mmol) of 4-bromo crotonyl chloride dropwise. The mixture was stirred for additional 0.5 hour at 0° C. 50 ml of saturated sodium chloride solution was added to the reaction mixture and then it was extracted with ethyl acetate. The ethyl acetate solution was dried over sodium sulfate and added to a solution of 6.6 ml (64 mmol) diethyl amine in 5 ml of THF at 0° C. dropwise. The solution was stirred an additional hour at 0° C. The mixture was poured into diluted sodium bicarbonate solution. The organic layer was separated and dried over sodium sulfate. The residue was chromatographed and followed by recrystallization to give 0.62 grams of white solid: mass spectrum (electrospray, m/e): M+H 482.0.

EXAMPLE 205

4-Morpholin-4-yl-but-2-enoic acid [4-(3-chloro-4-fluoro-phenylamino)-3-cyano-7-methoxy-quinolin-6-yl]-amide To a mixture of 1.2 g (3.5 mmol) of 4-[(3-chloro-4-fluorophenyl)amino]-7-methoxy-6-amino-quinoline-3-carbonitrile and 2.44 ml (14 mmol) of Hunig's base in 50 ml of dry THF at 0° C., with stirring, was added a THF solution containing 2.57 g (14 mmol) of 4-bromo crotonyl chloride dropwise. The mixture was stirred for an additional hour at 0° C. 50 ml of saturated sodium chloride solution was added to the reaction mixture, then it was extracted with ethyl acetate. The ethyl acetate solution was dried over sodium sulfate and then was added to a solution of 4.58 ml (52.5 mmol) morpholine in mL of THF at 0° C. dropwise. The solution was stirred an overnight at 0° C. The mixture was poured into diluted sodium bicarbonate solution. The organic layer dried over sodium sulfate. Chromatography gave 0.83 grams off-white solid: mass spectrum (electrospray, m/e): M+H 496.0.

EXAMPLE 206

4-(3-Bromo-4-fluoro-phenylamino)-7-methoxy-6-nitro-quinoline-3-carbonitrile

A mixture of 3.52 g (9.7 mmol) of 4-chloro-7-methoxy-6-nitro-3-quinolinecarbonitrile and 2.0 g (10.7 mmol) of 3-bromo-4-fluoro aniline in 150 ml of methoxyethanol was refluxed under nitrogen for 5.5 hours. The reaction mixture was diluted with ethyl acetate and wash with sodium bicarbonate solution and sodium chloride solution. The organic layer was dried with sodium sulfate and then solvent was removed under vacuum. The residue was chromatographed on silica gel eluting with mixture of ethyl acetate and methanol to give 3 g of yellow solid: mass spectrum (electrospray, m/e): 416.8 and 418.8.

EXAMPLE 207

6-Amino-4-(3-bromo-4-fluoro-phenylamino)-7-methoxy-quinoline-3-carbonitrile

A mixture of 2.9 g (6.95 mmol) of 4-[(3-bromo-4-fluorophenyl)amino]7-methoxy-6-nitro-quinoline-3-carbonitrile, 6.5 g (121.6 mmol) of ammonium chloride and 4.05 g (73 mmol) of iron in 50 ml of water and 50 ml of methanol for 6 hours. The mixture was diluted with hot ethyl acetate and the hot mixture was filtered. The filtration was washed with saturated sodium chloride solution then the organic layer was dried over sodium sulfate. The solvent was removed and the residue was chromatographed on silica gel eluting with mixture of ethyl acetate and methanol to give 2.11 g of light yellow solid: mass spectrum (electrospray, m/e): M+H 386.7 and 388.8.

EXAMPLE 208

4-Dimethylamino-but-2-enoic acid [4-(3-bromo-4-fluoro-phenylamino)-3-cyano-7-methoxy-quinolin-6-yl]-amide To a mixture of 0.77 g (1.98 mmol) of 4-(3-bromo-4-fluorophenyl)amino]-7-methoxy-6-amino-quinoline-3-carbonitrile and 3.5 ml (20 mmol) of Hunig's base in 35 ml of dry THF at 0° C., with stirring, was added a THF solution containing 2.2 g (12 mmol) of 4-bromo crotonyl chloride dropwise. The mixture was stirred for additional 30 minutes at 0° C. 50 ml of saturated sodium chloride solution was added to the reaction mixture, then it was extracted with ethyl acetate. The ethyl acetate solution was dried over sodium sulfate and then was added to 15 ml of dimethyl amine (2.0 M in THF) at 0° C. dropwise. The solution was stirred an additional hour at room temperature. The mixture was poured into diluted sodium bicarbonate solution. The organic layer was dried over sodium sulfate and the solvent was removed under vacuum. The residue was chromatographed gave 0.55 g beige solid: mass spectrum (electrospray, m/e): M+H 498.0 and 500.0.

EXAMPLE 209

4Diethylamino-but-2-enoic acid [4(3-bromo-4-fluoro-phenylamino)-3-cyano-7-methoxy-quinolin-6-yl]-amide To a mixture of 0.77 g (1.98 mmol) of 4-[(3-bromo-4-fluorophenyl)amino]-7-methoxy-6-amino-quinoline-3-carbonitrile and 3.5 ml (20 mmol) of Hunig's base in 35 ml of dry THF at 0° C., with stirring, was added a THF solution containing 2.2 g (12 mmol) of 4-bromo crotonyl chloride dropwise. The mixture was stirred for additional 30 minutes at 0° C. 50 ml of saturated NaCl solution was added to the reaction mixture, then it was extracted with ethyl acetate. The ethyl acetate solution was dried over sodium sulfate and then was added to a solution of 3.1 ml (30 mmol) of diethyl amine in 5 ml of THF at 0° C. dropwise. The solution was stirred an additional hour at 0° C. and 30 minutes at room temperature. The mixture was poured into diluted sodium bicarbonate solution. The organic layer was dried over sodium sulfate and solvent was removed under vacuum. The residue was chromatographed to give 0.4 g off-white solid: mass spectrum (electrospray, m/e): M+H 525.9 and 527.9.

EXAMPLE 210

7-Ethoxy-4-hydroxy-quinoline-3-carbonitrile

A mixture of 10 g (73 mmol) of 3-ethoxy aniline and 12.3 g (73 mmol) of ethyl (ethoxymethylene) cyanoacetate was heated in 90 ml of Dowther at 140° C. for 7 hours. To this mixture was added 250 ml of Dowther. The solution was stirred and refluxed under nitrogen for 12 hours with periodically distilling out the eliminated ethanol. The mixture was cooled to room temperature and the solid was collected and washed with hexane. The crude solid was treated with boiling ethanol and then filtered to give 9.86 g of brown solid: mass spectrum (electrospray, m/e): M+H 214.7.

EXAMPLE 211

7-Ethoxy-4-hydroxy-6-nitro-quinoline-3-carbonitrile

To a suspension of 5 g (23 mmol) of 7-Ethoxy-4-hydroxy-quinoline-3-carbonitrile in 75 ml of trifluroacetic anhydride was added 5.5 g (69 mmol) of ammonium nitrate over a period of 6 hours at room temperature. Excess anhydride was removed at reduced pressure at 45° C. The residue was stirred with 300 ml of water. The solid was collected and treated with boiling ethanol to give 3.68 g of tin solid: mass spectrum (electrospray, m/e) M+H 259.8.

EXAMPLE 212

4-Chloro-7-ethoxy-6-nitro-quinoline-3-carbonitrile

A mixture of 3.45 g (13 mmol) of 7-Ethoxy-4-hydroxy-6-nitro-quinoline-3-carbonitrile, 5.55 g (26 mmol) of phosphorous pentachloride, and 10 ml of phosphorous oxychloride was refluxed for 3 hours. The mixture was diluted with hexane and the solid was collected. The solid was dissolved in 500 ml of ethyl acetate and washed with cold diluted sodium hydroxide solution. The solution was dried over magnesium sulfate and filtered through a pad of silica gel. The solvent was removed giving 2.1 g of beige solid: mass spectrum (electrospray, m/e) M+H 277.7.

EXAMPLE 213

4-(3-Bromo-phenylamino)-7-ethoxy-6-nitro-quinoline-3-carbonitrile

A mixture of 2.1 g (7.6 mmol) of 4-chloro-7-ethoxy-6-nitro-3-quinolinecarbonitrile and 0.91 ml (8.3 mmol) of 3-bromo aniline in 100 ml ethanol was refluxed under nitrogen for 4.5 hours. The reaction mixture was poured into diluted sodium bicarbonate solution. Ethanol was removed under vacuum. The mixture was diluted with ethyl acetate and the organic layer was separated and dried over sodium sulfate. The solution was concentrated and solid was collected and then washed with hexane. Upon drying, 2.6 g of yellow solid obtained: mass spectrum (electrospray, m/e) M+H 412.8 and 414.9.

EXAMPLE 214

6-Amino-4-(3-bromo-phenylamino)-7-ethoxy-quinoline-3-carbonitrile

A mixture of 2.5 g (6 mmol) of 4-[(3-bromophenyl)amino]-7-ethoxy-6-nitro-quinoline-3-carbonitrile, 2.4 g (45 mmol) of ammonium chloride, and 1.5 g (27 mmol) iron was stirred at reflux in 40 ml of water and 40 ml of methanol for 4 hours. The mixture was diluted with 500 ml of hot ethyl acetate and the hot mixture was filtered. The filtration was washed with saturated sodium chloride solution and then the organic layer was dried over sodium sulfate. The solution was concentrated and 1.5 of beige solid was collected: mass spectrum (electrospray, m/e): M+H 382.8 and 384.8.

EXAMPLE 215

4-Bromo-but-2-enoic acid [4-(3-bromo-phenylamino)-3-cyano-7-ethoxy-quinolin-6-yl]-amide To a mixture of 1.34 g (3.5 mmol) of 4-[3-bromo-phenyl)amino]-7-ethoxy-6-amino-3-quinolinecarbonitrile and 3.66 ml (21 mmol) of Hunig's base in 80 ml of dry THF at 0° C., with stirring, was added a THF solution containing 3.85 g (21 mmol) of 4-bromo crotonyl chloride dropwise. The mixture was stirred for additional 30 minutes at 0° C. 50 ml of saturated sodium chloride solution was added to the reaction mixture, then it was extracted with ethyl acetate. The ethyl acetate solution was dried over sodium sulfate and then the drying agent was filtered off. This solution was used without further characterization.

EXAMPLE 216

4-Dimethylamino-but-2-enoic acid [4-(3-bromo-phenylamino)-3-cyano-7-ethoxy-quinolin-6-yl]-amide A one-third portion of the solution from example 18 was added dropwise to 8.75 ml (17.5 mmol) of dimethyl amine at 0° C. The mixture was stirred for an additional 30 minutes at 0° C. The mixture was diluted with sodium bicarbonate solution and then the organic layer was separated and dried. The solvent was removed under vacuum and the residue was chromatographed on silica gel eluting with a mixture of ethyl acetate and methanol giving 0.32 g beige solid: mass spectrum (electrospray, m/e) M+H, 494.0 and 496.0.

EXAMPLE 217

4-Diethylamino-but-2-enoic acid [4-(3-bromo-phenylamino)-3-cyano-7-ethoxy-quinolin-6-yl]-amide A one-third portion of the solution from example 18 was added dropwise to a solution of 1.81 ml (17.5 mmol) of diethyl amine in 5 ml of THF at 0° C. The mixture was stirred for an additional 30 minutes at 0° C. The mixture was diluted with sodium bicarbonate solution and then the organic layer was separated and dried. The solvent was removed under vacuum and the residue was chromatographed on silica gel eluting with a mixture of ethyl acetate and methanol giving 0.22 g beige solid: mass spectrum (electrospray, m/e) M+H, 522.0 and 524.0.

EXAMPLE 218

4-Morpholin-4-yl-but-2-enoic acid [4-(3-bromo-phenylamino)-3-cyano-7-ethoxy-quinolin-6-yl]-amide A one-third portion of the solution from example 18 was added dropwise to a solution of 1.57 ml (18 mmol) of morpholine in 5 ml of THF at 0° C. The mixture was stirred for an additional 30 minutes at 0° C. The mixture was diluted with sodium bicarbonate solution and then the organic layer was separated and dried. The solvent was removed under vacuum and the residue was chromatographed on silica gel eluting with a mixture of ethyl acetate and methanol giving 0.37 g white solid: mass spectrum (electrospray, m/e) M+H, 535.9 and 538.0.

EXAMPLE 219

8-Methoxy-4-hydroxy-6-nitro-quinoline-3-carbonitrile

A mixture of 12.6 g (75 mmol) of 2-methoxy-4-nitro aniline and 12.7 g (75 mmol) of ethyl (ethoxymethylene) cyanoacetate was heated in 100 ml of Dowther at 120° C. for overnight and 180° C. for 20 hours. To this mixture was added 300 ml of Dowther. The solution was stirred and refluxed under nitrogen for 12 hours with periodically distilling out the eliminated ethanol. The mixture was cooled to room temperature and the solid was collected and washed with hexane. The crude solid was treated with boiling ethanol and then filtered to give 12 g of brown solid: mass spectrum (electrospray, m/e): M+H 245.8.

EXAMPLE 220

4-Chloro-8-methoxy-6-nitro-quinoline-3-carbonitrile

A mixture of 4 g (16 mmol) of 8-Methoxy-4-hydroxy-6-nitro-quinoline-3-carbonitrile, 6.66 g (32 mmol) of phosphorous pentachloride, and 15 ml of phosphorous oxychloride was refluxed for 2.5 hours. The mixture was diluted with hexane and the solid was collected. The solid was dissolved in 500 ml of ethyl acetate and washed with cold diluted sodium hydroxide solution. The solution was dried over magnesium sulfate and filtered through a pad of silica gel. The solvent was removed giving 2.05 g of tan solid: mass spectrum (electrospray, m/e) M+H 263.7.

EXAMPLE 221

6-nitro-4-(3-bromo-phenylamino)-8-methoxy-quinoline-3-carbonitrile

A mixture of 1.9 g (7.6 mmol) of 4-chloro-8-methoxy-6-nitro-quinoline-3-carbonitrile and 0.86 ml (8.3 mmol) of 3-bromo aniline in 95 ml ethanol was refluxed under nitrogen for 5 hours. The reaction mixture was poured into diluted sodium bicarbonate solution. Ethanol was removed under vacuum. The mixture was diluted with ethyl acetate and the organic layer was separated and dried over sodium chloride. The solution was concentrated and solid was collected and then washed with hexane. Upon drying, 2.3 g of yellow solid obtained: mass spectrum (electrospray, m/e) M+H 398.8 and 400.8.

EXAMPLE 222

6-Amino-4-(3-bromo-phenylamino)-8-methoxy-quinoline-3-carbonitrile

A mixture of 2.15 g (5 mmol) of 4-[(3-bromophenyl)amino]-8-methoxy-6-nitro-quinoline-3-carbonitrile, 1.95 g (37.5 mmol) of ammonium chloride, and 1.26 g (22.5 mmol) iron was stirred at reflux in 40 ml of water and 40 ml of methanol for 3 hours. The mixture was diluted with 500 ml of hot ethyl acetate and the hot mixture was filtered. The filtration was washed with saturated sodium chloride solution and then the organic layer was dried over sodium sulfate. The solution was concentrated and 0.43 of dark yellow solid was collected: mass spectrum (electrospray, m/e): M+H 368.9 and 370.9.

EXAMPLE 223

4-Bromo-but-2-enoic acid [4-(3-bromo-phenylamino)-3-cyano-8-methoxy-quinolin-6-yl]-amide To a mixture of 1.05 g (2.8 mmol) of 4-[3-bromo-phenyl) amino]-8-methoxy-6-amino-3-quinolinecarbonitrile and 3.9 ml (22.4 mmol) of Hunig's base in 50 ml of dry THF at 0° C., with stirring, was added a THF solution containing 4.11 g (22.4 mmol) of 4-bromo crotonylchloride dropwise. The mixture was stirred for additional 1 hour at 0° C. 50 mL of saturated sodium chloride solution was added to the reaction mixture, then it was extracted with ethyl acetate. The ethyl acetate solution was dried over sodium sulfate and then the drying agent was filtered off. This solution was used without further characterization.

EXAMPLE 224

4-Dimethylamino-but-2-enoic acid [4-(3-bromo-phenylamino)-3-cyano-8-methoxy-quinolin-6-yl]-amide A one-third portion of the solution form example 26 was added dropwise to a solution of 7 ml (14 mmol) of dimethyl amine (2.0 M in THF) at 0° C. The mixture was stirred for an additional 30 minutes at 0° C. The mixture was diluted with sodium bicarbonate solution and then the organic layer was separated and dried. The solvent was removed under vacuum and the residue was chromatographed on silica gel eluting with a mixture of ethyl acetate and methanol giving 0.22 g tin solid: mass spectrum (electrospray, m/e) M+H, 480.0 and 482.0.

EXAMPLE 225

4-Diethylamino-but-2-enoic acid [4-(3-bromo-phenylamino)-3-cyano-8-methoxy-quinolin-6-yl]-amide A one-third portion of the solution from example 26 was added dropwise to a solution of 1.4 ml (14 mmol) of diethyl amine in 5 ml of THF at 0° C. The mixture was stirred for an additional 30 minutes at 0° C. The mixture was diluted with sodium bicarbonate solution and then the organic layer was separated and dried. The solvent was removed under vacuum and the residue was chromatographed on silica gel eluting with a mixture of ethyl acetate and methanol giving 95 mg tin solid: mass spectrum (electrospray, m/e) M+H, 509.9 and 511.0.

EXAMPLE 226

4-Morpholin-4-yl-but-2-enoic acid [4-(3-bromo-phenylamino)-3-cyano-8-methoxy-quinolin-6-yl]-amide A one-third portion of the solution from example 26 was added dropwise to a solution of 1.2 ml (14 mmol) of morpholine in 5 ml of THF at 0° C. The mixture was stirred for an additional 30 minutes at 0° C. The mixture was diluted with sodium bicarbonate solution and then the organic layer was separated and dried. The solvent was removed under vacuum and the residue was chromatographed on silica gel eluting with a mixture of ethyl acetate and methanol giving 0.21 g yellow solid: mass spectrum (electrospray, m/e) M+H, 522.0 and 524.0.

EXAMPLE 227

4-Dimethylamino-but-2-ynoic acid [4-(3-bromo-phenylamino)-3-cyano-7-methoxy-quinol-6-yl]-amide Isobutyl chloroformate 6.9 ml (5.4 mmol) and N-methylmorpholine 1.19 ml (10.8 mmol) were added to an ice-cold solution of 1.37 g (10.8 mmol) of 4-dimethylamino-2-butynoic acid in 60 ml of THF. After stirring for 10 minutes, a solution of 1 g (2.7 mmol) 4-[(3-bromophenyl)amino]-7-methoxy-6-amino-quinoline-3-carbonitrile in 10 ml of pyridine was introduced. The reaction mixture was stirred overnight at 0° C. The solvent was evaporated and the residue was stirred in diluted sodium bicarbonate. The solution was then extracted with ethyl acetate. The ethyl acetate solution was dried and removed under vacuum. The residue was chromatographed to give 0.18 g of tin solid: mass spectrum (electrospray, m/e) 478.0 and 480.0.

EXAMPLE 228

4-(4-Chloro-2-fluoro-phenylamino)-6,7-dimethoxy-quinoline-3-carbonitrile

A mixture of 2.0 g of 4-chloro-6,7-dimethoxy-3-quinolinecarbonitrile, 1.46 g of 4-chloro-2-fluoroaniline, 0.925 g of pyridine hydrochloride, and 125 ml of ethoxyethanol was stirred under nitrogen, at reflux temperature for 1 h. The mixture was cooled and added to 1000 ml of water. To this mixture was added sodium carbonate to pH 9. The product was collected, washed with water, and dried to give 2.61 g of 4-(4-chloro-2 -fluoro-phenylamino)-6,7-dimethoxy-quinoline-3-carbonitrile as a solid, mp 139–141° C.; mass spectrum (electrospray, m/e): M+H 357.9.

EXAMPLE 229

4(3-Hydroxy-4-methyl-phenylamino)-6,7-dimethoxyquinoline-3-carbonitrile

A mixture of 2.98 g of 4chloro-6,7-dimethoxy-3-quinolinecarbonitrile, 1.85 g of 5-amino-o-cresol, 1.39 g of pyridine hydrochloride, and 200 ml of ethoxyethanol was stirred under nitrogen, at reflux temperature for 1 h. The mixture was cooled and added to 1000 ml of water. To this mixture was added sodium carbonate to pH 9. The product was collected, washed with water, and dried to give 3.27 g of 4-(3-hydroxy-4-methyl-phenylamino)-6,7-dimethoxy-quinoline-3-carbonitrile as a solid, mp 222–224° C.; mass spectrum (EI, m/e): M 335.1269.

EXAMPLE 230

4-Hydroxy-6,7,8-trimethoxy-quinoline-3-carbonitrile

A mixture of 4.82 g of methyl 3,4,5-trimethoxyanthranilate in 20 ml of N,N-dimethylformamide dimethyl acetal was refluxed for 18 hours and concentrated in vacuo. The crude amidine product was used in the next step without further purification. To 25 ml of tetrahydrofuran at −78° C. was added 17.6 ml of 2.5M n-butyllithium in hexanes. Then 2.35 ml of acetonitrile in 45 ml of tetrahydrofuran was added dropwise. The mixture was stirred at −78° C. for 15 minutes. Then a solution of the crude amidine in 30 ml of tetrahydrofuran was added dropwise. The mixture was stirred at −78° C. for minutes, then 5.7 ml of acetic acid was added. The mixture was warmed to room temperature, and 100 ml of water was added. The product was collected, washed with water, and dried to give 4.14 g of 4-hydroxy-6,7,8-trimethoxy-quinoline-3-carbonitrile as a solid, mp 280° C. (decomposed); mass spectrum (electrospray, m/e): M+H 261.2.

EXAMPLE 231

4-Chloro-6,7,8-trimethoxy-quinoline-3-carbonitrile

A stirred mixture of 1.30 g of 4-hydroxy-6,7,8-trimethoxy-quinoline-3-carbonitrile, 10 ml of phosphorous oxychloride, and 1 drop of N,N-dimethylformamide was refluxed for 10 minutes and evaporated free of volatile matter. The residue was stirred with 20 ml of 5% methyl alcohol in ethyl acetate. The product was collected and dried to give 1.12 g of 4-chloro-6,7,8-trimethoxy-quinoline-3-carbonitrile as a solid, mp 161–163° C.; mass spectrum (EI, m/e): M 278.0452.

EXAMPLE 232

4-(3-Dimethylamino-phenylamino)-6.7.8-trimethoxy-quinoline-3-carbonitrile

A mixture of 0.279 g of 4-chloro-6,7,8-trimethoxy-quinoline-3-carbonitrile, 0.23 g of N,N-dimethyl-1,3-phenylenediamine dihydrochloride, 0.2 ml of pyridine, and 15 ml of ethoxyethanol was stirred under nitrogen, at reflux temperature for 30 minutes. The mixture was cooled and added to 100 ml of water. To this mixture was added sodium carbonate to pH 9. The product was collected, washed with water, and dried to give 0.251 g of 4-(3-dimethylamino-phenylamino)-6,7,8-trimethoxy-quinoline-3-carbonitrile as a solid, mp 142–144° C.; mass spectrum (EI, m/e): M 378.1685.

EXAMPLE 233

4-(3-Hydroxy-4-methyl-phenylamino)-6,7,8-trimethoxy-quinoline-3-carbonitrile

A mixture of 0.279 g of 4-chloro-6,7,8-trimethoxy-quinoline-3-carbonitrile, 0.148 g of 5-amino-o-cresol, and 10 ml of ethoxyethanol was stirred under nitrogen, at reflux temperature for 30 minutes. The mixture was cooled and added to 100 ml of water. To this mixture was added sodium carbonate to pH 9. The product was collected, washed with water, and dried to give 0.279 g of 4-(3-hydroxy-4-methyl-phenylamino)-6,7,8-trimethoxy-quinoline-3-carbonitrile as a solid, mp 200° C. (decomposed); mass spectrum (EI, m/e): M 365.1356.

EXAMPLE 234

4-(4-Chloro-2-fluoro-phenylamino)-6,7,8-trimethoxy-quinoline-3-carbonitrile

A mixture of 0.279 g of 4-chloro-6,7,8-trimethoxy-quinoline-3-carbonitrile, 0.177 g of 4-chloro-2-fluoroaniline, and 10 ml of ethoxyethanol was stirred under nitrogen, at reflux temperature for 30 minutes. The mixture was cooled and added to 100 ml of water. To this mixture was added sodium carbonate to pH 9. The product was extracted with ethyl acetate, washed with water, dried and concentrated in vacuo. The solid thus obtained was chromatographed on silica gel eluting with hexanes-ethyl acetate 9:1 to 2:1. Solvent was removed from product fractions giving 0.261 g of 4-(4 -chloro-2-fluoro-phenylamino)-6,7,8-trimethoxy-quinoline-3-carbonitrile as a yellow solid: mp 166–168° C.; mass spectrum (EI, m/e): M 387.0777.

EXAMPLE 235

2-(Dimethylamino-methyleneamino)-3,6-dimethoxy-benzoic acid methylester

A mixture of 3.46 g of 2-amino-3,6-dimethoxybenzoic acid (Manouchehr Azadi-Ardakani and Timothy W. Wallace, Tetrahedron, Vol. 44, No. 18, pp. 5939 to 5952, 1988) in 20 ml of N,N-dimethylformamide dimethyl acetal was refluxed for 18 hours and concentrated in vacuo. To the residue was added 180 ml of ethyl acetate. The mixture was filtered, and 200 ml of hexanes was added to the filtrate. The mixture was then concentrated to 100 ml. The product was collected and dried to give 3.25 g of 2-(dimethylamino-methyleneamino)-3,6-dimethoxy-benzoic acid methylester as a solid, mp 81–83° C.; mass spectrum (EI, m/e): M 266.1263.

EXAMPLE 236

4-Hydroxy-5,8-dimethoxy-quinoline-3-carbonitrile

To 12.5 ml of tetrahydrofuran at −78° C. was added 8.8 ml of 2.5M n-butyllithium in hexanes. Then 1.18 ml of acetonitrile in 25 ml of tetrahydrofuran was added dropwise. The mixture was stirred at −78° C. for 15 minutes. Then a solution of 2-(dimethylamino-methyleneamino)-3,6-dimethoxy-benzoic acid methylester in 62 ml of tetrahydrofuran was added dropwise. The mixture was stirred at −78° C. for 10 minutes, then warmed to room temperature in 15 minutes. Acetic acid (3 ml) was added, followed by 200 ml of water. The product was collected, washed with water, and dried to give 1.57 g of 4-hydroxy-5,8-dimethoxy-quinoline-3-carbonitrile as a solid, mp 300–305° C.; mass spectrum (EI, m/e): M 230.0685.

EXAMPLE 237

4-Chloro-5,8-dimethoxy-quinoline-3-carbonitrile

A stirred mixture of 1.30 g of 4-hydroxy-5,8-dimethoxy-quinoline-3-carbonitrile, 10 ml of phosphorous oxychloride, and 2 drops of N,N-dimethylformamide was refluxed for 10 minutes and evaporated free of volatile matter. The residue was stirred with 50 ml of water. The product was collected and dried to give 1.74 g of 4-chloro-5,8 -dimethoxy-quinoline-3-carbonitrile as a solid, mp 165–167° C.; mass spectrum (EI, m/e): M 248.0346.

EXAMPLE 238

4-(4-Chloro-2-fluoro-phenylamino)-5,8-dimethoxyquinoline-3-carbonitrile

A mixture of 0.148 g of 4-chloro-5,8-dimethoxy-3-quinolinecarbonitrile, 0.102 g of 4-chloro-2-fluoroaniline, and 5 ml of ethoxyethanol was stirred under nitrogen, at reflux temperature for 30 minutes. The mixture was cooled and added to 50 ml of water. To this mixture was added sodium carbonate to pH 9. The product was collected, washed with water, dried, and washed with 10 ml of hexanes-ethyl acetate (4:1) to give 0.168 g of 4-(4-chloro-2-fluoro-phenylamino)-5,8-dimethoxy-quinoline-3-carbonitrile as a solid, mp 197–199° C.; mass spectrum (EI, m/e): M 329.7609.

EXAMPLE 239

4-(3-Hydroxy-4-methyl-phenylamino)-5,8-dimethoxy-quinoline-3-carbonitrile

A mixture of 0.148 g of 4-chloro-5,8-dimethoxy-3-quinolinecarbonitrile, 0.087 g of 5-amino-o-cresol, and 5 ml of ethoxyethanol was stirred under nitrogen, at reflux temperature for 30 minutes. The mixture was cooled and added to 50 ml of water. To this mixture was added sodium carbonate to pH 9. The product was collected, washed with water, dried, and washed with 10 ml of hexanes-ethyl acetate (4:1) to give 0.168 g of 4-(3-hydroxy-4-methyl-phenylamino)-5,8-dimethoxy-quinoline-3-carbonitrile as a solid, mp 240–242° C.; mass spectrum (EI, m/e): M 335.1260.

EXAMPLE 240

4-(3-Bromo-phenylamino)-5,8-dimethoxy-quinoline-3-carbonitrile

A mixture of 0.148 g of 4-chloro-5,8-dimethoxy-3-quinolinecarbonitrile, 0.12 g of m-bromoaniline, and 5 ml of ethoxyethanol was stirred under nitrogen, at reflux temperature for 30 minutes. The mixture was cooled and added to 50 ml of water. To this mixture was added sodium carbonate to pH 9. The product was collected, washed with water, dried, and washed with 10 ml of hexanes-ethyl acetate (4:1) to give 0.213 g of 4-(3-bromo-phenylamino)-5,8-dimethoxy-quinoline-3-carbonitrile as a solid, mp 72–74° C.; mass spectrum (EI, m/e): M 383.0265.

EXAMPLE 241

4-(3-Bromo-phenylamino)-6,7,8-trimethoxy-quinoline-3-carbonitrile

A mixture of 0.167 g of 4-chloro-6,7,8-trimethoxy-3-quinolinecarbonitrile, 0.12 g of m-bromoaniline, and 5 ml of ethoxyethanol was stirred under nitrogen, at reflux temperature for 30 minutes. The mixture was cooled and added to 50 ml of water. To this mixture was added sodium carbonate to pH 9. The product was collected, washed with water, dried, and washed with 10 ml of hexanes-ethyl acetate (4:1) to give 0.212 g of 4-(3-bromo-phenylamino)-6,7,8-trimethoxy-quinoline-3-carbonitrile as a solid, mp 211–213° C.; mass spectrum (EI, m/e): M 413.0377.

EXAMPLE 242

4-(3-Dimethylamino-phenylamino)-5,8-dimethoxy-quinoline-3-carbonitrile

A mixture of 0.148 g of 4-chloro-5,8-dimethoxy-3-quinolinecarbonitrile, 0.146 g of N,N-dimethyl-1,3-phenylenediamine dihydrochloride, 0.2 ml of pyridine, and 5 ml of ethoxyethanol was stirred under nitrogen, at reflux temperature for 30 minutes. Then the mixture was partitioned between ethyl acetate and saturated sodium chloride solution. The organic layer was dried and concentrated in vacuo. The residue thus obtained was chromatographed on silica gel eluting with ethyl acetate. Solvent was removed from product fractions giving 0.160 g of 4-(3-dimethylamino-phenylamino)-5,8-dimethoxy-quinoline-3-carbonitrile as a solid, mp 103–105° C.; mass spectrum (EI, m/e): M 348.1588.

EXAMPLE 243

4-(4-Chloro-2-fluoro-5-hydroxy-phenylamino)-5,8-dimethoxy-quinoline-3-carbonitrile A mixture of 0.223 g of 4-chloro-5,8-dimethoxy-3-quinolinecarbonitrile, 0.22 g of the methyl carbonate of 4-chloro-2-fluoro-5-hydroxy-aniline, and 15 ml of ethoxyethanol was stirred under nitrogen, at reflux temperature for 30 minutes. The mixture was cooled and added to 100 ml of water. To this mixture was added sodium carbonate to pH 9. The product was collected, washed with water, and dried. The solids thus obtained were dissolved in a mixture of 30 ml of methyl alcohol and 20 ml of acetone. To this mixture was added 1.5 ml of 28–30% ammonium hydroxide solution. The mixture was heated at 50° C. for 30 minutes and concentrated. The product was collected, washed with ethyl acetate, and dried to give 0.237 g of 4-(4 -chloro-2-fluoro-5-hydroxy-phenylamino)-5,8-dimethoxy-quinoline-3-carbonitrile as a solid, mp 240° C. (decomposed); mass spectrum (electrospray, m/e): M+H 373.9.

EXAMPLE 244

4-(4-Chloro-2-fluoro-5-hydroxy-phenylamino)-6,7,8-trimethoxy-quinoline-3-carbonitrile A mixture of 0.279 g of 4-chloro-6,7,8-trimethoxy-3-quinolinecarbonitrile, 0.22 g of the methyl carbonate of 4-chloro-2-fluoro-5-hydroxy-aniline, and 15 ml of ethoxyethanol was stirred under nitrogen, at reflux temperature for 30 minutes. The mixture was cooled and added to 100 ml of water. To this mixture was added sodium carbonate to pH 9. The product was collected, washed with water, and dried. The solids thus obtained were dissolved in a mixture of 30 ml of methyl alcohol and 20 ml of acetone. To this mixture was added 1.5 ml of 28–30% ammonium hydroxide solution. The mixture was heated at 50° C. for 30 minutes and concentrated. The product was collected, washed with ethyl acetate, and dried to give 0.162 g of 4-(4-chloro-2-fluoro-5-hydroxy-phenylamino)-6,7,8-trimethoxy-quinoline-3-carbonitrile as a solid, mp 223–225° C.; mass spectrum (EI, m/e): M 403.0731.

EXAMPLE 245

4-(3-Hydroxy-2-methyl-phenylamino)-6,7-dimethoxy-quinoline-3-carbonitrile

A mixture of 0.249 g of 4-chloro-6,7-dimethoxy-3-quinolinecarbonitrile, 0.123 g of 3-amino-o-cresol, 20 mg of pyridine hydrochloride, and 10 ml of ethoxyethanol was stirred under nitrogen, at reflux temperature for 30 minutes. The mixture was cooled and added to 40 ml of water. To this mixture was added sodium carbonate and concentrated hydrogen chloride to adjust pH to 7. The product was collected, washed with water, and dried to give 0.174 g of 4-(3-hydroxy-2-methyl-phenylamino)-6,7-dimethoxy-quinoline-3-carbonitrile as a solid, mp 255–257° C.; mass spectrum (electrospray, m/e): M+H 335.9.

EXAMPLE 246

4-(2-Hydroxy-6-methyl-phenylamino)-6,7-dimethoxy-quinoline-3-carbonitrile

A mixture of 0.249 g of 4-chloro-6,7-dimethoxy-3-quinolinecarbonitrile, 0.123 g of 2-amino-m-cresol, 20 mg of pyridine hydrochloride, and 10 ml of ethoxyethanol was stirred under nitrogen, at reflux temperature for 30 minutes. The mixture was cooled and added to 40 ml of water. To this mixture was added sodium carbonate and concentrated hydrogen chloride to adjust pH to 7. The product was collected, washed with water, and dried to give 0.216 g of 4-(2-hydroxy-6-methyl-phenylamino)-6,7-dimethoxy-quinoline-3-carbonitrile as a solid, mp 245–247° C.; mass spectrum (electrospray, m/e): M+H 336.1363.

EXAMPLE 247

3-(3-Cyano-6,7-dimethoxy-quinolin-4-ylamino)-benzamide

A mixture of 0.249 g of 4-chloro-6,7-dimethoxy-3-quinolinecarbonitrile, 0.136 g of 3-aminobenzamide, 20 mg of pyridine hydrochloride, and 10 ml of ethoxyethanol was stirred under nitrogen, at reflux temperature for 30 minutes. The mixture was cooled and added to 40 ml of water. To this mixture was added sodium carbonate and concentrated hydrogen chloride to adjust pH to 7. The product was collected, washed with water, and dried to give 0.321 g of 3-(3-cyano-6,7-dimethoxy-quinolin-4-ylamino)-benzamide as a solid, mp 253–255° C.; mass spectrum (electrospray, m/e): M 349.1301.

EXAMPLE 248

4-(3-Bromo-4-methyl-phenylamino)-6,7-dimethoxy-quinoline-3-carbonitrile

A mixture of 0.249 g of 4-chloro-6,7-dimethoxy-3-quinolinecarbonitrile, 0.186 g of 3-bromo-4-methylaniline, 20 mg of pyridine hydrochloride, and 10 ml of ethoxyethanol was stirred under nitrogen, at reflux temperature for 30 minutes. The mixture was cooled and added to 40 ml of water. To this mixture was added sodium carbonate and concentrated hydrogen chloride to adjust pH to 7. The product was collected, washed with water, and dried to give 0.286 g of 4-(3-bromo-4-methyl-phenylamino)-6,7-dimethoxy-quinoline-3-carbonitrile as a solid, mp 292–294° C.; mass spectrum (EI, m/e): M 397.0446.

EXAMPLE 249

4-(3-Chloro-4-hydroxy-phenylamino)-6,7-dimethoxy-quinoline-3-carbonitrile

A mixture of 0.249 g of 4-chloro-6,7-dimethoxy-3-quinolinecarbonitrile, 0.144 g of 4-amino-2-chlorophenol, 20 mg of pyridine hydrochloride, and 10 ml of ethoxyethanol was stirred under nitrogen, at reflux temperature for 30 minutes. The mixture was cooled and added to 40 ml of water. To this mixture was added sodium carbonate and concentrated hydrogen chloride to adjust pH to 7. The product was collected, washed with water, and dried to give 0.256 g of 4-(3-chloro-4-hydroxy-phenylamino)-6,7-dimethoxy-quinoline-3-carbonitrile as a solid, mp 230–232° C.; mass spectrum (EI, m/e): M 355.0719.

EXAMPLE 250

6,7-Dimethoxy-4-(2-methylsulfanyl-phenylamino)-quinoline-3-carbonitrile

A mixture of 0.249 g of 4-chloro-6,7-dimethoxy-3-quinolinecarbonitrile, 0.139 g of 2-(methylmercapto)aniline, 20 mg of pyridine hydrochloride, and 10 ml of ethoxyethanol was stirred under nitrogen, at reflux temperature for 30 minutes. The mixture was cooled and added to 40 ml of water. To this mixture was added sodium carbonate and concentrated hydrogen chloride to adjust pH to 7. The product was collected, washed with water, and dried to give 0.184 g of 6,7-dimethoxy-4-(2-methylsulfanyl-phenylamino)-quinoline-3-carbonitrile as a solid, mp 245–247° C.; mass spectrum (EI, m/e): M 351.1051.

EXAMPLE 251

Methyl 2-(dimethylaminomethyleneamino)-4,5-diethoxybenzoate

To a stirred solution of methyl 2-amino-4,5-diethoxybenzoate (4.79 g, 20 mmol) in 20 ml of DMF at 0° C. was added phosphorous oxychloride (2.24 ml, 24 mmol) during 15 m. The mixture was warmed to 55° C. and stirred for 45 m. The resulting solution was diluted with methylene chloride, cooled to 0° C., and treated with 80 ml of pre-cooled N/1 sodium hydroxide during 5 m. The organic layer was separated and washed at 0° C. with with water. The solution was dried and concentrated to give an amber oil; NMR (CDCl$_3$) δ 3.00(s, ME$_2$N).

EXAMPLE 252

1,4-Dihydroquinoline-6,7-diethoxy-4-oxo-3-carbonitrile

To a stirred solution of n-butylllithium (17.6 ml of 2.5 M in hexane; 44 mmol) in 25 ml of THF at −78° C. was added a solution of acetonitrile (2.35 ml, 45 mmol) in 44 ml of THF during 10 m. After stirring at −78° C. for 15 m, the mixture was treated with a solution of ethyl 2-(dimethylaminomethyleneamino)-4,5-diethoxybenzoate (5.83 g, 19.8 mmol) in 30 ml of THF during 30 m. After 30 m at −78° C. the mixture was treated with 5.7 ml (100 mmol) of acetic acid and evaporated to dryness. The residue was stirred in water, and the resulting precipitate was filtered off, washed with water, and dried to give 4.01 g of off-white solid; NMR (DMSO-d$_6$) d 8.58(s, 2-H).

EXAMPLE 253

4-Chloro-6,7-diethoxy-3-quinolinecarbonitrile

In the manner of Example 115 treatment of 1,4-dihydroquinoline-6,7-diethoxy-4-oxo-3-carbonitrile with phosphorous oxychloride gave the tide compound as a pink solid, mp 170–175° C.

EXAMPLE 254

4-[3-Chloro-4-(phenylthio)phenylamino]-6,7-diethoxy-3-quinolinecarbonitrile

In the manner of Example 105 reaction of 4-chloro-6,7-diethoxy-3-quinolinecarbonitrile with 3-chloro-4-(phenylthio)aniline gave the title compound as a tan solid, mp 88–94° C.

EXAMPLE 255

4-[3-Chloro-4-(phenylthio)phenylamino]-6,7-dimethoxy-3-quinolinecarbonitrile

In the manner of Example 105 reaction of 4-chloro-6,7-dimethoxy-3-quinolinecarbonitrile with 3-chloro-4-

EXAMPLE 256

4-(3-Chloro-4-fluorophenylamino)-6,7-diethoxy-3-quinolinecarbonitrile

In the manner of Example 105 reaction of 4-chloro-6,7-diethoxy-3-quinolinecarbonitrile with 3-chloro-4-fluoroaniline gave the title compound as an off-white solid, mp 194–198° C.

EXAMPLE 257

4-(3-acetylphenylamino)-6.7-diethoxy-3-quinolinecarbonitrile

In the manner of Example 105 reaction of 4-chloro-6,7-diethoxy-3-quinolinecarbonitrile with 3-aminoacetophenone gave the tide compound as an off-white solid, mp 191–194° C.

EXAMPLE 258

4-(N-Methylphenylamino)-6,7-diethoxy-3-quinolinecarbonitrile

In the manner of Example 105 reaction of 4-chloro-6,7-diethoxy-3-quinolinecarbonitrile with N-methylaniline gave the title compound as a tan solid, mp 153–155° C.

EXAMPLE 259

4-(Phenylamino)-6,7-diethoxy-3-quinolinecarbonitrile

In the manner of Example 105 reaction of 4-chloro-6,7-diethoxy-3-quinolinecarbonitrile with aniline gave the title compound as a tan solid, mp 168–170° C.

EXAMPLE 260

4-(4-fluorophenylamino)-6,7-diethoxy-3-quinolinecarbonitrile

In the manner of Example 105 reaction of 4-chloro-6,7-diethoxy-3-quinolinecarbonitrile with 4-fluoroaniline gave the title compound as a tan solid, mp 177–181° C.

EXAMPLE 261

4-(4-Fluoro-2-methylphenylamino)-6,7-diethoxy-3-quinolinecarbonitrile

In the manner of Example 105 reaction of 4-chloro-6,7-diethoxy-3-quinolinecarbonitrile with 4-fluoro-3-methylaniline gave the title compound as a tan solid, mp 105–108° C.

EXAMPLE 262

4-(3-Chlorophenylamino)-6,7-diethoxy-3-quinolinecarbonitrile

In the manner of Example 105 reaction of 4-chloro-6,7-diethoxy-3-quinolinecarbonitrile with 4-fluoroaniline gave the title compound as a tan solid, mp 188–190° C.

EXAMPLE 263

4-(3-Fluorophenylamino)-6,7-diethoxy-3-quinolinecarbonitrile

In the manner of Example 105 reaction of 4-chloro-6,7-diethoxy-3-quinolinecarbonitrile with 3-fluoroaniline gave the title compound as a tan solid, mp 192–195° C.

EXAMPLE 264

4-(3-Aminophenylamino)-6,7-dimethoxy-3-quinolinecarbonitrile

A stirred mixture of 4-chloro-6,7-dimethoxy-3-quinolinecarbonitrile (3.73 g, 15 mmol), 1,3-diaminobenzene (4.86 g, 45 mmol), pyridine (1.21 ml, 15 mmol), and 45 ml of ethoxyethanol was refluxed for 30 m, cooled, and stirred with aqueous sodium bicarbonate. The resulting solid was filtered, washed with water, and dried. Recrystallization from ethanol gave a brown solid, mp 222–228° C.

EXAMPLE 265

4-(3-Acetamidophenylamino)-6,7-dimethoxy-3-quinolinecarbonitrile

To a stirred solution of 4-(3-aminophenylamino)-6,7-dimethoxy-3-quinolinecarbonitrile (0.96 g, 3.0 mmol) in 9.0 ml of acetic acid at 25° C. was added 0.85 ml (9.0 mmol) of acetic anhydride. After 2 h the solution was evaporated to dryness, and the residue was stirred with methanol. This solution was evaporated, and the residue was recrystallized from ethanol to give 0.50 g of amber solid, mp 147–150° C.

EXAMPLE 266

4-[3-(2-Butynoylamino)phenylamino)]-6.7-dimethoxy-3-quinolinecarbonitrile

Isobutyl chloroformate (0.26 ml, 2.0 mmol) and N-methylmorpholine (0.22 ml, 2.0 mmol) were added to an ice-cold solution of 2-butynoic acid (0.21 g, 2.5 mmol) in 8.5 ml of THF. After 10 m a suspension of 4-(3-aminophenylamino)-6,7-dimethoxy-3-quinolinecarbonitrile (0.32 g, 1.0 mmol) in 6.5 ml of THF was added, and the resulting mixture was stirred at 25° C. for 16 h and diluted with water. The resulting solid was filtered off, washed with water, dried, and recrystallized from methanol to give 0.12 g of off-white solid, mp 193–196° C.

EXAMPLE 267

4-[3-(Hydroxymethyl)phenylamino]-6,7-dimethoxy-3-quinolinecarbonitrile

A stirred mixture of 4-chloro-6,7-dimethoxy-3-quinolinecarbonitrile (7.46 g, 30 mmol), 3-aminobenzyl alcohol (7.39 g, 60 mmol), pyridine (2.43 ml, 30 mmol), and 90 ml of ethoxyethanol was refluxed for 5 h, cooled, and stirred with aqueous sodium bicarbonate. The resulting solid was filtered, washed with water, and dried. Recrystallization from methanol gave a brown solid, mp 250–255° C.

EXAMPLE 268

4-[3-(Chloromethyl)phenylamino]-6,7-dimethoxy-3-quinolinecarbonitrile

To 14 ml of DMF was added phosphorous trichloride (0.70 ml, 8.0 mmol) with stirring at 25–30° C. After 60 m, the mixture was cooled to 0° C., and a suspension of 4-[3-(hydroxymethyl)phenylamino]-6,7-dimethoxy-3-quinolinecarbonitrile (1.34 g, 4.0 mmol) in 6 ml of DMF was added. The mixture was warmed to 25° C., stirred 15 m, recooled in ice bath, and partitioned with methylene chloride-aqueous sodium bicarbonate. The organic layer was washed with water, dried, and concentrated to give 1.15 g of an amber solid; NMR (CDCl$_3$) δ 4.79(s, CH$_2$Cl).

(phenylthio)aniline gave the title compound as a tan solid, mp 124–130° C.

EXAMPLE 269

4-[3-(Acetylthiomethyl)phenylamino]-6,7-dimethoxy-3-quinolinecarbonitrile

To a stirred solution of 4-[3-(chloromethyl)phenylamino]-6,7-dimethoxy-3-quinolinecarbonitrile (0.97 g, 2.7 mmol) in 5.4 ml of DMF was added potassium thioacetate (0.93 g, 8.1 mmol) at 25° C. After 30 m the mixture was partitioned with methylene chloride and water. The organic layer was washed with water, dried, and concentrated. The residue was recrystallized from ethyl acetate to give 0.43 g of yellow solid, mp 172–177° C.

EXAMPLE 270

4-[3-(Thiomethyl)phenylamino]-6,7-dimethoxy-3-quinolinecarbonitrile

A stirred mixture of 4-[3-(acetylthiomethyl)phenylamino]-6,7-dimethoxy-3-quinolinecarbonitrile (1.23 g, 3.13 mmol), 12.5 ml of concentrated ammonium hydroxide, 63 ml of ethanol, and 32 ml of DMF was heated at 85° C. for 2.5 h and then concentrated to dryness. The residue was partitioned with methylene chloride and water. The organic layer was washed with water, dried, and concentrated. The residue was subjected to chromatography on silica gel with methylene chloride-ethyl acetate-methanol to give an off-white solid; mass spectrum (electrospray, m/e) M+H 352.1.

EXAMPLE 271

2-(Dimethylamino-methyleneamino)-3-methoxy-benzoic acid methyl ester

A reaction mixture of 5.0 g (29.9 mmol) of 2-amino-3-methoxy-benzoic acid in 25.0 mL of DMF-DMA was heated at 100–105° C. for 2.5 hr, and then the solvent was removed to give a red-purple viscous oil. After standing in a refrigerator, the oil solidified to give 5.8 g of the product as a red-purple solid in 82.8% yield, mass spectrum (electrospray, m/e): M+H 236.9

EXAMPLE 272

1,4-Dihydro-8-methoxy-4-oxo-3-quinolinecarbonitrile

To 35.0 mL of THF was added 26.6 mL (66.4 mmol) of n-BuLi solution during 5 min at −78° C. To the stirred solution was added a solution of 3.55 mL (67.9 mmol) of CH$_3$CN in 65 mL of THF during 10 min which time the solution became white suspension, and then continued to stir for 15 min at −78° C. To the suspension was added a solution of 5.8 g (24.5 mmol) of 2-(Dimethylamino-methyleneamino)-3-methoxy-benzoic acid methyl ester in 45 mL of THF during 30 min, and then continued to stir 30 min at −78° C. during which time the mixture gradually became clear. The solution was quenched with 8.5 mL of HOAc. The resulting thick slurry was stirred and warmed to room temperature. After most of the solvent was evaporated, the residue was diluted with cold water. The separate solid was collected by filtration and washed with water. After drying in vacuo, this afforded 3.8 g of the product as an off white solid in 77.6% of yield, m.p. 270° C. (dec.), mass spectrum (electrospray, m/e): M+H 201.1

EXAMPLE 273

4-Chloro-8-methoxy-3-quinolinecarbonitrile

A mixture of 3.8 g (19 mmol) of 1,4-dihydro-8-methoxy-4-oxo-3-quinolinecarbonitrile and 40 mL of phosphorous oxochloride and 5 drops of DMF was refluxed for 0.5 hours. The mixture was evaporated to dryness and diluted with hexanes. The solid was collected and mixed with cold dilute sodium carbonate solution and extracted several times with ethyl acetate. The organic layer was dried over sodium sulfate and filtered through a pad of silica gel. Removal of the solvent gave 3.8 g of 4-chloro-8-methoxy-3-quinolinecarbonitrile as an off white solid in 91% yield, mass spectrum (electrospray, m/e): M+H 219.1.

EXAMPLE 274

4-[(3-Bromophenyl)amino]-8-methoxy-3-quinolinecarbonitrile

A solution of 328.0 mg (1.5 mmol) of 4-chloro-8-methoxy-3-quinolinecarbonitrile, 309.7 mg (1.8 mmol) of 3-bromoaniline and 173.3 mg (1.5 mmol) of pyridine hydrochloride in 15 ml of 2-ethoxyethanol was refluxed under nitrogen for 0.5 hours. The solvent was removed and the residue was diluted with water followed by neutralization to pH 7–8 with diluted sodium carbonate solution. The precipitate was collected and washed with ether and dried in vacuo to give 476.1 mg (89.6%) of the product as a yellow solid, m.p. 210–212° C.; mass spectrum (electrospray, m/e): M+H 353.8, 355.8.

EXAMPLE 275

4-(4-Chloro-2-fluoro-phenylamino)-8-methoxy-quinoline-3-carbonitrile

Using an analogous procedure to that described in Example 274. A reaction mixture of 328.0 mg (1.5 mmol) of 4-chloro-8-methoxy -3-quinolinecarbonitrile, 173.3 mg (1.5 mmol) of pyridine hydrochloride and 240.0 mg (1.7 mmol) of 2-fluoro-4-chloroaniline in 15 mL of 2-ethoxyethanol was heated at 100° C. for 2 hr. After the work up, 431.3 mg (87.9%) of the product was obtained as an off white solid, m.p. 127° C. (dec.), mass spectrum (electrospray, m/e): M+H 327.8, 329.9.

EXAMPLE 276

4-(3-Hydroxy-4-methyl-phenylamino)-8-methoxy-quinoline-3-carbonitrile

Using an analogous procedure to that described in Example 274. A reaction mixture of 328.0 mg (1.5 mmol) of 4-chloro-8-methoxy -3-quinolinecarbonitrile, 173.3 mg (1.5 mmol) of pyridine hydrochloride and 203.2 mg (1.7 mmol) of 3-hydroxy-4-methylaniline in 15 mL of 2-ethoxyethanol was heated at 100° C. for 1.5 hr. After the work up, 407.7 mg (89.4%) of the product was obtained as a yellow solid, m.p. 148–150° C., mass spectrum (electrospray, m/e): M+H 306.9.

EXAMPLE 277

4(3-Dimethylamino-phenylamino)-8-methoxy-quinoline-3-carbonitrile

Using an analogous procedure to that described in Example 274. A reaction mixture of 250.0 mg (1.1 mmol) of 4-chloro-8-methoxy -3-quinolinecarbonitrile, 273.3 mg (3.0 mmol) of pyridine and 261.4 mg (1.25 mmol) of 3-dimethylaminoaniline hydrochloride in 10 mL of 2-ethoxyethanol was heated at 100° C. for 1.5 hr. The work up gave 294.8 mg (73.4%) of the product as a deep greenish yellow solid, m.p. 222–225° C., mass spectrum (electrospray, m/e): M+H 319.0.

EXAMPLE 278

4-(4-Bromo-3-hydroxy-phenylamino)-8-methoxy-quinoline-3-carbonitrile

Using an analogous procedure to that described in Example 274. A reaction mixture of 250.0 mg (1.1 mmol) of 4-chloro-8-methoxy-3-quinolinecarbonitrile, 131.7 mg (1.1 mmol) of pyridine hydrochloride and 286.7 mg (1.3 mmol) of 4-bromo-3-hydroxy-aniline in 10 mL of 2-ethoxyethanol was heated at 100° C. for 1.5 hr. The work up gave 374.1 mg (88.6%) of the product as a pink solid, m.p. 146° C. (dec.), mass spectrum (electrospray, m/e): M+H 369.9.

EXAMPLE 279

4-(3-Hydroxy-4-methoxy-phenylamino)-8-methoxy-quinoline-3-carbonitrile

Using an analogous procedure to that described in Example 274. A reaction mixture of 200.0 mg (0.92 mmol) of 4-chloro-8-methoxy-3-quinolinecarbonitrile, 105.7 mg (0.92 mmol) of pyridine hydrochloride and 140.6 mg (1.0 mmol) of 5-amino-2-methoxyphenol in 10 mL of 2-ethoxyethanol was heated at 100° C. for 2 hr. The work up gave 261.6 mg (89.0%) of the product as a deep yellow solid, m.p. 138–140° C. (dec.), mass spectrum (electrospray, m/e): M+H 321.9.

EXAMPLE 280

8-Methoxy-4-(2,4,6-trifluoro-phenylamino)-quinoline-3-carbonitrile

Using an analogous procedure to that described in Example 274. A reaction mixture of 200.0 mg (0.92 mmol) of 4-chloro-8-methoxy-3-quinolinecarbonitrile, 105.7 mg (0.92 mmol) of pyridine hydrochloride and 148.6 mg (1.0 mmol) of 2,4,6-trifluoro-aniline in 10 mL of 2-ethoxyethanol was heated at 100° C. for 2 hr. The work up gave 112.6 mg (37.4%) of the product as a yellow solid, m.p. 297° C. (dec.), mass spectrum (electrospray, m/e): M+H 330.0.

EXAMPLE 281

4-(3-hydroxy-4-methyl-phenylamino)-7-methoxy-quinoline-3-carbonitrile

To a suspension of 200 mg (0.91 mmol) of -chloro-7-methoxy-3-quinolinecarbonitrile and 135.5 mg (1.10 mmol) of 5-amino-o-cresol in 10 mL of 2-ethoxy ethanol was added 105.6 mg (0.91 mmol) of pyridine hydrochloride. The resulting reaction mixture was refluxed for 1 hr, and then the solvent was removed to give a residue. To the residue was added about 30 mL of water and neutralized to pH 7–8 by addition of diluted sodium carbonate solution. The precipitate was collected by filtration and washed with water and ether. After drying in vacuo, this afforded 277 mg (99%) of the product as a yellow solid, m.p.>250° C., mass (electrospray, m/e): M+H 305.9.

EXAMPLE 282

4-(4-Chloro-2-fluoro-5-hydroxy-phenylamino)-7-methoxy-quinoline-3-carbonitrile The method of Example 281 was used with 218.6 mg (1.0 mmol) of 4-chloro-7-methoxy-3-quinolinecarbonitrile, 263.5 mg (1.2 mmol) of the aniline and 115.6 mg (1.0 mmol) of pyridine hydrochloride in 10 mL of 2-ethoxyethanol. This afforded a red oil residue. To the residue were added 10 mL of methanol and 1 mL of $NH_4OH$ (28–30%). The resulting mixture was heated at 50° C. for 302 mm, and the n the solvent was removed to give a residue. To the residue was added water. The separated solid was collected by filtration and washed with water and ether/ethyl acetate (1:1). After drying in vacuo, 142.1 mg (41.4%) of the product was obtained as a brown solid, m.p. 240° C. (dec.); mass (electrospray, m/e): M+H 343.9, 345.8.

EXAMPLE 283

4-(4-Chloro-2-fluoro-phenylamino)-6-methoxy-quinoline-3-carbonitrile

The method of Example 281 was used with 218.6 mg (1 mmol) of 4-chloro-6-methoxy-3-quinolinecarbonitrile, 174.7 mg (1.2 mmol) of 4-chloro-2-fluoro-aniline and 115.6 mg (1 mmol) of pyridine hydrochloride in 10 mL of 2-ethoxyethanol. This afforded 319.8 mg of the product as a yellow solid, m.p.>250° C., mass (electrospray, m/e): M+H 325.9, 327.9

EXAMPLE 284

4-(3-Hydroxy-4-methyl-phenylamino)-6-methoxy-quinoline-3-carbonitrile

To a suspension of 218.6 mg (1.0 mmol) of 4-chloro-6-methoxy-3-quinolinecarbonitrile and 147.8 mg (1.20 mmol) of 5-amino-o-cresol in 10 mL of 2-ethoxyethanol was added 115.6 mg (1.0 mmol) of pyridine hydrochloride. The resulting reaction mixture was refluxed for 1 hr, and then the solvent was removed to give a residue. To the residue was added about 30 mL of water and neutralized to pH 7–8 by addition of diluted sodium carbonate solution. The precipitate was collected by filtration and washed with water and ether. After drying in vacuo, this afforded 278.3 mg (91%) of the product as a yellow solid, m.p.>250° C. (dec.), mass (electrospray, m/e): M+H 305.9.

EXAMPLE 285

4-(4-Chloro-2-fluoro-5-hydroxy-phenylamino)-6-methoxy-quinoline-3-carbonitrile The method of Example 282 was used with 218.6 mg (1.0 mmol) of 4-chloro-6-methoxy-3-quinolinecarbonitrile and 263.5 mg (1.2 mmol) of the aniline (cat 800906) in 10 mL of 2-ethoxyethanol was added 115.6 mg (1.0 mmol) of pyridine hydrochloride. This afforded a dark oil residue. To the residue was added 10 mL of methanol and 1 mL of $NH_4OH$ (28–30%). The resulting mixture was heated at 50° C. for 30 min, and then the solvent was removed and the residue was triturated with water and ether in an ice bath. The separated solid was filtered off and washed with water and ether. After drying in vacuo, 83.2 mg (24.2%) of the product was obtained as a light brown solid, m.p. 228–230° C., mass (electrospray, m/e): M+H 343.8, 345.8.

EXAMPLE 286

4-(3,5-Dichloro-4-hydroxy-phenylamino)-6,7-dimethoxy-quinoline-3-carbonitrile A reaction mixture of 248.7 mg (1 mmol) of 4-chloro-6,7-dimethoxy-3-quinolinecarbonitrile, 213.6 mg (1.2 mmol) of 4-amino-2,6-dichlorophenol and 115.6 mg (1 mmol) of pyridine hydrochloride in 10 mL of 2-ethoxyethanol was refluxed under N$_2$ for 1 hr. After removal of the solvent, the residue was diluted with water and neutralized to pH 7–8 with diluted sodium carbonate solution. The precipitate was filtered and washed with water and ether/ethyl acetate (1:1). After drying in vacuo, this yielded 346.7 mg (88.8%) of the product as a yellow solid, m.p.>250° C., mass (electrospray, m/e): M+H 389.8, 391.8.

Example 287

4-(2-Hydroxy-4-methyl-phenylamino)-6,7-dimethoxy-quinoline-3-carbonitrile

Using an analogous procedure to that described in Example 286, 248.7 mg (1 mmol) of 4-chloro-6,7-dimethoxy-3-quinolinecarbonitrile in 10 mL of 2-ethoxyethanol and in the presence of 115.6 mg (1 mmol) of pyridine hydrochloride was reacted with 147.8 mg (1.2 mmol) of 6-amino-m-cresol to give 287.5 mg (85.8%) of the product as a light brown solid, m.p.>250° C., mass (electrospray, m/e): M+H 335.9.

EXAMPLE 288

4-(4-Hydroxy-3,5-dimethyl-phenylamino)-6,7-dimethoxy-quinoline-3-carbonitrile

Using an analogous procedure to that described in Example 286, 248.7 mg (1 mmol) of 4-chloro-6,7-dimethoxy-3-quinolinecarbonitrile in 10 mL of 2-ethoxyethanol and in the presence of 115.6 mg (1 mmol) of pyridine hydrochloride was reacted with 164.6 mg (1.2 mmol) of 4-amino-2,5-dimethylphenol to give 232.9 mg (66.7%) of the product as a light brown solid, m.p. 234–236° C., mass (electrospray, m/e): M+H 349.9.

EXAMPLE 289

4-(3-Cyano-6,7-dimethoxy-quinolin-4-ylamino)-benzamide

Using an analogous procedure to that described in Example 286, 248.7 mg (1 mmol) of 4-chloro-6,7-dimethoxy-3-quinolinecarbonitrile in 10 mL of 2-ethoxyethanol and in the presence of 115.6 mg (1 mmol) of pyridine hydrochloride was reacted with 163.4 mg (1.2 mmol) of 4-amino-benzamide to give 255.7 mg (73.4%) of the product as a light yellow solid, m.p.>250° C., mass (electrospray, m/e): M+H 348.9.

EXAMPLE 290

4-(5-Chloro-2-hydroxy-phenylamino)-6,7-dimethoxy-quinoline-3-carbonitrile

Using an analogous procedure to that described in Example 286, 248.7 mg (1 mmol) of 4-chloro-6,7-dimethoxy-3-quinolinecarbonitrile in 15 mL of 2-ethoxyethanol and in the presence of 115.6 mg (1 mmol) of pyridine hydrochloride was reacted with 172.3 mg (1.2 mmol) of 2-amino-chlorophenol to give 326.4 mg (91.9%) of the product as a yellow solid, m.p.>250° C., mass (electrospray, m/e): M+H 355.8.

EXAMPLE 291

4-(3,5-Dibromo-4-hydroxy-phenylamino)-6,7-dimethoxy-quinoline-3-carbonitrile

Using an analogous procedure to that described in Example 286, 248.7 mg (1 mmol) of 4-chloro-6,7-dimethoxy-3-quinolinecarbonitrile in 15 mL of 2-ethoxyethanol and in the presence of 115.6 mg (1 mmol) of pyridine hydrochloride was reacted with 320.3 mg (1.2 mmol) of 4-amino-2,6-dibromophenol to give 427.1 mg (89.2%) of the product as a gray solid, m.p.>250° C., mass (electrospray, m/e): M+H 479.7, 481.6.

EXAMPLE 292

4-(4-Hydroxy-2-methyl-phenylamino)-6,7-dimethoxy-quinoline-3-carbonitrile

Using an analogous procedure to that described in Example 286, 248.7 mg (1 mmol) of 4-chloro-6,7-dimethoxy-3-quinolinecarbonitrile in 15 mL of 2-ethoxyethanol and in the presence of 115.6 mg (1 mmol) of pyridine hydrochloride was reacted with 147.8 mg (1.2 mmol) of 4-amino-m-cresol to give 304.6 mg (90.9%) of the product as a salmon solid, m.p.>250° C., mass (electrospray, m/e): M+H 335.9

EXAMPLE 293

6,7-Dimethoxy-4-(pyridin-3-ylamino)-quinoline-3-carbonitrile

Using an analogous procedure to that described in Example 286, 248.7 mg (1 mmol) of 4-chloro-6,7-dimethoxy-3-quinolinecarbonitrile in 15 mL of 2-ethoxyethanol and in the presence of 115.6 mg (1 mmol) of pyridine hydrochloride was reacted with 112.9 mg (1.2 mmol) of 3-amino-pyridine to give 60.6 mg (19.8%) of the product as an orange solid, m.p. 231–233° C., mass (electrospray, m/e): M+H 306.8.

EXAMPLE 294

6,7-Dimethoxy-4-(3-methilsulfanyl-phenylamino)-quinoline-3-carbonitrile

Using an analogous procedure to that described in Example 286, 248.7 mg (1 mmol) of 4-chloro-6,7-dimethoxy-3-quinolinecarbonitrile in 15 mL of 2-ethoxyethanol and in the presence of 115.6 mg (1 mmol) of pyridine hydrochloride was reacted with 167.1 mg (1.2 mmol) of 3-(methylthio)aniline to give 134.1 mg (38.2%) of the product as an off white solid, m.p.>250° C., mass (electrospray, m/e): M+H 351.9.

EXAMPLE 295

4-(2-Hydroxy-5-methyl-phenylamino)-6,7-dimethoxy-quinoline-3-carbonitrile

Using an analogous procedure to that described in Example 286, 248.7 mg (1 mmol) of 4-chloro-6,7-dimethoxy-3-quinolinecarbonitrile, in 15 mL of 2-ethoxyethanol and in the presence of 115.6 mg (1 mmol) of pyridine hydrochloride was reacted with 147.8 mg (1.2 mmol) of 2-amino-p-cresol to give 315.0 mg (94.0%) of the product as a yellow solid, m.p. 198–200° C., mass (electrospray, m/e): M+H 335.8.

EXAMPLE 296

4-(2-Chloro-4-hydroxy-phenylamino)-6,7-dimethoxy-quinoline-3-carbonitrile

Using an analogous procedure to that described in Example 286, 248.7 mg (1 mmol) of 4-chloro-6,7- dimethoxy-3-quinolinecarbonitrile in 15 mL of 2-ethoxyethanol and in the presence of 115.6 mg (1 mmol) of pyridine hydrochloride was reacted with 270.1 mg (1.5 mmol) of 4-amino-3-chlorophenol to give 299.2 mg (84.3%) of the product as a light brown solid, m.p.>250° C., mass (electrospray, m/e): M+H 355.8, 357.8.

EXAMPLE 297

2-(3-Cyano-6,7-dimethoxy-quinolin-4-ylamino)-benzamide

Using an analogous procedure to that described in Example 286, 248.7 mg (1 mmol) of 4-chloro-6,7-dimethoxy-3-quinolinecarbonitrile in 12 mL of 2-ethoxyethanol and in the presence of 115.6 mg (1 mmol) of pyridine hydrochloride was reacted with 177.0 mg (1.3 mmol) of anthranilamide to give 292.4 mg (84.0%) of the product as a deep yellow solid, m.p. 238–240.5° C., mass (electrospray, m/e): M+H 348.9.

EXAMPLE 298

6,7-Dimethoxy-4-(4-methylsulfanyl-phenylamino)-quinoline-3-carbonitrile

Using an analogous procedure to that described in Example 286, 248.7 mg (1 mmol) of 4-chloro-6,7-dimethoxy-3-quinolinecarbonitrile in 12 mL of 2-ethoxyethanol and in the presence of 115.6 mg (1 mmol) of pyridine hydrochloride was reacted with 181.0 mg (1.3 mmol) of 4-(methylmercapto)-aniline to give 334.1 mg (95.2%) of the product as a yellow solid, m.p. 235–237° C., mass (electrospray, m/e): M+H 351.9, 352.9, 353.8, 354.9.

EXAMPLE 299

4-[4-(2-Hydroxy-ethyl)-phenylamino]-6,7-dimethoxy-quinoline-3-carbonitrile

Using an analogous procedure to that described in Example 286, 248.7 mg (1 mmol) of 4-chloro-6,7-dimethoxy-3-quinolinecarbonitrile in 12 mL of 2-ethoxyethanol and in the presence of 115.6 mg (1 mmol) of pyridine hydrochloride was reacted with 178.3 mg (1.3 mmol) of 4-aminophenethyl alcohol to give 327.8 mg (93.9%) of the product as an off white yellow solid, m.p. 208–210° C., mass (electrospray, m/e): M+H 349.9.

EXAMPLE 300

4-(2,4-Dihydroxy-phenylamino)-6,7-dimethoxy-quinoline-3-carbonitrile

Using an analogous procedure to that described in Example 286, 248.7 mg (1 mmol) of 4-chloro-6,7-dimethoxy-3-quinolinecarbonitrile in 12 mL of 2-ethoxyethanol and in the presence of 115.6 mg (1 mmol) of pyridine hydrochloride was reacted with 210.0 mg (1.3 mmol) of 4-aminoresorcinol to give 330.4 mg (98.0%) of the product as a deep purple solid, m.p.>250° C., mass (electrospray, m/e): M+H 337.9.

EXAMPLE 301

4-[2-(2-Hydroxy-ethyl)-phenylamino]-6,7-dimethoxy-quinoline-3-carbonitrile

Using an analogous procedure to that described in Example 286, 248.7 mg (1 mmol) of 4-chloro-6,7-dimethoxy-3-quinolinecarbonitrile in 12 mL of 2-ethoxyethanol and in the presence of 115.6 mg (1 mmol) of pyridine hydrochloride was reacted with 178.3 mg (1.3 mmol) of 2-aminophenethyl alcohol to give 218.4 mg (64.4%) of the product as a pink solid, m.p 159–162° C., mass (electrospray, m/e): M+H 349.9.

EXAMPLE 302

4-(3-Bromophenylamino)-6,7-dihydroxy-3-quinolinecarbonitrile

A stirred mixture of 4-(3-bromophenylamino)-6,7-dimethoxy-3-quinolinecarbonitrile (15.4 g, 40 mmol) and 100 g of pyridine hydrochloride was heated at 210° C. for 20 m, cooled to 0° C., treated with 100 ml of concentrated ammonium hydroxide, and concentrated to dryness. The residue was stirred with 1 L of water, and the resulting amber solid was filtered off, washed with water, and dried; mass spectrum (electrospray, m/e) M+H 356.1, 358.1.

EXAMPLE 303

4-(3-Bromophenylamino)-6,7-di-n-propoxy-3-quinolinecarbonitrile

To a stirred mixture of 4(3-bromophenylamino)-6,7-dihydroxy-3-quinolinecarbonitrile (1.07 g, 3.0 mmol), potassium carbonate (1.66 g, 12.0 mmol), and 12 ml of DMF at 0° C. was added 1-iodopropane (1.17 ml, 12.0 mmol). The mixture was warmed to 25° C., stirred for 5 h, and then partioned at 0° C. with ethyl acetate and water containing HCl to give pH-8. The organic layer was separated, washed with water, dried, and concentrated. The residue was subjected to chromatography on silica gel with methylene chloride-ethyl acetate-acetic acid to give an amorphous solid; mass spectrum (electrospray, m/e) M+H 440.2, 442.2.

EXAMPLE 304

4-[(3-Bromophenyl)-N-acetylamino]-6,7-dihydroxy-3-quinolinecarbonitrile

A solution of 4-(3-bromophenylamino)-6,7-dihydroxy-3-quinolinecarbonitrile (1.78 g, 5.0 mmol), dimethylaminopyridine (60 mg, 0.50 mmol), 5.0 ml of acetic anhydride, and 10 ml of pyridine was stirred at reflux temperature for 1.5 h and concentrated to dryness. The residue was stirred with 50 ml of methanol, 5 ml of water, and sodium bicarbonate (2.1 g, 25 mmol) at 25° C. for 16 h and concentrated to dryness. The residue was stirred with water containing acetic acid to give pH-4–5, and the resulting solid was filtered off, washed with water, and dried. A solution of the resulting solid in THF was passed through a pad of silica gel; the filtrate was concentrated to give a tan solid; mass spectrum (electrospray, m/e) M–H 396.3, 398.3.

EXAMPLE 305

4(3-Bromophenylamino)-6,7-di-n-butoxy-3-quinolinecarbonitrile

A stirred mixture of 4-[(3-bromophenyl)-N-acetylamino]-6,7-dihydroxy-3-quinolinecarbonitrile (0.40 g, 1.0 mmol), 1-bromobutane (0.41 g, 3.0 mmol), potassium carbonate (0.30 g, 2.2 mmol), and 2.0 ml of DMF was stirred at 65–70° C. for 5 h, concentrated to dryness, and partitioned with ethyl acetate and water containing acetic acid to give pH-6. The organic layer was washed with water, dried and concentrated. The residue was stirred with potassium carbonate (0.55 g, 4.0 mmol), and 10 ml of methanol at reflux temperature for 60 m and then evaporated to dryness. The residue was partitioned with methylene chloride and water saturated with carbon dioxide (pH-8–9). The organic layer was separated and washed with water, dried, and concentrated. A solution of the residue in 60:30:1 heptane-ethyl acetate-acetic was filtered through a pad of silica gel. The filtrate was evaporated to give an amorphous solid; mass spectrum (electrospray, m/e) M+H 467.9, 469.9.

EXAMPLE 306

4-Chloro-7-methoxy-3-quinolinecarbonitrile

In the manner of Example 115 treatment of 1,4-dihydroquinolin-7-methoxy-4-oxo-3-carbonitrile with phosphorous oxychloride gave the title compound as a tan solid; mass spectrum (electrospray, m/e) M+H 219.2, 221.2.

EXAMPLE 307

4-(4-Chloro-2-fluorophenylamino)-7-methoxy-3-quinolinecarbonitrile

In the manner of Example 274 reaction of 4chloro-7-methoxy-3-quinolinecarbonitrile with 4-chloro-2-fluoroaniline gave the title compound as an amber solid, mp 208–210° C.

EXAMPLE 308

4-(4-Chloro-2-fluorophenylamino)-7-hydroxy-3-quinolinecarbonitrile

In the manner of Example 302 reaction of 4-(4-chloro-2-fluorophenylamino)-7-methoxy-3-quinolinecarbonitrile with pyridine hydrochloride at 210° C. gave the title compound, mp 295–305° C.

EXAMPLE 309

4-[(4-Chloro-2-fluorophenylamino)-N-acetylamino]-7-hydroxy-quinolinecarbonitrile In the manner of Example 304 peracetylation of 4-(4-chloro-2-fluorophenylamino)-7-hydroxy-3-quinolinecarbonitrile with acetic anhydride in the presence of dimethylaminopyridine followed by de-O-acetylation with sodium bicarbonate in aqueous methanol gave the title compound as an amber solid, mp 182–191° C.

EXAMPLE 310

4-(4-Chloro-2-fluorophenylamino)-7-ethoxy-3-quinolinecarbonitrile

In the manner of Example 305 alkylation of 4-[(4-Chloro-2-fluorophenylamino)-N-acetylamino]-7-hydroxy-3-quinolinecarbonitrile with ethyl iodide in the presence of potassium carbonate in DMF followed by de-N-acetylation with potassium carbonate in aqueous methanol gave the title compound as a white solid, mp 221–224° C.

EXAMPLE 311

4-[(3-Bromophenyl)amino]-6,7-bis(2-methoxyethoxy)-3-quinolinecarbonitrile

In the manner of Example 305 alkylation of 4-(3-bromophenylamino)-6,7-dihydroxy-3-quinolinecarbonitrile with 2-bromoethyl methyl ether in the presence of potassium carbonate in DMF gave the title compound as a light yellow solid, mp 135–138° C.

EXAMPLE 312

4-(4-Hydroxy-2-methyl-phenylamino)-6-methoxy-7-(3-morpholin-4-yl-propoxy)-quinoline-3-carbonitrile A mixture of 0.3 g of 4chloro-6-methoxy-7-(3-morpholin-4-yl-propoxy)-quinoline-3-carbonitrile derivative, 0.12 g of 4amino-m-cresol, 0.1 g of pyridine hydrochloride and 4 ml of 2-ethoxy ethanol was stirred under nitrogen at reflux temperature for 1.5 hr. The mixture was cooled and added to the mixture of ethyl acetate and saturated solution of sodium bicarbonate, stirred for 15 minutes. Following separation of layers, the organic layer was dried over anhydrous sodium sulfate, filtered and filtrate was evaporated to yield dark oil. The oil was purified by silica gel flash chromatography utilizing a gradient of methylene chloride/methanol (95:5 to 90:10 ) to give 0.23 g of the title compound as a tan solid, mp120–126 C; mass spectrum (electrospray, m/e):M+H 449.

EXAMPLE 313

4-(3-Bromo-phenylamino)-6-methoxy-7-(3-morpholin-4-yl-propoxy)-quinoline-3-carbonitrile The method of Example 312 was used as well as 0.3 g of 4-chloro-6-methoxy-7-(3-morpholin-4-yl-propoxy)-quinoline-3-carbonitrile, 0.12 ml of 3-bromo aniline, 0.1 g of pyridine hydrochloride and 4.0 ml of 2-ethoxy ethanol. This afforded an oil which was purified by silica gel flash chromatography utilizing a gradient of methylene chloride/methanol (96:4 to 92:8) to give 0.22 g of the tide compound as an off white solid, mp 115–118 C; mass spectrum (ES, m/e):M+H499.

EXAMPLE 314

6-Methoxy-4-(2-methylsulfanyl-phenylamino)-7-(3-morpholin-4-yl-propoxy)-quinoline-3-carbonitrile The method of Example 312 was used as well as 0.3 g of 4-chloro-6-methoxy-7-(3-morpholin-4-yl-propoxy)-quinoline-3-carbonitrile, 0.14 ml of 2-(methyl mercapto) aniline, 0.1 g of pyridine hydrochloride and 4.0 ml of 2-ethoxy ethanol. This afforded an oil which was purified by silica gel flash chromatography [methylene chloride/methanol (96:4) ] to give 0.16 g of the title compound as an off white solid, mp 179–180 C; mass spectrum (ES, m/e) :M+H465.

EXAMPLE 315

4-(4-Hydroxy-3,5-dimethyl-phenylamino)-6-methoxy-7-morpholin-4-yl-propoxy)-quinoline-3-carbonitrile The method of Example 312 was used as well as 0.25 g of 4-chloro-6-methoxy-7-(3-morpholin-4-yl-propoxy)-quinoline-3-carbonitrile, 0.12 ml of 4-amino, 2–5 dimethyl phenol, 0.1 g of pyridine hydrochloride and 4.0 ml of 2-ethoxy ethanol. This afforded an oil which was purified by silica gel flash chromatography utilizing a gradient of methylene chloride/methanol (96:4 to 92:8) to give 0.20 g of the title compound as a tan foam, mp 122–125 C; mass spectrum (ES, m/e):M+H481.

EXAMPLE 316

4-(2-Aminphenylmethylamino)-6,7-diethoxy-3-quinolinecarbonitrile

In the manner of Example 61 reaction of 4-chloro-6,7-diethoxy-3-quinolinecarbonitrile with 2-aminobenzylamine gave the tide compound as an off-white solid, mp 173–177° C.

EXAMPLE 317

4-(3,4-Difluorophenylmethylamino)-6,7-diethoxy-3-quinolinecarbonitrile

In the manner of Example 61 reaction of 4-chloro-6,7-diethoxy-3-quinolinecarbonitrile with 3,4-difluorobenzylamine gave the title compound as a tan solid, mp167–169° C.

EXAMPLE 318

4-Methoxy-but-2-enoic acid [4-(3-bromo-phenylamino)-quinazolin-6-yl]-amide

To a solution of 1 g (3.17 mmol) of 6-amino-4-[(3-bromophenyl)amino]-3-quinolinecarbonitrile and 0.6 g of disopropylethylamine in 21 ml of tetrahydrofuran was added 0.47 g (3.5 mmol) of 4-methoxycrotonoyl chloride at 0° C. with stirring. After 1.5 hr at 0° C. another 0.15 g of acid chloride was added. The mixture was diluted with 75 ml of tetrahydrofuran and stirred with a mixture of brine and saturated sodium bicarbonate. 50 ml of ethyl acetate was added and the organic layer was separated and dried over magnesium sulfate. Solvent was removed and the residue was purified by chromatography on silica gel. Recrystalization from 1-butanol gave 1.25 g of a yellow powder: mass spectrum (electrospray, m/e): M+H 415.0 and 415.9.

EXAMPLE 319

4-(4-Chloro-2-fluoro-5-hydroxy-phenylamino)-6,7-dimethoxyquinoline-3-carbonitrile A mixture of 0.25 g of 4-chloro-6,7-dimethoxy-3-quinolinecarbonitrile, 0.195 g of 4-chloro-2-fluoro-5-hydroxyaniline, 0.116 g of pyridine hydrochloride, and 3 ml of ethoxyethanol was stirred under nitrogen, at reflux temperature for 1 h. The mixture was cooled and added to 10 ml of water. To this mixture was added sodium carbonate until pH 9. The product was collected, washed with water, and dried to give 0.327 g of 4-(4-chloro-2-fluoro-5-hydroxy-phenylamino)-6,7-dimethoxy-quinoline-3-carbonitrile as a solid, dec >260° C. ; mass spectrum (electrospray, m/e): M+H 373.9.

EXAMPLE 320

7-benzyloxy-4-hydroxy-6-methoxy-quinoline-3-carbonitrile

To a stirred solution of 26.9 ml of n-butyllithium (2.5 M in hexane) in 50 ml of THF at −78° C. was added a 3.51 ml of acetonitrile in 20 ml of THF during 10 min. After stirring at −78° C. for 30 min, the mixture was treated with 10 g of L17741-150 (B. Floyd) in 20 ml of THF during 5 min. After 15 min at −78° C. the stirred mixture was warmed to 0° C. for a further 30 min. It was then treated with 5 ml of acetic acid, warmed to 25° C. and stirred for 30 min. The mixture was evaporated to dryness, and diluted with aqueous sodium bicarbonate. The resulting off-white solid was filtered, washed with water, ethyl acetate and ether. After drying, 4.5 g of 7-benzyloxy-4-hydroxy-6-methoxy-quinoline-3-carbonitrile was obtained as an off-white solid, dec >255° C. ; mass spectrum (electrospray, m/e) M+H 307.

EXAMPLE 321

7-benzyloxy-4-chloro-6-methoxy-quinoline-3-carbonitrile

To a stirred suspension of 1 g of 7-benzyloxy-4-hydroxy-6-methoxy-quinoline-3-carbonitrile in 10 ml of methylene chloride was added 5 ml of oxalyl chloride (2M in methylene chloride), and 2 drops of N,N-dimethylformamide. The mixture was refluxed for 20 min and to it was slowly added aqueous sodium bicarbonate until the bubbling ceased. Following separation of the layers, the organic layer was evaporated to a small volume, then passed through a plug of magnesol. Elution with 50 ml methylene chloride, followed by evaporation provided 0.6 g of 7-benzyloxy-4-chloro-6-methoxy-quinoline-3-carbonitrile as a pale yellow solid, mp 282–284° C.; mass spectrum (electrospray, m/e) M+H 325.

EXAMPLE 322

7-Benzyloxy-4-(4-chloro-2-fluoro-phenylamino)-6-methoxy-quinoline-3-carbonitrile A mixture of 0.200 g of 7-benzyloxy-4chloro-6-methoxy-quinoline-3-carbonitrile 0.108 g of 4-chloro-2-fluoroaniline, 0.071 g of pyridine hydrochloride, and 3 ml of ethoxyethanol was stirred under nitrogen, at reflux temperature for 1 h. The mixture was cooled and added to 10 ml of water. To this mixture was added sodium carbonate until pH 9. The product was collected, washed with water, and dried to give 0. 150 g of 7-Benzyloxy-4-(4-chloro-2-fluoro-phenylamino)-6-methoxy-quinoline-3-carbonitrile hydrochloride as a solid, mp 241–243° C.; mass spectrum (electrospray, m/e): M+H 433.9.

EXAMPLE 323

4-(4-Chloro-2-fluoro-5-hydroxy-phenylamino)-7-methoxy-6-(3-morpholin-4-yl)-propoxyl-quinoline-3-carbonitrile A mixture of 0.35 g of 4-chloro-7-methoxy-6-(3-morpholin-4-yl-propoxy))-3-quinolinecarbonitrile, 0.188 g of 4-chloro-2-fluoro-5-hydroxyaniline, 0.112 g of pyridine hydrochloride, and 4 ml of ethoxyethanol was stirred under nitrogen, at reflux temperature for 1 h. The mixture was cooled and added to 10 ml of water. To this mixture was added sodium carbonate until pH 9. The product was collected, washed with water, and dried to give 0.210 g of 4-(4-Chloro-2-fluoro-5-hydroxy-phenylamino)-7-methoxy-6-(3-morpholin-4-yl)-propoxyl-quinoline-3-carbonitrile as a solid, mp 125–128° C.; mass spectrum (electrospray, m/e): M+H 487.0.

EXAMPLE 324

4(3-acetylphenylamino)-6,7-dimethoxy-3-quinolinecarbonitrile

In the manner of Example 274 reaction of 4-chloro-6,7-dimethoxy-3-quinolinecarbonitrile with 3-aminoacetophenone gave the tide compound as a tan solid, mp 204–206° C.

EXAMPLE 325

4-(3-Bromophenylamino)-6,7-di-methoxymethyl-3-quinolinecarbonitrile

In the manner of Example 305 treatment of 4-(3-bromophenylamino)-6,7-dihydroxy-3-quinolinecarbonitrile with potassium carbonate and chloromethyl ether in dimethylformamide gave the title compound as a yellow solid: mp=113–116° C.

EXAMPLE 326

N-[4-(3-Bromo-phenylamino)-3-cyano-quinolin-6-yl]-3-chloro-(E) acrylamide and

EXAMPLE 327

N-[4-(3-Bromo-phenylamino)-3-cyano-quinolin-6-yl]-3-chloro-(Z)-acrylamide

To a solution of 0.5 g (1.47 mmol) of of 6-amino-4-[(3-bromophenyl)amino]-3-quinolinecarbonitrile and 0.24 g (1.8 mmol) of diisopropylethyl amine in 3 ml of terahydrofuran at 0° C. with stirring was added 0.21 g (1.7 mmol) of 3-chloro-acryloyl chloride (cis/trans mixture) in 2 ml of tetrahydrofuran. After 40 min at 0° C., the mixture was poured into a saturated solution of sodium bicarbonate and then extracted ether. The organic solution was dried over magnesium sulfate and the sovent was removed. The residue chromatographed on silica gel giving 0.16 g of N-[4-(3-bromo-phenylamino)-3-cyano-quinolin-6-yl]-3-chloro-(E) acrylamide: mass spectrum (electrospray, m/e,): M+H 424.9, 427.0, and 0.12 g of N-[4-(3-bromo-phenylamino)-3-cyano-quinolin-6-yl]-3-chloro-(Z) acrylamide acrylamide: mass spectrum (electrospray, m/e,): M+H 425.0, 427.0

EXAMPLE 328

N-[4-[(3-Bromophenyl)amino]-3-cyano-6-quinolinyl]-4-morpholino-2-butynamide

Isobutyl chloroformate (0.161 g, 1.18 mmol) was dropwise added into an ice cold solution of 4-morpholino-2-butynoic acid (0.25 g, 1.48 mmol) and N-methylmorpholine (0.15 g, 1.48 mmol) in 8 mL of tetrahydrofuan under $N_2$. After stirring for 30 min, a solution of 025 g (0.74 mmol) of 6-amino-4-[(3-bromophenyl)amino]-3-quinolinecarbonitrile in 6 mL of pyridine was added dropwise and the mixture was stirred at 0° C. for 2 hr. The reaction was quenched with ice water, poured into saturated sodium bicarbonate and brine, and extracted with ethyl acetate. The ethyl acetate layer was concentrated and purified by thin-layer chromatography eluted with 15% methanol in ethyl acetate. The product was collected, and dried in vacuo to give 0.096 g (27%) of yellow solid; :mass spectrum (electrospray, m/e,) 490.1, 492.1 (M+H$^+$); mp 145–148° C.

EXAMPLE 329

N-[4-[(3-Bromophenyl)amino]-3-cyano-6-quinolinyl]-4-dimethylamino-2-butynamide

Isobutyl chloroformate (0.342 g, 2.5 mmol) was dropwise added into an ice cold solution of 4-dimethylamino-2-butynoic acid (0.9 g, 3.8 mmol) and N-methylmorpholine (0.384 g, 3.8 mmol) in 50 mL of tetrahydrofuan under $N_2$. After stirring for 30 min, a solution of 0.644 g (1.9 mmol) of 6-amino-4-[(3-bromophenyl)amino]-3-quinolinecarbonitrile in 10 mL of pyridine was added dropwise and the mixture was stirred at 0° C. for 2.5 hr. The reaction was quenched with ice water, poured into saturated sodium bicarbonate and brine, and extracted with ethyl acetate. The ethyl acetate layer was concentrated and purified by thin-layer chromatography eluted with 15% methanol in ethyl acetate. The product was collected, and dried in vacuo to give 0.144 g (21%) of yellow solid; : mass spectrum (electrospray, m/e,): 447.9, 450.2 (M+H$^+$); mp 180° C. (dec.).

EXAMPLE 330

N-[4-[(3-Bromophenyl)amino]-3-cyano-6-quinolinyl]-4-methoxy-2-butynamide

Isobutyl chloroformate (0.432 g, 3.2 mmol) was dropwise added into an ice cold solution of 4-methoxy-2-butynoic acid (0.72 g, 6.32 mmol) and N-methylmorpholine (0.959 g, 9.78 mmol) in 20 mL of tetrahydrofuan under $N_2$. After stirring for 30 min, a solution of 0.5 g (1.58 mmol) of 6-amino-4-[(3-bromophenyl)amino]-3-quinoline-carbonitrile in 8 mL of pyridine was added dropwise and the mixture was stirred at 0° C. for 2 hr. The reaction was quenched with ice water, poured into saturated sodium bicarbonate and brine, and extracted with ethyl acetate. The ethyl acetate layer was concentrated and purified by thin-layer chromatography eluted with 5% methanol in chlorform. The product was collected, and dried in vacuo to give 0.27 g (41%) of yellow solid; mass spectrum (electrospray, m/e,): 435.1, 437.0 (M+H$^+$); mp 197° C. (dec.).

EXAMPLE 331

N-[4-[(3-Bromophenyl)amino]-3-cyano-6-quinolinyl]-4-t-butyldimethylsiloxy-2-butynamide Isobutyl chloroformate (0.214 g, 1.57 mmol) was dropwise added into an ice cold solution of 4-t-butyldimethylsiloxy-2-butynoic acid (0.336 g, 1.57 mmol) and N-methylmorpholine (0.19 g, 1.88 mmol) in 15 mL of tetrahydrofuan under $N_2$. After stirring for 30 min, the reaction mixture was added dropwise into a solution of 0.4 g (1.18 mmol) of 6-amino-4-[(3-bromophenyl)amino]-3-quinolinecarbonitrile in 3 mL of tetrahydrofuran and 1.5 mL of pyridine and stirred at 0° C. for 1 hr. The reaction was quenched with ice water, poured into saturated sodium bicarbonate and brine, and extracted with ethyl acetate. The ethyl acetate layer was concentrated and purified by column chromatography eluted with 60% ethyl acetate in hexane. The product was collected, and dried in vacuo to give 0.22 g (35%) of yellow solid;: mass spectrum (electrospray, m/e,): 535.1189 (M$^+$.).

EXAMPLE 332

N-[4-[(3-Bromophenyl)amino]-3-cyano-6-quinolinyl]-4-hydroxy-2-butynamide

N-[4-[(3-Bromophenyl)amino]-3-cyano-6-quinolinyl]-4-t-butyldimethylsiloxy-2-butynamide (60 mg, 0.122 mmol) was dissolved in a solution of acetic acid, tetrahydrofuran and water (3:1:1) and stirred overnight at room temperature. The solution was diluted with ethyl acetate and washed with saturated sodium bicarbonate and brine. The ethyl acetate was concentrated to give 42.2 mg (90%) of yellow solid; : mass spectrum (electrospray, m/e,): 421.0311 (M$^+$.).

EXAMPLE 333

4-(3-Hydroxymethyl-2-methylphenylamino)-6,7-dimethoxyquinoline-3-carbonitrile

A mixture of 0.248 g (1 mmol) of 4-chloro-6,7-dimethoxy-quinoline-3-carbonitrile, 0.151 g (1.1 mmol) of 3-amino-2-methylbenzyl alcohol, 0.116 g (1 mmol) pyridine hydrochloride and 12 ml of 2-ethoxyethanol was heated in a 138–140° C. oil bath for 6 hours; progress of the reaction was monitored by TLC. When TLC indicated the disappearance of starting material, the reaction was cooled and concentrated in vacuo to a thick oil. To this oil was added 50 ml of water followed by 5 ml of 1M $NaHCO_3$, approximately pH 8. The resulting precipitate was collected, washed with water and diethyl ether, and dried in vacuo at 65° C. to give 0.32 g (91.5%) of the desired product as light tan crystals. MP 123–125° C.; : mass spectrum (electrospray, m/e,): 349.9(M+H)$^+$.

EXAMPLE 334

4-(2-Amino-4,5-dimethylphenylamino)-6,7-dimethoxy-quinoline-3-carbonitrile

A mixture of 0.248 g (1 mmol) of 4-chloro-6,7-dimethoxy-quinoline-3-carbonitrile, 0.410 g (3.0 mmol) of 4,5- dimethyl-1,2-diphenylenediamine, 0.116 g (1 mmol) pyridine hydrochloride and 12 ml of 2-ethoxyethanol was heated in a 138–140° C. oil bath for 1 hour; progress of the reaction was monitored by TLC. When TLC indicated the disappearance of starting material, the reaction was cooled and concentrated in vacuo to a thick oil. To this oil was added 50 ml of water followed by 5 ml of 1M NaHCO$_3$, approximately pH 8. The resulting precipitate was collected, washed with water and diethyl ether, and dried in vacuo at 65° C. to give 0.587 g of the desired product (impure). The impure product was digested with 50 ml of chloroform and 50 ml of ethyl acetate for 0.5 hour, collected, washed with chloroform and dried to give 0.307 g (88%) of the desired pure product as yellow crystals. MP 260–262° C.; :mass spectrum (electrospray, m/e,): 348.1582(HR).

EXAMPLE 335

4(4-Ethylphenylamino)-6,7-dimethoxyquinoline-3-carbonitrile

A mixture of 0.248 g (1 mmol) of 4-chloro-6,7-dimethoxy-quinoline-3-carbonitrile, 0.14 ml (1.1 mmol) of 4-ethylaniline, 0.116 g (1 mmol) pyridine hydrochloride and 12 ml of 2-ethoxyethanol was heated in a 138–140° C. oil bath for 1 hour; progress of the reaction was monitored by TLC. When TLC indicated the disappearance of starting material, the reaction was cooled and concentrated in vacuo to a thick oil. To this oil was added 50 ml of water followed by 5 ml of 1M NaHCO$_3$, approximately pH 8. The resulting precipitate was collected, washed with water and diethyl ether, and dried in vacuo at 65° C. to give 0.325 g (97.5%) of the desired product as light cream crystals. MP 248–250° C.; : mass spectrum (electrospray, m/e,): 333.1462.

EXAMPLE 336

4-(4-Chloro-2-methylphenylamino)-6,7-dimethoxyquinoline-3-carbonitrile

A mixture of 0.248 g (1 mmol) of 4-chloro-6,7-dimethoxy-quinoline-3-carbonitrile, 0.156 g (1.1 mmol) of 4-chloro-2-methylaniline, 0.116 g (1 mmol) pyridine hydrochloride and 12 ml of 2-ethoxyethanol was heated in a 138–140° C. oil bath for 24 hours; progress of the reaction was monitored by TLC. After 24 hours an additional 0.156 g of of 4-chloro-2-methylaniline was added and the heating continued for 24 hours. When TLC indicated the disappearance of starting material, the reaction was cooled and concentrated in vacuo to a thick oil. To this oil was added 50 ml of water followed by 5 ml of 1M NaHCO$_3$, approximately pH 8. The gummy solid was dissolved in chloroform and passed through a pad of hydrous magnesium silicate. The liquid was concentrated in vacuo and the residue triturated 5 times with hexane. The resulting precipitate was collected, washed with hexane, and dried in vacuo at 65° C. to give 0.250 g (71%) of the desired product as brown crystals. MP 227–229° C.;: mass spectrum (electrospray, m/e,): 353.8(M+H)$^+$.

EXAMPLE 337

6,7-Dimethoxy-4(3-phenoxyphenylamino)quinoline-3-carbonitrile

A mixture of 0.248 g (1 mmol) of 4-chloro-6,7-dimethoxy-quinoline-3-carbonitrile, 0.204 g (1.1 mmol) of 3-phenoxyaniline, 0.116 g (1 mmol) pyridine hydrochloride and 12 ml of 2-ethoxyethanol was heated in a 138–140° C. oil bath for 3 hours; progress of the reaction was monitored by TLC. When TLC indicated the disappearance of starting material, the reaction was cooled and concentrated in vacuo to a thick oil. To this oil was added 50 ml of water followed by 5 ml of 1M NaHCO$_3$, approximately pH 8. The resulting precipitate was collected, washed with water and diethyl ether, and dried in vacuo at 65° C. to give 0.309 g (78%) of the desired product as cream crystals. MP 253–254° C.; : mass spectrum (electrospray, m/e,): 397.0(M+H)$^+$.

EXAMPLE 338

4-(4-Chloro-3-trifluoromethylphenylamino)-6,7-dimethoxyquinoline-3-carbonitrile

A mixture of 0.248 g (1 mmol) of 4-chloro-6,7-dimethoxy-quinoline-3-carbonitrile, 0.215 g of 4-chloro-3-trifluoromethylaniline, 0.116 g (1 mmol) pyridine hydrochloride and 12 ml of 2-ethoxyethanol was heated in a 138–140° C. oil bath for 1.5 hours; progress of the reaction was monitored by TLC. When TLC indicated the disappearance of starting material, the reaction was cooled and concentrated in vacuo to a thick oil. To this oil was added 50 ml of water followed by 5 ml of 1M NaHCO$_3$, approximately pH 8. The resulting precipitate was collected, washed with water and diethyl ether, and dried in vacuo at 65° C. to give 0.266 g (65.5%) of the desired product as cream crystals. MP 265–267° C.;: mass spectrum (electrospray, m/e,): 408.2 (M+H)$^+$.

EXAMPLE 339

4-(3-Hydroxy-phenylamino)-6,7-dimethoxy-quinoline-3-carbonitrile

Using the method described in Example 105, 0.7 g of 4-chloro-6,7-dimethoxy-3-quinolinecarbonitrile and 0.38 g of 3-aminophenol was converted to 0.83 g of the title compound: mass spectrum (electrospray, m/e,): 321.9, 322.8 (M+H)$^+$

EXAMPLE 340

4-(4-methyl-phenylamino)-6,7-dimethoxy-quinoline-3-carbonitrile

Using the method described in Example 105, 0.7 g of 4-chloro-6,7-dimethoxy-3-quinolinecarbonitrile and 0.317 g of 4-methylphenol was converted to 0.79 g of the tide compound: MP=128–130° C.

EXAMPLE 341

4-(3-Hydroxy-4-methyl-phenylamino)-8-methoxy-6-nitro-quinoline-3-carbonitrile

Using the method described in Example 105, 0.5 g of 4-chloro-8-methoxy-6-nitro-3-quinolinecarbonitrile and 0.28 g of 3-hydroxy-4-methylphenol was converted to 0.3 g of the title compound: mass spectrum (electrospray, m/e,): 350.9, 351.9 (M+H)$^+$

EXAMPLE 342

4-(4-chloro-2-fluoro-phenylamino)-8-methoxy-6-nitro-quinoline-3-carbonitrile

Using the method described in Example 105, 0.5 g of 4chloro-8-methoxy-6-nitro-3-quinolinecarbonitrile and 0.25 ml of 4-chloro-2-fluoro phenol was converted to 0.08 g of the title compound: mass spectrum (electrospray, m/e,): 372.8, 374.8 (M+H)$^+$

EXAMPLE 343

4-(3-hydroxy-4-methoxy-phenylamino)-8-methoxy-6-nitro-quinoline-3-carbonitrile

Using the method described in Example 105, 0.5 g of 4chloro-8-methoxy-6-nitro-3-quinolinecarbonitrile and 0.31 g of 3-hydroxy-4-methoxy phenol was converted to 0.21 g of the title compound: mass spectrum (electrospray, m/e,): 366.9, 367.9 (M+H)+

EXAMPLE 344

6-Amino-4-(3-hydroxy-4-methyl-phenylamino)-8-methoxy -quinoline-3-carbonitrile

Using the method described in Example 196, 0.2 g of 4-(3-hydroxy-4-methyl-phenylamino)-8-methoxy-6-nitro-quinoline-3-carbonitrile and 0.1 g of iron was converted to 0.14 g of the title compound: :MP=227° C. (dec)

EXAMPLE 345

6-Amino-4-(3-hydroxy-4-methoxy-phenylamino)-8-methoxy-quinoline-3-carbonitrile

Using the method described in Example 196, 0.1 g of 4-(3-hydroxy-4-methoxy-phenylamino)-8-methoxy-6-nitro-quinoline-3-carbonitrile and 0.09 g of iron was converted to the title compound: :MP=215° C. (dec)

EXAMPLE 346

N-{4-[(3-Bromo-4-fluorophenyl)amino]-3-cyano-7-methoxy-6-quinolinyl}-4-bromo-2-butenamide By using the method described in Example 172 and not reacting with dimethylamine, a portion of 6-amino-4(3-bromo-fluoro-phenylamino)-7-methoxy-quinoline-3-carbonitrile was converted to the title compound: mass spectrum (electrospray, m/e,): 532.8, 534.8, 536.8 (M+H)+

EXAMPLE 347

N-{4-[(3-Bromophenyl)amino]-3-cyano-7-methoxy-6-quinolinyl}-4-chloro-2-butenamide In the method described in Example 198, a side product was isolated that proved to be the title compound: mass spectrum (electrospray, m/e,): 471.25, 473.3(M+H)+

EXAMPLE 348

N-{3-Cyano-4-[(3-iodophenyl)amino]-6-quinolinyl}-2-butynamide

Dissolved 275 mg (3.27 mmol) 2-butynoic acid in 20 ml THF under $N_2$ and chilled to 0° C. Added 420 µl (3.23 mmol) isobutyl chloroformate and 355 µl (3.24 mmol) N-methylmorpholine and stirred for 10 minutes. Added dropwise a solution of 500 mg (1.30 mmol) 6-amino-4-[(3-iodophenyl)amino]-3-quinolinecarbonitrile and after 15 minutes, removed ice bath and stirred overnight at 25° C. Stripped solvent, washed with water and collected solids. Boiled in ethyl acetate, collected, and dried in vacuo, giving 228 mg of orange-brown solid: mass spectrum (electrospray m/e): M+H=453.1.

EXAMPLE 349

N-{3-Cyano-4-[(3-methylphenyl)amino]-6-quinolinyl}-2-propenamide

Dissolved 500 mg (1.82 mmol) of 6-amino-4-[(3-methylphenyl)amino]-3-quinolinecarbonitrile in 1.0 ml DMF and 6 ml THF and chilled to 0° C. under $N_2$. Added 280 µl (2.00 mmol) triethylamine and 166 µl (2.00 mmol) acryloyl chloride. Removed ice bath at 15 minutes and at 1 hour, stripped solvent and slurried residue with dilute sodium bicarbonate. Collected crystals and washed with water. Boiled solids in ethyl acetate, collected and dried in vacuo, giving 238 mg of yellow-orange solid: mass spectrum (electrospray m/e): M+H=329.1.

EXAMPLE 350

N-{4-r(4Bromophenyl)amino]-3-cyano-6-quinolinyl}-2-butynamide

Dissolved 310 mg (3.68 mmol) 2-butynoic acid in 20 ml THF and chilled to 0° C. under $N_2$. Added 480 µl (3.68 mmol) isobutyl chloroformate and 410 µl (3.72 mmol) N-methylmorpholine. Stirred for 20 minutes and dropwise added a solution of 500 mg (1.47 mmol) 6amino-4-[(4-bromophenyl)amino]-3-quinolinecarbonitrile in 1 ml DMF and 10 ml THF. Removed ice bath after 15 minutes and stirred at 25° C. overnight. Stripped solvent, slurried residue with water and collected solids. Boiled solids in ethyl acetate, collected, and dried in vacuo, giving 341 mg of yellow solid: mass spectrum (electrospray m/e): M+H= 405.1, 407.1.

EXAMPLE 351

N-{4-[(3-Chloro-4-thiophenoxyphenyl)amino]-3-cyano-6-quinolinyl}-2-propenamide

Dissolved 1.00 g (2.48 mmol) 6-amino-4-[(3-chloro-4-thiophenoxyphenyl)amino]-3-quinolinecarbonitrile in 2.0 ml DMF and 12 ml THF and chilled to 0° C under $N_2$. Added 380 µl (2.73 mmol) triethylamine and 227 µl (2.73 mmol) acryloyl chloride. Removed ice bath at 15 minutes and at 1.5 hours stripped solvent and slurried residue with dilute sodium bicarbonate. Collected solids and washed with water. Recrystallized from ethyl acetate and dried in vacuo, giving 293 mg of yellow-orange solid: mass spectrum (electrospray m/e): M+H=457.3. 459.3.

EXAMPLE 352

N-{3-Cyano-4-[(3,4-difluorophenyl)amino]-6-quinolinyl}-2-butynamide

Dissolved 425 mg (5.06 mmol) 2-butynoic acid in 40 ml THF and chilled to 0° C. under $N_2$. Added 556 µl (5.06 mmol) N-methylmorpholine and 658 µl (5.06 mmol) isobutyl chloroformate and stirred for 10 minutes. Added dropwise a solution of 1.00 g (3.37 mmol) 6-amino-4-[(3,4-difluorophenyl)amino]-3-quinolinecarbonitrile in 2.0 ml hot DMF and 20 ml THF. Removed ice bath at 15 minutes and stirred at 25° C. overnight. Stripped solvent, slurried residue with water, and collected solids. Boiled in ethyl acetate, collected solids, and dried in vacuo, giving 735 mg of yellow solid: mass spectrum (electrospray m/e): M+H=363.3

EXAMPLE 353

N-{4-[(3-Chlorophenyl)amino]-3-cyano-6-quinolinyl]-2-butynamide

Dissolved 428 mg (5.09 mmol) 2-butynoic acid in 40 ml THF and chilled to 0° C. under $N_2$. Added 560 µl (5.09 mmol) N-methylmorpholine and 662 µl (5.09 mmol) isobutyl chloroformate and stirred for 10 minutes. Added dropwise a solution of 1.00 g (3.39 mmol) 6-amino-4-[(3- chlorophenyl)amino]-3-quinolinecarbonitrile in 2 ml DMF and 20 ml THF. Removed ice bath at 15 minutes and stirred at 25° C. overnight. Stripped solvent, slurried residue with water and collected solids. Boiled in ethyl acetate, collected and dried in vacuo, giving 975 mg of yellow solid: mass spectrum (electrospray m/e): M+H=361.1, 363.2.

EXAMPLE 354

N-{3-Cyano-4-[(3-isopropylphenyl)amino]-6-quinolinyl}-2-butynamide

Dissolved 695 mg (8.27 mmol) 2-butynoic acid in 40 ml THF and chilled to 0° C. under $N_2$. Added 1.08 ml (8.30 mmol) isobutyl chloroformate and 910 µl (8.27 mmol) N-methylmorpholine and stirred for 10 minutes. Dropwise added a solution of 1.00 g (3.31 mmol) 6-amino-4-[(3-isopropylphenyl)amino]-3-quinolinecarbonitrile in 2.0 ml DMF and 15 ml THF. Removed ice bath at 15 minutes and stirred at 25° C. overnight. Stripped solvent, slurried residue with water, and collected solid. Recrystallized from ethyl acetate and dried in vacuo, giving 329 mg of yellow-green solid: mass spectrum (electrospray m/e): M+H=369.2.

EXAMPLE 355

N-{3-Cyano-4-[(3-isopropylphenyl)amino]-6-quinolinyl}-2-propenamide

Dissolved 1.00 g (3.31 mmol) 6-amino-4-[(3-isopropylphenyl)amino]-3-quinolinecarbonitrile in 2.0 ml hot DMF, added 12 ml THF, and chilled to 0° C. under $N_2$. Added 507 µl (3.64 mmol) triethylamine and 303 µl (3.64 mmol) acryloyl chloride. Removed ice bath at 15 minutes and at 1 hour stripped solvent. Slurried residue with dilute sodium bicarbonate, collected solids and washed with water. Recrystallized from ethyl acetate and dried in vacuo, giving 366 mg of orange solid: mass spectrum (electrospray m/e): M+H=357.1.

EXAMPLE 356

6-Amino-4-[(3-isopropylphenyl)amino]-3-quinolinecarbonitrile

Added 0.5 g 10% palladium on carbon to a flask under $N_2$ and covered with 250 ml ethanol. To this added 4.818 g (14.5 mmol) 4-[(3-isopropylphenyl)amino]-6-nitro-3-quinolinecarbonitrile and 1.14 ml (36.2 mmol) anhydrous hydrazine and heated to reflux. At 1.5 hours, filtered hot mixture through celite, stripped solvent, and dried in vacuo, giving 4.30 g of yellow solid: mass spectrum (electrospray m/e): M+H=303.1.

EXAMPLE 357

4-[(3-Isopropylphenyl)amino]-6-nitro-3-quinolinecarbonitrile

A mixture of 5.00 g (21.5 mmol) 4-chloro-6-nitro-3-quinolinecarbonitrile, 200 ml ethanol, and 3.48 g (25.8 mmol) 3-isopropylaniline was heated to reflux under $N_2$. At 4 hours, removed heat and made basic with saturated sodium bicarbonate. Stripped solvents and azeotroped with ethanol. Slurried residue with hexane and collected solids. Dissolved in ethyl acetate, stirred with Darco, filtered through celite, stripped solvent and dried in vacuo, giving 5.289 g of yellow solid: mass spectrum (electrospray m/e): M+H=333.1.

EXAMPLE 358

4-(3-Bromo-phenylamino)-6-(3-pyrrolidin-1-yl-propylamino)-quinoline-3-carbonitrile Dissolved 0.64 g (3.69 mmol) 3-(pyrrolidin-1-yl) propionaldehyde dimethyl acetal in 10 ml water and acidified to pH 1 with concentrated HCl. Heated to 40° C. for 90 minutes, removed heat and neutralized with sodium bicarbonate. Dissolved 500 mg (1.47 mmol) 6-amino-4-(3-bromo-phenylamino)-quinoline-3-carbonitrile in 100 ml ethanol and added acetic acid until pH was 3 to 4. Added the deprotected aldehyde to the amine solution and stirred at 25° C. for 0.5 hour. Gradually added 94 mg (1.47 mmol) sodium cyanoborohydride and stirred overnight. Stripped solvent, partitioned between chloroform and water. Washed organic layer with brine and dried with sodium sulfate. Stripped solvent and filtered through a pad of silica gel, first with 10% methanol/chloroform, then 20% methanol/chloroform/1% ammonium hydroxide. Stripped solvent and dried in vacuo, giving 143 mg of yellow-brown solid: mass spectrum (electrospray m/e): M+H=450,452.1.

EXAMPLE 359

4-(3-Azido-phenylamino)-6,7-dimethoxy-quinoline-3-carbonitrile

Dissolved 643 mg (2.00 mmol) 4-(3-amino-phenylamino)-6,7-dimethoxy-quinoline-3-carbonitrile in 25 ml 80% acetic acid in water. Chilled to 0° C. and added 152 mg (2.21 mmol) sodium nitrite in 2.2 ml water. After 10 minutes, added 144 mg (2.21 mmol) sodium azide in 2.2 ml water. At 1.5 hours stripped solvent and dissolved residue in hot ethyl acetate. Washed with saturated sodium bicarbonate, water and brine and dried with sodium sulfate. Stripped solvent and redissolved in 60% ethyl acetate/ methylene chloride and filtered through a pad of silica gel. Stripped solvent and dried in vacuo, giving 526 mg of brown solid: mass spectrum (electrospray m/e): M+H=347.1.

EXAMPLE 360

6-Amino-4-[(4-Chloro-2-fluorophenyl)amino]-7-methoxy-3-quinolinecarbonitrile

A mixture of 500 mg (1.34 mmol) 4-[(4-chloro-2-fluorophenyl)amino]-7-methoxy-6-nitro-3-quinolinecarbonitrile, 20 ml ethanol and 1.52 ml (6.71 mmol) tin chloride dihydrate was heated to reflux under $N_2$. At 3 hours, removed heat, added ice water and made basic with sodium bicarbonate. Stirred for several hours and extracted with chloroform. Dried organic layer with sodium sulfate, stripped solvent and dried in vacuo, giving 350 mg of green solid: mass spectrum (electrospray m/e): M+H= 342.9, 344.8.

EXAMPLE 361

4-[(4-Chloro-2-fluorophenyl)amino]-7-methoxy-6-nitro-3-quinolinecarbonitrile

A mixture of 5.017 g (19.0 mmol) 4-chloro-7-methoxy-6-nitro-3-quinolinecarbonitrile, 250 ml ethanol, and .2.55 ml 22.8 mmol) 4-chloro-2-fluoroaniline was heated to reflux under $N_2$. At 3.5 hours, removed heat and made basic with saturated sodium bicarbonate. Stripped solvents and azeotroped with ethanol. Slurried residue with hexane, collected solids, and washed with water. Dissolved in ethyl acetate, stirred with Darco, filtered, stripped solvent, and dried in vacuo, giving 6.54 g of yellow solid: mass spectrum (electrospray m/e): M+H=372.8, 374.8.

EXAMPLE 362

4-[(3,4-dichlorophenyl)amino]-6-nitro-3-quinolinecarbonitrile

A mixture of 5.00 g (21.5 mmol) 4chloro-6-nitro-3quinolinecarbonitrile, 250 ml ethanol, and 4.17 g (25.6 mmol) 3,4-dichloroaniline was heated to reflux under N$_2$. At 3.5 hours, removed head and made basic with saturated sodium bicarbonate. Stripped solvents and azeotroped with ethanol. Slurried residue with hexane, collected solids and washed with water. Dissolved in ethyl acetate, stirred with Darco, filtered, stripped solvent and dried in vacuo, giving 2.106 g of yellow solid: mass spectrum (electrospray m/e): M+H=359.1, 361.0.

EXAMPLE 363

6-Amino-4-[(3-methylsulfanylphenyl)amino]-3-quinolinecarbonitrile

A mixture of 4.55 g (13.5 mmol) 4-[(3-methylsulfanylphenyl)amino]-6-nitro-3-quinolinecarbonitrile, 250 ml ethanol, 0.46 g 10% palladium on carbon, and 1.06 ml (33.8 mmol) anhydrous hydrazine was heated to reflux. At 4 hours, added 0.5 equivalents of hydrazine, and at 5 hours, filtered the hot mixture through celite. Stripped the solvent and dried in vacuo, giving 4.068 g brown solid: mass spectrum (electrospray m/e): M+H= 307.1.

EXAMPLE 364

4-[(3-Methylsulfanylphenyl)amino]-6-nitro-3-quinolinecarbonitrile

A mixture of 5.00 g (21.5 mmol) 4-chloro-6-nitro-3-quinolinecarbonitrile, 200 ml ethanol, and 3.18 ml (25.8 mmol) 3-methylsulfanylaniline was heated to reflux under N$_2$. At 2 hours, removed heat and made basic with saturated sodium bicarbonate. Stripped solvents and air dried. Washed residue with hexane, collected solids and washed with water. Dissolved in ethyl acetate, stirred with Darco, stripped solvent and dried in vacuo, giving 4.848 g of yellow solid: mass spectrum (electrospray m/e): M+H=337.1.

EXAMPLE 365

4-[(3-Trifluoromethoxyphenyl)amino]-6-nitro-3-quinolinecarbonitrile

A mixture of 5.00 g (21.5 mmol) 4-chloro-6-nitro-3-quinolinecarbonitrile, 200 ml ethanol, and 3.4 ml (25.3 mmol) 3-trifluoromethoxyaniline was heated to reflux. At 5 hours, removed heat and made basic with saturated sodium bicarbonate. Stripped solvents, slurried residue with hexane, collected, and washed with water. Dissolved in ethyl acetate, stirred with Darco, filtered, stripped solvent, and dried in vacuo, giving 4.537 g of yellow-orange solid: mass spectrum (electrospray m/e): M+H=374.8.

EXAMPLE 366

4-(3-Dimethylamino-phenylamino)-6,7-dimethoxy-quinoline-3-carbonitrile

A 1.25 gram (5 mmole) portion of 4-chloro, 6,7-dimethoxy-quinoline-3-carbonitrile and a 1.05 gram (5 mmole) portion of N, N-dimethyl-1,3-phenylenediamine in 10 ml of 2-methoxyethanol were refluxed for 2 hours in an oil bath at 154 deg. Cooling gave a solid which was recrystallized from water to give 0.4 grams (19%) of 4-(3-Dimethylamino-phenylamino)-6,7-dimethoxy-quinoline-3-carbonitrile which melted at 246–249° C.: mass spectrum (electrospray m/e):.(M+H)=349.2., (M+2H)$^{+2}$=174.9.

EXAMPLE 367

6,7-Dimethoxy-4-(4-methoxy -2-methyl-phenylamino)-quinoline-3-carbonitrile

A reaction mixture of 248.7 mg (1 mmol) of 4-chloro-6, 7-dimethoxy-3-quinolinecarbonitrile, 164.6 mg (1.2 mmol) of 4-methoxy-2-methyl-aniline and 115.6 mg (1 mmol) of pyridine hydrochloride in 10 mL of 2-ethoxyethanol was refluxed under N$_2$ for 3 hr. After removal of the solvent, the residue was diluted with water and neutralized to pH 7–8 with diluted sodium carbonate solution. The precipitate was filtered and washed with water and ether. After drying in vacuo, this yielded 250.2 mg (71.7%) of the product as a off red solid, m.p.>131° C(dec.), mass (electrospray, m/e): M+H 349.9.

EXAMPLE 368

3-(3-Cyano-6,7-dimethoxy-quinolin-4-ylamino)-2-methyl-benzoic acid

Using an analogous procedure to that described in Example 367, 248.7 mg (1 mmol) of 4-chloro-6,7-dimethoxy-3-quinolinecarbonitrile in 12 mL of 2-ethoxyethanol and in the presence of 115.6 mg (1 mmol) of pyridine hydrochloride was reacted with 196.5 mg (1.3 mmol) of 3-amino-2-methylbenzoic acid to give 89.6 mg (24.7%) of the product as a gray solid, m.p. 242–245° C., mass (electrospray, m/e): M+H 364.0.

EXAMPLE 369

4-(3-Hydroxy-4-methoxy-phenylamino)-6,7-dimethoxy-quinoline-3-carbonitrile

Using an analogous procedure to that described in Example 367, 248.7 mg (1 mmol) of 4-chloro-6,7-dimethoxy-3-quinolinecarbonitrile in 10 mL of 2-ethoxyethanol and in the presence of 115.6 mg (1 mmol) of pyridine hydrochloride was reacted with 167.0 mg (1.2 mmol) of 5-amino-2-methoxyphenol to give 313.3 mg (89.3%) of the product as a gray solid, m.p. 254–256° C., mass (electrospray, m/e): M+H351.2.

Example 370

4-(3-Chloro-4-methyl-phenylamino)-6,7-dimethoxy-quinoline-3 carbonitrile

Using an analogous procedure to that described in Example 367, 248.7 mg (1 mmol) of 4-chloro-6,7-dimethoxy-3-quinolinecarbonitrile in 10 mL of 2-ethoxyethanol and in the presence of 115.6 mg (1 mmol) of pyridine hydrochloride was reacted with 170.0 mg (1.2 mmol) of 2-chloro-4-amino-toluene to give 350.9 mg (99.4%) of the product as a yellow solid, m.p.>250° C., mass (electrospray, m/e): M+H 353.9,355.8.

EXAMPLE 371

6,7-Dimethoxy-4-(4-phenoxy-phenylamino)-quinoline-3-carbonitrile

Using an analogous procedure to that described in Example 367, 248.7 mg (1 mmol) of 4-chloro-6,7-dimethoxy-3-quinolinecarbonitrile in 12 mL of 2-ethoxyethanol and in the presence of 115.6 mg (1 mmol) of pyridine hydrochloride was reacted with 222.3 mg (1.2 mmol) of 4-phenoxyaniline to give 283.0 mg (71.3%) of the product as a light yellow solid, m.p. 239–241° C., mass (electrospray, m/e): M+H 397.9.

EXAMPLE 372

4-(5-Chloro-2-methoxy-phenylamino)-6,7-dimethoxy-quinoline-3-carbonitrile

Using an analogous procedure to that described in Example 367, 248.7 mg (1 mmol) of 4-chloro-6,7- dimethoxy-3-quinolinecarbonitrile in 12 mL of 2-ethoxyethanol and in the presence of 115.6 mg (1 mmol) of pyridine hydrochloride was reacted with 189.1 mg (1.2 mmol) of 5-chloro-o-anisidine to give 240.5 mg (65.0%) of the product as a cream solid, m.p. 200–202° C., mass (electrospray, m/e): M+H 369.9, 371.8.

EXAMPLE 373

4-(4-Chloro-2-fluoro-phenylamino)-6,7-dihydroxy-quinoline-3-carbonitrile

A mixture of 0.358 g of 4-(4-chloro-2-fluoro-phenylamino)-6,7-dimethoxy-quinoline-3-carbonitrile and 3 g of pyridine hydrochloride was stirred under nitrogen at 210–220° C. for 20 minutes. The mixture was cooled and added to 50 ml of 3% ammonium hydroxide solution. The product was collected, washed with water, and dried to give 0.302 g of 4-(4-chloro-2-fluoro-phenylamino)-6,7-dihydroxy-quinoline-3-carbonitrile as a solid, mp 270–272° C.; mass spectrum (EI, m/e): M 329.0363.

EXAMPLE 374

4-(3-Hydroxy-2-methyl-phenylamino)-6,7-dimethoxy-quinoline-3-carbonitrile

A mixture of 0.249 g of 4-chloro-6,7-dimethoxy-3-quinolinecarbonitrile, 0.123 g of 3-amino-o-cresol, 20 mg of pyridine hydrochloride, and 10 ml of ethoxyethanol was stirred under nitrogen, at reflux temperature for 30 minutes. The mixture was cooled and added to 40 ml of water. To this mixture was added sodium carbonate and concentrated hydrogen chloride to adjust pH to 7. The product was collected, washed with water, and dried to give 0.174 g of 4-(3-hydroxy-2-methyl-phenylamino)-6,7-dimethoxy-quinoline-3-carbonitrile as a solid, mp 255–257° C.; mass spectrum (electrospray, m/e): M+H 335.9.

EXAMPLE 375

4-(3-Chloro-4-methoxy-phenylamino)-6,7-dimethoxy-quinoline-3-carbonitrile

A mixture of 0.249 g of 4-chloro-6,7-dimethoxy-3-quinolinecarbonitrile, 0.158 g of 3-chloro-p-anisidine, 20 mg of pyridine hydrochloride, and 10 ml of ethoxyethanol was stirred under nitrogen, at reflux temperature for 30 minutes. The mixture was cooled and added to 40 ml of water. To this mixture was added sodium carbonate and concentrated hydrogen chloride to adjust pH to 7. The product was collected, washed with water, and dried to give 0.324 g of 4-(3-chloro-4-methoxy-phenylamino)-6,7-dimethoxy-quinoline-3-carbonitrile as a solid, mp 278–280° C.; mass spectrum (EI, m/e): M 369.0860.

EXAMPLE 376

6,7-Dimethoxy-4-(4-trifluoromethyl-phenylamino)-quinoline-3-carbonitrile

A mixture of 0.249 g of 4-chloro-6,7-dimethoxy-3-quinolinecarbonitrile, 0.322 g of 4-(trifluoromethyl)aniline, 20 mg of pyridine hydrochloride, and 10 ml of ethoxyethanol was stirred under nitrogen, at reflux temperature for 30 minutes. The mixture was cooled and added to 40 ml of water. To this mixture was added sodium carbonate and concentrated hydrogen chloride to adjust pH to 7. The product was collected, washed with water, and dried to give 0.268 g of 6,7-dimethoxy-4-(4-trifluoromethyl-phenylamino)-quinoline-3-carbonitrile as a solid, mp 116–118° C.; mass spectrum (EI, m/e): M 373.1031.

EXAMPLE 377

4-(3,4-Dibromophenylamino)-6-nitroquinoline-3-carbonitrile

A mixture of 6.20 g (26.6 mmol) of 4-chloro-6-nitroquinoline-3-carbonitrile and 8.00 g (31.9 mmol) of 3,4-dibromoaniline in 160 mL of EtOH was refluxed under $N_2$ for 5 hr. Satd $NaHCO_3$ was added and volatile material was removed. The residue was slurried with hexane, collected, washed with hexane and $H_2O$ and dried. The insoluble material was repeatedly extracted with boiling EtOAc and the solution was then filtered through silica gel. The solvent was removed to give 3.80 g of 4-(3,4-dibromophenylamino)-6-nitroquinoline-3-carbonitrile as a green solid: mass spectrum (electrospray, m/e): M+H 448.9.

EXAMPLE 378

6-Amino-4-(3-trifluoromethylphenylamino)quinoline-3-carbonitrile

A mixture of 6.0 g (16.8 mmol) of 6-nitro-4-(3-trifluoromethylphenylamino)quinoline-3-carbonitrile and 18.9 g (83.8 mmol) of $SnCl_2.2H_2O$ in 240 mL of EtOH was refluxed under $N_2$ for 1 hr. Ice water was added followed by $NaHCO_3$ to pH 8. The mixture was stirred for 2 hr and then extracted with $CHCl_3$. Darco was added and the extracts were filtered through anhyd $MgSO_4$ and evaporated. The residue was filtered through silica gel with 10% MeOH in $CHCl_3$. Solvent evaporation and drying in vacuo (40° C.) gave 4.87 g of 6-amino-4(3-tifluoromethylphenylamino)quinoline-3-carbonitrile as a brown solid: mass spectrum (electrospray, m/e): M+H 329.1.

EXAMPLE 379

6-Amino-4-(3,4-dibromophenylamino)quinoline-3-carbonitrile

Prepared from 4.90 g of 4-(3,4-dibromophenylamino)-6-nitroquinoline-3-carbonitrile and 12.4 g of $SnCl_2.2H_2O$ in the same manner as Example 378. There was obtained 1.25 g of 6-amino-4-(3,4-dibromophenylamino)quinoline-3-carbonitrile as a brown solid: mass spectrum (electrospray, m/e): M+H 416.9, 418.9.

EXAMPLE 380

N-[3-Cyano-4(3,4-dibromophenylamino)quinolin-6-yl]acrylamide

6-Amino-4-(3,4-dibromophenylamino)quinoline-3-carbonitrile (0.750 g. 1.79 mmol) in mL of THF was treated with 0.217 g (2.15 mmol) of EtN and 0.195 g (2.15 mmol) of acryloyl chloride at 0° C. under $N_2$. After stirring overnight at 25° C., the solvent was evaporated and the residue was slurried with water and collected. The residue was boiled twice with EtOAc and then dried in vacuo (50° C.) to give 0.609 g of N-[3-cyano-4-(3,4-dibromophenylamino) quinolin-6-yl]acrylamide as a brown solid: mass spectrum (electrospray, m/e): 470.9, 472.9.

EXAMPLE 381

N-[4-(3-Bromophenylamino)-3-cyanoquinolin-6-yl] propionamide

Prepared from 1.00 g of 6-amino-4-(3-bromophenylamino)quinoline-3-carbonitrile, 0.359 g of Et₃N and 0.328 g of propionyl chloride in the same manner as Example 380. The yield of N-[4-(3-bromophenylamino)-3-cyanoquinolin-6-yl]propionamide was 0.722 g as a yellow solid: mass spectrum (electrospray, m/e): M+H 395.1, 397.0.

EXAMPLE 382

(E)-But-2-enoic Acid [4-(3-Bromophenylamino)-3-cyanoquinolin-6-yl]amide

A solution of 0.637 g (7.40 mmol) of E-but-2-enoic acid in 25 mL of THF under $N_2$ was chilled in ice. Isobutyl chloroformate (1.01 g, 7.40 mmol) and N-methylmorpholine (0.747 g, 7.40 mmol) were added and the solution was stirred cold for 10 min. A slurry of 1.00 g (2.96 mmol) of 6-amino-4-(3-bromophenylamino)-quinoline-3-carbonitrile in 15 mL of THF was added and the mixture was stirred at 25° C. overnight. The mixture was evaporated and the residue was slurried in water, collected and dried. The residue was boiled twice with EtOAc and dried in vacuo (50° C.) to give 0.965 g of (E)-but-2-enoic acid [4-(3-bromophenylamino)-3-cyano-quinolin-6-yl]amide as a yellow solid: mass spectrum (electrospray, m/e): M+H 406.9, 408.9.

EXAMPLE 383

N-[4-(3-Bromophenylamino)-3-cyanoquinolin-6-yl]-2-methylacrylamide

Prepared from 0.500 g of 6-amino-4(3-bromophenylamino)quinoline-3-carbonitrile, 0.194 g of Et₃N and 0.202 g of methacryloyl chloride in the same manner as Example 380. There was obtained 0.317 g of N-[4-(3-bromophenylamino)-3-cyanoquinolin-6-yl]-2-methylacrylamide as a yellow solid: mass spectrum (electrospray, m/e): M+H 406.8, 408.8.

EXAMPLE 384

4-(3-Fluorophenylamino)-6-nitroquinoline-3-carbonitrile

Prepared from 5.00 g of 4-chloro-6-nitroquinoline-3-carbonitrile and 2.86 g of 3-fluoroaniline in the same manner as Example 377. The crude product was dissolved in a large volume of EtOAc, treated with Darco and filtered through Celite. Solvent removal and drying in vacuo (50° C.) gave 5.77 g of 4-(3-fluorophenylamino)-6-nitroquinoline-3-carbonitrile as a yellow-orange solid: mass spectrum (electrospray, m/e): M+H 309.2.

EXAMPLE 385

6-Amino-4-(3-fluorophenylamino)quinoline-3-carbonitrile

Prepared from 5.04 g of 4-(3-fluorophenylamino)-6-nitroquinoline-6-carbonitrile and 18.5 g of $SnCl_2.2H_2O$ in the same manner as Example 378. Filtration through silica was unnecessary. There was obtained 4.30 g of 6-amino-4-(3-fluorophenylamino)-quinoline-3-carbonitrile as yellow-brown crystals: mass spectrum (electrospray, m/e): M+H 279.1.

EXAMPLE 386

4-(3-Dimethylaminophenylamino)-6-nitroquinoline-3-carbonitrile

Prepared from 5.00 g of 4-chloro-6-nitroquinoline-3-carbonitrile, 5.38 g of 3-dimethylaminoaniline dihydrochloride and 5.17 g of triethylamine in the same manner as Example 377. The crude product was taken up in EtOAc, treated with Darco, filtered through Celite, evaporated and dried in vacuo (50° C.). The yield of 4-(3-dimethylaminophenylamino)-6-nitroquinoline-3-carbonitrile was 5.62 g as brick red crystals: mass spectrum (electrospray, m/e): M+H 334.2.

EXAMPLE 387

4-(4-Dimethylaminophenylamino)-6-nitroquinoline-3-carbonitrile

Prepared from 5.00 g of 4-chloro-6-nitroquinoline-3-carbonitrile, 5.38 g of 4-dimethylaminoaniline dihydrochloride and 5.17 g of triethylamine in the same manner as Example 386. The yield of 4-(4dimethylaminophenylamino)-6-nitroquinoline-3-carbonitrile was 5.58 g as brick red crystals: mass spectrum (electrospray, m/e): M+H 334.2.

EXAMPLE 388

6-Amino-4-(3-dimethylaminophenylamino)quinoline-3-carbonitrile

A mixture of 5.00 g (15.0 mmol) of 4-(3-dimethylaminophenylamino)-6-nitro-quinoline-3-carbonitrile, 1.20 g (37.5 mmol) of anhyd hydrazine and 0.5 g of 10% Pd/C in 250 mL of EtOH was refluxed under $N_2$ for 1.3 hr. The reaction was filtered through Celite, the Celite was washed with EtOH and the filtrate and washes were combined. Solvent evaporation and drying in vacuo (50° C.) gave 6-amino-4-(3 -dimethylaminophenylamino)quinoline-3-carbonitrile as a red brown solid: mass spectrum (electrospray, m/e): 303.9.

EXAMPLE 389

6-Amino-4-(4-dimethylaminophenylamino)quinoline-3-carbonitrile

Prepared from 4-(4-dimethylaminophenylamino)-6-nitroquinoline-3-carbonitrile (5.00 g), 1.20 g of anhyd hydrazine and 0.500 g of 10% Pd/C in the same manner as Example 388 155179. After washing first with MeOH (discarded), the product was eluted with DMF. The latter solvent was collected separately, evaporated and the residue was dried in vacuo (50° C.). The yield of 6-amino-4-(4-dimethylaminophenylamino)quinoline-3-carbonitrile was 4.00 g as a yellow solid: mass spectrum (electrospray, m/e): M+H 303.9.

EXAMPLE 390

But-2-ynoic Acid [4-(3-Fluorophenylamino)-3-cyanoquinolin-6-yl]amide

Prepared from 0.756 g of but-2-ynoic acid, 1.23 g of isobutyl chloroformate, 0.908 g of N-methylmorpholine and 1.00 g of 6-amino-4-(3-fluorophenylamino)quinoline-3-carbonitrile in the same manner as Example 382. The yield of but-2-ynoic acid [4-(3-fluorophenylamino)-3-cyanoquinolin-6-yl]amide was 1.07 g as a yellow solid: mass spectrum (electrospray, m/e): 345.1.

EXAMPLE 391

N-[3-Cyano-4-(3-dimethylaminophenylamino)quinolin-6-yl]acrylamide

Prepared from 1.00 g of 6-amino-4-(3-dimethylaminophenylamino)quinoline-3-carbonitrile, 0.400 g of triethylamine and 0.360 g of acryloyl chloride in the same manner as Example 88. The yield of N-[3-cyano-4-(3-dimethylaminophenylamino)-quinolin-6-yl]acrylamide was 0.880 g as an orange solid: mass spectrum (electrospray, m/e): 358.1.

EXAMPLE 392

N-[³-Cyano-4-(4)-dimethylaminophenylamino) quinolin-6-yl]acrylamide

Prepared from 1.00 g of 6-amino-4-(4-dimethylaminophenylamino)quinoline-3-carbonitrile, 0.400 g of triethylamine and 0.360 g of acryloyl chloride in the same manner as Example 380. The yield of N-[3-cyano-4-(4-dimethylaminophenylamino)-quinolin-6-yl]acrylamide was 0.990 g of brown-orange solid: mass spectrum (electrospray, m/e): 358.2.

EXAMPLE 393

But-2-ynoic Acid [3-Cyano-4-(3-dimethylaminophenylamino)quinolin-6-yl]amide

Prepared from 0.694 g of but-2-ynoic acid, 1.13 g of isobutyl chloroformate, 0.833 g of N-methylmorpholine and 1.00 g of 6-amino-4-(3-dimethylaminophenylamino) quinoline-3-carbonitrile in the same manner as Example 382. The yield of but-2-ynoic acid [3-cyano-4-(3-dimethylaminophenylamino)quinolin-6-yl]amide was 0.967 g as an orange solid: mass spectrum (electrospray, m/e): M+H 370.2.

EXAMPLE 394

But-2-ynoic Acid [3-Cyano-4(4-dimethylaminophenylamino)quinolin-6-yl]amide

Prepared from 0.694 g of but-2-ynoic acid, 1.13 g of isobutyl chloroformate, 0.833 g of N-methylmorpholine and 1.00 g of 4(4-dimethylaminophenylamino)quinoline-3-carbonitrile in the same manner as Example 382. The yield of but-2-ynoic acid [3-cyano-4-(4-dimethylaminophenylamino)quinolin-6-yl]amide was 1.13 g as a brick red solid: mass spectrum (electrospray, m/e): M+H 370.2.

EXAMPLE 395

4-(3-Bromophenylamino)-6-dimethylaminoquinoline-3-carbonitrile Hydrochloride

Prepared from 0.400 g of 4-chloro-6-dimethylaminoquinoline-3-carbonitrile and 3-bromoaniline in the same manner as Example 377. The crude product was boiled twice with EtOAc and dried in vacuo (50° C.). The yield of 4(3-bromophenylamino)-6-dimethylaminoquinoline-3-carbonitrile hydrochloride was 0.621 g as a brown powder: mass spectrum (electrospray, m/e) M+H 366, 368.9.

EXAMPLE 396

6-Dimethylamino-4-(3-methoxyphenylamino) quinoline-3-carbonitrile Hydrochloride

Prepared from 0.400 g of 4-chloro-6-dimethylaminoquinoline-3-carbonitrile and 0.256 g of 3-methoxyaniline in the same manner as Example 395. The yield of 6-dimethylamino-4-(3-methoxyphenylamino) quinoline-3-carbonitrile was 0.532 g of brown powder: mass spectrum (electrospray, m/e): M+H 318.9.

EXAMPLE 397

2-Bromo-N-[4-(3-bromophenylamino)-3-cyanoquinolin-6-yl]acetamide

Prepared from 1.50 g of 6-amino-4-(3-bromophenylamino)quinoline-3-carbonitrile, 0.538 g of triethylamine and 1.08 g of bromoacetyl bromide in the same manner as Example 380. The yield of 2-bromo-N-[4-(3-bromophenylamino)-3-cyanoquinolin-6-yl]acetamide was 1.55 g as a yellow-brown solid: mass spectrum (electrospray, m/e): M+H 458.9, 460.9.

EXAMPLE 398

6-Iodo-4-(3-methoxyphenylamino)quinoline-3-carbonitrile

Prepared from 1.00 g of 4-chloro-6-iodoquinoline-3-carbonitrile and 0.469 g of 3-methoxyaniline in the same manner as Example 377. The crude product was filtered through silica gel with 20% EtOAc in CH$_2$Cl$_2$, evaporated and dried in vacuo (50° C.). The yield of 6-iodo-4-(3-methoxyphenylamino)quinoline-3-carbonitrile was 1.09 g as yellow crystals: mass spectrum (electrospray, m/e): M+H 401.9.

We claim:
1. A compound of the formula

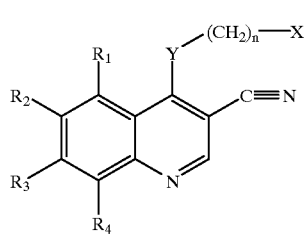

1 wherein:
X is cycloalkyl of 3 to 7 carbon atoms, which may be optionally substituted with one or more alkyl of 1 to 6 carbon atom groups; or is a pyridinyl, pyrimidinyl, or phenyl ring; wherein the pyridinyl, pyrimidinyl, or phenyl ring optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

n is 0–1;
Y is —NH—, —O—, —S—, or —NR—;
R is alkyl of 1–6 carbon atoms;

$R_1$, $R_2$, $R_3$, and $R_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, aminoalkyl of 1–4 carbon atoms, N-alkylaminoalkyl of 2–7 carbon atoms, N,N-dialkylaminoalkyl of 3–14 carbon atoms, phenylamino, benzylamino,

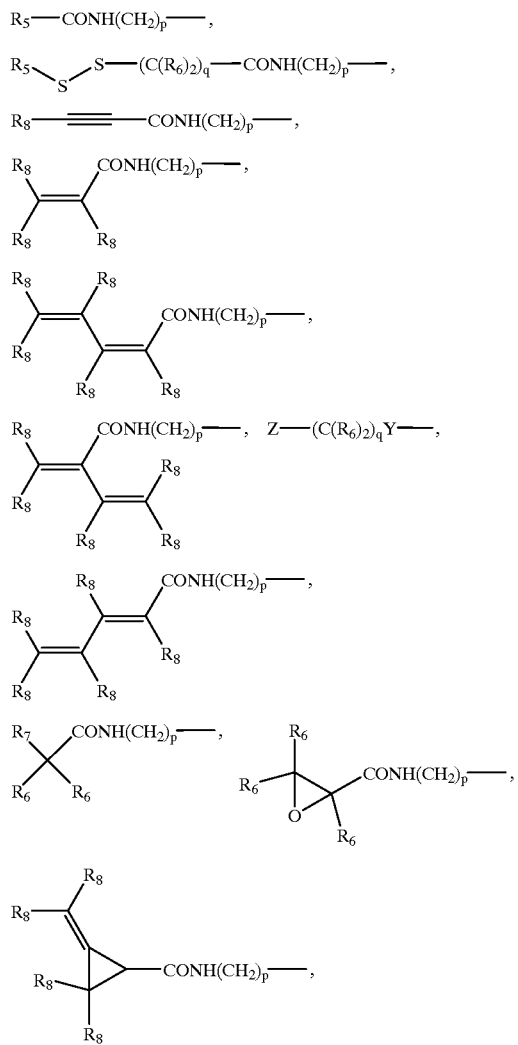

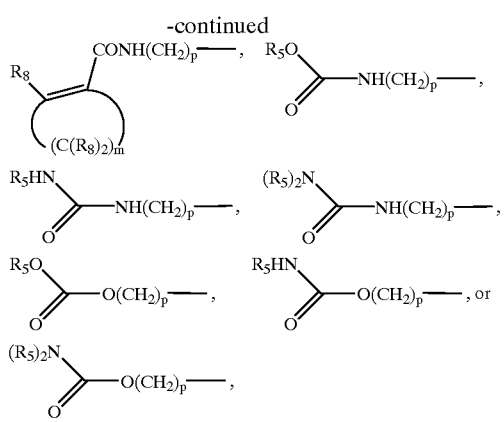

$R_5$ is alkyl of 1–6 carbon atoms, alkyl optionally substituted with one or more halogen atoms, phenyl, or phenyl optionally substituted with one or more halogen, alkoxy of 1–6 carbon atoms, trifluoromethyl, amino, nitro, cyano, or alkyl of 1–6 carbon atoms groups;

$R_6$ is hydrogen, alkyl of 1–6 carbon atoms, or alkenyl of 2–6 carbon atoms;

$R_7$ is chloro or bromo $R_8$ is hydrogen, alkyl of 1–6 carbon atoms, aminoalkyl of 1–6 carbon atoms, N-alkylaminoalkyl of 2–9 carbon atoms, N,N-dialkylaminoalkyl of 3–12 carbon atoms, N-cycloalkylaminoalkyl of 4–12 carbon atoms, N-cycloalkyl-N-alkylaminoalkyl of 5–18 carbon atoms, N,N-dicycloalkylaminoalkyl of 7–18 carbon atoms, morpholino-N-alkyl wherein the alkyl group is 1–6 carbon atoms, piperidino-N-alkyl wherein the alkyl group is 1–6 carbon atoms, N-alkyl-piperidino-N-alkyl wherein either alkyl group is 1–6 carbon atoms, azacycloalkyl-N-alkyl of 3–11 carbon atoms, hydroxyalkyl of 1–6 carbon atoms, alkoxyalkyl of 2–8 carbon atoms, carboxy, carboalkoxy of 1–6 carbon atoms, phenyl, carboalkyl of 2–7 carbon atoms, chloro, fluoro, or bromo; Z is amino, hydroxy, alkoxy of 1–6 carbon atoms, alkylamino wherein the alkyl moiety is of 1–6 carbon atoms, dialkylamino wherein each of the alkyl moieties is of 1–6 carbon atoms, morpholino, piperazino, N-alkylpiperazino wherein the alkyl moiety is of 1–6 carbon atoms, or pyrrolidino;

m=1–4, q=1–3, and p=0–3;

any two of the substituents $R_1$, $R_2$, $R_3$, or $R_4$ that are located on contiguous carbon atoms can together be the divalent radical —O—C($R_8$)$_2$—O—;

or a pharmaceutically acceptable salt thereof with the proviso that when Y is —NH—, $R_1$, $R_2$, $R_3$, and $R_4$ are hydrogen, and n is 0, X is not 2-methylphenyl further provided that $R^3 \neq Cl$.

2. The compound according to claim 1 wherein Y is —NH— and n=0 or a pharmaceutically acceptable salt thereof.

3. The compound according to claim 2 wherein X is optionally substituted phenyl or a pharmaceutically acceptable salt thereof.

4. The compound according to claim 3 wherein $R_1$ and $R_4$ are hydrogen or a pharmaceutically acceptable salt thereof.

5. The compound according to claim 1 which is 4-[(3-bromophenyl)amino]-6,7-diethoxy-3-quinolinecarbonitrile or a pharmaceutically acceptable salt thereof.

6. The compound according to claim 1 which is 4dimethylamino-but-2-enoic acid [4-(3-chloro-4-fluorophenylamino)-3-cyano-7-methoxy-quinolin-6-yl]-amide or a pharmaceutically acceptable salt thereof.

7. The compound according to claim 1 which is 4-diethylamino-but-2-enoic acid [4-(3-chloro-4-fluoro-phenylamino)-3-cyano-7-methoxy-quinolin-6-yl]-amide or a pharmaceutically acceptable salt thereof.

8. The compound according to claim 1 which is 4-dimethylamino-but-2-enoic acid [4-(3-bromo-4-fluoro-phenylamino)-3-cyano-7-methoxy-quinolin-6-yl]-amide or a pharmaceutically acceptable salt thereof.

9. The compound according to claim 1 which is 4dimethylamino-but-2-enoic acid [4-(3-bromo-phenylamino)-3-cyano-7-ethoxy-quinolin-6-yl]-amide or a pharmaceutically acceptable salt thereof.

10. The compound according to claim 1 which is 4-diethylamino-but-2-enoic acid [4-(3-bromo-phenylamino)-3-cyano-7-ethoxy-quinolin-6-yl]-amide or a pharmaceutically acceptable salt thereof.

11. The compound according to claim 1 which is 4-morpholin-4-yl-but-2-enoic acid [4-(3-chloro-4-fluoro-phenylamino)-3-cyano-7-methoxy-quinolin-6-yl]-amide or a pharmaceutically acceptable salt thereof.

12. The compound according to claim 1 which is 4-dimethylamino-but-2-enoic acid [4-(3-bromo-phenylamino)-3-cyano-7-methoxy-quinolin-6-yl]-amide or a pharmaceutically acceptable salt thereof.

13. The compound according to claim 1 which is N-[4-[(3-bromophenyl)amino]-3-cyano-6-quinolinyl]-4-methoxy-2-butynamide or a pharmaceutically acceptable salt thereof.

14. The compound according to claim 1 which is N-{4-[(3-chloro-4-fluorophenyl)-amino]-3-cyano-6-quinolinyl}-4-dimethylamino-2-butenamide or a pharmaceutically acceptable salt thereof.

15. A compound according to claim 1 which is
a) 4-[(3-bromophenyl)amino]-7-methoxy-3-quinolinecarbonitrile;
b) 4-[(3-bromophenyl)amino]-7-methoxy-6-nitro-3-quinolinecarbonitrile;
c) 6-amino-4-[(3-bromophenyl)amino]-7-methoxy-3-quinolinecarbonitrile;
d) N-[4-[(3-bromophenyl)amino]-3-cyano-7-methoxy-6-quinolinyl]-2-butynamide;
e) N-[4-[(3-bromophenyl)amino]-3-cyano-7-methoxy-6-quinolinyl]-2-propenamide;
f) 4-[(3-bromophenyl)amino]-6-nitro-3-quinolinecarbonitrile;
g) 6-amino-4-[(3-bromophenyl)amino]-3-quinolinecarbonitrile;
h) N-[4-[(3-bromophenyl)amino]-3-cyano-6-quinolinyl]-2-butynamide;
i) N-[4-[(3-bromophenyl)amino]-3-cyano-6-quinolinyl]acetamide;
j) N-[4-[(3-bromophenyl)amino]-3-cyano-6-quinolinyl]butanamide;
k) N-[4-[(3-bromophenyl)amino]-3-cyano-6-quinolinyl]-2-propenamide;
l) N-[4-[(3-bromophenyl)amino]-3-cyano-6-quinolinyl]-2-chloroacetamide;
m) 4-[(3,4-dibromophenyl)amino]-6-nitro-3-quinolinecarbonitrile;
n) 6-amino-4-[(3,4-dibromophenyl)amino]-3-quinolinecarbonitrile;
o) N-[4-[(3,4-dibromophenyl)amino]-3-cyano-6-quinolinyl]-2-butynamide;
p) 6-nitro-4-[(3-trifluoromethylphenyl)amino]-3-quinolinecarbonitrile;
q) 6-amino-4-[(3-trifluoromethylphenyl)amino]-3-quinolinecarbonitrile;
r) N-[4-[(3-trifluoromethylphenyl)amino]-3-cyano-6-quinolinyl]-2-butynamide;
s) 4-[(3-bromophenyl)amino]-6,7-dimethoxy-3-quinolinecarbonitrile;
t) 4-[(3-fluorophenyl)amino]-6,7-dimethoxy-3-quinolinecarbonitrile;
u) 4-(cyclohexyamino)-6,7-dimethoxy-3-quinolinecarbonitrile;
v) 4-[(3-bromophenyl)amino]-6,7-dihydroxy-3-quinolinecarbonitrile;
w) 8-[(3-bromophenyl)amino]-[1,3]-dioxolo[4,5-g]quinoline-7-carbonitrile;
x) 4-[(3-chlorophenyl)amino]-6,7-dimethoxy-3-quinolinecarbonitrile;
y) 4-[(3-trifluoromethylphenyl)amino]-6,7-dimethoxy-3-quinolinecarbonitrile;
z) 4-[(3,4-dimethoxyphenyl)amino]-6,7-dimethoxy-3-quinolinecarbonitrile;
aa) 4-[(methylphenyl)amino]-6,7-dimethoxy-3-quinolinecarbonitrile;
bb) 4-[(3-cyanophenyl)amino]-6,7-dimethoxy-3-quinolinecarbonitrile;
cc) 4-[(4-fluorophenyl)amino]-6,7-dimethoxy-3-quinolinecarbonitrile;
dd) 4-[(3-(hydroxymethyl)phenyl)amino]-6,7-dimethoxy-3-quinolinecarbonitrile;
ee) 4-(3-bromophenoxy)-6,7-dimethoxy-3-quinolinecarbonitrile;
ff) 4-[(4-bromophenyl)sulfanyl]-6,7-dimethoxy-3-quinolinecarbonitrile;
gg) N-[4-[(3-bromophenyl)amino]-3-cyano-6-quinolinyl]-3(E)-chloro-2-propenamide;
hh) N-[4-[(3-bromophenyl)amino]-3-cyano-6-quinolinyl]-3(Z)-chloro-2-propenamide;
ii) N-[4-[(3-bromophenyl)amino]-3-cyano-6-quinolinyl]-2-methyl-2-propenamide;
jj) N-[4-[(3,4-dibromophenyl)amino]-3-cyano-6-quinolinyl]-2-propenamide;
kk) N-[4-[(5-bromo-3-pyridinyl)amino]-6,7-dimethoxy-3-quinolinecarbonitrile;
ll) 4-[(3-bromophenyl)amino]-6,7-bis(methoxymethoxy)-3-quinolinecarbonitrile;
mm) N-[4-[(3-bromophenyl)amino]-3-cyano-6-quinolinyl]-4-hydroxy-2-butynamide;
nn) N-[4-[(3-bromophenyl)amino]-3-cyano-6-quinolinyl]-4-morpholino-2-butynamide;
oo) N-[4-[(3-bromophenyl)amino]-3-cyano-6-quinolinyl]-4-dimethylamino-2-butynamide;
pp) N-[4-[(3-bromophenyl)amino]-3-cyano-6-quinolinyl]-4-methoxy-2-butynamide;
qq) 4-(3-bromophenylmethylamino)-6,7-diethoxy-3-quinolinecarbonitrile;
rr) 4-(3-phenylmethylamino)-6,7-diethoxy-3-quinolinecarbonitrile;
ss) 4-(3,4-dimethoxyphenylmethylamino)-6,7-diethoxy-3-quinolinecarbonitrile;
tt) 4-(3,4-dichlorophenylmethylamino)-6,7-diethoxy-3-quinolinecarbonitrile;

uu) 4-methoxy-but-2-enoic acid [4-(3-bromo-phenylamino)-3-cyanoquinolin-6-yl]-amide;

vv) 4-(4-chloro-2-fluoro-phenylamino)-7-(3-chloropropoxy)-6-methoxy-quinoline-3-carbonitrile;

ww) 4-(4-chloro-2-fluoro-phenylamino)-6-methoxy-7-(3-morpholin-4-yl-propoxy)-quinoline-3-carbonitrile;

xx) 7-(2-dimethylamino-ethoxy)-4-(3-hydroxy-4-methyl-phenylamino)-6-methoxy-quinoline-3-carbonitrile;

yy) 4-(3-hydroxy-4-methyl-phenylamino)-6-methoxy-7-(2-morpholin-4-yl-ethoxy)-quinoline-3-carbonitrile; or zz) 4-(4-chloro-2-fluoro-5-hydroxy-phenylamino)-7-(3-dimethylamino-propoxy)-6-methoxy-quinoline-3-carbonitrile;

or a pharmaceutically acceptable salt thereof.

16. A compound according to claim 1 which is a) 4-(4-chloro-2-fluoro-5-hydroxy-phenylamino)-6-methoxy-7-(3-morpholin-4-yl-propoxy)-quinoline-3-carbonitrile;

b) 4-(4-chloro-2-fluoro-5-hydroxy-phenylamino)-7-(2-dimethylamino-ethoxy)-6-methoxy-quinoline-3-carbonitrile;

c) 4-(4-chloro-2-fluoro-5-hydroxy-phenylamino)-6-methoxy-7-(2-morpholin-4-yl-ethoxy)-quinoline-3-carbonitrile;

d) N-[3-cyano-4-(3-fluorophenylamino)quinolin-6-yl] acrylamide;

e) 6,7-dimethoxy-4-(3-nitrophenylamino)quinoline-3-carbonitrile;

f) 4-(3-bromophenylamino)-6-ethoxy-7-methoxyquinoline-3-carbonitrile;

g) 6-ethoxy-4-(3-hydroxy-4-methylphenylamino)-7-methoxyquinoline-3-carbonitrile;

h) 4-dimethylamino-but-2-enoic acid [4-(3-bromo-phenylamino)-3-cyano-quinolin-6-yl]-amide;

i) 4-diethylamino-but-2-enoic acid [4-(3-bromo-phenylamino)-3-cyano-quinolin-6-yl]-amide;

j) 4-methylamino-but-2-enoic acid [4-(3-bromo-phenylamino)-3-cyano-quinolin-6-yl]-amide;

k) 4-[(3-bromophenyl)amino]-8-methyl-6-nitro-3-quinolinecarbonitrile;

l) 4-[(3-bromophenyl)amino]-8-dimethylaminomethyl-6-nitro-3-quinolinecarbonitrile;

m) 6-amino-4-[(3-bromophenyl)amino]-8-dimethylaminomethyl-3-quinolinecarbonitrile;

n) N-{4-[(3-bromophenyl)amino]-3-cyano-8-dimethylaminomethyl-6-quinolinyl}-2-butynamide;

o) N-{4-[(3-bromophenyl)amino]-3-cyano-8-dimethylaminomethyl-6-quinolinyl}-2-propenamide;

p) N-[4-[(3-bromophenyl)amino]-3-cyano-8-dimethylaminomethyl-6-quinolinyl}acetamide;

q) 4-[(3-chloro-4-fluorophenyl)amino]-7-methoxy-6-(morpholinopropoxy)-3-quinolinecarbonitrile;

r) 4-[(3-bromophenyl)amino]-7-methoxy-6-(morpholinopropoxy)-3-quinolinecarbonitrile;

s) 4-[(4chloro-2-fluorophenyl)amino]-7-methoxy-6-(morpholinopropoxy)-3-quinolinecarbonitrile;

t) 4-[(3-hydroxy-4-methylphenyl)amino]-7-methoxy-6-(morpholinopropoxy)-3-quinolinecarbonitrile;

u) N-{3-cyano-4-[(3-iodophenyl)amino]-6-quinolinyl}-2-propenamide;

v) 6-amino-4-[(3-iodophenyl)amino]-3-quinolinecarbonitrile;

w) 4-[(3-iodophenyl)amino]-6-nitro-3-quinolinecarbonitrile;

x) N-{3-cyano-4-[(3-methylphenyl)amino]-6-quinolinyl}-2-butynamide;

y) 6-amino-4-[(3-methylphenyl)amino]-3-quinolinecarbonitrile;

z) 6-nitro-4-[(3-methylphenyl)amino]-3-quinolinecarbonitrile;

aa) N-{4-[(3-chlorophenyl)amino]-3-cyano-6-quinolinyl}-2-propenamide;

bb) 6-amino-4-[(3-chlorophenyl)amino]-3-quinolinecarbonitrile;

cc) 4-[(3-chlorophenyl)amino]-6-nitro-3-quinolinecarbonitrile;

dd) N-{3-cyano-4-[(3-methoxyphenyl)amino]-6-quinolinyl}-2-propenamide;

ee) N-{3-cyano-4-[(3-methoxyphenyl)amino]-6-quinolinyl}-2-butynamide;

ff) N-{3-cyano-4-[(3-methoxyphenyl)amino]-6-quinolinyl}-4-piperidino-2-butynamide;

gg) 6-amino-4-[(3-methoxyphenyl)amino]-3-quinolinecarbonitrile;

hh) 4-[(3-methoxyphenyl)amino]-6-nitro-3-quinolinecarbonitrile;

ii) N-{4-[(3-chloro-4-fluoro-phenyl)amino]-3-cyano-6-quinolinyl}-2-butynamide;

jj) N-{4-[(3-chloro-4fluorophenyl)amino]-3-cyano-6-quinolinyl}-2-propenamide;

kk) N-{4-[(3-chloro-4-fluorophenyl)amino]-3-cyano-6-quinolinyl}-4-diethylamino-2-butenamide;

ll) N-{4-[(3-chloro-4-fluorophenyl)amino]-3-cyano-6-quinolinyl}-4-morpholino-2-butenamide;

mm) N-{4-[(3-chloro-4-fluorophenyl)amino]-3-cyano-6-quinolinyl}-2-morpholin-4-ylmethyl-2-propenamide;

nn) 6-amino-[(3-chloro-4-fluorophenyl)amino]-3-quinolinecarbonitrile;

oo) 4-[(3-chloro-4-fluorophenyl)amino]-6-nitro-3-quinolinecarbonitrile;

pp) N-{4-[(4-bromophenyl)amino]-3-cyano-6-quinolinyl}-2-propenamide;

qq) 6-amino-4-[(4-bromophenyl)amino]-3-quinolinecarbonitrile;

rr) [(4-bromophenyl)amino]-6-nitro-3-quinolinecarbonitrile;

ss) N-{3-cyano-4-[(3,4-difluorophenyl)amino]-6-quinolinyl]-2-propenamide;

tt) 6-amino-4-[(3,4difluorophenyl)amino]-3-quinolinecarbonitrile;

uu) 4-[(3,4-difluorophenyl)amino]-6-nitro-3-quinolinecarbonitrile;

ww) N-{4-[(3-chloro-4-thiophenoxyphenyl)amino]-3-cyano-6-quinolinyl}-2-butynamide;

xx) 6-amino-4-[(3-chloro-4-thiophenoxyphenyl)amino]-3-quinolinecarbonitrile;

yy) 4-[(3-chloro-4-thiophenoxyphenyl)amino]-6-nitro-3-quinolinecarbonitrile; or zz) N-(3-cyano-4-[(3-cyanophenyl)amino]-6-quinolinyl}-2-propenamide;

or a pharmaceutically acceptable salt thereof.

17. A compound according to claim 1 which is a) N-{3-cyano-4-[(3-cyanophenyl)amino]-6-quinolinyl}-4-piperidino-2-butynamide;

b) 6-amino-4-[(3-cyanophenyl)amino]-3-quinolinecarbonitrile;
c) 4-[(3-cyanophenyl)amino]-6-nitro-3-quinolinecarbonitrile;
d) N-{3-cyano-4-[(3-ethynylphenyl)amino]-6-quinolinyl}-2-butynamide;
e) N-{3-cyano-4-[(3-ethynylphenyl)amino]-6-quinolinyl}-2-propenamide;
f) N-{3-cyano-4-[(3-ethynylphenyl)amino]-6-quinolinyl}-4-piperidino-2-butynamide;
g) 6-amino-4-[(3-ethynylphenyl)amino]-3-quinolinecarbonitrile;
h) 4-[(3-ethynylphenyl)amino]-6-nitro-3-quinolinecarbonitrile;
i) N-{4-[(3-bromophenyl)amino]-3-cyano-6-quinolinyl}-4-piperidino-2-butynamide;
j) N-{4-[(3-bromophenyl)amino]-3-cyano-6-quinolinyl}-4-dipropylamino-2-butynamide;
k) N-{4-[(3-bromophenyl)amino]-3-cyano-6-quinolinyl}-2-morpholin-4-ylmethyl-2-propenamide;
l) N-{4-[(3-bromo-4-fluorophenyl)amino]-3-cyano-6-quinolinyl}-4-dimethylamino-2-butenamide;
m) N-{4-[(3-bromo-4-fluorophenyl)amino]-3-cyano-6-quinolinyl}-4-diethylamino-2-butenamide;
n) N-{4-[(3-bromo-4-fluorophenyl)amino]-3-cyano-6-quinolinyl}-4-morpholino-2-butenamide;
o) N-{4-[(3-bromo-4-fluorophenyl)amino]-3-cyano-7-methoxy-6-quinolinyl}-4-morpholino-2-butenamide;
p) 4-[(3-bromophenyl)amino]-7-ethoxy-6-methoxy-3-quinolinecarbonitrile;
q) 7-ethoxy-4-[(3-hydroxy-4-methylphenyl)amino]-6-methoxy-3-quinolinecarbonitrile;
r) N-[4-[(3-chloro-4-fluorophenyl)amino]-3-cyano-6-quinolinyl]-4-dimethylamino-(z)-2-butenamide;
s) N-[4-[(3-chloro-4-fluorophenyl)amino]-3-cyano-6-quinolinyl]-4-methoxy-(z)-2-butenamide;
t) 4-[[4[(3-bromophenyl)amino]-3-cyano-6-quinolinyl]amino]-2-methylene-4-oxo-butanoic acid;
u) N-[4-[(3-bromophenyl)amino]-3-cyano-6-quinolinyl]-4-diethylamino-2-butynamide;
v) N-[4-[(3-bromophenyl)amino]-3-cyano-6-quinolinyl]-4-(n-ethylpiperazino)-2-butynamide;
w) N-[4-[(3-chloro-4-fluorophenyl)amino]-3-cyano-6-quinolinyl]-4-diethylamino-2-butynamide;
x) N-[4-[(3-bromophenyl)amino]-3-cyano-6-quinolinyl]-4-(n-methylpiperazino)-2-butynamide;
y) N-[4-[(3-bromophenyl)amino]-3-cyano-6-quinolinyl]-4-(n-isopropyl-n-methylamino)-2-butynamide;
z) N-[4-[(3-bromophenyl)amino]-3-cyano-6-quinolinyl]-4-diisopropylamino-2-butynamide;
aa) N-[4-[(3-chloro-4-fluorophenyl)amino]-3-cyano-6-quinolinyl]-4-dimethylamino-2-butynamide;
bb) N-[4-[-(3-chloro-4-fluorophenyl)amino]-3-cyano-6-quinolinyl]-4-methoxy-2-butynamide;
cc) 4-[(3-bromo-4-fluorophenyl)amino]-6-nitro-3-quinolinecarbonitrile;
dd) 6-amino-4-[(3-bromo-4-fluorophenyl)amino]-3-quinolinecarbonitrile;
ee) N-[4-[(3-bromo-4-fluorophenyl)amino]-3-cyano-6-quinolinyl]-4-dimethylamino-2-butynamide;
ff) 4-diethylamino-but-2-enoic acid [4-(3-bromo-phenylamino)-3-cyano-7-methoxy-quinolin-6-yl]-amide;
gg) 4-morpholin-4-yl-but-2-enoic acid [4-(3-bromo-phenylamino)-3-cyano-7-methoxy-quinolin-6-yl]-amide;
hh) 4-(3-chloro-4-fluoro-phenylamino)-7-methoxy-6-nitro-quinoline-3-carbonitrile;
ii) 6-amino-4-(3-chloro-4-fluoro-phenylamino)-7-methoxy-quinoline-3-carbonitrile;
jj) 4-(3-bromo-4-fluoro-phenylamino)-7-methoxy-6-nitro-quinoline-3-carbonitrile;
kk) 6-amino-4-(3-bromo-4-fluoro-phenylamino)-7-methoxy-quinoline-3-carbonitrile;
ll) 4-diethylamino-but-2-enoic acid [4-(3-bromo-4-fluoro-phenylamino)-3-cyano-7-methoxy-quinolin-6-yl]-amide;
mm) 4-(3-bromo-phenylamino)-7-ethoxy-6-nitro-quinoline-3-carbonitrile;
nn) 6-amino-4-(3-bromo-phenylamino)-7-ethoxy-quinoline-3-carbonitrile;
oo) 4-bromo-but-2-enoic acid [4-(3-bromo-phenylamino) 3-cyano-7-ethoxy-quinolin-6-yl]-amide;
pp) 4-morpholin-4-yl-but-2-enoic acid [4(3-bromo-phenylamino)-3-cyano-7-ethoxy-quinolin-6-yl]-amide;
qq) 6-amino-4-(3-bromo-phenylamino)-8-methoxy-quinoline-3-carbonitrile;
rr) 6-amino-4-(3-bromo-phenylamino)-8-methoxy-quinoline-3-carbonitrile;
ss) 4-bromo-but-2-enoic acid [4-(3-bromo-phenylamino)-3-cyano-8-methoxy-quinolin-6-yl]-amide;
tt) 4-dimethylamino-but-2-enoic acid [4-(3-bromo-phenylamino)-3-cyano-8-methoxy-quinolin-6-yl]-amide;
uu) 4-diethylamino-but-2-enoic acid [4(3-bromo-phenylamino)-3-cyano-8-methoxy-quinolin-6-yl]-amide;
vv) 4-morpholin-4-yl-but-2-enoic acid [4-(3-bromo-phenylamino)-3-cyano-8-methoxy-quinolin-6-yl]-amide;
ww) 4-dimethylamino-but-2-ynoic acid [4-(3-bromo-phenylamino)-3-cyano-7-methoxy-quinol-6-yl]-amide;
xx) 4-(4-chloro-2-fluoro-phenylamino)-6,7-dimethoxy-quinoline-3-carbonitrile;
yy) 4-(3-hydroxy-4-methyl-phenylamino)-6,7-dimethoxy-quinoline-3-carbonitrile; or
zz) 4-(3-dimethylamino-phenylamino)-6,7,8-trimethoxy-quinoline-3-carbonitrile;
or a pharmaceutically acceptable salt thereof.

18. A compound according to claim 1 which is
a) 4-(3-hydroxy-4-methyl-phenylamino)-6,7,8-trimethoxy-quinoline-3-carbonitrile;
b) 4-(4-chloro-2-fluoro-phenylamino)-6,7,8-trimethoxy-quinoline-3-carbonitrile;
c) 4-(4-chloro-2-fluoro-phenylamino)-5,8-dimethoxy-quinoline-3-carbonitrile;
d) 4-(3-hydroxy-4-methyl-phenylamino)-5,8-dimethoxy-quinoline-3-carbonitrile;
e) 4-(3-bromo-phenylamino)-5,8-dimethoxy-quinoline-3-carbonitrile;
f) 4-(3-bromo-phenylamino)-6,7,8-trimethoxy-quinoline-3-carbonitrile;
g) 4-(3-dimethylamino-phenylamino)-5,8-dimethoxy-quinoline-3-carbonitrile;
h) 4-(4-chloro-2-fluoro-5-hydroxy-phenylamino)-5,8-dimethoxy-quinoline-3-carbonitrile;

i) 4-(4-chloro-2-fluoro-5-hydroxy-phenylamino)-6,7,8-trimethoxy-quinoline-3-carbonitrile;
j) 4-(3-hydroxy-2-methyl-phenylamino)-6,7-dimethoxy-quinoline-3-carbonitrile;
k) 4-(2-hydroxy-6-methyl-phenylamino)-6,7-dimethoxy-quinoline-3-carbonitrile;
l) 4-(3-bromo-4-methyl-phenylamino)-6,7-dimethoxy-quinoline-3-carbonitrile;
m) 4-(3-chloro-4-hydroxy-phenylamino)-6,7-dimethoxy-quinoline-3-carbonitrile;
n) 6,7-dimethoxy-4(2-methylsulfanyl-phenylamino)-quinoline-3-carbonitrile;
o) 1,4-dihydroquinoline-6,7-diethoxy-4oxo-3-carbonitrile;
p) 4-[3-chloro-4-(phenylthio)phenylamino]-6,7-diethoxy-3-quinolinecarbonitrile;
q) 4-[3-chloro-4-(phenylthio)phenylamino]-6,7-dimethoxy-3-quinolinecarbonitrile;
r) 4-(3-chloro-4fluorophenylamino)-6,7-diethoxy-3-quinolinecarbonitrile;
s) 4-(3-acetylphenylamino)-6,7-diethoxy-3-quinolinecarbonitrile;
t) 4-(n-methylphenylamino)-6,7-diethoxy-3-quinolinecarbonitrile;
u) 4-(phenylamino)-6,7-diethoxy-3-quinolinecarbonitrile;
v) 4-(4-fluorophenylamino)-6,7-diethoxy-3-quinolinecarbonitrile;
w) 4-(4-fluoro-2-methylphenylamino)-6,7-diethoxy-3-quinolinecarbonitrile;
x) 4-(3-chlorophenylamino)-6,7-diethoxy-3-quinolinecarbonitrile;
y) 4-(3-fluorophenylamino)-6,7-diethoxy-3-quinolinecarbonitrile;
z) 4-(3-aminophenylamino)-6,7-dimethoxy-3-quinolinecarbonitrile;
aa) 4-(3-acetamidophenylamino)-6,7-dimethoxy-3-quinolinecarbonitrile;
bb) 4-[3-(2-butynoylamino)phenylamino)]-6,7-dimethoxy-3-quinolinecarbonitrile;
cc) 4-[3-(hydroxymethyl)phenylamino]-6,7-dimethoxy-3-quinolinecarbonitrile;
dd) 4-[3-(chloromethyl)phenylamino]-6,7-dimethoxy-3-quinolinecarbonitrile; ee) 4-[3-(acetylthiomethyl)phenylamino]-6,7-dimethoxy-3-quinolinecarbonitrile;
ff) 4-[3-(thiomethyl)phenylamino]-6,7-dimethoxy-3-quinolinecarbonitrile;
gg) 4-[(3-bromophenyl)amino]-8-methoxy-3-quinolinecarbonitrile;
hh) 4-(4-chloro-2-fluoro-phenylamino)-8-methoxy-quinoline-3-carbonitrile;
ii) 4-(3-hydroxy-4-methyl-phenylamino)-8-methoxy-quinoline-3-carbonitrile;
jj) 4-(3-dimethylamino-phenylamino)-8-methoxy-quinoline-3-carbonitrile;
kk) 4-(4-bromo-3-hydroxy-phenylamino)-8-methoxy-quinoline-3-carbonitrile;
ll) 4-(3-hydroxy-4-methoxy-phenylamino)-8-methoxy-quinoline-3-carbonitrile;
mm) 8-methoxy-4-(2,4,6-trifluoro-phenylamino)-quinoline-3-carbonitrile;
nn) 4-(3-hydroxy-4-methyl-phenylamino)-7-methoxy-quinoline-3-carbonitrile;
oo) 4-(4-chloro-2-fluoro-5-hydroxy-phenylamino)-7-methoxy-quinoline-3-carbonitrile;
pp) 4-(4-chloro-2-fluoro-phenylamino)-6-methoxy-quinoline-3-carbonitrile;
qq) 4-(3-hydroxy-4-methyl-phenylamino)-6-methoxy-quinoline-3-carbonitrile;
rr) 4-(4-chloro-2-fluoro-5-hydroxy-phenylamino)-6-methoxy-quinoline-3-carbonitrile;
ss) 4-(3,5-dichloro-4-hydroxy-phenylamino)-6,7-dimethoxy-quinoline-3-carbonitrile;
tt) 4-(2-hydroxy-4-methyl-phenylamino)-6,7-dimethoxy-quinoline-3-carbonitrile;
uu) 4-(4hydroxy-3,5-dimethyl-phenylamino)-6,7-dimethoxy-quinoline-3-carbonitrile;
vv) 4-(5-chloro-2-hydroxy-phenylamino)-6,7-dimethoxy-quinoline-3-carbonitrile;
ww) 4-(3,5-dibromo-4-hydroxy-phenylamino)-6,7-dimethoxy-quinoline-3-carbonitrile;
xx) 4-(4-hydroxy-2-methyl-phenylamino)-6,7-dimethoxy-quinoline-3-carbonitrile;
yy) 6,7-dimethoxy-4-(pyridin-3-ylamino)-quinoline-3-carbonitrile; or
zz) 6,7-dimethoxy-4-(3-methylsulfanyl-phenylamino)-quinoline-3-carbonitrile;

or a pharmaceutically acceptable salt thereof.

19. A compound according to claim 1 which is
a) 4-(2-hydroxy-5-methyl-phenylamino)-6,7-dimethoxy-quinoline-3-carbonitrile;
b) 4-(2-chloro-4-hydroxy-phenylamino)-6,7-dimethoxy-quinoline-3-carbonitrile;
c) 6,7-dimethoxy-4-(4-methylsulfanyl-phenylamino)-quinoline-3-carbonitrile;
d) 4-[4-(2-hydroxy-ethyl)-phenylamino]-6,7-dimethoxy-quinoline-3-carbonitrile;
e) 4-(2,4-dihydroxy-phenylamino)-6,7-dimethoxy-quinoline-3-carbonitrile;
f) 4-[2-(2-hydroxy-ethyl)-phenylamino]-6,7-dimethoxy-quinoline-3-carbonitrile;
g) 4-(3-bromophenylamino)-6,7-dihydroxy-3-quinolinecarbonitrile;
h) 4-(3-bromophenylamino)-6,7-di-n-propoxy-3-quinolinecarbonitrile;
i) 4-[(3-bromophenyl)-n-acetylamino]-6,7-dihydroxy-3-quinolinecarbonitrile;
j) 4-(3-bromophenylamino)-6,7-di-n-butoxy-3-quinolinecarbonitrile;
k) 4-(4-chloro-2-fluorophenylamino)-7-methoxy-3-quinolinecarbonitrile;
l) 4-(4-chloro-2-fluorophenylamino)-7-hydroxy-3-quinolinecarbonitrile;
m) 4-[(4-chloro-2-fluorophenylamino)-n-acetylamino]-7-hydroxy-3-quinolinecarbonitrile;
n) 4-(4-chloro-2-fluorophenylamino)-7-ethoxy-3-quinolinecarbonitrile;
o) 4-[(3-bromophenyl)amino]-6,7-bis(2-methoxyethoxy)-3-quinolinecarbonitrile;
p) 4-(2-aminphenylmethylamino)-6,7-diethoxy-3-quinolinecarbonitrile;
q) 4-(3,4-difluorophenylmethylamino)-6,7-diethoxy-3-quinolinecarbonitrile;
r) 4-methoxy-but-2-enoic acid [4-(3-bromo-phenylamino)-quinazolin-6-yl]-amide;

s) 7-benzyloxy-4-(4-chloro-2-fluoro-phenylamino)-6-methoxy-quinoline-3-carbonitrile;

t) 4-(4-chloro-2-fluoro-5-hydroxy-phenylamino)-7-methoxy-6-(3-morpholin-4-yl)-propoxyl-quinoline-3-carbonitrile;

u) N-[4-(3-bromo-phenylamino)-3-cyano-quinolin-6-yl]-3-chloro-(e) acrylamide;

v) N-[4-(3-bromo-phenylamino)-3-cyano-quinolin-6-yl]-3-chloro-(z)-acrylamide;

w) N-[4-[(3-bromophenyl)amino]-3-cyano-6-quinolinyl]-4-morpholino-2-butynamide;

x) N-[4-[(3-bromophenyl)amino]-3-cyano-6-quinolinyl]-4-dimethylamino-2-butynamide;

y) N-[4-[(3-bromophenyl)amino]-3-cyano-6-quinolinyl]-4-t-butyldimethylsiloxy-2-butynamide;

z) N-[4-[(3-bromophenyl)amino]-3-cyano-6-quinolinyl]-4-hydroxy-2-butynamide;

aa) 4-(3-hydroxymethyl-2-methylphenylamino)-6,7-dimethoxyquinoline-3-carbonitrile;

bb) 4-(2-amino-4,5-dimethylphenylamino)-6,7-dimethoxyquinoline-3-carbonitrile;

cc) 4-(4-ethylphenylamino)-6,7-dimethoxyquinoline-3-carbonitrile;

dd) 4-(4-chloro-2-methylphenylamino)-6,7-dimethoxyquinoline-3-carbonitrile;

ee) 6,7-dimethoxy-4-(3-phenoxyphenylamino)quinoline-3-carbonitrile;

ff) 4-(4-chloro-3-trifluoromethylphenylamino)-6,7-dimethoxyquinoline-3-carbonitrile;

gg) 4-(3-hydroxy-phenylamino)-6,7-dimethoxy-quinoline-3-carbonitrile;

hh) 4-(4-methyl-phenylamino)-6,7-dimethoxy-quinoline-3-carbonitrile;

ii) 4-(3-hydroxy-4-methyl-phenylamino)-8-methoxy-6-nitro-quinoline-3-carbonitrile;

jj) 4-(4-chloro-2-fluoro-phenylamino)-8-methoxy-6-nitro-quinoline-3-carbonitrile;

kk) 4-(3-hydroxy-4-methoxy-phenylamino)-8-methoxy-6-nitro-quinoline-3-carbonitrile;

ll) 6-amino-4-(3-hydroxy-4-methyl-phenylamino)-8-methoxy-quinoline-3-carbonitrile;

mm) 6-amino-4-(3-hydroxy-4-methoxy-phenylamino)-8-methoxy-quinoline-3-carbonitrile;

nn) N-{4-[(3-bromo-4-fluorophenyl)amino]-3-cyano-7-methoxy-6-quinolinyl}-4-bromo-2-butenamide;

oo) N-{4-[(3-bromophenyl)amino]-3-cyano-7-methoxy-6-quinolinyl}-4-chloro-2-butenamide;

pp) N-{3-cyano-4[(3-iodophenyl)amino]-6-quinolinyl}-2-butynamide;

qq) N-{3-cyano-4-[(3-methylphenyl)amino]-6-quinolinyl}-2-propenamide;

rr) N-{4-[(4-bromophenyl)amino]-3-cyano-6-quinolinyl}-2-butynamide;

ss) N-{4-[(3-chloro-4-thiophenoxyphenyl)amino]-3-cyano-6-quinolinyl}-2-propenamide;

tt) N-{3-cyano-4-[(3,4-difluorophenyl)amino]-6-quinolinyl}-2-butynamide;

uu) N-{4-[(3-chlorophenyl)amino]-3-cyano-6-quinolinyl}-2-butynamide;

vv) N-{3-cyano-4-[(3-isopropylphenyl)amino]-6-quinolinyl}-2-butynamide;

ww) N-{3-cyano-4-[(3-isopropylphenyl)amino]-6-quinolinyl}-2-propenamide;

xx) 6-amino-4-[(3-isopropylphenyl)amino]-3-quinolinecarbonitrile;

yy) 4-[(3-isopropylphenyl)amino]-6-nitro-3-quinolinecarbonitrile; or zz) 4-(3-bromo-phenylamino)-6-(3-pyrrolidin-1-yl-propylamino)-quinoline-3-carbonitrile;

or a pharmaceutically acceptable salt thereof.

20. A compound according to claim 1 which is a) 4-(3-azido-phenylamino)-6,7-dimethoxy-quinoline-3-carbonitrile;

b) 6-amino-4-[(4-chloro-2-fluorophenyl)amino]-7-methoxy-3-quinolinecarbonitrile;

c) 4-[(4-chloro-2-fluorophenyl)amino]-7-methoxy-6-nitro-3-quinolinecarbonitrile;

d) 4-[(3,4dichlorophenyl)amino]-6-nitro-3-quinolinecarbonitrile;

e) 6-amino-4-[(3-methylsulfanylphenyl)amino]-3-quinolinecarbonitrile;

f) 4-[(3-methylsulfanylphenyl)amino]-6-nitro-3-quinolinecarbonitrile;

g) 4-[(3-trifluoromethoxyphenyl)amino]-6-nitro-3-quinolinecarbonitrile;

h) 4-(3-dimethylamino-phenylamino)-6,7-dimethoxy-quinoline-3-carbonitrile;

i) 6,7-dimethoxy-4-(4-methoxy-2-methyl-phenylamino)-quinoline-3-carbonitrile;

j) 4-(3-hydroxy-4-methoxy-phenylamino)-6,7-dimethoxy-quinoline-3-carbonitrile;

k) 4-(3-chloro-4-methyl-phenylamino)-6,7-dimethoxy-quinoline-3-carbonitrile;

l) 6,7-dimethoxy-4-(4-phenoxy-phenylamino)-quinoline-3-carbonitrile;

m) 4-(5-chloro-2-methoxy-phenylamino)-6,7-dimethoxy-quinoline-3-carbonitrile;

n) 3-(3-cyano-6,7-dimethoxy-quinolin-4-ylamino)-2-methyl-benzoic acid;

o) 4-(4-chloro-2-fluoro-phenylamino)-6,7-dihydroxy-quinoline-3-carbonitrile;

p) 4-(3-hydroxy-2-methyl-phenylamino)-6,7-dimethoxy-quinoline-3-carbonitrile;

q) 4-(3-chloro-4-methoxy-phenylamino)-6,7-dimethoxy-quinoline-3-carbonitrile;

r) 6,7-dimethoxy-4-(4-trifluoromethyl-phenylamino)-quinoline-3-carbonitrile;

s) 4-(3,4-dibromophenylamino)-6-nitroquinoline-3-carbonitrile;

t) 6-amino-4-(3-trifluoromethylphenylamino)quinoline-3-carbonitrile;

u) 6-amino-4-(3,4-dibromophenylamino)quinoline-3-carbonitrile;

v) N-[3-cyano-4-(3,4-dibromophenylamino)quinolin-6-yl]acrylamide;

w) N-[4-(3-bromophenylamino)-3-cyanoquinolin-6-yl] propionamide;

x) (e)-but-2-enoic acid [4-(3-bromophenylamino)-3-cyanoquinolin-6-yl]amide; y) N-[4-(3-bromophenylamino)-3-cyanoquinolin-6-yl]-2-methylacrylamide;

z) 4-(3-fluorophenylamino)-6-nitroquinoline-3-carbonitrile;

aa) 6-amino-4-(3-fluorophenylamino)quinoline-3-carbonitrile; bb) 4(3-dimethylaminophenylamino)-6-nitroquinoline-3-carbonitrile;

cc) 4-(4-dimethylaminophenylamino)-6-nitroquinoline-3-carbonitrile;

dd) 6-amino-4-(3-dimethylaminophenylaminoquinoline-3-carbonitrile;

ee) 6-amino-4-(4-dimethylaminophenylamino)quinoline-3-carbonitrile;

ff) but-2-ynoic acid [4-(3-fluorophenylamino)-3-cyanoquinolin-6-yl]amide;

gg) N-[3-cyano-4-(3-dimethylaminophenylamino) quinolin-6-yl]acrylamide;

hh) N-[3-cyano-4-(4-dimethylaminophenylamino) quinolin-6-yl]acrylamide;

ii) but-2-ynoic acid [3-cyano-4-(3-dimethylaminophenylamino)quinolin-6-yl]amide;

jj) but-2-ynoic acid [3-cyano-4-(4dimethylaminophenylamino)quinolin-6-yl]amide;

kk) 4-(3-bromophenylamino)-6-dimethylaminoquinoline-3-carbonitrile hydrochloride;

ll) 6-dimethylamino-4-(3-methoxyphenylamino) quinoline-3-carbonitrile hydrochloride;

mm) 2-bromo-n-[4-(3-bromophenylamino)-3-cyanoquinolin-6-yl]acetamide;

nn) 6-iodo-4-(3-methoxyphenylamino)quinoline-3-carbonitrile;

oo) 4-(4-hydroxy-2-methyl-phenylamino)-6-methoxy-7-(3-morpholin-4-yl-propoxy)-quinoline-3-carbonitrile;

pp) 4-(3-bromo-phenylamino)-6-methoxy-7-(3-morpholin-4-yl-propoxy)-quinoline-3-carbonitrile;

qq) 6-methoxy-4-(2-methylsulfanyl-phenylamino)-7-(3-morpholin-4-yl-propoxy)-quinoline-3-carbonitrile; or rr) 4-(4-hydroxy-3,5-dimethyl-phenylamino)-6-methoxy-7-(3-morpholin-4-yl-propoxy)-quinoline-3-carbonitrile;

or a pharmaceutically acceptable salt thereof.

21. A method of inhibiting the biological effects of a deregulated protein kinase in a mammal which comprises administering to said mammal an effective amount of a compound having the formula

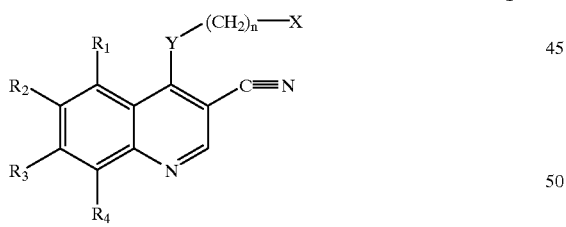

wherein:

X is cycloalkyl of 3 to 7 carbon atoms, which may be optionally substituted with one or more alkyl of 1 to 6 carbon atom groups; or is a pyridinyl, pyrimidinyl, or phenyl ring; wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

n is 0–1;

Y is —NH—, —O—, —S—, or —NR—,

R is alkyl of 1–6 carbon atoms;

$R_1$, $R_2$, $R_3$, and $R_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, aminoalkyl of 1–4 carbon atoms, N-alkylaminoalkyl of 2–7 carbon atoms, N,N-dialkylaminoalkyl of 3–14 carbon atoms, phenylamino, benzylamino,

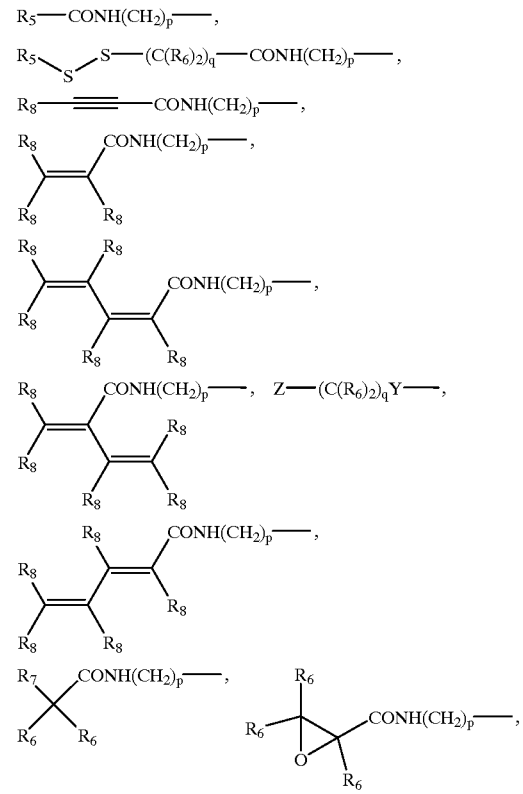

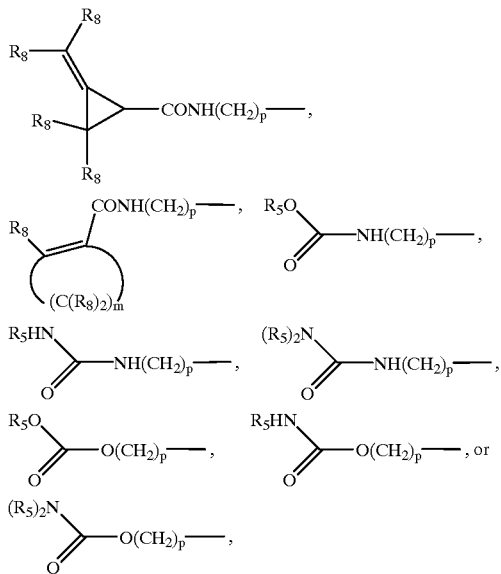

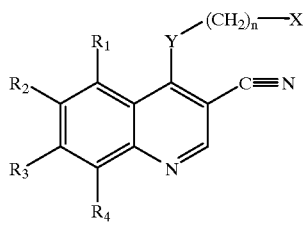

R₅ is alkyl of 1–6 carbon atoms, alkyl optionally substituted with one or more halogen atoms, phenyl, or phenyl optionally substituted with one or more halogen, alkoxy of 1–6 carbon atoms, trifluoromethyl, amino, nitro, cyano, or alkyl of 1–6 carbon atoms groups;

R₆ is hydrogen, alkyl of 1–6 carbon atoms, or alkenyl of 2–6 carbon atoms;

R₇ is chloro or bromo

R₈ is hydrogen, alkyl of 1–6 carbon atoms, aminoalkyl of 1–6 carbon atoms, N-alkylaminoalkyl of 2–9 carbon atoms, N,N-dialkylaminoalkyl of 3–12 carbon atoms, N-cycloalkylaminoalkyl of 4–12 carbon atoms, N-cycloalkyl-N-alkylaminoalkyl of 5–18 carbon atoms, N,N-dicycloalkylaminoalkyl of 7–18 carbon atoms, morpholino-N-alkyl wherein the alkyl group is 1–6 carbon atoms, piperidino-N-alkyl wherein the alkyl group is 1–6 carbon atoms, N-alkyl-piperidino-N-alkyl wherein either alkyl group is 1–6 carbon atoms, azacycloalkyl-N-alkyl of 3–11 carbon atoms, hydroxyalkyl of 1–6 carbon atoms, alkoxyalkyl of 2–8 carbon atoms, carboxy, carboalkoxy of 1–6 carbon atoms, phenyl, carboalkyl of 2–7 carbon atoms, chloro, fluoro, or bromo;

Z is amino, hydroxy, alkoxy of 1–6 carbon atoms, alkylamino wherein the alkyl moiety is of 1–6 carbon atoms, dialkylamino wherein each of the alkyl moieties is of 1–6 carbon atoms, morpholino, piperazino, N-alkylpiperazino wherein the alkyl moiety is of 1–6 carbon atoms, or pyrrolidino;

m=1–4, q=1–3, and p=0–3;

any of the substituents R₁, R₂, R₃, or R₄ that are located on contiguous carbon atoms can together be the divalent radical —O—C(R₈)₂—O—;

or a pharmaceutically acceptable salt thereof with the proviso that when Y is —NH—, R₁, R₂, R₃, and R₄ are hydrogen, and n is 0, X is not 2-methylphenyl.

22. A method of treating, inhibiting the growth of, or eradicating a neoplasm in a mammal in need thereof which comprises administering to said mammal an effective amount of a compound having the formula wherein:

X is cycloalkyl of 3 to 7 carbon atoms, which may be optionally substituted with one or more alkyl of 1 to 6 carbon atom groups; or is a pyridinyl, pyrimidinyl, or phenyl ring; wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

n is 0–1;

Y is —NH—, —O—, —S—, or —NR—;

R is alkyl of 1–6 carbon atoms;

R₁, R₂, R₃, and R₄ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, aminoalkyl of 1–4 carbon atoms, N-alkylaminoalkyl of 2–7 carbon atoms, N,N-dialkylaminoalkyl of 3–14 carbon atoms, phenylamino, benzylamino,

R₅—CONH(CH₂)ₚ—,

R₅\_S\_S—(C(R₆)₂)_q—CONH(CH₂)ₚ—,

R₈≡≡≡—CONH(CH₂)ₚ—,

-continued

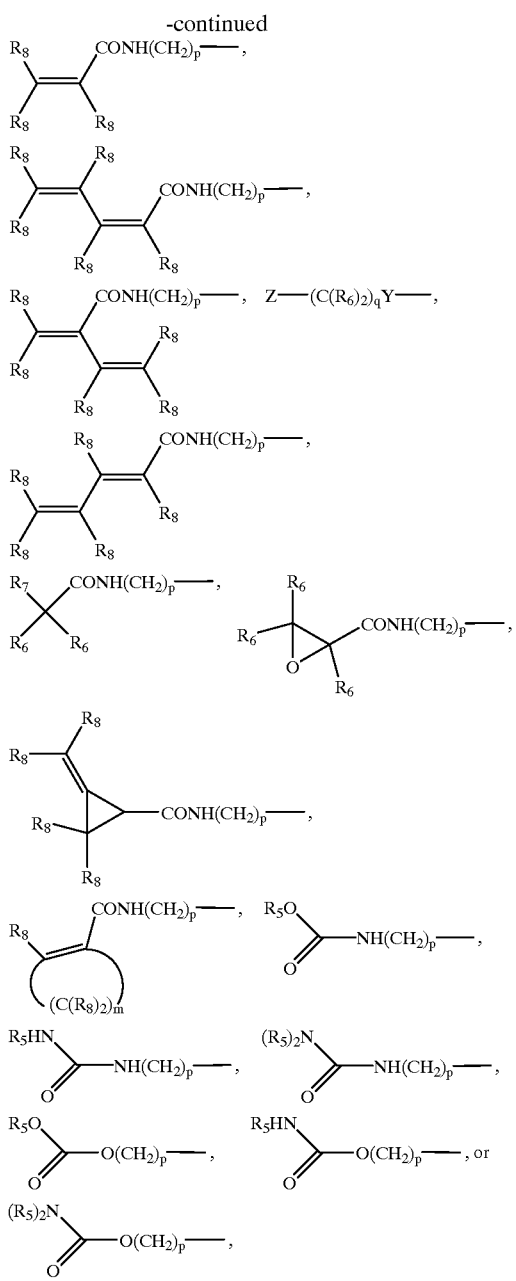

R$_5$ is alkyl of 1–6 carbon atoms, alkyl optionally substituted with one or more halogen atoms, phenyl, or phenyl optionally substituted with one or more halogen, alkoxy of 1–6 carbon atoms, trifluoromethyl, amino, nitro, cyano, or alkyl of 1–6 carbon atoms groups;

R$_6$ is hydrogen, alkyl of 1–6 carbon atoms, or alkenyl of 2–6 carbon atoms;

R$_7$ is chloro or bromo

R$_8$ is hydrogen, alkyl of 1–6 carbon atoms, aminoalkyl of 1–6 carbon atoms, N-alkylaminoalkyl of 2–9 carbon atoms, N,N-dialkylaminoalkyl of 3–12 carbon atoms, N-cycloalkylaminoalkyl of 4–12 carbon atoms, N-cycloalkyl-N-alkylaminoalkyl of 5–18 carbon atoms, N,N-dicycloalkylaminoalkyl of 7–18 carbon atoms, morpholino-N-alkyl wherein the alkyl group is 1–6 carbon atoms, piperidino-N-alkyl wherein the alkyl group is 1–6 carbon atoms, N-alkyl-piperidino-N-alkyl wherein either alkyl group is 1–6 carbon atoms, azacycloalkyl-N-alkyl of 3–11 carbon atoms, hydroxyalkyl of 1–6 carbon atoms, alkoxyalkyl of 2–8 carbon atoms, carboxy, carboalkoxy of 1–6 carbon atoms, phenyl, carboalkyl of 2–7 carbon atoms, chloro, fluoro, or bromo;

Z is amino, hydroxy, alkoxy of 1–6 carbon atoms, alkylamino wherein the alkyl moiety is of 1–6 carbon atoms, dialkylamino wherein each of the alkyl moieties is of 1–6 carbon atoms, morpholino, piperazino, N-alkylpiperazino wherein the alkyl moiety is of 1–6 carbon atoms, or pyrrolidino;

m=1–4, q=1–3, and p=0–3;

any of the substituents R$_1$, R$_2$, R$_3$, or R$_4$ that are located on contiguous carbon atoms can together be the divalent radical —O—C(R$_8$)$_2$—O—;

or a pharmaceutically acceptable salt thereof with the proviso that when Y is —NH—, R$_1$, R$_2$, R$_3$, and R$_4$ are hydrogen, and n is 0, X is not 2-methylphenyl.

23. The method according to claim 22 wherein the neoplasm expresses EGFR.

24. The method according to claim 22 wherein the neoplasm expresses MAPK.

25. The method according to claim 22 wherein the neoplasm expresses ECK.

26. The method according to claim 22 wherein the neoplasm expresses KDR.

27. The method according to claim 22 wherein the neoplasm is selected from the group consisting of breast, kidney, bladder, mouth, larynx, esophagus, stomach, colon, ovary, and lung.

28. A method of treating, inhibiting the progression of, or eradicating polycystic kidney disease in a mammal which comprises administering to said mammal an effective amount of a compound having the formula

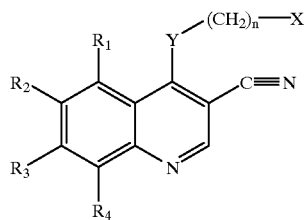

wherein:

X is cycloalkyl of 3 to 7 carbon atoms, which may be optionally substituted with one or more alkyl of 1 to 6 carbon atom groups; or is a pyridinyl, pyrimidinyl, or phenyl ring; wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

n is 0–1;

Y is —NH—, —O—, —S—, or —NR—;

R is alkyl of 1–6 carbon atoms;

$R_1$, $R_2$, $R_3$, and $R_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, aminoalkyl of 1–4 carbon atoms, N-alkylaminoalkyl of 2–7 carbon atoms, N,N-dialkylaminoalkyl of 3–14 carbon atoms, phenylamino, benzylamino,

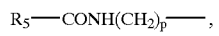

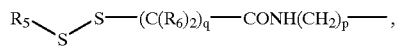

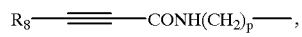

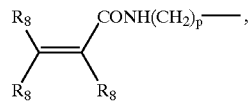

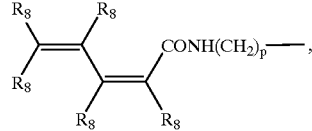

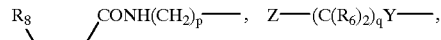

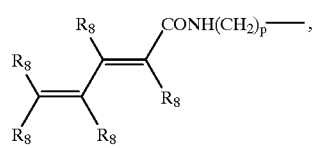

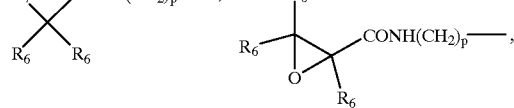

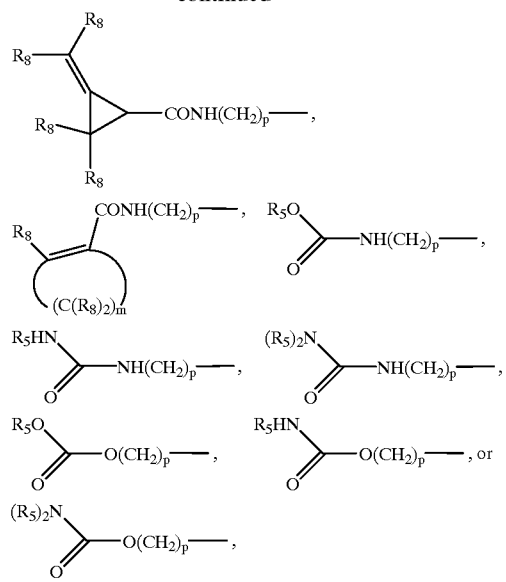

$R_5$ is alkyl of 1–6 carbon atoms, alkyl optionally substituted with one or more halogen atoms, phenyl, or phenyl optionally substituted with one or more halogen, alkoxy of 1–6 carbon atoms, trifluoromethyl, amino, nitro, cyano, or alkyl of 1–6 carbon atoms groups;

$R_6$ is hydrogen, alkyl of 1–6 carbon atoms, or alkenyl of 2–6 carbon atoms;

$R_7$ is chloro or bromo $R_8$ is hydrogen, alkyl of 1–6 carbon atoms, aminoalkyl of 1–6 carbon atoms, N-alkylaminoalkyl of 2–9 carbon atoms, N,N-dialkylaminoalkyl of 3–12 carbon atoms, N-cycloalkylaminoalkyl of 4–12 carbon atoms, N-cycloalkyl-N-alkylaminoalkyl of 5–18 carbon atoms, N,N-dicycloalkylaminoalkyl of 7–18 carbon atoms, morpholino-N-alkyl wherein the alkyl group is 1–6 carbon atoms, piperidino-N-alkyl wherein the alkyl group is 1–6 carbon atoms, N-alkyl-piperidino-N-alkyl wherein either alkyl group is 1–6 carbon atoms, azacycloalkyl-N-alkyl of 3–11 carbon atoms, hydroxyalkyl of 1–6 carbon atoms, alkoxyalkyl of 2–8 carbon atoms, carboxy, carboalkoxy of 1–6 carbon atoms, phenyl, carboalkyl of 2–7 carbon atoms, chloro, fluoro, or bromo;

Z is amino, hydroxy, alkoxy of 1–6 carbon atoms, alkylamino wherein the alkyl moiety is of 1–6 carbon atoms, dialkylamino wherein each of the alkyl moieties is of 1–6 carbon atoms, morpholino, piperazino, N-alkylpiperazino wherein the alkyl moiety is of 1–6 carbon atoms, or pyrrolidino;

m=1–4, q=1–3, and p=0–3;

any of the substituents $R_1$, $R_2$, $R_3$, or $R_4$ that are located on contiguous carbon atoms can together be the divalent radical —O—C($R_8$)$_2$—O—;

or a pharmaceutically acceptable salt thereof with the proviso that when Y is —NH—, $R_1$, $R_2$, $R_3$, and $R_4$ are hydrogen, and n is 0, X is not 2-methylphenyl.

29. A pharmaceutical composition which comprises a compound having the formula

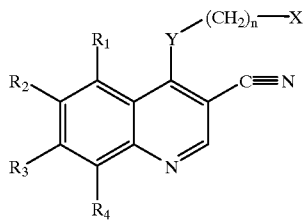

wherein:

X is cycloalkyl of 3 to 7 carbon atoms, which may be optionally substituted with one or more alkyl of 1 to 6 carbon atom groups; or is a pyridinyl, pyrimidinyl, or phenyl ring; wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

n is 0–1;

Y is —NH—, —O—, —S—, or —NR—;

R is alkyl of 1–6 carbon atoms;

$R_1$, $R_2$, $R_3$, and $R_4$ are each, independently, hydrogen, halogen, alkyl of 1–6 carbon atoms, alkenyl of 2–6 carbon atoms, alkynyl of 2–6 carbon atoms, alkenyloxy of 2–6 carbon atoms, alkynyloxy of 2–6 carbon atoms, hydroxymethyl, halomethyl, alkanoyloxy of 1–6 carbon atoms, alkenoyloxy of 3–8 carbon atoms, alkynoyloxy of 3–8 carbon atoms, alkanoyloxymethyl of 2–7 carbon atoms, alkenoyloxymethyl of 4–9 carbon atoms, alkynoyloxymethyl of 4–9 carbon atoms, alkoxymethyl of 2–7 carbon atoms, alkoxy of 1–6 carbon atoms, alkylthio of 1–6 carbon atoms, alkylsulphinyl of 1–6 carbon atoms, alkylsulphonyl of 1–6 carbon atoms, alkylsulfonamido of 1–6 carbon atoms, alkenylsulfonamido of 2–6 carbon atoms, alkynylsulfonamido of 2–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzyl, amino, hydroxyamino, alkoxyamino of 1–4 carbon atoms, alkylamino of 1–6 carbon atoms, dialkylamino of 2 to 12 carbon atoms, aminoalkyl of 1–4 carbon atoms, N-alkylaminoalkyl of 2–7 carbon atoms, N,N-dialkylaminoalkyl of 3–14 carbon atoms, phenylamino, benzylamino,

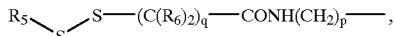
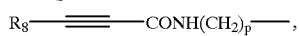

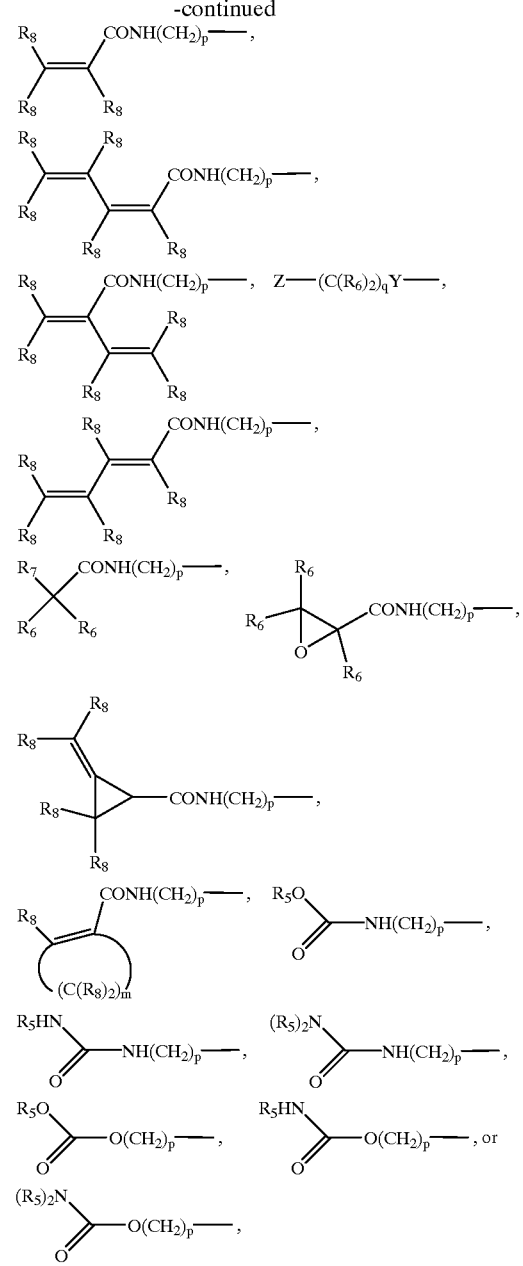

$R_5$ is alkyl of 1–6 carbon atoms, alkyl optionally substituted with one or more halogen atoms, phenyl, or phenyl optionally substituted with one or more halogen, alkoxy of 1–6 carbon atoms, trifluoromethyl, amino, nitro, cyano, or alkyl of 1–6 carbon atoms groups;

$R_6$ is hydrogen, alkyl of 1–6 carbon atoms, or alkenyl of 2–6 carbon atoms;

$R_7$ is chloro or bromo $R_8$ is hydrogen, alkyl of 1–6 carbon atoms, aminoalkyl of 1–6 carbon atoms, N-alkylaminoalkyl of 2–9 carbon atoms, N,N-dialkylaminoalkyl of 3–12 carbon atoms, N-cycloalkylaminoalkyl of 4–12 carbon atoms, N-cycloalkyl-N-alkylaminoalkyl of 5–18 carbon atoms, N,N-dicycloalkylaminoalkyl of 7–18 carbon atoms, morpholino-N-alkyl wherein the alkyl group is 1–6 carbon atoms, piperidino-N-alkyl wherein the alkyl group is 1–6 carbon atoms, N-alkyl-piperidino-N-alkyl wherein either alkyl group is 1–6 carbon atoms, azacycloalkyl-N-alkyl of 3–11 carbon atoms, hydroxyalkyl of 1–6 carbon atoms, alkoxyalkyl of 2–8 carbon atoms, carboxy, carboalkoxy of 1–6 carbon atoms, phenyl, carboalkyl of 2–7 carbon atoms, chloro, fluoro, or bromo;

Z is amino, hydroxy, alkoxy of 1–6 carbon atoms, alkylamino wherein the alkyl moiety is of 1–6 carbon atoms, dialkylamino wherein each of the alkyl moieties is of 1–6 carbon atoms, morpholino, piperazino, N-alkylpiperazino wherein the alkyl moiety is of 1–6 carbon atoms, or pyrrolidino;

m=1–4, q=1–3, and p=0–3;

any of the substituents $R_1$, $R_2$, $R_3$, or $R_4$ that are located on contiguous carbon atoms can together be the divalent radical —O—C($R_8$)$_2$—O—;

or a pharmaceutically acceptable salt thereof with the proviso that when Y is —NH—, $R_1$, $R_2$, $R_3$, and $R_4$ are hydrogen, and n is 0, X is not 2-methylphenyl and a pharmaceutically acceptable carrier.

* * * * *